(12) United States Patent  
Mohler et al.

(10) Patent No.: US 7,190,994 B2  
(45) Date of Patent: Mar. 13, 2007

(54) METHOD AND SYSTEM FOR GENERATING A LIKELIHOOD OF CARDIOVASCULAR DISEASE, ANALYZING CARDIOVASCULAR SOUND SIGNALS REMOTELY FROM THE LOCATION OF CARDIOVASCULAR SOUND SIGNAL ACQUISITION, AND DETERMINING TIME AND PHASE INFORMATION FROM CARDIOVASCULAR SOUND SIGNALS

(75) Inventors: Sailor Hampton Mohler, Columbia, MD (US); Dan Mulholland, Arlington, VA (US); Alan Figgatt, Reston, VA (US); Warren Holford, Fairfax, VA (US)

(73) Assignee: Sonomedica, Inc., Vienna, VA (US)

( * ) Notice: Subject to any disclaimer, the term of this patent is extended or adjusted under 35 U.S.C. 154(b) by 430 days.

(21) Appl. No.: 10/390,172

(22) Filed: Mar. 18, 2003

(65) Prior Publication Data  
US 2003/0229289 A1 Dec. 11, 2003

Related U.S. Application Data

(60) Provisional application No. 60/364,605, filed on Mar. 18, 2002.

(51) Int. Cl.  
*A61B 5/04* (2006.01)

(52) U.S. Cl. .................................................. 600/514
(58) Field of Classification Search ................ 600/586, 600/513, 514  
See application file for complete search history.

(56) References Cited

U.S. PATENT DOCUMENTS 6,629,937 B2 * 10/2003 Watrous ...................... 600/586

* cited by examiner

*Primary Examiner*—Scott M. Getzow  
(74) *Attorney, Agent, or Firm*—Bingham McCutchen LLP

(57) ABSTRACT

A system, method, and computer executable code for generating a likelihood of cardiovascular disease from acquired cardiovascular sound signals is diesclosed, where the generated likelihood of cardiovascular disease is based at least on an overlapping in time of bruit candidates in one heart cycle or in different heart cycles. Also disclosed is a system, method, and computer executable code for collecting, forwarding, and analyzing cardiovascular sound signals, where the collecting and analyzing may occur at locations that are remote from each other. Further disclosed is a system, method, and computer executable code for determining the time and phase information contained in cardiovascular sound signals, for use in analyzing those cardiovascular sound signals.

48 Claims, 81 Drawing Sheets

Autocorrelation Peaks as a Function of Time Displacement

Math Model Envelope Calculated from Convolution Sub-Peak Parameters

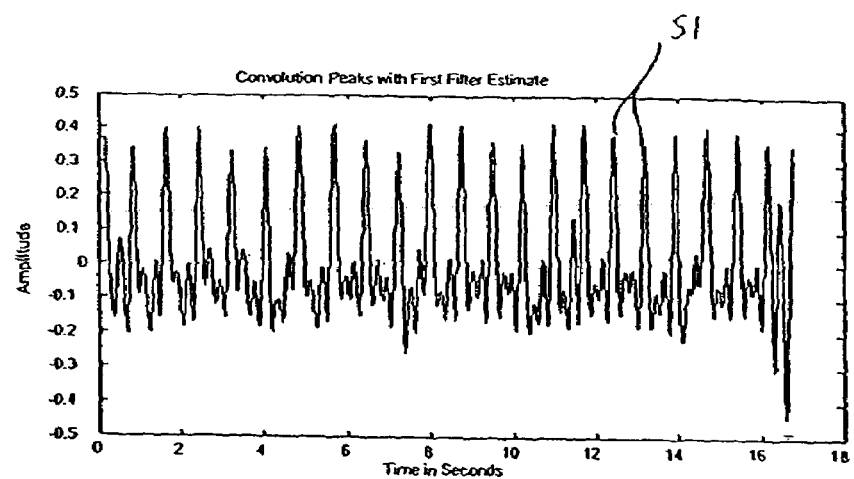
Fig. 20: Convolution Peak Search for Beats Using First Estimate
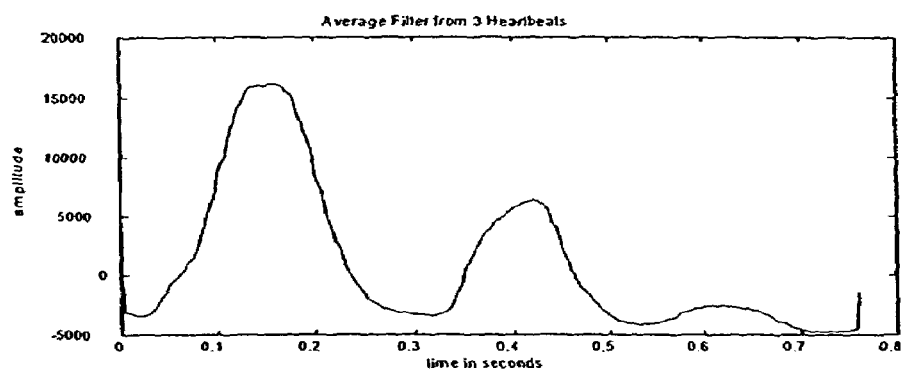
Fig. 21: Bootstrap Heartbeat Envelope Estimated from a 3-Beat Average
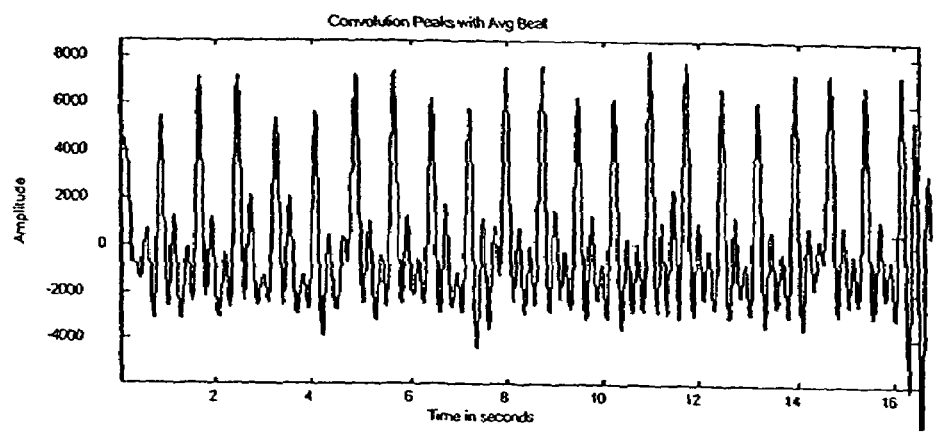
Fig. 22: Correlation Peaks from 5-Beat Average Marking Start of Beats Input: Filtered and Smoothed Narrowband Time Data – shown above
Interim Processing Steps:
AutoCorrelation of Heart Audio NB Time Data (selected segment)
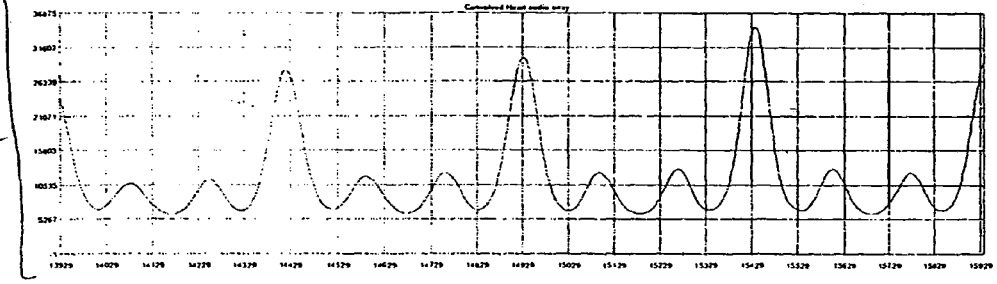
3310
Math Model Heart Filter (hfilt) and BootStrap Filters (kfilt):
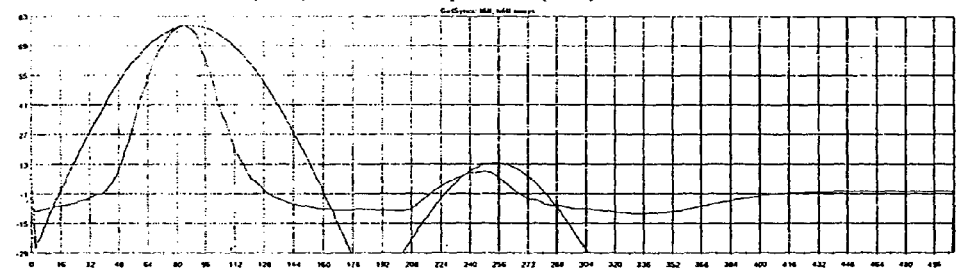
3320
Output:
Synch Locations – Mark the start of the HeartBeat. Shown here for the NB HA data
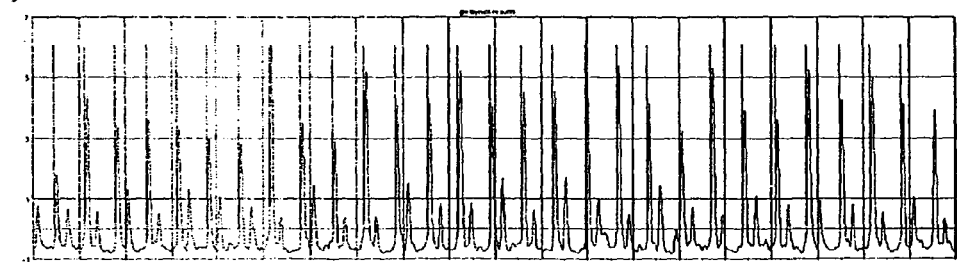
3330
Parsing Score, Synch Array and Duration Array:
Parsing Score = 0.98
FIG. 33

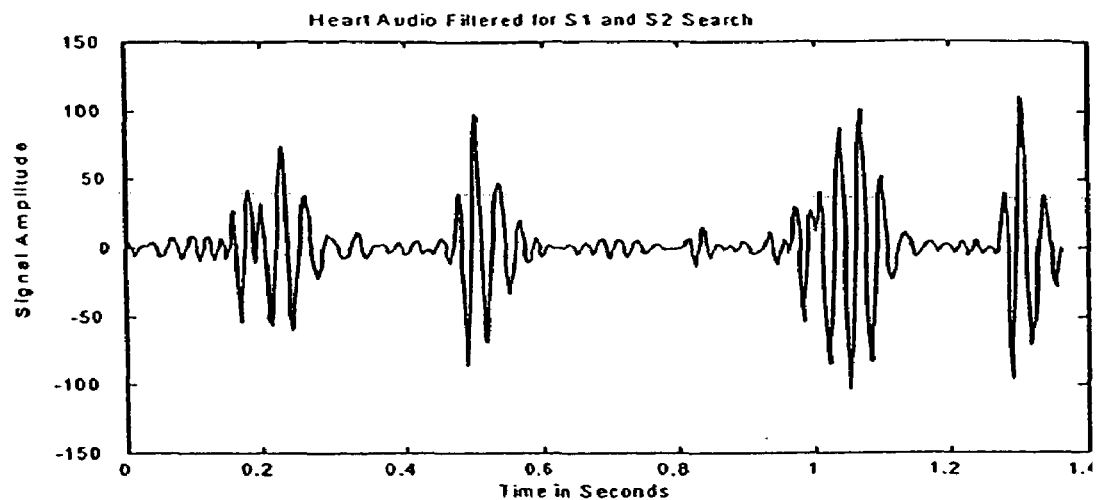
Fig. 46: Heartbeat Audio Filtered to Enhance S1 and S2
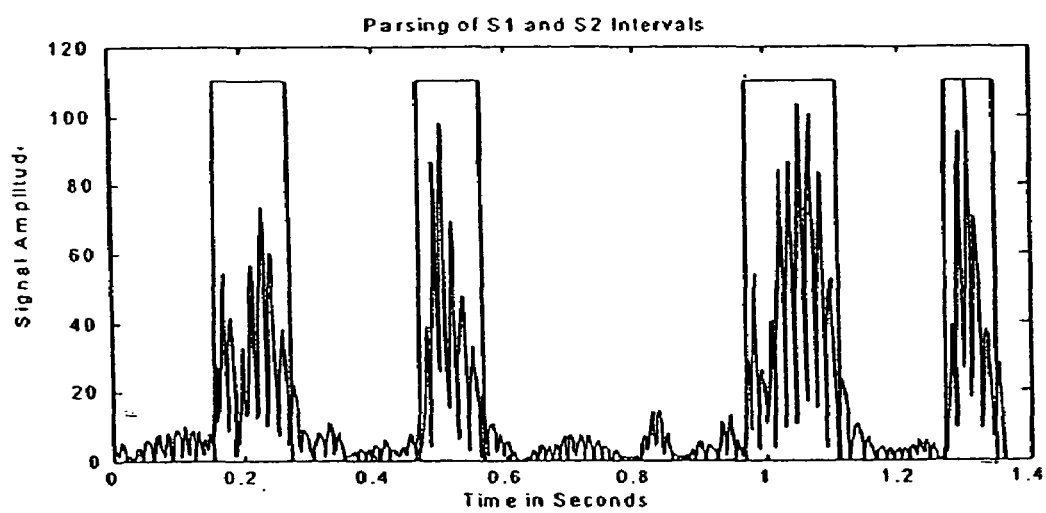
Fig. 47: Parsing of the S1 and S2 Intervals of the Heartbeats Input: Filtered NarrowBand Heart Audio Time Data, Synch Array, Duration Array Interim steps:

Chart shows the Assign Phaze Window and Pksax array

4810

Output: s_inxs array marking S1, S2, S3, S4 regions

| | | |
|---|---|---|
| S_inxs(1,1) (1,2) | 15 | 80 |
| S_inxs(2,1) (2,2) | 186 | 248 |
| S_inxs(3,1) (3,2) | 349 | 367 |
| S_inxs(4,1) (4,2) | 426 | 466 |

4820

Input: Filtered Narrowband Time Data, Synch Array, Duration Array, s_inxs Array

Output: Pulse arrays, Statistics Arrays

Size of Pulse Arrays = 91 pulses detected, First 12 shown here

4910

| Index | Pulse Start | Pulse Length | Pulse Power |
|---|---|---|---|
| 1 | 47 | 141 | 28 |
| 2 | 245 | 69 | 1 |
| 3 | 351 | 270 | 111 |
| 4 | 640 | 38 | 1 |
| 5 | 732 | 19 | 1 |
| 6 | 805 | 169 | 289 |
| 7 | 1013 | 51 | 21 |
| 8 | 1081 | 19 | 0 |
| 9 | 1322 | 141 | 174 |
| 10 | 1514 | 103 | 51 |
| 11 | 1812 | 317 | 235 |
| 12 | 2264 | 150 | 188 |

Pulse Statistics Array for each heartbeat:

4920

| | S1 | | | S2 | | | S3 | | | S4 | | |
|---|---|---|---|---|---|---|---|---|---|---|---|---|
| Beat | Start | Length | Pwr | Start | Length | Pwr | Start | Length | Pwr | Start | Length | Pwr |
| 1 | 3 | 158 | 65 | 162 | 150 | 47 | 384 | 19 | 1 | 457 | 25 | 43 |
| 2 | 1 | 144 | 246 | 183 | 70 | 21 | 0 | 0 | 0 | 0 | 0 | 0 |
| 3 | 4 | 141 | 174 | 196 | 103 | 51 | 0 | 0 | 0 | 494 | 15 | 11 |
| 4 | 1 | 160 | 119 | 162 | 142 | 105 | 0 | 0 | 0 | 442 | 45 | 56 |
| 5 | 1 | 128 | 128 | 187 | 134 | 48 | 361 | 59 | 1 | 442 | 33 | 1 |
| 6 | 1 | 142 | 149 | 186 | 78 | 41 | 352 | 87 | 3 | 463 | 18 | 1 |
| 7 | 1 | 120 | 152 | 189 | 126 | 36 | 360 | 30 | 1 | 444 | 50 | 123 |
| 8 | 1 | 158 | 388 | 179 | 58 | 19 | 0 | 0 | 0 | 0 | 0 | 0 |
| 9 | 1 | 145 | 191 | 193 | 98 | 58 | 408 | 33 | 1 | 442 | 63 | 3 |
| 10 | 13 | 129 | 156 | 162 | 121 | 15 | 360 | 28 | 1 | 461 | 34 | 74 |
| 11 | 1 | 141 | 308 | 162 | 95 | 18 | 0 | 0 | 0 | 483 | 17 | 26 |
| 12 | 1 | 142 | 217 | 192 | 125 | 59 | 0 | 0 | 0 | 454 | 68 | 91 |
| 13 | 1 | 131 | 175 | 189 | 97 | 31 | 0 | 0 | 0 | 472 | 25 | 72 |
| 14 | 1 | 131 | 317 | 162 | 112 | 27 | 348 | 44 | 1 | 0 | 0 | 0 |
| 15 | 1 | 142 | 226 | 193 | 101 | 65 | 359 | 70 | 2 | 452 | 68 | 115 |

FIG. 49

Fig. 50 – The waveform of one heartbeat (top),
and a magnified view of bruits (bottom)

| File | Row | Beat | Skew | Time | PkPwr | PkFreq | TimePwr | mbProb | SynTime | DurTime |
|---|---|---|---|---|---|---|---|---|---|---|
| 77340pw8.tmi | 1 | 1 | 0.435 | 1.654 | 17.5 | 345 | 0.194 | 0.000 | 1.111 | 1.156 |
| 77340pw8.tmi | 2 | 1 | 0.271 | 1.669 | 24.2 | 310 | 0.171 | 0.000 | 1.111 | 1.156 |
| 77340pw8.tmi | 3 | 4 | 0.334 | 5.123 | 18.7 | 310 | 0.267 | 0.000 | 4.619 | 1.175 |
| 77340pw8.tmi | 4 | 4 | 0.363 | 5.137 | 20.0 | 345 | 0.254 | 0.000 | 4.619 | 1.175 |
| 77340pw8.tmi | 5 | 5 | 0.538 | 6.821 | 20.6 | 310 | 0.226 | 0.000 | 5.794 | 1.170 |
| 77340pw8.tmi | 6 | 5 | 0.411 | 6.835 | 20.9 | 310 | 0.216 | 0.000 | 5.794 | 1.170 |
| 77340pw8.tmi | 7 | 5 | 0.566 | 6.922 | 18.4 | 310 | 0.208 | 0.000 | 5.794 | 1.170 |
| 77340pw8.tmi | 8 | 6 | 0.651 | 7.517 | 19.3 | 310 | 0.196 | 0.000 | 6.964 | 1.098 |
| 77340pw8.tmi | 9 | 6 | 0.393 | 7.532 | 27.3 | 310 | 0.279 | 0.000 | 6.964 | 1.098 |
| 77340pw8.tmi | 10 | 6 | 0.363 | 7.546 | 22.7 | 310 | 0.212 | 0.000 | 6.964 | 1.098 |
| 77340pw8.tmi | 11 | 7 | 0.436 | 9.041 | 15.9 | 345 | 0.223 | 0.000 | 8.061 | 1.091 |
| 77340pw8.tmi | 12 | 9 | 0.515 | 11.421 | 14.5 | 1585 | 0.222 | 0.000 | 10.324 | 1.125 |
| 77340pw8.tmi | 13 | 10 | 0.425 | 12.002 | 18.2 | 310 | 0.231 | 0.000 | 11.449 | 1.086 |
| 77340pw8.tmi | 14 | 10 | 0.554 | 12.350 | 24.9 | 310 | 0.265 | 0.000 | 11.449 | 1.086 |
| 77340pw8.tmi | 15 | 10 | 0.455 | 12.365 | 14.0 | 413 | 0.276 | 0.000 | 11.449 | 1.086 |
| 77340pw8.tmi | 16 | 11 | 0.499 | 13.061 | 14.4 | 310 | 0.266 | 0.000 | 12.535 | 1.109 |
| 77340pw8.tmi | 17 | 12 | 0.381 | 14.353 | 15.5 | 482 | 0.220 | 0.000 | 13.644 | 1.073 |
| 77340pw8.tmi | 18 | 13 | 0.391 | 15.267 | 15.8 | 310 | 0.295 | 0.000 | 14.717 | 0.980 |
| 77340pw8.tmi | 19 | 14 | 0.472 | 16.239 | 14.5 | 413 | 0.244 | 0.000 | 15.696 | 1.200 |
| 77340pw8.tmi | 20 | 14 | 0.990 | 16.675 | 15.4 | 345 | 0.206 | 0.000 | 15.696 | 1.200 |
| 77340pw8.tmi | 21 | 15 | 0.338 | 17.473 | 32.7 | 310 | 0.251 | 0.000 | 16.896 | 1.127 |
| 77340pw8.tmi | 22 | 15 | 0.306 | 17.488 | 21.9 | 310 | 0.204 | 0.000 | 16.896 | 1.127 |
| 77340pw8.tmi | 23 | 18 | 0.647 | 21.000 | 14.4 | 1654 | 0.239 | 0.000 | 20.229 | 1.104 |
| 77340pw8.tmi | 24 | 18 | 0.547 | 21.014 | 15.0 | 310 | 0.235 | 0.000 | 20.229 | 1.104 |
| 77340pw8.tmi | 25 | 19 | 0.574 | 21.827 | 14.6 | 1275 | 0.186 | 0.000 | 21.333 | 1.141 |
| 77340pw8.tmi | 26 | 19 | 0.572 | 21.899 | 18.9 | 310 | 0.297 | 0.000 | 21.333 | 1.141 |
| 77340pw8.tmi | 27 | 22 | 0.543 | 25.368 | 15.5 | 482 | 0.182 | 0.000 | 24.714 | 1.136 |
| 77340pw8.tmi | 28 | 22 | 0.414 | 25.803 | 16.0 | 310 | 0.207 | 0.000 | 24.714 | 1.136 |
| 77340pw8.tmi | 29 | 23 | 0.330 | 26.427 | 22.2 | 310 | 0.189 | 0.000 | 25.850 | 1.152 |

Fig. 66

Probability of Bruit as a function of the Spectral SNR

| P(Skew) = 1 | P(Skew) = 1 | P(Skew) = 1 | P(Skew) = 0.7 | P(Skew) = 0.5 | P(Skew) = 0.7 | P(Skew) = 1 | P(Skew) = 1 | P(Skew) = 1 |
|---|---|---|---|---|---|---|---|---|

(avg. heartbeat period ÷ narrow band SR) entries

**INVERSE TIME DOMAIN GAUSSIAN
DISTRIBUTION ARRAY FOR BRUIT 1**

FIG. 75

Fig. 76: Sample Probability of a Bruit on the Time Axis, Given one Anomaly

| P(Amplitude) = 1 | P(Amplitude) = 1 | P(Amplitude) = 1 | P(Amplitude) = 0.8 | P(Amplitude) = 0.3 | P(Amplitude) = 0.8 | P(Amplitude) = 1 | P(Amplitude) = 1 | P(Amplitude) = 1 |
|---|---|---|---|---|---|---|---|---|

▲─────────────────────────── 64 entries ───────────────────────────▲

INVERSE FREQUENCY DOMAIN GAUSSIAN
DISTRIBUTION ARRAY FOR BRUIT 1

Fig. 77

Fig. 78: Sample Probability of a Bruit on the Frequency Axis, Given one Anomaly

TWO-DIMENSIONAL GAUSSIAN DISTRIBUTION
TABLE FOR EACH ENTRY IN BRUIT CANDIDATE
TABLE

INVERSE GAUSSIAN DISTRIBUTION ARRAY
FOR BRUIT 1

INVERSE GAUSSIAN DISTRIBUTION ARRAY FOR
BRUIT 2 (NOT PREVIOUSLY ILLUSTRATED EXPLICITLY)

METHOD AND SYSTEM FOR GENERATING A LIKELIHOOD OF CARDIOVASCULAR DISEASE, ANALYZING CARDIOVASCULAR SOUND SIGNALS REMOTELY FROM THE LOCATION OF CARDIOVASCULAR SOUND SIGNAL ACQUISITION, AND DETERMINING TIME AND PHASE INFORMATION FROM CARDIOVASCULAR SOUND SIGNALS

RELATED APPLICATIONS

The present application claims priority to U.S. Provisional Application No. 60/364,605, filed Mar. 18, 2002, the disclosure of which is incorporated herein by reference in its entirety.

FIELD OF THE INVENTION

The invention relates to systems and methods for generating a likelihood of cardiovascular disease based on acquired cardiovascular sound signals, analyzing the cardiovascular sound signals at a location that is remote from the location of cardiovascular sound signal acquisition, and determining time and phase information from the cardiovascular sound signals.

BACKGROUND

Occlusions in arteries and other portions of the cardiovascular system are often associated with various types of cardiovascular disease, such as coronary heart disease. Many of these occlusions are believed to be the source of turbulent flow and abnormal high frequency sounds approximately in the 200 to 2000 Hz, usually 300 to 1800 Hz, audio band. These sounds, generically referred to as "bruits," are known to occur at many different time locations within a heart cycle, such as bruits that are believed to occur during diastole when the maximum pressure from the aorta surges into the arteries. Detection of bruits can provide physicians with valuable information that can be used to assess whether a patient has cardiovascular disease, such as coronary heart disease ("CHD"). Numerous techniques have attempted to detect and analyze high frequency signals from the cardiovascular sounds of a patient, some of which use averaging, neural networks, wavelet transforms, and linear prediction analysis. However, none of these conventional techniques are believed to provide a reliable probability of the likelihood that a patient has cardiovascular disease.

SUMMARY OF THE INVENTION

In light of the foregoing problems associated with conventional techniques for detecting the presence of cardiovascular disease, generally speaking, one object of the invention is to provide a system, method, and computer executable code for generating a likelihood of cardiovascular disease from acquired cardiovascular sound signals, where the generated likelihood of cardiovascular disease is based at least on an overlapping in time of bruit candidates in one heart cycle or in different heart cycles so as to emphasize the repetitive nature of bruits that occur in one or multiple heart cycle signals. Another object of the invention is to provide a system, method, and computer executable code for collecting, forwarding, and analyzing cardiovascular sound signals, where the collecting and analyzing may occur at locations that are remote from each other. Still another object of the invention is to provide a system, method, and computer executable code for determining the time and phase information contained in cardiovascular sound signals, for use in analyzing those cardiovascular sound signals.

Other objects, advantages and features associated with the invention will become more readily apparent to those skilled in the art from the following detailed description. As will be realized, the invention is capable of other and different embodiments, and its several details are capable of modification in various obvious aspects, all without departing from the invention. Accordingly, the drawings and the description are to be regarded as illustrative in nature, and not limitative.

BRIEF DESCRIPTION OF THE DRAWINGS

FIG. 20 depicts a signal consisting of a set of leveled peaks that result from correlating a math model envelope against the smoothed heart signals, and then dividing by a set of automatic gain control values.

FIG. 21 illustrates a bootstrap filter that results from averaging multiple heart cycles signals.

FIG. 22 depicts a signal consisting of a set of peaks that result from convolving the bootstrap filter with the filtered cardiovascular sound signals.

FIG. 33 is a sequence of signals showing various stages of processing signals

FIG. 46 is a filtered heart audio signal showing enhanced S1 and S2 pulses.

FIG. 47 is a signal representing the parsing process that identifies the S1 and S2 intervals of the heart cycle signals.

FIG. 49 shows a portion of a pulse array and a portion of a pulse statistics array.

FIG. 66 is a portion of a bruit candidate table.

FIG. 75 depicts an inverse time domain Gaussian distribution array for a first bruit.

FIG. 77 depicts an inverse frequency domain Gaussian distribution array for a first bruit.

DETAILED DESCRIPTION OF THE PREFERRED EMBODIMENTS

System Overview

Figure 1:
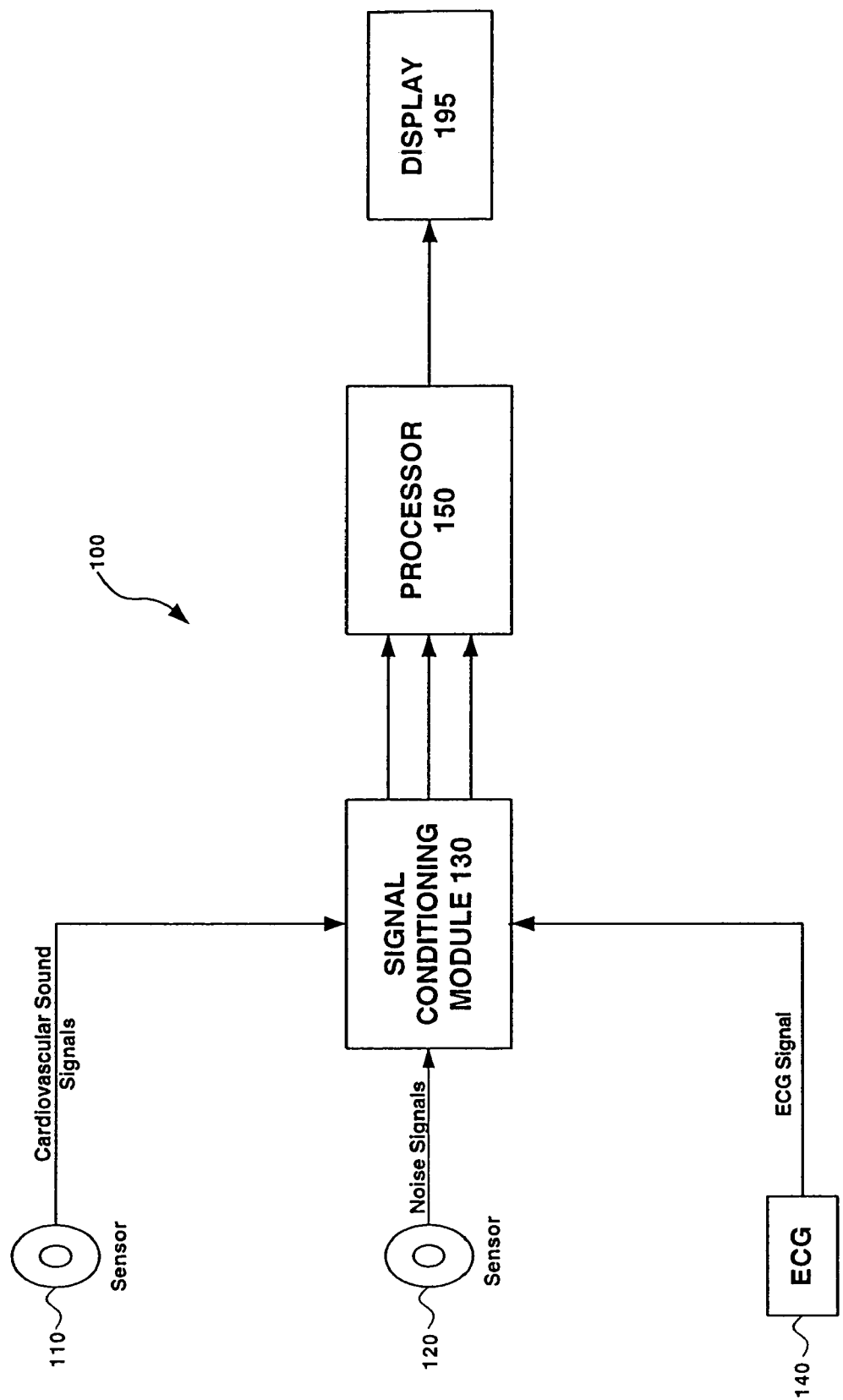
FIG. 1 depicts a system for acquiring and analyzing cardiovascular sound signals in accordance with one embodiment of the invention.

By way of an overview, the embodiments of the invention described herein concern systems and methods for identifying cardiovascular sound signals that are indicative of one or more bruits, i.e., bruit candidates, and for generating a likelihood of cardiovascular disease that emphasizes the occurrence of multiple bruits in one or multiple heart cycles.

Occlusions and other anomolies in the cardiovascular system are often associated with various types of cardiovascular disease, such as coronary heart disease. The presence of occlusions and other abnormalities in the cardiovascular system, such as in the heart and blood vessels, is believed to be the source of abnormal sounds, referred to herein as "bruits," that are associated with many different varieties of cardiovascular disease. As used herein, "cardiovascular disease" refers to any of the abnormal conditions associated with the cardiovascular system, especially the heart and blood vessels. Set forth below are some examples of cardiovascular diseases that are known to generate various types of bruits: acute alcoholic hepatitis; acute rheumatic fever (Carey Coombs murmur); anemia; aortic insufficiency (Austin Flint); arteriovenous fistula (systemic or pulmonic); atrial myxoma; atrial septal aneurysm; atrial septal defect; atrioventricular junctional rhythm; bacterial endocarditis; branch pulmonary stenosis; carotid occlusion; celiac mesenteric occlusion; chronic cor pulmonale; coarctation of aorta; complete heart block; congenital heart disease; high-to-low pressure shunts; rapid blood flow; secondary to localized arterial obstruction; cor triatriatum; coronary artery disease; coronary heart disease; coronary occlusion; diffuse endomyocardial disease; Ebstein's malformation; femoral occlusion; heart trauma, direct or indirect; hemiangioma; hpyerthyroidism; hyperemia of neoplasm (hepatoma renal cell carcinoma, Paget's disease); hypertensive heart disease; hyperthyroidism; hypertrophic cardiomyopathy; hypertrophic subaortic stenosis; intercostal muscle contractions; intraventricular tumors or other masses; left atrial tumor; left-to-right atrial shunting (Lutembacher's syndrome, mitral atresia plus atrial septal defect); mammary soufflé; marfan syndrome; mediastinal emphysema; membraneous ventricular septal aneurysm; mitral commisurotomy; mitral insufficiency; mitral stenosis; mitral valve prolapse; myocarditis nylon chordae; papillary muscle dysfunction; pericardial effusion; pericardial heart disease; pleural or pericardial adhesions; pneumoperitoneum; pneumothorax; polyarteritis nodosa; pulmonary septal defect (patent ductus arteriosus); renal occlusion; spontaneous closure of ventricular septal defects; systemic artery to pulmonary artery (patent ductus arterious, aortopulmonary window; truncus arteriosus, pulmonary atresia, anomalous left coronary, bronchiectasis, sequestration of the lung); systemic artery to right heart (ruptured sinus of Valsalva, coronary artery fistula); systemic lupus erythematosus; torn porcine valve cusps; tricuspid valve prolapse; venous hum; venovenous shunts (anomalous pulmonary veins, portosystemic shunts); and ventricular septal defect.

There are many types of bruits that are associated with different forms of cardiovascular disease and that can be analyzed in accordance with embodiments of the invention. For example, a bruit may result from one or more of the following types of murmurs: aneurismal murmurs; aortic murmurs; apex murmurs; apical diastolic murmurs; arterial murmurs; attrition murmurs; Austin Flint murmurs; basal diastolic murmurs; Carey Coombs murmurs; continuous cardiac murmurs; cooing murmurs; crescendo murmurs; Cruveilheir-Baumgarten murmurs, diastolic murmurs; Duroziez's early diastolic murmurs; early systolic murmurs; ejection murmurs; extracardiac murmurs; friction murmurs; Gibson murmurs; Graham Steell's murmurs; Hamman's murmurs; hourglass murmurs; humming top murmurs; late systolic murmurs; mid-diastolic murmurs; midsystolic murmurs; mitral murmurs; organic murmurs; pansystolic murmurs; pericardial murmurs; pleuropericardial murmurs; prediastolic murmurs; presystolic murmurs; pulmonic murmurs; regurgitant murmurs; Roger's murmurs; seagull murmurs; stenosal murmurs; Still's murmurs; subclavicular murmurs; systolic murmurs; tricuspid murmurs; vascular murmurs; venous murmurs; and other known and yet to be known murmurs. Categories of some bruits associated with cardiovascular disease include: bruits d'airain; aneurysmal bruits; bruits de bois; bruits de canon; bruits de clapotement; bruits de claquement; bruits de craquement; bruits de cuir neuf; bruits de diable; bruits de drapeau; false bruits; bruits de froissement; bruits de frolement; bruits de frottement; bruits de gallop; bruits de grelot; bruits de lime; bruits de Moulin; bruits de parchemin; bruits de piaulement; bruits placentaire; bruits de pot fele; bruits de rape; bruits de rappel; bruits de Roger; bruits de scie; bruits skodique; bruits de soufflet; systolic bruits; bruits de tabourka; bruits de tambour; and Verstraeten's bruits.

For purposes of illustration, the following description concerns bruits associated with occlusions in the cardiovascular system of humans an other mammals, which typically have frequency components that range from 200–2000 Hz, often between 300–1800 Hz, more often between 400–1500 Hz, and most often between 400–1200 Hz. As will be appreciated, alternative embodiments of the invention can be directed to bruits falling below 200 Hz and above 2000 Hz. Also, while some bruits are observed in systole, for purposes of illustration, the following description focuses on bruits occurring in diastole. As will be apparent, the invention is also applicable to bruits occurring in systole.

FIG. 1 illustrates a system 100 for acquiring and analyzing cardiovascular sounds in accordance with one embodiment of the invention. The system 100 includes a sensor 110, which is a device capable of acquiring (i.e., sensing, detecting, or gathering) cardiovascular sound signals from a patient when placed on or near the patient. Examples of sensors 110 that are suitable for the system 100 include those described in U.S. Pat. No. 6,053,872, the entire disclosure of which is hereby incorporated by reference.

Cardiovascular sound signals acquired by the sensor 110 may include those sound signals emanating from the heart, blood vessels (i.e., arteries, veins, capillaries, etc.) and/or other portions of the cardiovascular system of mammals. For purposes of illustration, the following description concerns an embodiment of the invention in which the sensor 110 is placed on a patient's precordium to acquire cardiovascular sound signals that include heart sound signals. However, the sensor 110 may be placed at other locations. For example, in accordance with one embodiment of the invention, the sensor 110 is placed on a patient's back to acquire cardiovascular sound signals. In a further embodiment, the sensor 110 is placed on the neck or leg of a patient to acquire cardiovascular sound signals.

Figure 2:
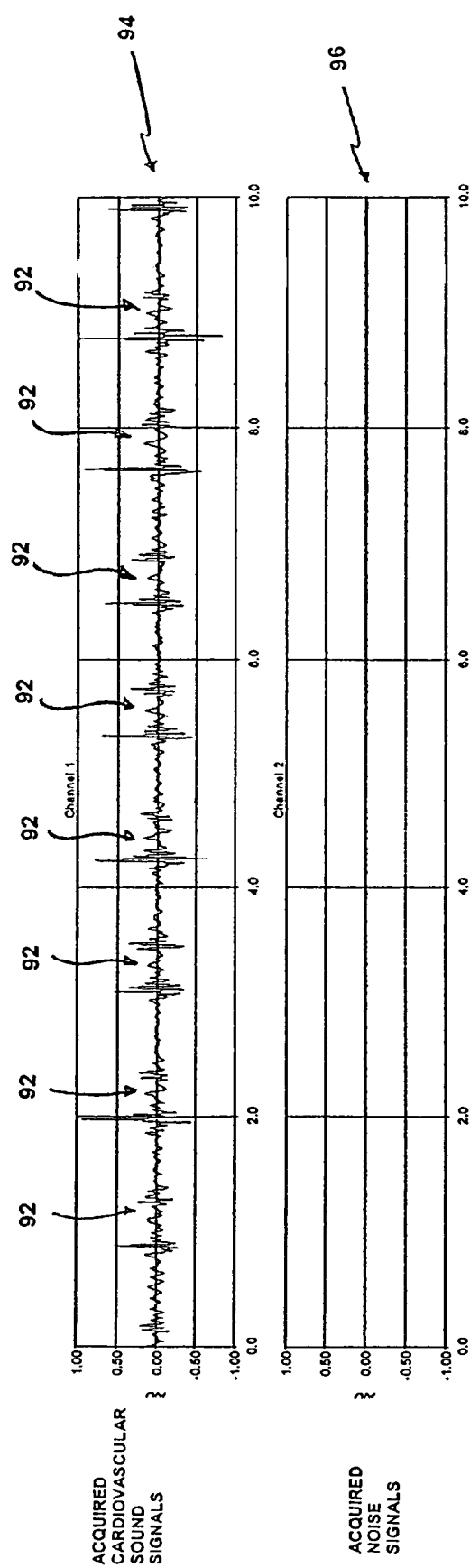
FIG. 2 depicts one embodiment of acquired cardiovascular sound signals and acquired noise sound signals.
Figure 3:
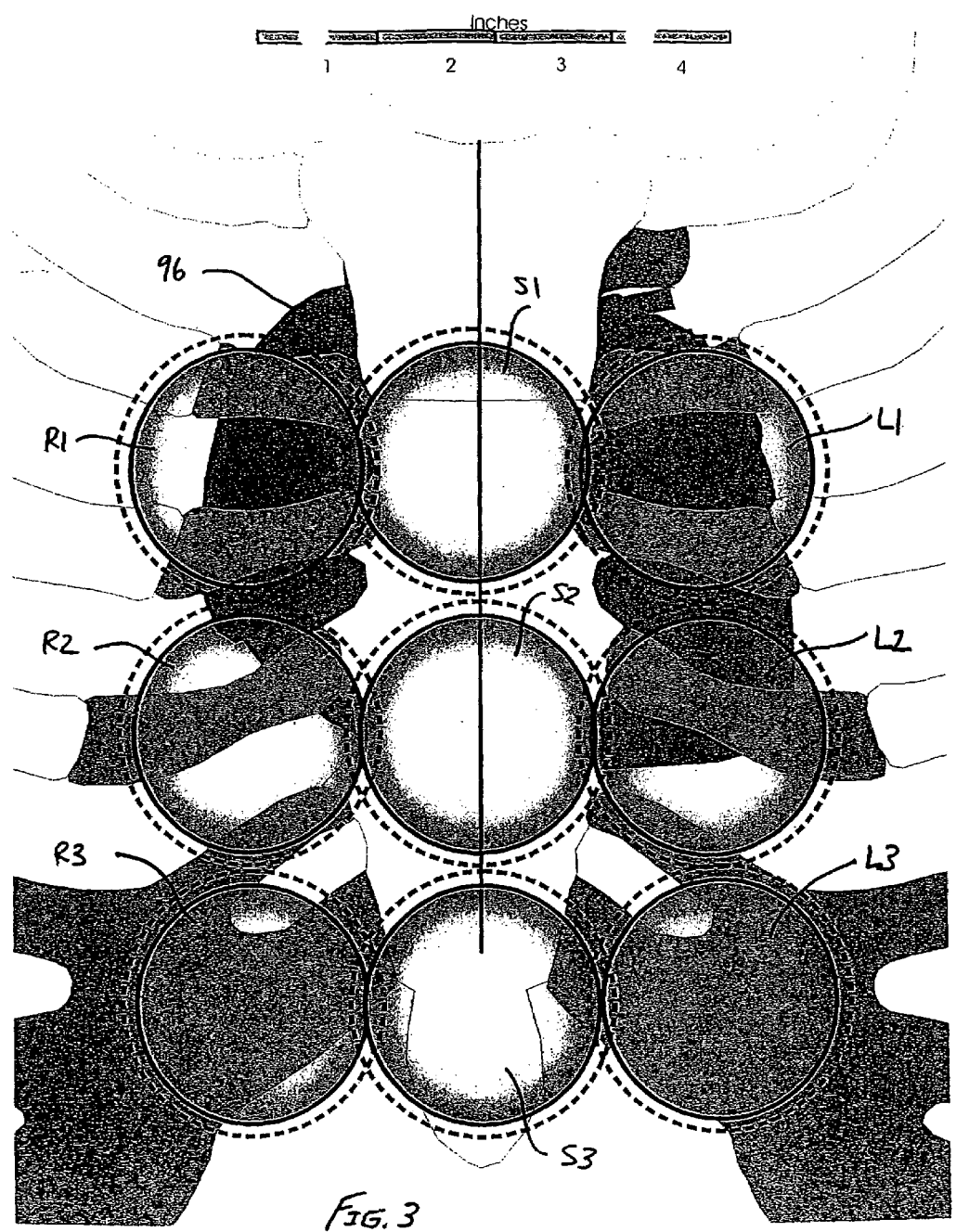
FIG. 3 is a partial view of the nine locations where cardiovascular sound signals are acquired in accordance with one embodiment of the invention.

In the illustrated embodiment of the invention, the sensor 110 is a single sensor that is placed at different locations on the patient for sequentially acquiring cardiovascular sound signals from the patient for a specified period of time. In this manner, the cardiovascular sound signals are said to be gathered in series from different locations. As is illustrated in FIG. 2, the cardiovascular sound signals acquired from one location on the patient's percordium include a plurality (at least two) heart cycle signals 92 to define one heart waveform signal 94. Similar waveforms of other cardiovascular sound signals may be acquired from other areas of the body. In FIG. 2, the vertical axis is representative of the amplitude of the acquired cardiovascular sound signals and the horizontal axis is representative of time. In accordance with the illustrated embodiment, the sensor 110 is placed at nine different locations on a patient's precordium to acquire a heart waveform 94 from each location for a total of nine acquired waveforms. More particularly, and as is illustrated in FIG. 3, the sensor 110 is placed at nine locations R1, R2, R3, S1, S2, S3, L1, L2, and L3 on the patient's precordium that form a 3×3 grid roughly over the patient's heart. Hence, the sensor 110 will acquire cardiovascular sound signals having nine different heart waveform signals 94, where each heart waveform signal has a plurality of heart cycles 92. In the preferred embodiment, the sensor 110 is located at each location R1, R2, R3, S1, S2, S3, L1, L2, and L3 for approximately one minute to acquire the different heart waveform signals in series. In subsequent processing, the serially gathered physiological signals are processed non-coherently. In another embodiment of the invention, two or more sensors 110 are used to acquire cardiovascular sound signals in parallel. In subsequent processing, the parallel-acquired cardiovascular sound signals are processed coherently.

The cardiovascular sound signals acquired by the sensor 110 include at least those frequencies where bruits are found. However, other frequencies may also be of interest or use. Hence, in the illustrated embodiment of the system 100, cardiovascular sound signals are acquired in frequencies between dc and 2000 Hz so as to also encompass audible or possibly inaudible acoustic signals emanating from the cardiovascular system, such as normal sounds of the heart and/or its adjacent veins and arteries. As will be appreciated, because the heart is not isolated from the body, the acquired cardiovascular sound signals will typically include other sounds as well, such as the sounds of air moving through the lungs. In an alternative embodiment of the invention, the acquired cardiovascular sound signals only include frequencies in a limited frequency band, e.g., a 200–2000 Hz, 300–1800 Hz, 400–1500 Hz, or 400–1200 Hz band. This may be accomplished with filters as is apparent. To provide ample frequency resolution for the identification of bruit candidates in the acquired cardiovascular sound signals, in the illustrated embodiment of the system 100, the cardiovascular sound signals are acquired in frequencies between dc and 2000 Hz at a sampling rate of greater than 4000 Hz, preferably at 8000 Hz. However, the cardiovascular sound signals can be sampled at a lower or greater rate than 8000Hz. For example, in an alternative embodiment, the cardiovascular sound signals are sampled at 2000 Hz or at 6000 Hz.

As is also illustrated in FIG. 1, the system 100 also includes a background sensor 120 that acquires background (noise) sound signals. The background sensor 120 is a device capable of measuring, detecting, or gathering background sound signals from the patient and/or the patient's surroundings. In the illustrated embodiment, the background sensor 120 is an omni-directional microphone. The background sound signals acquired by the background sensor 120 typically include various acoustic vibrations, electrical interference, etc., that are generated by or within proximity to the patient and that are generally considered "noise" or interference to the cardiovascular sound signals described above. These acquired background sounds signals are used to reduce and/or eliminate their effects on the acquired cardiovascular sound signals as will become apparent. In the illustrated embodiment, the background sensor is located on a stable surface or table near the patient to acquire any background sound signals while the cardiovascular sound signals are acquired via the sensor 110. FIG. 2 also illustrates an example of a noise waveform 96 acquired by the background sensor 120 in parallel with the heart waveform signal 94 acquired by the sensor 110, where the vertical axis is represents amplitude and the horizontal axis represents time.

As is illustrated in FIG. 1, the cardiovascular sound signals that have been acquired by the sensor 110 and the noise signals that have been acquired by the background sensor 120 are forwarded, either sequentially or in parallel, to a signal conditioning module 130 for conversion into digital signals. The signal conditioning module 130 includes one or more electronic circuits that convert the analog sound signals from the sensor 110 into digital signals. In one embodiment of the invention, the signal conditioning module 130 is an off-the-shelf module such as a commercial multi-channel 16-bit or greater analog to digital converter. In a further embodiment, the signal conditioning is performed by the sensor 110, the sensor 120, and/or the processor 150.

In the illustrated embodiment, the signal conditioning module 130 also receives an electrocardiograph signal ("ECG signal") from an ECG instrument 140 that generates a record of the electrical currents associated with the patient's heart muscle activity. As is described below in further detail, the ECG signal is used to detect various phases of each heart beat cycle. Unfortunately, in some environments, an ECG signal is not available or produces an unreliable signal. In accordance with one embodiment of the system 100, the phases of each heart cycle of a given heart waveform signal are determined without the reference ECG signal.

The digital cardiovascular sound signals converted by the signal conditioning module 130 are forwarded to a processor 150, which is one or more devices that that processes the digital cardiovascular sound signals in accordance with programmed instructions, as set forth below in greater detail. The processor 150 is configured to generate a probability indicator indicative of the likelihood that a patient has cardiovascular disease in accordance with the previously programmed instructions. The processor 150 may be a computer, a separate digital signal processor, or other processing device as would be apparent. In the illustrated embodiment, the processor 150 includes a memory or recordable media that stores the acquired cardiovascular signals, intermediate results of processing, and the final output of the processor. The processor 150 may also include a preamplifier circuit, gain control circuits, filters, and sampling circuits. For example, in one embodiment, the processor 150 includes a signal analysis module, a digital signal processing module, and a commercially available personal computer. Various features of the processor 150 may be manually adjusted (e.g., gain control adjusted by the user) or automatically adjusted (e.g., automatic gain control) as would also be apparent. In a further embodiment, the previously described signal conditioning is also performed by the processor 150. The processor 150 immediately processes the cardiovascular sound signals and/or stores the cardiovascular sound signals for processing at a later time. For example, in one embodiment of the invention, the processor 150 is located at the point-of-care of the patient and immediately processes the cardiovascular sound signals at the point-of-care to generate the probability indicator indicative of the likelihood that the patient has cardiovascular disease. In another embodiment of the invention, the processor 150 is located at the point-of-care of the patient, stores the cardiovascular sound signals in a memory or computer storage media, and later processes the cardiovascular sound signals at the point-of-care to generate the probability indicator indicative of the likelihood that the patient has cardiovascular disease. In a further embodiment of the invention, the processor 150 is located at a location remote from the point-of-care of the patient. In this embodiment, the cardiovascular sound signals are forwarded from the point-of-care to the processor 150 at the remote location, where the processor processes the cardiovascular sound signals to generate the probability indicator indicative of the likelihood that the patient has cardiovascular disease. In a variation of this embodiment, the cardiovascular sound signals are stored and transmitted to the processor 150 at the remote location from an intermediate computer located at the patient's point-of-care (not otherwise illustrated). As will be appreciated, in this embodiment the intermediate computer could include the signal conditioning module 130. Additionally, the cardiovascular sound signals could be forwarded to the processor 150 in analog form, where the processor 150 defines the signal conditioning module 130 and performs the functions thereof. In various of these embodiments of the invention, the cardiovascular sound signals may additionally be stored for purposes of building a knowledge base over time for increasing the accuracy of generating the probability indicator indicative of the likelihood that the patient has cardiovascular disease.

In above-described embodiments of the invention where the cardiovascular sound and other signals are gathered or captured at the patient's point-of-care and transmitted to the processor 150 located elsewhere, the processor 150, subsequent to receiving the signals, generates a probability indicator indicative of the likelihood that the patient has cardiovascular disease, such as heart disease, and forwards the generated probability indicator to the patient and/or the patient's health care provider. These embodiments of the invention are akin to forwarding blood samples drawn at the patient's point of care to a laboratory where the blood samples are analyzed and the results are forwarded to the patient and/or the patient's health care provider. As would be apparent, the "laboratory" for determining the probability indicator indicative of the likelihood that the patient has cardiovascular disease (i.e., the processor 150) may be co-located with the point of care facility (i.e., within the doctor's office, the hospital, the hospital complex, etc.); may be associated or affiliated with the point of care facility (i.e., as with a managed healthcare provider); or may be a laboratory independent of the point of care facility (i.e., a local, regional, national, or international laboratory that processes the cardiovascular sound signals from various, different, point-of care facilities).

Various mechanisms exist for forwarding the captured cardiovascular sound signals from the point-of-care to the processor 150 and for forwarding the generated probability indicator from the processor or other device to the patient, the point-of-care, and/or the patient's health care provider. For example, in one embodiment of the invention, the cardiovascular sound signals are transmitted to the processor 150 over a network, such as the internet, a local area network, a wide area network, a dedicated network, etc., using various well known transmission protocols. These networks may include one or more wired or wireless connections such as, for example, between the intermediate computer processor and the processor 150, as would be apparent. In one embodiment, the cardiovascular sound signals are transmitted to the processor 150 via telephone lines. Likewise, in accordance with these embodiments, the generated probability indicator is transmitted to the patient, the point-of-care, and/or the patient's health care provider over a network, such as to the intermediate computer at the point-of-care. In a further embodiment, the cardiovascular sound and other signals are stored on a computer readable/writable medium, such as a magnetic disk, an optical disk, or portable RAM or ROM, which medium is then forwarded to the laboratory, via mail, courier, or otherwise, where the processor 150 is located. The processor 150 retrieves the heart sound and other signals from the portable memory and then generates the probability indicator. The generated probability indicator is then recorded on a paper or another portable memory and forwarded to the patient, the point-of-care, and/or the patient's health care provider for analysis and consideration as would be apparent.

In one embodiment of the invention, the cardiovascular sound signals are encrypted or secured in some fashion to address privacy concerns associated with the patient as well as to address authentication, authorization, and integrity matters associated with the signals. Data encryption and/or data security are generally well known. In these embodiments, an identifier of the patient known to the patent and/or patient's health care provider may be transmitted and/or stored with the signals as would be apparent.

As is also illustrated in FIG. 1, the system 100 also include a display device 195 that generates a graphical user interface for viewing and interpreting intermediate and/or final results of the processing performed by the processor 150. As will be appreciated, the signal conditioning module 130, the processor 150, the display 195, and their associated components may be part of a computer, workstation, or other computing device.

Signal Processing Overview

Figure 4:
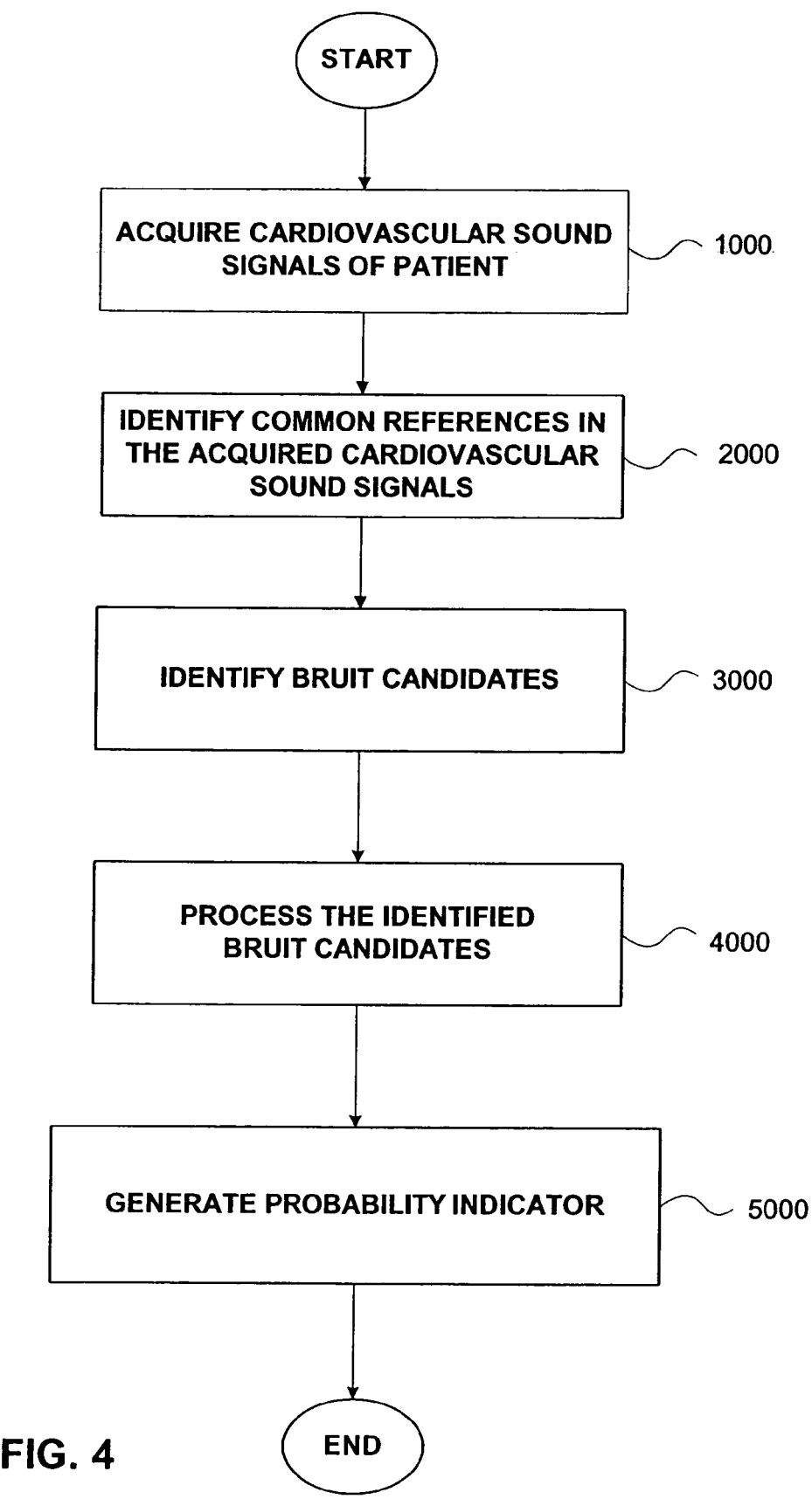
FIG. 4 is a flow chart that depicts the overall process by which cardiovascular sound signals are processed to generate a probability indicator indicative of the likelihood that a patient has cardiovascular disease, such as coronary heart disease (CHD), according to one embodiment of the invention.

The flowchart in FIG. 4 depicts an overview of the process by which the system 100, and more particularly the processor 150, processes the received cardiovascular signals to eventually generate at a step 5000 the probability indicator indicative of the likelihood that the patient has cardiovascular disease (also referred to herein as the Flow Murmur Score). In a step 1000, the cardiovascular sound signals of the patient are acquired as set forth above. In the illustrated embodiment, the cardiovascular sound signals include nine heart waveform signals each corresponding to a different location where the cardiovascular sound signals were acquired and each including a number of heart cycle signals. Once the cardiovascular sound signals have been acquired in step 1000, parameters for subsequent processing are initialized, such as filter parameters and sample rates associated with the audio data. These parameters are based on constraints associated with signal sources, measurement objectives, and experimentation. Examples of such parameters are listed below in Table 1.

TABLE 1

Parameters for the calculation of Likelihood of Cardiovascular Disease

| Parameter | Description | Value | Range |
|---|---|---|---|
| Desired Wide Band Sample Rate | Effective rate for decimated Wide Band Time Data | 4.4 KHz | 4 to 8 KHz |
| Desired Narrowband Band Sample Rate | Effective rate for decimated Narrowband Band Time Data | 440 Hz | 300 to 1 KHz |
| High Beat per Second Limit | Defines Maximum Heart Rate search limit | 2.5 | 2. to 4. |
| Low Beat per Second Limit | Defines Minimum Heart Rate search limit | 0.6 | 0.3 to 1. |
| Heartbeat Duration Count Tolerance | Defines Next Heartbeat Duration Tolerance Window | 0.8 | 0.5 to 1.5 |
| Minimum Beat Factor Default | Default Minimum Heart-beat Duration as fraction of mean Heartbeat Duration | 0.65 | 0.5 to 1.5 |
| Minimum Beat Seconds | Absolute Minimum Time in Seconds to Next Heartbeat | 0.36 | 0.1 to 1 |
| Minimum Beat Factor Low | Minimum HeartBeat Duration as Fraction of Mean Heartbeat Duration After Adjustment for S1–S2 Spacing | 0.51 | 0.2 to 1.0 |
| Correlation Window Fraction | S1–S2 Interval Windowed for Matching | 0.65 | 0.5 to 1.0 |
| Match Filter Envelope Width | Fraction of Heart Beat Duration Count To Use As Width of Cosine Envelope in Building the Match Filter | 0.125 | 0.05 to 0.2 |
| Gap Run Threshold | Minimum gap in Seconds to hold a Pulse Active | 0.055 | 0.01 to 0.2 |
| Pulse Length Threshold | Minimum Pulse Length Threshold in Seconds | 0.035 | 0.01 to 0.2 |
| Signal Fraction Threshold | Minimum Fraction Threshold of Pulse Signal Max to Determine End of Pulse Component | 0.2 | 0.01 to 0.5 |
| Vernier Synch Shift Limit | Max Shift Permitted in Vernier Synch Function expressed as a Fraction of the Heartbeat Duration | 0.03 | 0.01 to 0.1 |
| FFTSize | FFT Size for Bruit Spectral Processing | 128 | 64 to 256 |
| FFT Overlap Ratio | Overlap Ratio for FFT Segments for Bruit Spectral Processing | 0.50 | 0.1 to 1.0 |
| Bruit Low Frequency Limit | Low Frequency Bruit Detection Limit | 300 | 200 to 500 |
| Bruit High Frequency Limit | High Frequency Bruit Detection Limit | 1800 | 500 to 2000 |
| Averaging Window Factor in Heartbeats | Width of Spectral Averaging Window as Fraction of Mean Heartbeat Duration For Bruit Processing | 1.0 | 0.25 to 2 |
| Noise Cancel Frequency Separation | Frequency Separation Limit for Cancellation | 1200 | 0 to 2000 |
| Noise Cancel Time Separation | Time Separation Limit in seconds for Cancellation | 0.02 | 0 to 0.1 |
| Noise Cancel Level | Skew Level Applied to Suppress Noise Bruit | 0.99 | 0.0 to 1.0 |
| 2nd Pass Noise Cancel Frequency Separation | Frequency Separation Limit for 2nd Pass Noise Cancellation | 780 | 0 to 2000 |
| Bruit Power Detect Cutoff | Lowest Bruit Spectral Power Considered | 14.0 dB | 10 to 30 dB |
| Bruit Power Detect Midrange | 50 Percent Bruit Spectral Power Probability Level | 18.5 dB | 10 to 30 dB |
| Bruit Power Detect 90 percent confidence | 90 Percent Bruit Spectral Power Probability Level | 24.0 dB | 10 to 30 dB |

TABLE 1-continued

Parameters for the calculation of Likelihood of Cardiovascular Disease

| Parameter | Description | Value | Range |
|---|---|---|---|
| Skew Cutoff | Highest Skew Ratio Level Considered | 0.75 | 0. to 1. |
| Skew Midrange Value | 50 Percent Skew Ratio Probability Level | 0.56 | 0. to 1. |
| Skew 90 percent confidence | 90 Percent Skew Ratio Probability Level | 0.38 | 0. to 1. |
| Prob(Bruit) rejection cutoff | Lowest Bruit Probability Considered | 0.09 | 0. to 0.9 |
| Bruits per Respiration Cycle | Expected Number Bruits per Respiration | 2.0 | 0.1 to 5 |
| Variance in Bruit Frequency | Uncertainty of Bruit Frequency Measurement | 75 Hz | 0 to 500 Hz |
| Variance in Bruit Time | Uncertainty of Bruit Time Measurement | 20 ms | 0 to 100 ms |
| Probability Site Covariance | Probability Processing Covariance factor | 0.5 | 0 to 1 |
| Probability Time Diastolic Window | Probability Processing Diastolic Time Window Cutoff in Seconds After S2 | 0.6 secs | 0 to 3.0 |

In summary, after the above parameters have been initialized, the cardiovascular sound signals are processed to identify common references in a step 2000. Thereafter, bruit candidates are identified in a step 3000, which are then processed in a step 4000. As a result of the processing of the bruit candidates, a probability indicator is generated in a step 5000 that indicates the likelihood that a patient has cardiovascular disease based, among other things, on the recurring nature of identified bruit candidates. In the embodiment set forth below, the above noted parameters are set for the detection of bruit candidates indicative of coronary heart disease. As will be appreciated the parameters can be set such that the system 100 identifies other bruits that are indicative of other cardiovascular diseases and generates one or more probability indicators indicative of such other cardiovascular diseases.

Identifying Common References in the Acquired Cardiovascular Sound Signals

The applicants have realized that the occurrence of bruit candidates at nearly the same time in different heart cycles can be, among other things, a strong indication of cardiovascular disease, especially coronary heart disease. Hence, as set forth above, one embodiment of the invention concerns emphasizing the repetitive nature of bruit candidates that occur in multiple heart cycle signals. To identify when bruit candidates occur at nearly the same time in different heart cycles, it is preferable to identify a common reference in each heart waveform, preferably in each heart cycle, from which the time location of the bruit candidates can be measured. Without such a common reference, it is difficult to determine when bruit candidates occur at roughly the same time in different heart cycles.

As is known, a heart cycle typically has two main components, termed "S1" and "S2." S1 is the heart sound occurring during closure of the mitral and tricuspid valves, often heard as a "lubb" sound. S1 begins with an inaudible, low-frequency vibration occurring at the onset of ventricular systole, followed by two intense higher frequency vibrating bursts associated with mitral and tricuspid valve closure, and ending with several variable low-intensity vibrations. S2 is the heart sound occurring during closure of the two semi-lunar valves at the beginning of diastole, often heard as a "dupp" sound. S2 typically includes two sharp higher frequency vibrations representing closure of the aortic then pulmonary valves. Some heart cycles also include components termed "S3" and "S4." S3 is the heart sound associated with lower frequency vibration of the ventricular walls during rapid ventricular filling in early diastole. S3 is often termed "S3 gallop rhythm." S4 is the heart sound associated with atrial contraction, occurring during the presystolic phase of diastole. S4 is often termed "S4 gallop rhythm." "Diastole" is the period of dilatation of the heart, especially of the ventricles; it coincides with the interval between S2 and the next S1. "Systole" is defined as the contraction, or period of contraction, of the heart, especially that of the ventricles, sometimes divided into components, as pre-ejection and ejection periods, or isovolumic and ejection. A typical waveform of a heart cycle will consist of an initial burst of energy (S1) lasting on the order of 150 milliseconds, a quiet period (systole) lasting about 200 milliseconds followed by a second burst of energy (S2) lasting about 100 milliseconds. The period from the end of S2 to the start of the next heartbeat (diastole) is usually quiet but may exhibit S3 and S4 under certain conditions. Cardiovascular diseases, such as arrhythmia or valve disease, may distort the S1 through S4 pulses. The energy of the S1 through S4 pulses is usually confined to a frequency band between zero and 150 Hz, where the peak frequency is usually on the order of 30 Hz.

Figure 5:
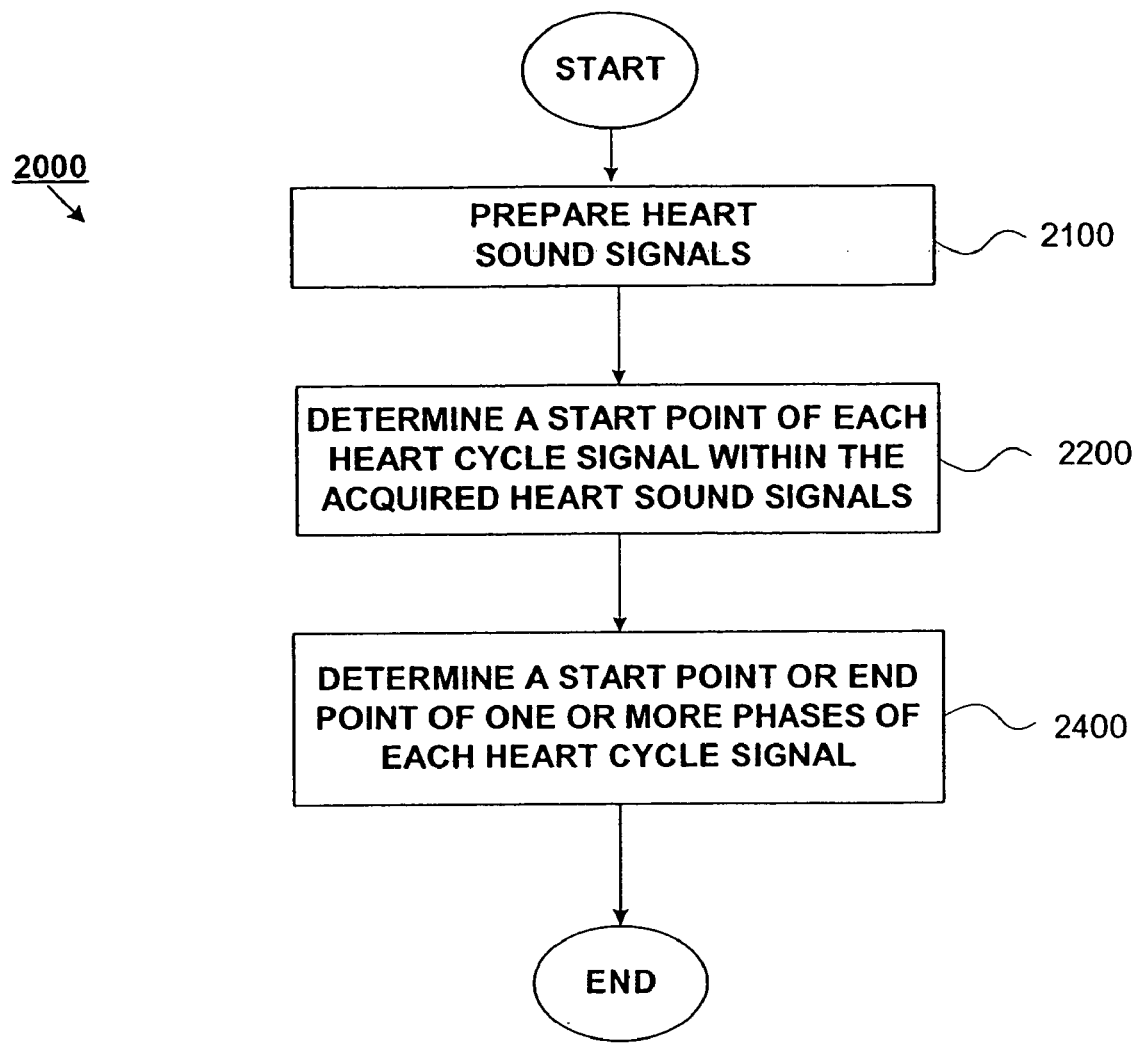
FIG. 5 is a flow chart showing the steps involved in identifying common references in the acquired cardiovascular sound signals of a patient, according to an embodiment of the invention.

As is known, a signal derived from electrical potential heart signals, such as a healthy ECG signal, typically includes one strong, narrow, bi-polar pulse occurring just prior to the onset of the S1 pulse. The other components of a typical ECG waveform are relatively weak. If well defined, the ECG signal provides an excellent medium in which to locate the start of each individual heart cycle, which can also serve as the common reference for each heart cycle. Alternative signals that may be used to locate the start of each heartbeat cycle include blood pressure or blood flow sensors, such as optical sensors. If an ECG or similar signal is available, then it is used at step 2000 to identify a common reference for each heart cycle. In many instances, however, an ECG or similar signal is not available, or, even if available, is not clear enough to provide a reliable indication of the start point of the heart cycle. Hence, in accordance with the illustrated embodiment of the invention, at step 2000 the system 100 processes the acquired cardiovascular sound signals to determine the common reference of each heart cycle without the assistance of a signal derived from electrical potential heart signals, such as an ECG or a similar signal. FIG. 5 illustrates one embodiment of processing the acquired cardiovascular sounds of a patient to determine a start point or an end point of one or more phases of each heart cycle signal, i.e., a common reference.

Figure 6:
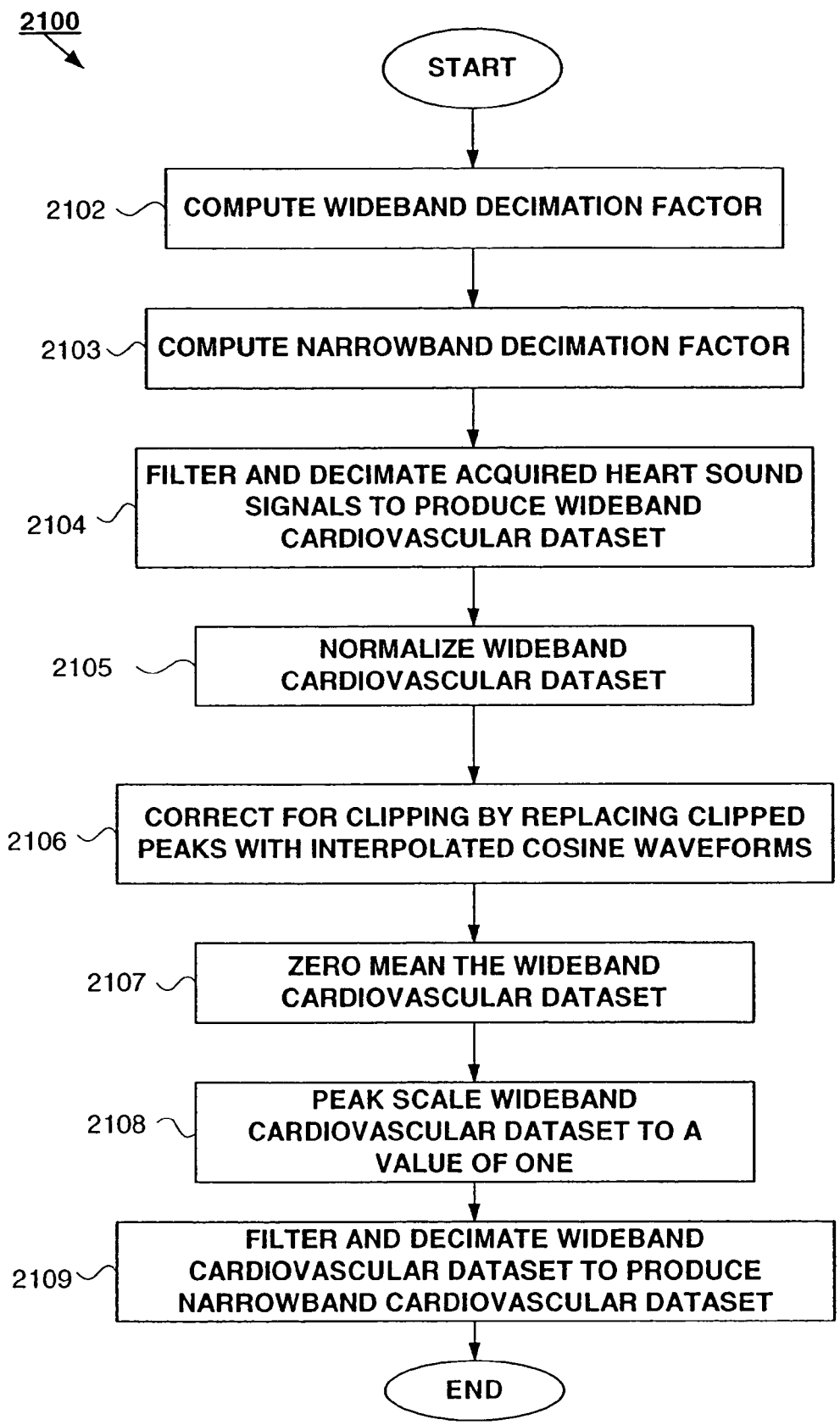
FIG. 6 is a flow chart with further detail on a method for preparing the acquired cardiovascular sound signals, according to an embodiment of the invention.

To determine the start point of each heart cycle without the assistance of an ECG, an estimate is made of where S1 and S2 generally fall within each heart cycle. The presence of both the S1 and S2 pulses in the heartbeat audio, coupled with the wide variations that can be present among individuals, makes it difficult to isolate S1 and S2 without an ECG signal. In a normal resting heartbeat, the recorded heart cycle signals for each heartbeat are essentially identical and occur repetitively at a nearly fixed rate. When these conditions are present, the determination of the periodicity of the heart rate is straightforward. In practice, however, many factors, such as arrhythmia, contribute to degrade the quality of each heart beat such that they are not identical and do not occur at a fixed rate. The processing of the cardiovascular sound signals at step 2000 is focused on the two principal pulses within each heartbeat (S1 and S2); the audio frequencies inherent to these pulses are typically below 100 Hz. As set forth above, the cardiovascular sound signals are acquired in frequencies between dc and 2 kHz at a sampling rate of greater than 4 kHz. To minimize the computing time for processing the cardiovascular sound signals, a narrow band version of the cardiovascular sound signals is produced by further re-sampling of the acquired cardiovascular sound signals at step 2100 to produce a reduced bandwidth wide band for each heart waveform. In sum, the acquired cardiovascular sound signals are filtered and decimated to a sample frequency upper limit of 4 kHz. This transformation to a lower sampling rate speeds up subsequent processing and reduces memory space requirements while maintaining a frequency resolution in excess of 2 kHz. FIG. 6 illustrates one preferred method of preparing the cardiovascular sound signals at step 2100 in greater detail.

In a step 2102, a wideband decimation factor is computed based on what is needed to reduce the input bandwidth to a nominal 2000 Hz bandwidth. This factor allows the acquired cardiovascular sound signals to be decimated by a particular factor to, among other things, reduce storage and computing requirements while not sacrificing audio quality. Similarly, in a step 2103, a narrowband decimation factor is computed based on what is needed to reduce the input bandwidth to a nominal 200 Hz bandwidth. In one embodiment, both the wideband and narrowband decimation factors are set equal to 10.

In a step 2104, the acquired cardiovascular sound signals are low pass filtered and decimated using the wideband decimation factor. In one embodiment, a rapid implementation of a low pass filter is a successive summing of heart waveforms displaced by sample counts according to the Fibonacci sequence, producing a wideband cardiovascular dataset (or wideband heart audio signal). Other similar low pass filter functions, such as a Bessel or Finite Impulse Response (FIR) filter, could also be used. In a step 2105, the wideband cardiovascular dataset is normalized, and in step 2106, correction for clipping (if it has occurred) takes place by replacing any clipped peaks with interpolated cosine transforms.

In a step 2107, the wideband cardiovascular dataset is further processed by performing a zero mean function on it. The zero mean function normalizes any A/D bias offset by subtracting the mean value of the wideband cardiovascular dataset from all sample points. In a step 2108, the normalized wideband cardiovascular dataset is then peak scaled to a value of one.

In a step 2109, the wideband cardiovascular dataset is low pass filtered using a Fibonacci sequence and decimated using the narrowband decimation factor. The filtering is a successive summing of waveform samples spaced according to the Fibonacci sequence, producing a narrowband cardiovascular dataset, which is stored in a memory for later use.

As is apparent, other sampling rates and frequency resolutions will suffice, so long as the Nyquist criteria are satisfied for the frequencies of interest. Hence, in accordance with another embodiment of the invention, step 2100 includes data sampled at 44 kHz and decimated to a bandwidth of 2200 Hz.

In one embodiment, a similar decimation process is carried out on the background noise to decimate and filter to a wideband sample rate for purposes of canceling anomalies induced by the noise. Once the cardiovascular sound signals have been prepared in step 2100 of FIG. 5, at a step 2200, the start point of each heart cycle signal (i.e., each heart beat) within the acquired cardiovascular sound signals is determined, as described in further detail below.

Determining a Start of Each Heart Cycle

As is illustrated in FIG. 5, after the cardiovascular signals have been prepared, at a step 2200, the start points of the heart cycles within each heart waveform of the acquired cardiovascular sound signals are then determined. To summarize this process, successive estimates of a heartbeat power envelope are used as a matching filter to locate heart beats in the cardiovascular sound signals. Correlations are then performed to find matches between a peak detect envelope and the cardiovascular sound signals. The peak detect envelope is a time domain representation of a signal that has peaks indicative of the estimated peaks in the heart waveform. An autocorrelation is performed to determine an initial estimate of heart rate, and the narrowband cardiovascular sound signals are then further processed to make an initial estimate of S1 to S2 spacing. Once the correlations are carried out, an analysis of the peaks is then conducted to isolate those peaks that most likely belong to the heartbeat sequence. During this analysis, a parsing score is carried along with the peak analysis results to quantify the quality of the process of predicting the start points of each heart cycle. If the parsing score for the peak analysis process based on the peak detect envelope reflects that detected peaks do not accurately align with all of the actual cardiovascular sound signals, then additional processing is carried out. During this additional processing, successive individual peak estimates from the peak detect envelope are correlated against all of the cardiovascular sound signals until a perfect match is found or until all of the successive heart cycle signal envelopes are processed. The peak analysis program processes each set of peak estimates and provides the parsing score for the set. If a perfect parsing score is obtained from one of the peak estimates from the peak detect envelope, the results are accepted without further processing. Step 2200 is now described in further detail below in reference to FIG. 7.

Figure 8:
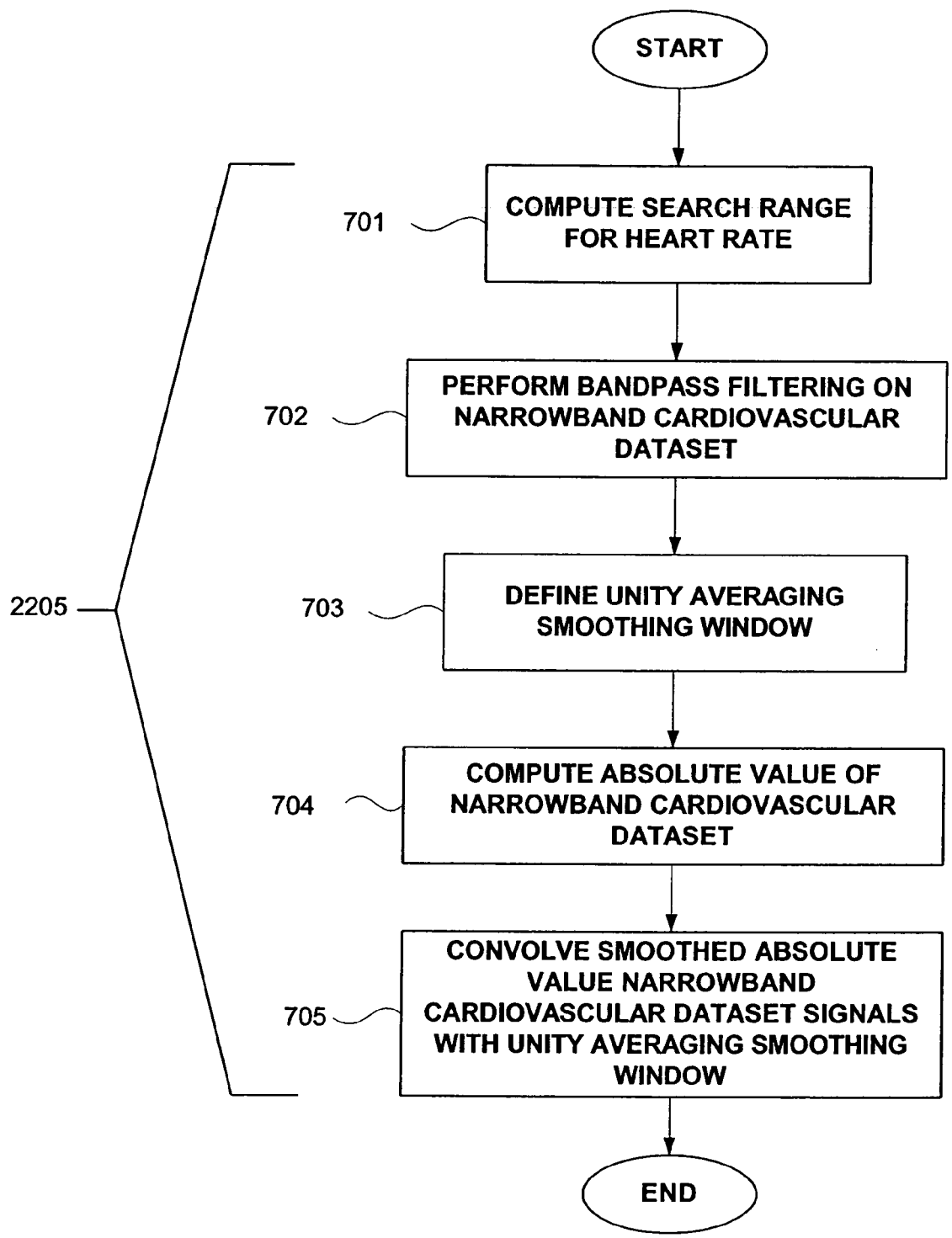
FIG. 8 is a flow chart showing the steps in generating smoothed cardiovascular sound signals, according to an embodiment of the invention.

In a step 2205, smoothed cardiovascular sound signals are generated in order to smooth the peaks in each heart cycle signal. In particular, as detailed in FIG. 8, a time sample search range is computed in narrowband time sample points in a step 701 for the heart rate of the cardiovascular sound signals. In an embodiment, a nominal heart rate search range with limits of 0.6 Hz to 3.0 Hz are divided into the sample rate to define the search limits. Next, in a step 702, a band-pass filter or similar filtering is applied to the narrowband cardiovascular dataset to help isolate the principal components that make up the S1 and S2 pulses in the heartbeat. In one embodiment, the band pass filter is centered at 40 Hz and has a 3 dB roll-off at +/−20 Hz away from center, although other filters could be used as would be apparent.

Figure 9:
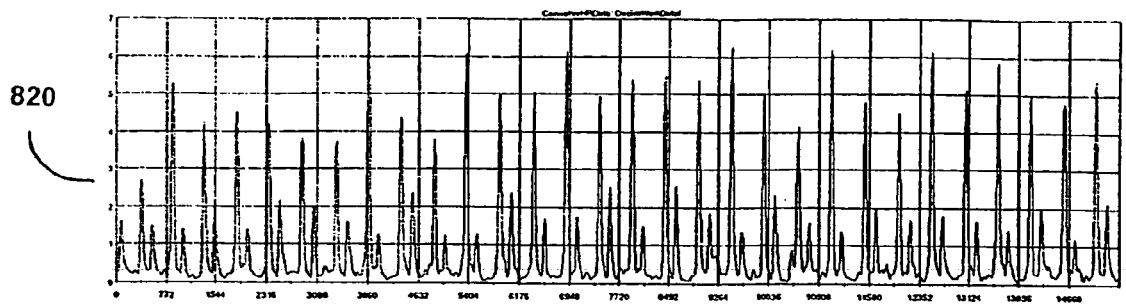
FIG. 9 illustrates smoothed cardiovascular sound signals of one heart waveform.
Figure 10:
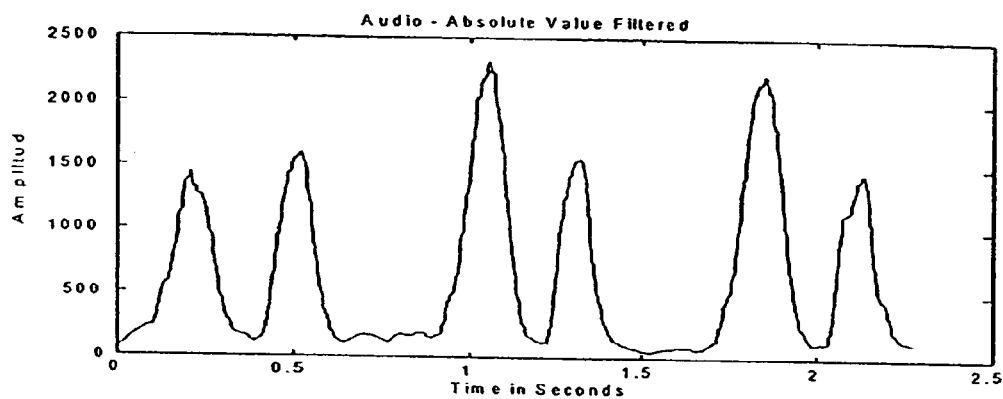
FIG. 10 depicts a portion of the smoothed cardiovascular sound signals of FIG. 9.

In a step 703, a 0.1 second time sample array of ones (i.e., a unity averaging smoothing window) is defined for use in a low pass filter process. In other embodiments, a Blackman, Gaussian, or Kaiser-Bessel window could be used. To avoid multiple peaks from high frequency components of S1 and S2 pulses within one each heart cycle, the band passed narrowband cardiovascular dataset is converted by an absolute value function in a step 704 and then low-pass filtered in a step 705 by convolving it against the unity averaging smoothing window. This convolution smoothes the envelopes of the beat structure to produce the smoothed cardiovascular sound signals. For example, FIG. 9 illustrates thirty seconds of one heart waveform 820 of the smoothed cardiovascular sound signals and FIG. 10 illustrates 2.5 seconds of smoothed cardiovascular sound signals.

Figure 11:
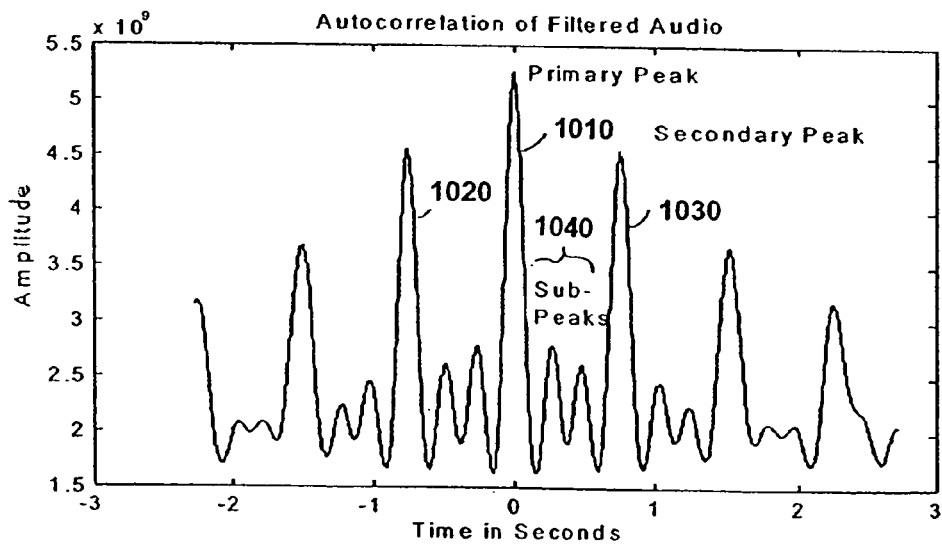
FIG. 11 depicts the autocorrelation peaks that result from convolving the smoothed cardiovascular sound signals with itself.

Referring again to FIG. 7, the smoothed cardiovascular sound waveform generated in step 2205 is then convolved with itself in a step 2210 to generate an autocorrelation that can be used as an initial estimate of the start point of each heart cycle signal within the acquired cardiovascular sound signals. Each point in the generated autocorrelation represents the sum of the products of the waveform with the same waveform shifted by incremental amounts. As is illustrated in FIG. 11, a typical generated autocorrelation has a central or primary peak 1010 where the waveform aligns with itself and a series of secondary peaks 1020, 1030 of reduced amplitude at spacings corresponding to the alignment of similar waveforms. Thus, the autocorrelation of a repetitive time waveform consists of well-defined central and secondary peaks with nominally equal spacings that match the heartbeat period. The spacing between the primary peak 1010 and adjacent secondary peaks 1020, 1030 is indicative of the nominal heart rate. In the example shown in FIG. 11, the primary to secondary peak separation is approximately 0.8 seconds implying a heart rate of approximately 75 beats per minute. This example also shows the presence of a pair of sub-peaks 1040 situated between primary peak 1010 and secondary peak 1030. Because of the similarity of the envelopes of the S1 and S2 sound pulses, the generated autocorrelation of the audio waveform will typically have additional peaks (sub-peaks 1040 in FIG. 11) in between the primary and secondary peaks. Heart cycle signals with a very weak S2 pulse may not have sub-peaks. When S2 is centrally located in the heartbeat interval, only one centered sub-peak will typically be present. When S2 is spaced away from the center of the heartbeat interval, two sub-peaks will typically be present, as shown in FIG. 11.

Figure 12:
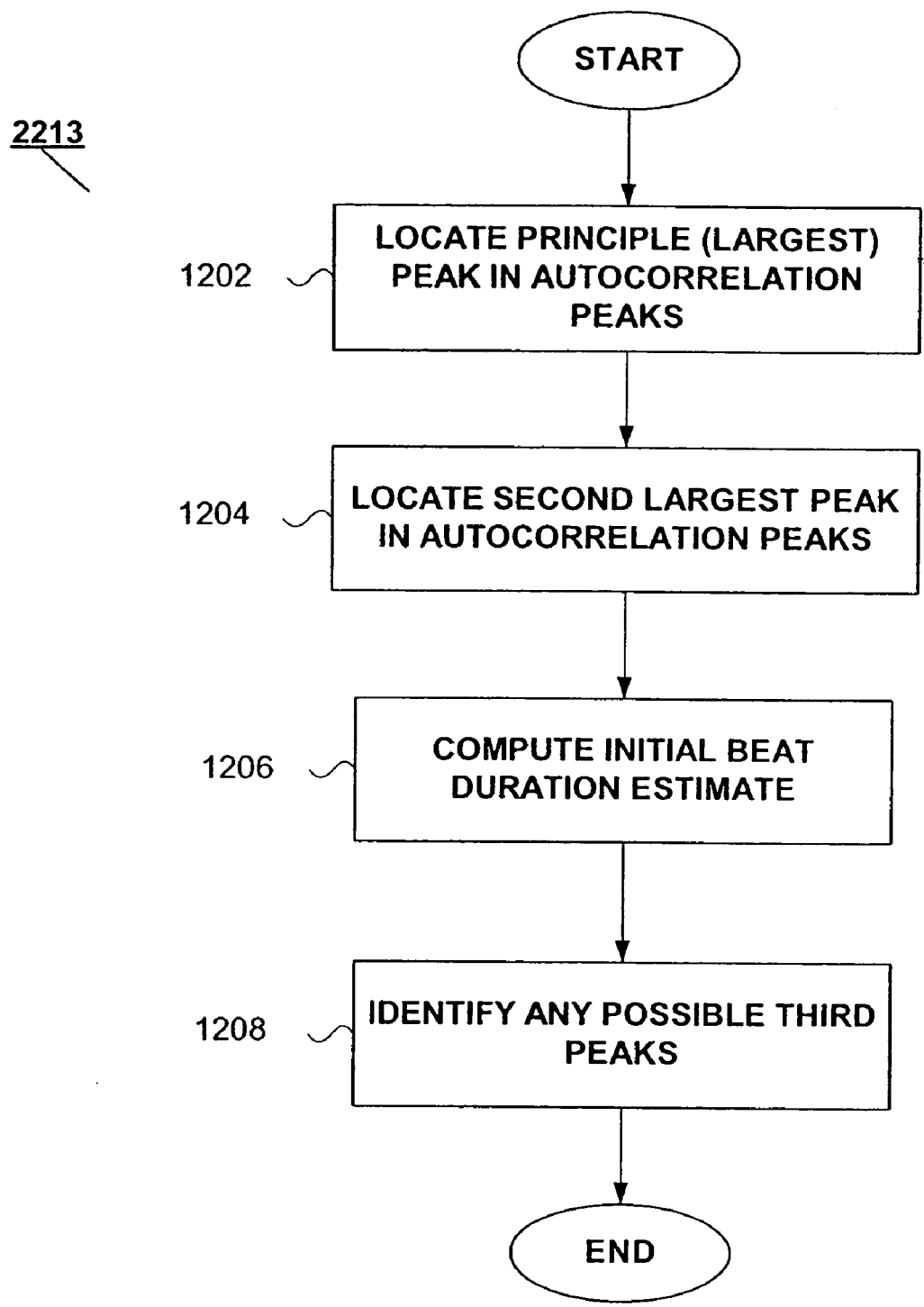
FIG. 12 is a flow chart depicting further detail on the process of generating a beat duration estimate, according to an embodiment of the invention.

Referring again to FIG. 7, from the autocorrelation that was calculated in step 2210, a beat duration estimate is generated in a step 2213 and a math model envelope is generated in a step 2215. The generation of the beat duration estimate is illustrated in FIG. 12 and provides an estimated value for the duration of one heart cycle. To calculate the beat duration estimate, the steps shown in FIG. 12 are carried out in accordance with one embodiment of the invention.

Figure 13:
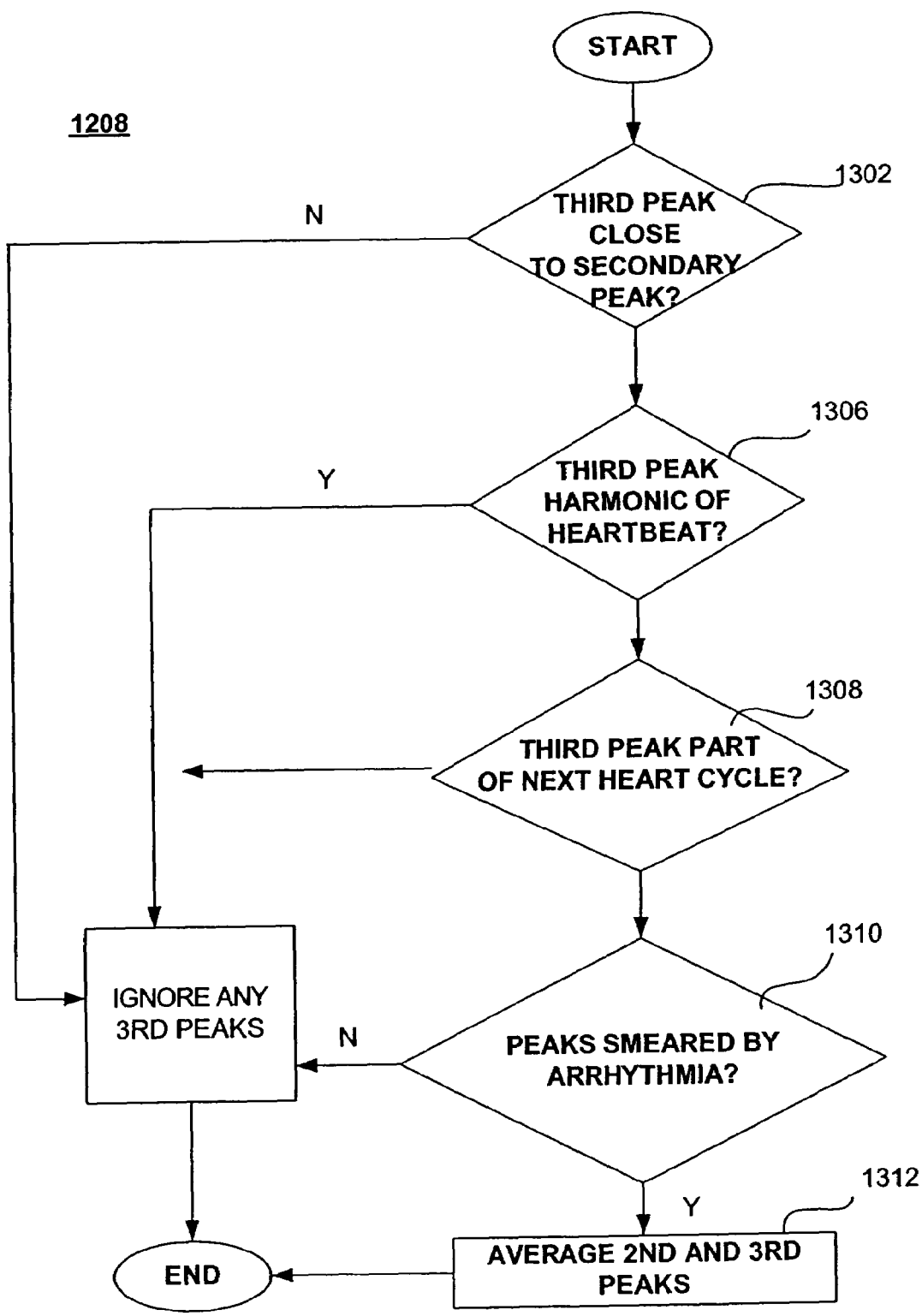
FIG. 13 is a flow chart depicting further detail on the process of identifying any possible third peaks, according to an embodiment of the invention.

As is illustrated in FIG. 12, in a step 1202 the principal (i.e., largest) peak in the autocorrelation array of autocorrelation peaks from the complete heart audio recording is located. This is typically the primary peak 1010 illustrated in FIG. 11. Next, in a step 1204 the secondary (or second largest) peak in the array of autocorrelation peaks is located. This is typically one of the secondary peaks 1020, 1030 illustrated in FIG. 11. Generally, the time between the principal peak and secondary peak will correspond to the period of the mean heart rate, so the separation of the principal peak and the secondary peak is stored as the heart rate. At a step 1206, the initial beat count (in samples) is stored as an initial beat duration estimate. The beat duration estimate represents the number of samples for one heart cycle signal. At a step 1208, the details of which are illustrated in FIG. 13, any other possible secondary peaks in the autocorrelation peaks indicative of a different beat count or heart rate are processed. These peak candidates could represent harmonics of the heartbeat or peaks that have been induced by arrhythmia. In particular, at a step 1302 of FIG. 13, a determination is made of whether a third peak candidate is close to the secondary peak. If so, tests are performed of whether this third peak should be considered as a valid peak. In a step 1306, a test determines whether the third peak is simply a harmonic of the heartbeat. If so, the third peak is ignored. In a step 1308, a test determines whether the third peak is actually part of the next heart cycle region and if so, the third peak is ignored. In a step 1310, a test determines if the widths of the peaks have been increased by arrhythmia. If the peaks have been affected by arrhythmia, they will be smeared or spread out over time. If the peaks are determined to be widened by arrhythmia, the secondary peak and the third peak are both determined to be secondary valid peaks. Accordingly, in a step 1312, the sample positions of the peaks are averaged. The heart rate estimate is based on the number of time samples between the primary and the secondary peak positions. After the beat duration estimate is generated, the math model envelope is generated.

Figure 14:
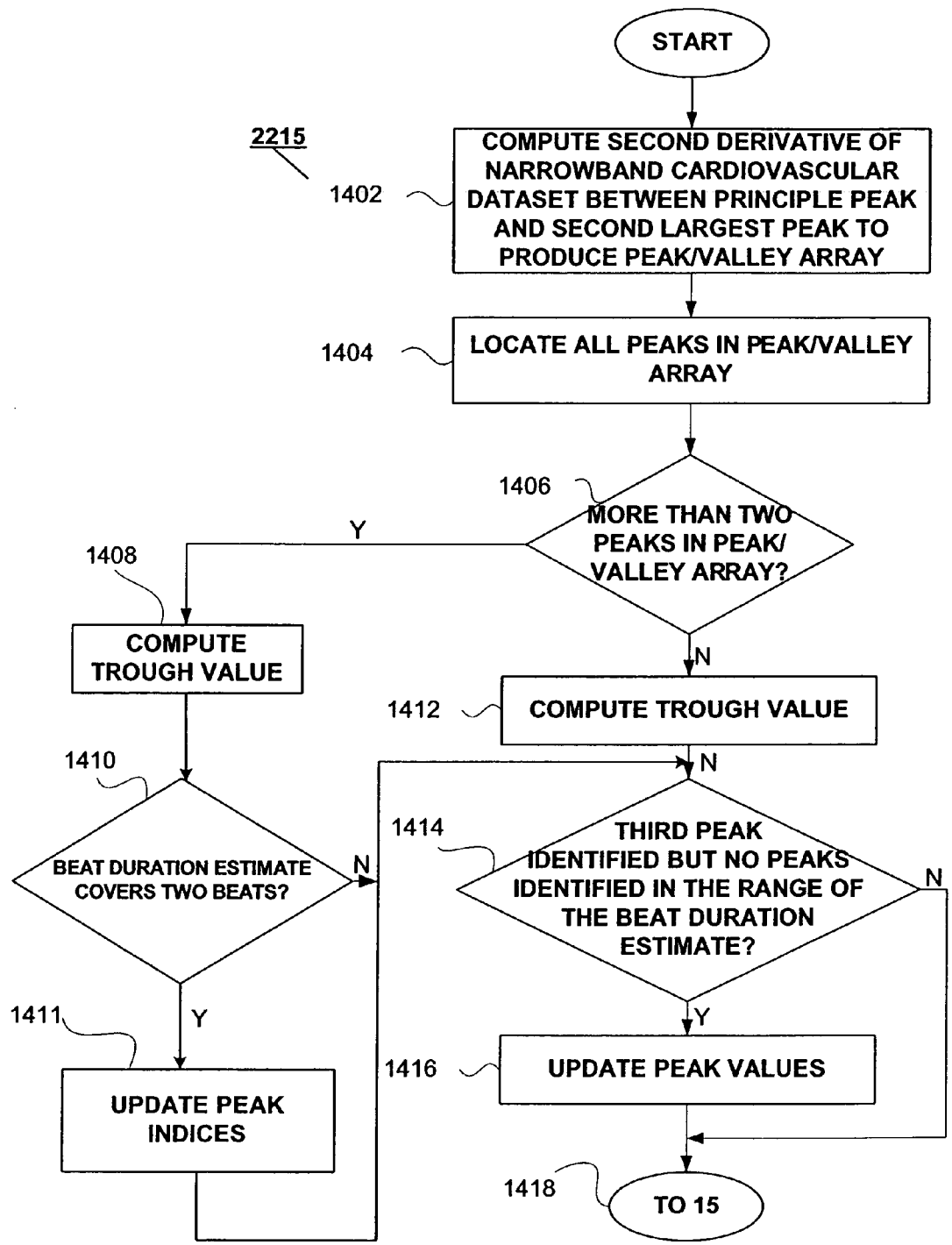
FIG. 14 is a flow chart depicting further detail on the process of generating a math model envelope, according to an embodiment of the invention.

Referring back to step 2215, using the number, location and amplitude of sub-peaks 1040, the math model envelope is generated, which is an estimate of the heartbeat power. The math model envelope approximates the positions of S1 and S2 in the heartbeat cycle, and the widths and relative amplitudes of the S1 and S2 pulses. The relative amplitude of S2 is estimated based on the amplitudes of sub-peaks 1040 relative to the primary peak 1010, and the position of S2 is estimated based upon the separation of the two sub-peaks 1040. The calculation of the math model envelope, according to an embodiment of the invention, is shown in the flow chart in FIG. 14. At a step 1402, the second derivative of the narrowband cardiovascular data set between the time domain locations of principal peak 1010 and secondary peak 1030 (i.e., one beat duration) is calculated. The calculation of the second derivative identifies all peaks and valleys in the narrowband cardiovascular sound signals. The results of the second derivative calculation are stored in a peak/valley array ("pkconv") in one embodiment of the invention. Once the peak/valley array is calculated and stored in step 1402, all peaks in the array are located in a step 1404. The peak locations are stored in a second array ("cpksix") according to an embodiment of the invention. A peak count is also stored, which is the number of peaks in the peak/valley array.

If more than two peaks are located in the pkconv array by a test in a step 1406, a valley value index (i.e., trough value) is determined in a step 1408 using the second index of the first valley in the pkconv array. A test is then performed at a step 1410 to determine if the previously calculated beat duration estimate covers two beats, since a strong second peak may actually be indicative of a true next beat. In an embodiment, the test is whether (1) the absolute value of two times the maximum peak location subtracted from the beat duration estimate is less than 2% of the beat duration estimate and (2) the amplitude of the peak location with the maximum value is greater than 85% of the second peak. If both conditions of step 1410 are true, the peak that meets those tests is considered to be the secondary peak, and the peak indices are updated in a step 1411. If there are not more than two peaks in the peak/valley array, control passes from step 1406 to a step 1412, where a valley value index (i.e., trough value) is determined using the index of the first sub-peak.

In a step 1414, a determination is made of whether any third peaks were identified in step 1406 but no peaks in the range of the beat duration estimate. If so, the peak indices in the peak/valley array are shifted in a step 1416 to account for the actual beat duration. At a step 1418, control passes to FIG. 15.

Figure 15:
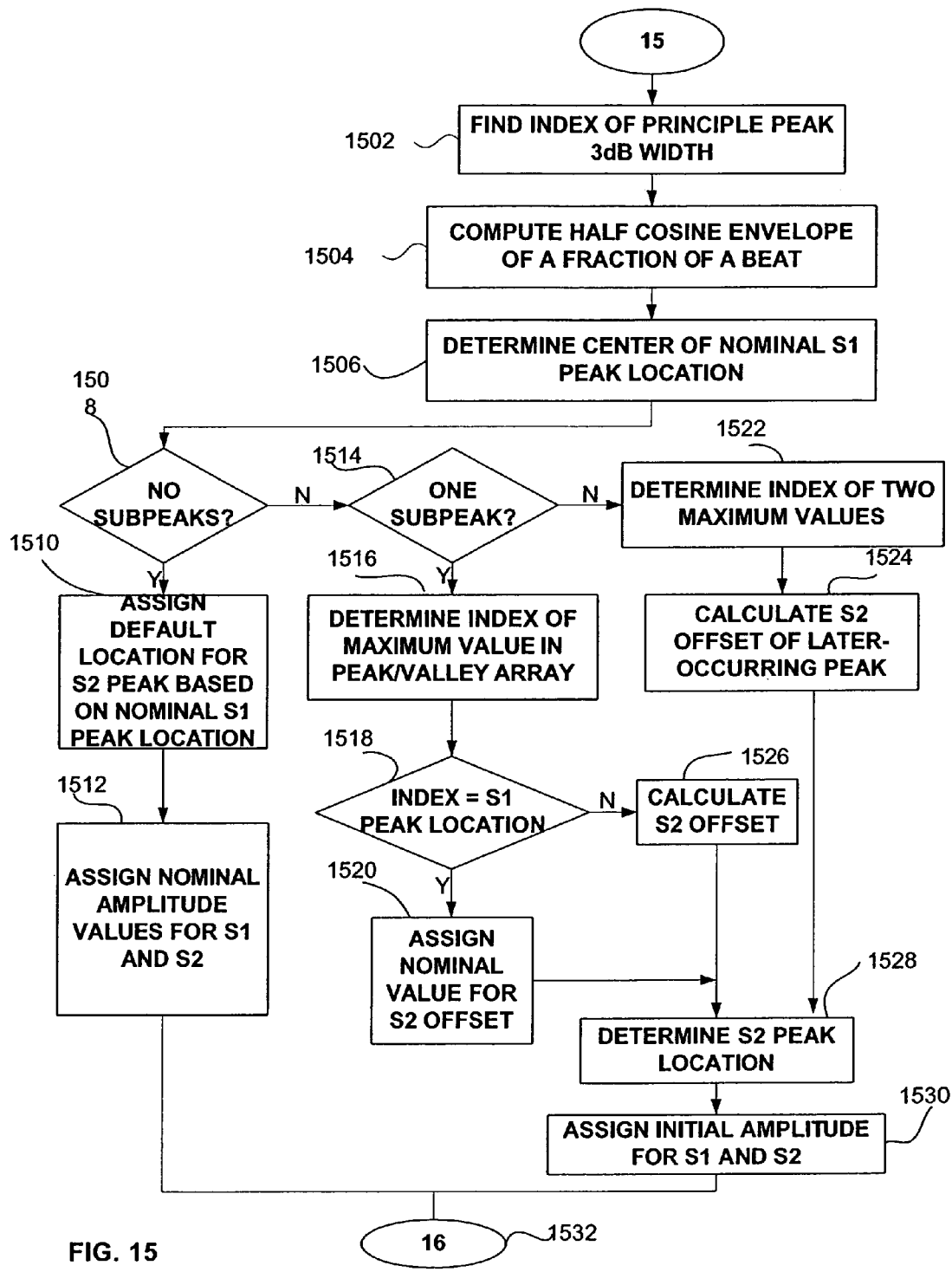
FIG. 15 is a flow chart depicting continued further detail on the process of generating a math model envelope, according to an embodiment of the invention.

In a step 1502 in FIG. 15, the sample index of the 3 dB roll off location of principal peak 1010 is determined. This will be used to determine an estimate of the proper width of the math model envelope. In one embodiment, this determination is made between the zero index of principal peak 1010 and 1/7 of the beat duration estimate. In a step 1504, a half cosine envelope of a fraction of a beat is computed, which will serve as the basis for the eventual calculation of the math model envelope. This is expanded by the 0.1 second smoothing filter width in narrowband sample points. Once the half cosine envelope is calculated, a determination is made in a step 1506 of the center index of a nominal S1 peak location. In an embodiment, the nominal S1 peak location ("s1pk") is determined by rounding the product of the half cosine envelope width and the value 1.5.

Once the nominal S1 peak location is determined, a set of tests are made to determine a nominal S2 peak location. In a step 1508, the peak count determined in step 1404 is tested to determine if it is zero (i.e., no peaks were identified). If so, a default location for the S2 peak is assigned in a step 1510, based on the nominal S1 peak location. In an embodiment, this default location for S2 is determined by rounding the product of the beat duration estimate and 0.35 and then adding the result to the nominal S1 peak location. Then, in a step 1512, nominal amplitude values for both S1 and S2 are assigned. In accordance with one embodiment, the nominal amplitude value for S1 is 1, and the nominal amplitude for S2 is less than 1 and greater than 0, such as 0.7 or 0.85.

If the check in step 1508 reveals that sub peaks were found in the autocorrelation, a check is then made in a step 1514 of whether just one sub peak was found or more than one sub peak was found. If only one sub peak was found, the index of the maximum value in the peak/valley array is determined in a step 1516. Once the index of the maximum value is determined, that index is checked against the index for the S1 peak location at a step 1518. If the values are the same, a nominal value for the S2 offset is assigned in a step 1520. If the values are not the same, an S2 offset is calculated in a step 1526, based upon the separation of the principal peak 1010 and the S2 subpeak. Next, a determination is made in a step 1528 of the actual S2 peak location.

Figure 16:
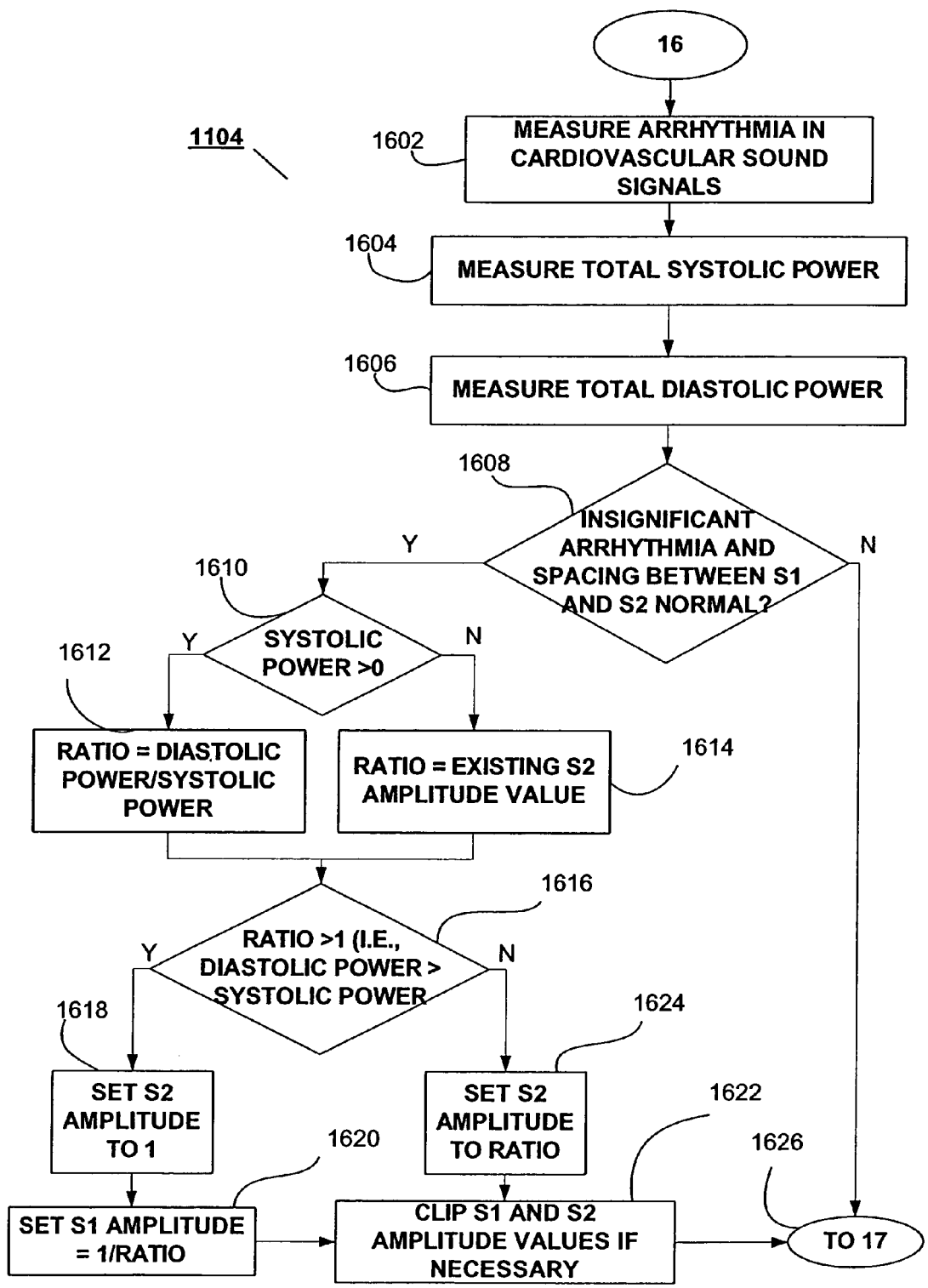
FIG. 16 is a flow chart depicting continued further detail on the process of generating a math model envelope, according to an embodiment of the invention.

If more than one sub peak was found in step 1514, the indices for the two maximum values are determined in a step 1522. In a step 1524, an S2 offset is calculated based on the separation of the principal peak 1010 and the later-occurring of the two peaks, followed by a determination of the actual S2 peak location in step 1528. If either one or more than one sub peak was found, the initial amplitudes for S1 and S2 are assigned in a step 1530. Control then passes to the flow chart shown in FIG. 16 at a step 1532.

In a step 1602, a measure is made of any arrhythmia in the cardiovascular sound signals by creating a histogram of single pulse intervals measured from S1 to S2 and S2 to S1. The location of the two major peaks in the histogram provides independent measures for the systolic and diastolic pulse intervals. An arrhythmia factor is calculated as the difference between the sum of these two average pulse intervals and the interval of the average heartbeat cycle. This measure will be insignificantly small if heartbeat cycle intervals are consistent. The difference will become large if significant arrhythmia spreads the range of diastolic intervals. Step 1604 finds the average power in the systolic pulses accumulated near the histogram peak of S1 pulses. Step 1606 finds the average power in the diastolic pulses accumulated near the histogram peak of S2 pulses. A power measurement is the means of the sum of the squares of the amplitudes of the time samples within the envelope under consideration (e.g., the S1 or S2 envelope).

In a step 1608, a test is done to determine whether (a) there is insignificant arrhythmia in the cardiovascular sound signals and (2) the spacing between the S1 and S2 peaks is normal. There is insignificant arrhythmia if the spacing between S1 and S2 is normal and does not vary by less than a threshold of 10 samples. If both conditions are true, a test is done then performed in a step 1610 of whether the systolic power is greater than zero. Then a power ratio is calculated in a step 1612 that is equal to the diastolic power divided by the systolic power, which will be used to determine the initial S1 and S2 amplitudes. If the systolic power is not greater than zero, the ratio is set to the existing S2 amplitude value. Next, in a step 1616, the ratio is tested to determine if the diastolic power is greater than the systolic power. If so, the S2 amplitude is normalized to a value of 1, and the S1 amplitude is set to a value of 1/ratio. If the diastolic power is not greater than the systolic power, the S2 amplitude is set in a step 1624 to the value of the ratio. Once the S1 and S2 amplitudes have been set, any necessary clipping of the S1 or S2 amplitudes (to a maximum value of one) is performed in a step 1622. Thereafter, the control then passes to FIG. 17 at a step 1626.

Figure 17:
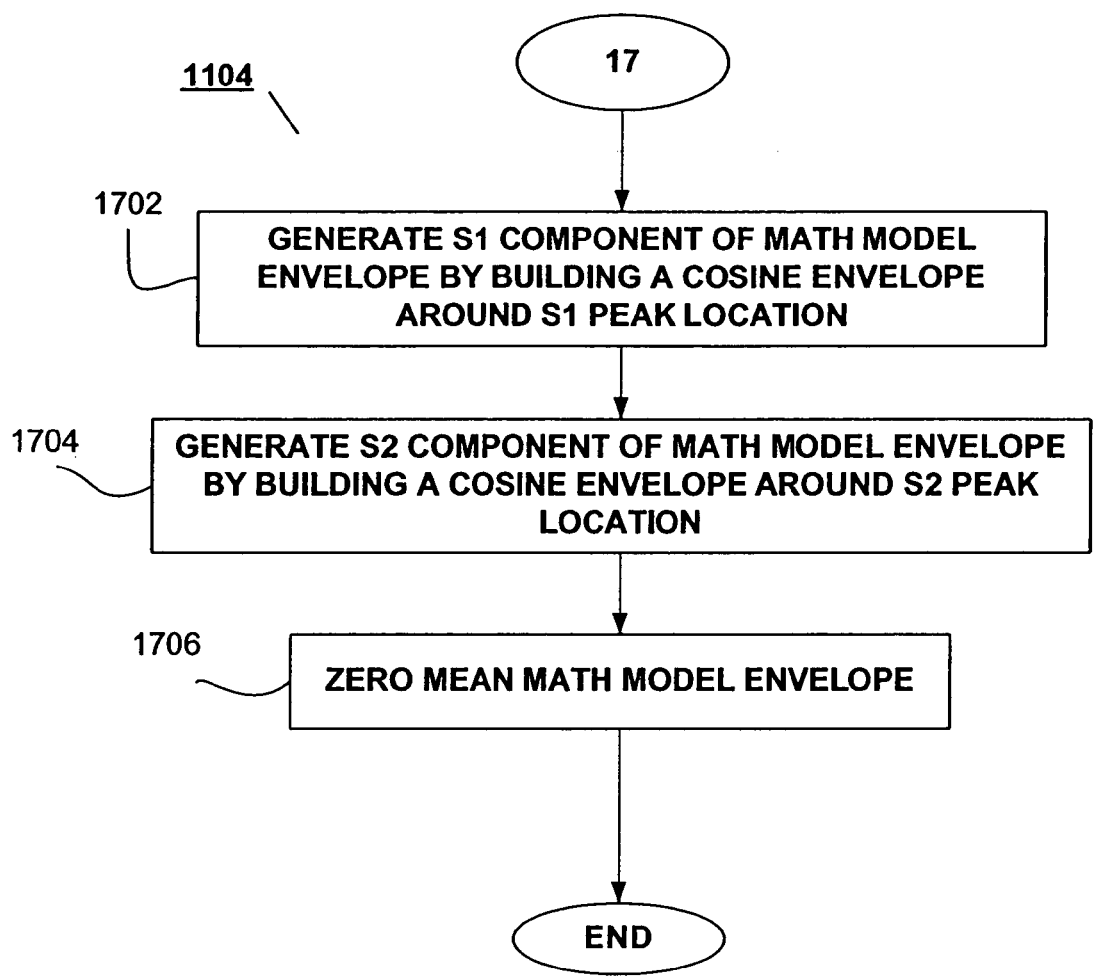
FIG. 17 is a flow chart depicting continued further detail on the process of generating a math model envelope, according to an embodiment of the invention.

In a step 1702 shown in the flowchart in FIG. 17, the S1 component of the math model envelope is calculated by building a cosine envelope using the values determined for the S1 peak location and duration in the previous steps. Likewise, in a step 1704, the S2 component of the math model envelope is generated. In a step 1706, a zero mean calculation is performed on the math model producing the final math model envelope of step 2215.

Figure 18:
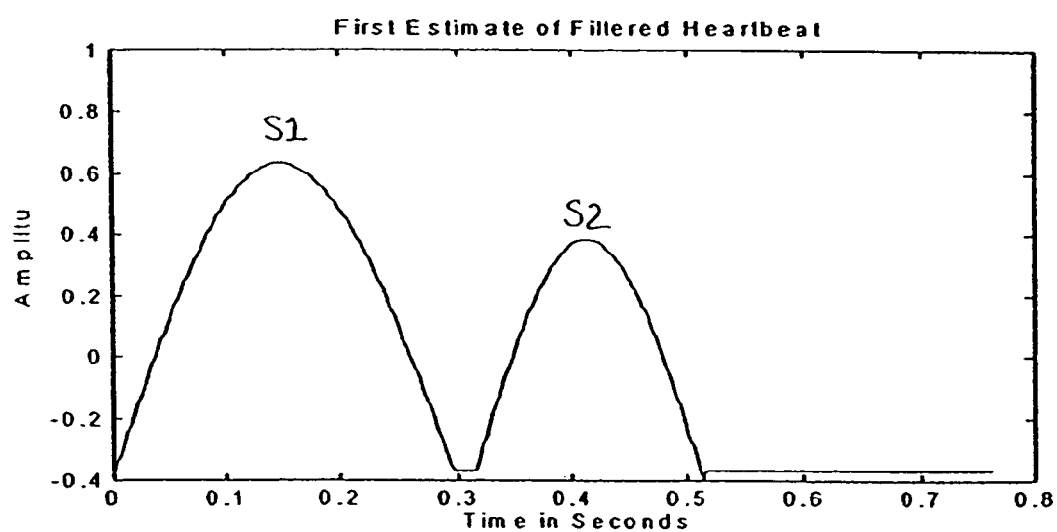
FIG. 18 depicts a math model envelope, calculated in accordance with an embodiment of the invention.

For the waveform shown in FIG. 10, the analysis of data from the autocorrelation results (including the two sub-peaks 1040) described above results in the mathematical model of the signal envelope (i.e., math model envelope) shown in FIG. 18. As will be appreciated, other math model envelops of S1 and S2 can be generated in other manners, such as a time scaled representation of a typical heart waveform.

Figure 19:
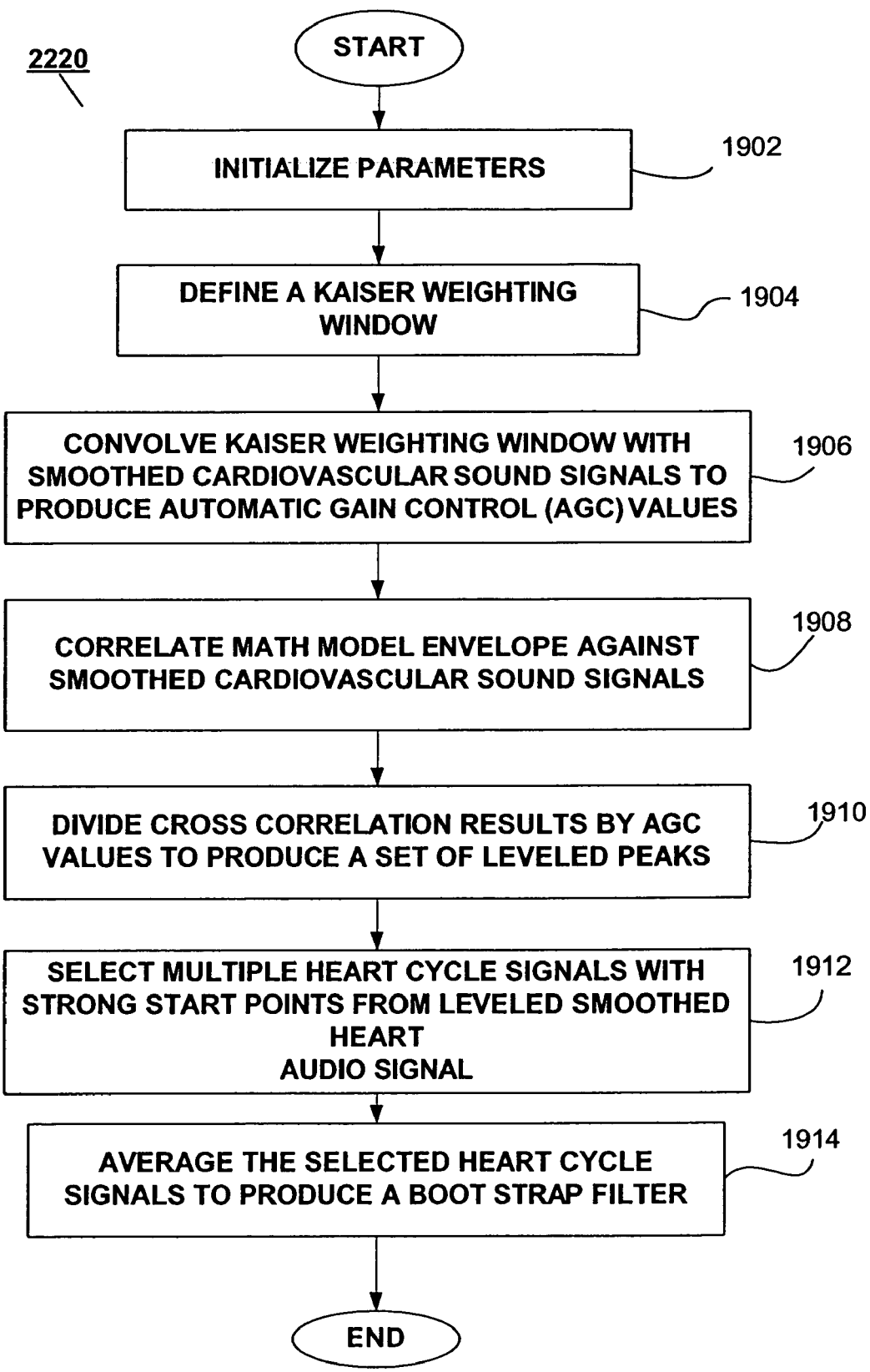
FIG. 19 is a flow chart depicting further details of the process of generating a bootstrap filter envelope, in accordance with an embodiment of the invention.

Referring back to FIG. 7, after the math model envelope and the beat duration have been estimated, at a step 2220, the start points of the heartbeats are determined and a bootstrap filter envelope is generated. The details of step 2220 are illustrated in FIG. 19. In reference to FIG. 19, a number of parameters are initialized in a step 1902 to control the selection of the beat correlation peaks in a correlation test. Table 2 sets forth a list of exemplary parameters that are based on the known parameters of patient heartbeats, along with a brief description thereof:

TABLE 2

Peak detection parameters

| | |
|---|---|
| Beat Count Tolerance = 0.8 | Fractional Heartbeat Tolerance |
| Correlation Window Factor = 0.7 | Fraction of Beat Count to Correlate |
| Minimum Beat Factor Default = 0.65 | Default minimum heart beat duration ratio limit |
| MinBeatFactLow = 0.51 | Minimum acceptable heart beat duration ratio cutoff |
| MinBeatRatio = value < 1.0 | Minimum acceptable beat duration as a fraction of the nominal beat count |
| MinBeatSeconds = 0.36 | Absolute minimum time in seconds to next heart beat |

Continuing in a step 1902, the minimum beat duration count to be acceptable for parsing is defined as the Minimum Beat Duration Ratio. If the S2 offset from the previous processing (step 1520 or 1526) is greater than zero, then a value is assigned to the Minimum Beat Duration Ratio equal to the S2 offset plus a constant offset. If the Minimum Beat Duration Ratio is less than the MinBeatFactLow parameter, it is set equal to the MinBeatFactLow value.

In a step 1904, a Kaiser-Bessel weighting window is defined, which will be used in an automatic gain control process to level out the amplitudes of the correlation pulses. To account for physiological variations in the strength of heartbeats, a gain normalization function (GN) may be applied, which will balance the level of energy in each heartbeat interval. In one embodiment, the GN utilizes a Kaiser weighting window or similar window with an extent equal to the average heartbeat, as would be apparent. This defines the left and right skirt amplitude to be 10 percent of the central maximum. In a step 1906, this window is then convolved with the low-pass filtered version of the smoothed cardiovascular sound signals in FIG. 9 to produce a GN value for every time sample. The waveform is then divided by the GN values so that the sum of the amplitudes under any heartbeat window is the same value. This process helps to level the series of start point peaks that might be found in the auto-correlation function described below.

Next, in a step 1908, the math model envelope, such as that shown in FIG. 18, is correlated against the smoothed cardiovascular sound signals, such as those shown in FIG. 9. The result of this correlation is then divided by the AGC values in a step 1910, which creates a signal consisting of a set of leveled peaks, such as shown in FIG. 20, for use in determining the start points of the heart cycle signals.

The leveled peaks shown in FIG. 20 represent the time indices at which the math model envelope of FIG. 18 best matches the individual heartbeat waveforms in FIG. 2. These time indices locate the onset of an S1 pulse that is a suitable heartbeat start point indicator in lieu of an ECG. In an alternate embodiment, an ECG can be used to provide these heartbeat start point indicators.

In the heart audio waveform used in this example, the envelopes of the S1 and S2 pulses are very well defined, which permits the analysis of the convolution process to provide a relatively accurate estimate of the heartbeat envelope which in turn will produce well defined peaks representing the start of each heartbeat. In one embodiment, step 2220 ends here if a parsing score of 1.00 is achieved, indicating no anomalies in the peaks from the correlation function. In some cases, however, the peaks are not so clear, such as when the heartbeat waveforms are distorted from various physical disorders of the heart. For this reason, additional steps are taken to provide a more accurate estimate of the heartbeat envelope.

The data corresponding to the waveform of FIG. 20 is next processed to locate the peaks that occur at times best fitting the nominal heart rate established in the steps described above. The process of finding the location of individual heart cycle signals generally requires a suitable heartbeat envelope that will correlate highly with all beats in the cardiovascular sound signals. A further refined model of the heartbeat envelope is derived from the parameters of the sub-peaks in the cross-correlation shown in FIG. 20. In general, a predetermined number of the strongest correlation peaks is used to identify actual heart cycle signals. The heart cycles associated with these peaks are averaged to form a bootstrap filter, which is more characteristic of the heart cycle signals corresponding to the heart cycles in the sampled audio.

More specifically, a bootstrap filter is created to further improve the waveform model and raise the parsing score. Using the predicted start positions of heartbeats from the math model filter, a predetermined number of strongly correlated matches (as determined by their amplitude) are selected at a step 1912 and then used to develop a new average waveform with which to search for the starts of heartbeats. This predetermined number of single heart cycle signals, selected from different intervals in the sample, is then at a step 1914 averaged to form a new estimate of the heartbeat waveform. In one embodiment, the predetermined number is five; in an alternative embodiment the predetermined number is three.

Since the heartbeat spacings from a patient with severe arrhythmia can depart widely from the expected spacing, as a final step in the formation of the bootstrap filter in one embodiment, a Kaiser filter is used to suppress points beyond the S2 location. While the best-fit algorithm seeks out the peaks that most likely represent the start of the heart beat cycle, the similarity of the S1 and S2 pulses within the heartbeat can often cause a subsequent S1 peak to affect the convolution waveform. Processing with the Kaiser window achieves the goal of minimizing the effects of any S1 signals early in subsequent heart cycles that might have contributed to the region after S2 (e.g., due to arrhythmia), by using a weighting factor that eliminates any potential contributions that spurious S1 signals might have caused.

The resulting average envelope is the bootstrap filter of step 2220 that bears a close resemblance to at least some of the heartbeats within the file. FIG. 21 illustrates one example of a bootstrap filter produced by the heartbeat averaging process in an embodiment using three beat averaging.

Referring back to FIG. 7, at a step 2225, the bootstrap filter shown in FIG. 21 is then convolved with the cardiovascular sound signals shown in FIG. 2 to produce a signal with peaks that more accurately represent the start of the heartbeats. FIG. 22 illustrates an example of a series of peaks resulting from this convolution process. The series of peaks in the start point detect signal are then parsed to determine if the bootstrap filter has accurately modeled the heart cycle signals.

Figure 7:
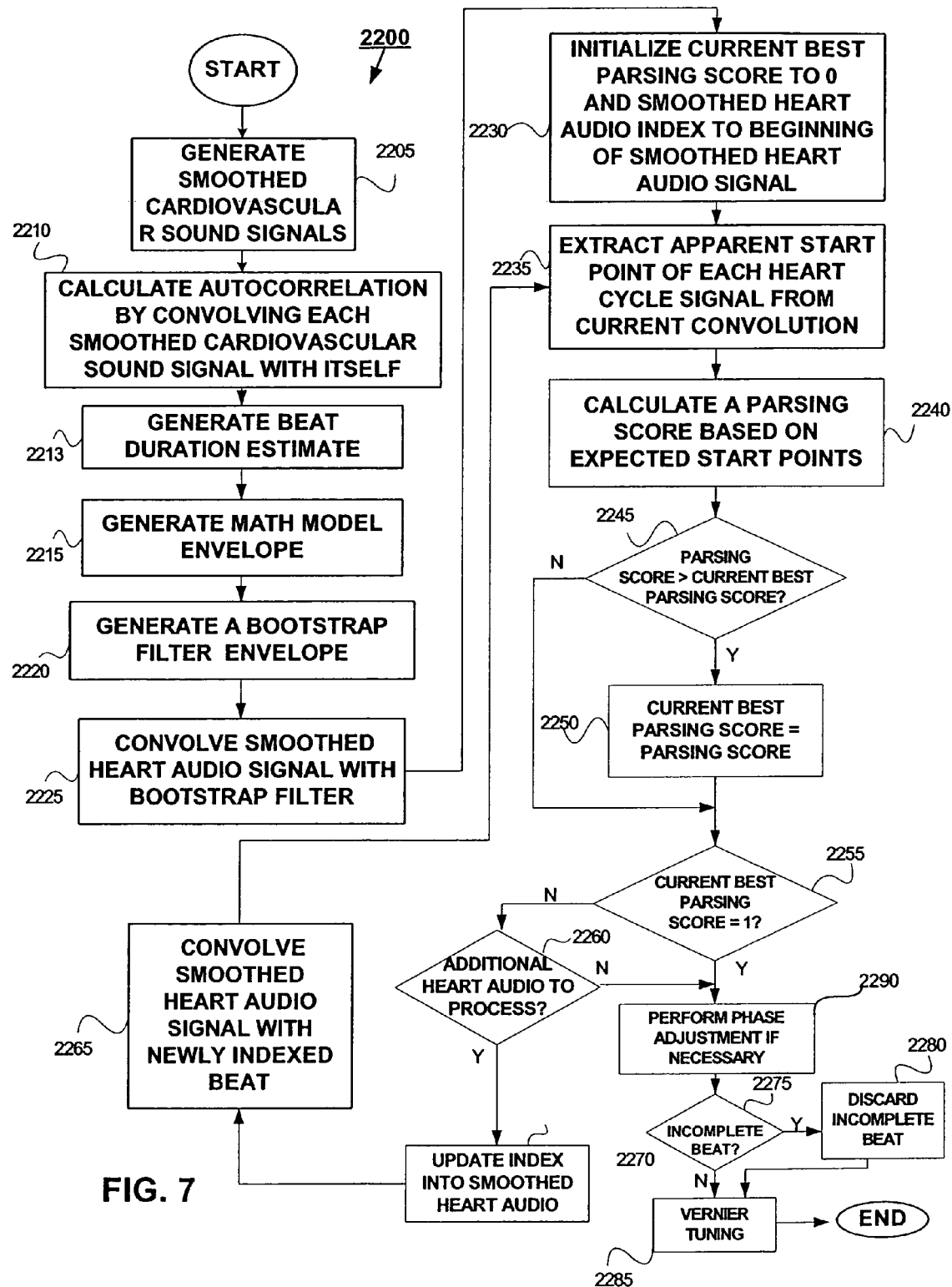
FIG. 7 is a flow chart showing the steps involved in determining a start point of each heart cycle signal within the acquired cardiovascular sound signals, according to an embodiment of the invention.

In particular, at a step 2230 of FIG. 7, a current best parsing score value and an index into the peak detect signal are initialized. In one embodiment, these are initialized to zero. Next, the set of peaks from the current convolution process (which, for the initial pass, will be the peak detect signal shown in FIG. 22) is parsed in a step 2235 to extract the apparent start point of each heartbeat interval.

Figure 23:
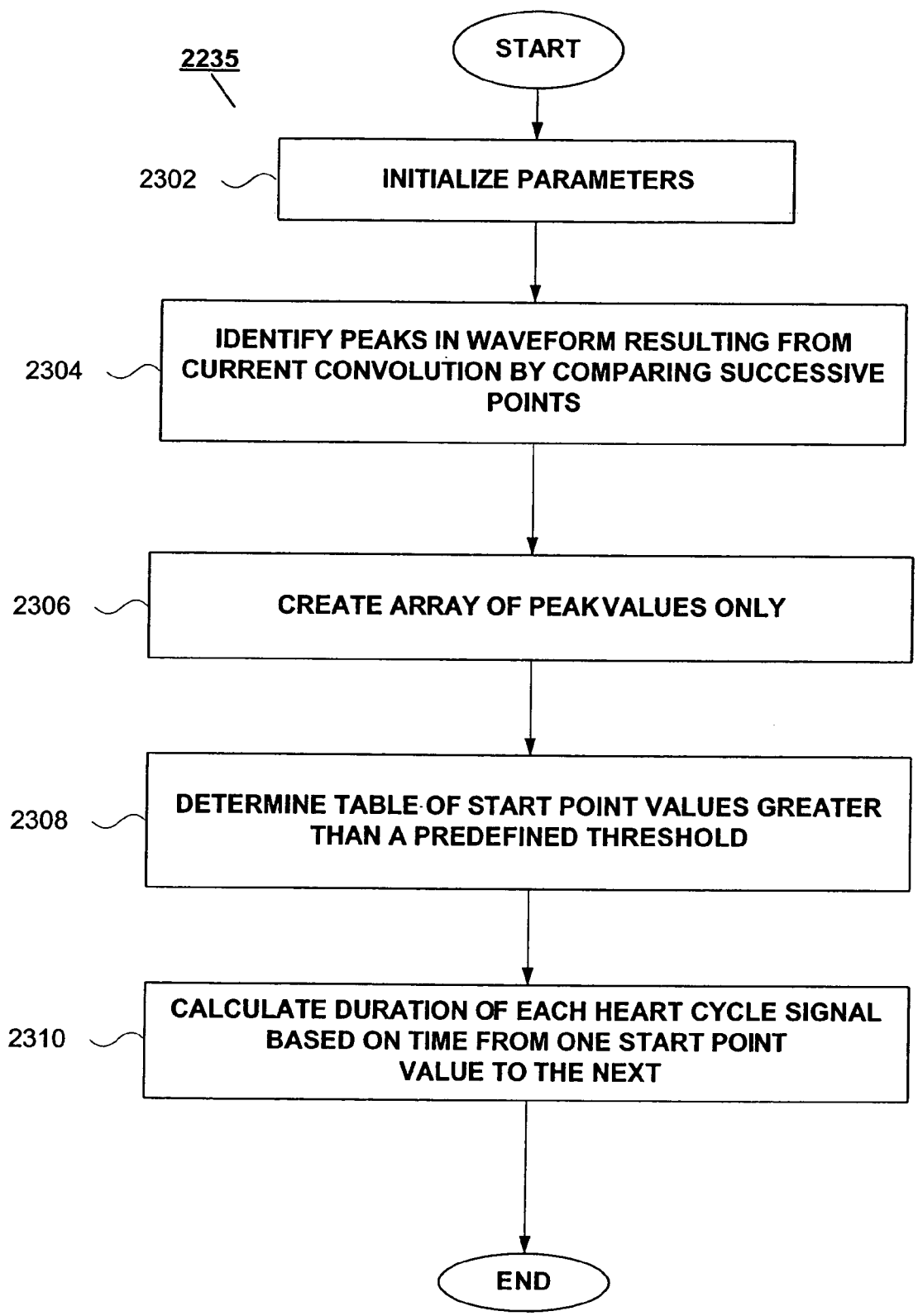
FIG. 23 is a flow chart depicting the extraction of the apparent start points of each heart cycle signal.

The flow chart in FIG. 23 depicts the details of the start point extraction process shown in step 2235 of FIG. 7. In a step 2302, parameters for the start point extraction process are initialized, including the beat duration estimate tolerance value, the minimum beat duration threshold, and the measured S1 peak to S2 peak offset.

In a step 2304, an array of peaks is generated from the correlation of the bootstrap waveform and the entire array of cardiovascular sound signals. The peaks are determined by a process of taking the sign of the difference of the sign of the difference between successive points in the array of the correlation peaks shown in FIG. 20 or FIG. 22. This results in an array with a value of −1 at the peak locations, +1 at the negative peaks, and a value of 0 elsewhere. Once the array of ones and zeroes is determined, negative peaks are discarded and the −1's are inverted to +1s. The entire array is then multiplied by the original smoothed narrowband cardiovascular sound signals in a step 2306, producing an array that contains the amplitude of each peak at a location corresponding to the heartbeat start time in the original cardiovascular sound signals.

Figure 24:
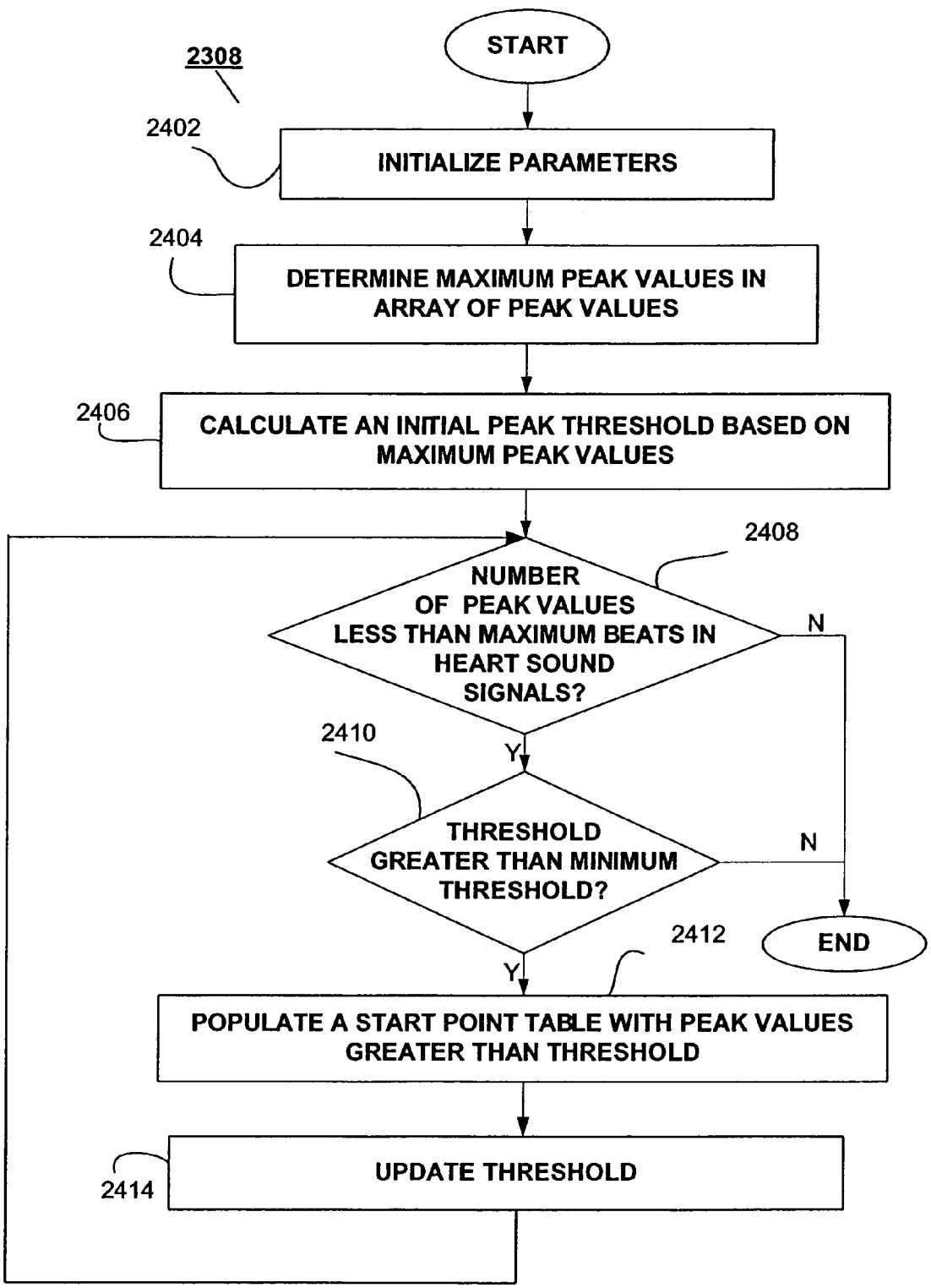
FIG. 24 is a flow chart depicting the generation of a table of start points of heart cycle signals that are greater than a predefined threshold.

Once the array of peak values is determined, that array is used in a step 2308 to determine a table of start point values that is greater than a predefined threshold. FIG. 24 provides further details of the generation of the table of start point values. In particular, at a step 2402 a set of parameters is initialized, including a counter of the number of candidate peaks, which, in one embodiment, is set to a value of 0. At a step 2404, the maximum number of peaks in the array of peak values is determined, and at a step 2406, a starting point for the predefined threshold is determined. In an embodiment of the invention, the starting point for that predefined threshold is a value 10% less than the maximum peak amplitude value in the array of peak values.

In a step 2408, a determination is made of whether the number of peak values above the predefined threshold in the array of peak values is less than the maximum number of beats expected in the cardiovascular sound signals. If so, it would mean that a start point value has not yet been determined for each heart cycle signal within the cardiovascular sound signals. Accordingly, in a step 2410, a test is first made of whether the current predefined threshold value is greater than the minimum threshold value. As long as the current predefined threshold value is greater than the minimum threshold value, the start point table is populated in a step 2412 with values greater than the predefined threshold and the predefined threshold is updated in a step 2414. This loop continues until either the number of peak values in the start point table is no longer less than the number of heart cycle signals in the cardiovascular sound signals, or the predefined threshold is no longer greater than the minimum threshold.

Referring again to FIG. 23, after determining the start point table in step 2308, the duration of each heart cycle signal is determined in a step 2310. These duration values are determined by calculating the number of sample points between each start point value in the start point table.

Figure 25:
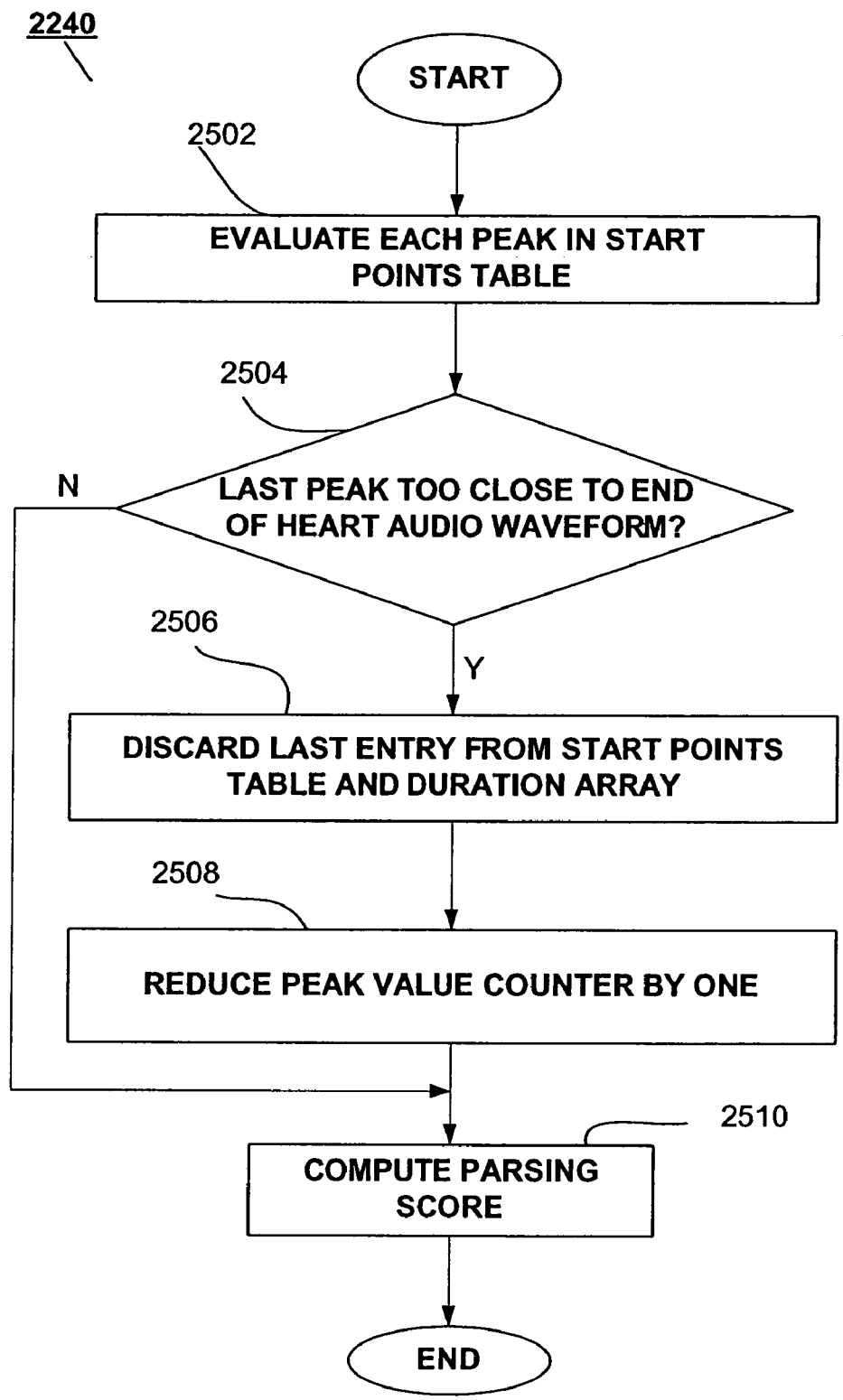
FIG. 25 is a flow chart depicting the calculation of a parsing score.

Referring to FIG. 7, at a step 2240, a parsing score is calculated based on the expected start points in the start point table determined in step 2308. FIG. 25 details step 2240. In particular, at a step 2502, each peak in the start point table is evaluated to determine if it is an actual start point.

Figure 26:
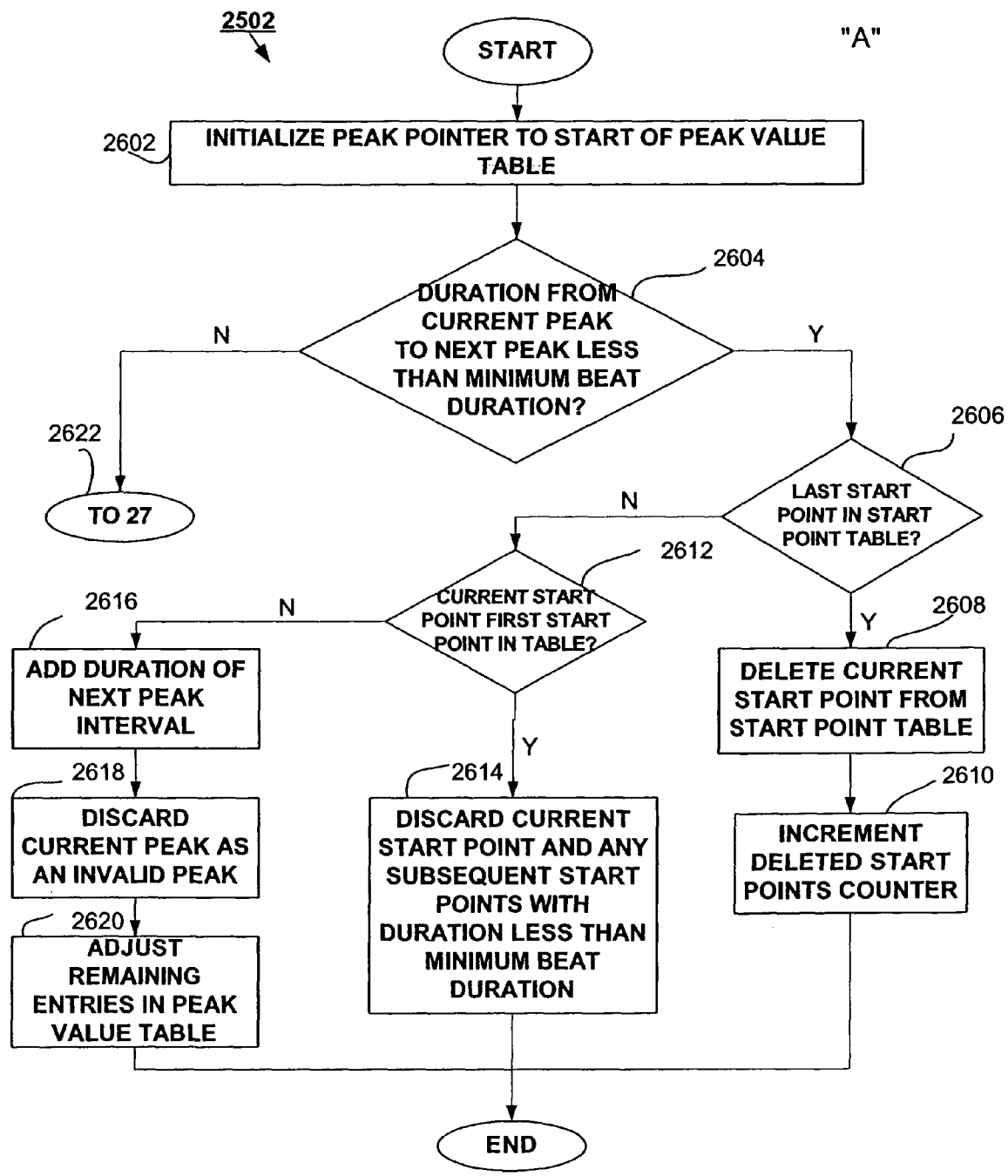
FIG. 26 is a flow chart depicting evaluation of peaks in the start points table.

FIG. 26 further details the process shown in step 2502 of evaluating each peak in the start point table. The evaluation of each peak generally falls into three categories. In the first category, as tested in a step 2604, the duration from the current peak to the next peak is less than the minimum beat duration. As detailed in subsequent flow charts, the other two categories are when the duration from the current peak to the next peak is within the beat count tolerance, and when the duration from the current peak to the next peak exceeds the beat count tolerance.

If the duration from the current peak to the next peak is less than the minimum beat duration, a further check is made in a step 2606 of whether the current start point is the last start point in the start point table. If so, the current start point is deleted from the start point table in a step 2608 and the deleted start points counter is incremented in a step 2610. If the current peak does not correspond to the last start point in the start points table, a check is then made in a step 2612 of whether the current start point is the first start point in the start points table. If so, the current start point and any immediately subsequent start points with a duration less than the minimum beat duration are discarded in a step 2614.

If, in step 2612, a determination is made that the current start point is not the first start point in the start points table, then the current start point is in the middle of the cardiovascular sound signals and must be processed. Accordingly, in a step 2616, the duration from the current peak to the next peak is added to the preceding duration and in a step 2618 the current peak is discarded as an invalid peak. Since the current peak has been discarded, the remaining entries in the peak value table are adjusted in a step 2620. In an embodiment of the invention, this adjustment consists of moving the remaining entries in the start points table down by one entry and adjusting all appropriate pointers and counters.

Figure 27:
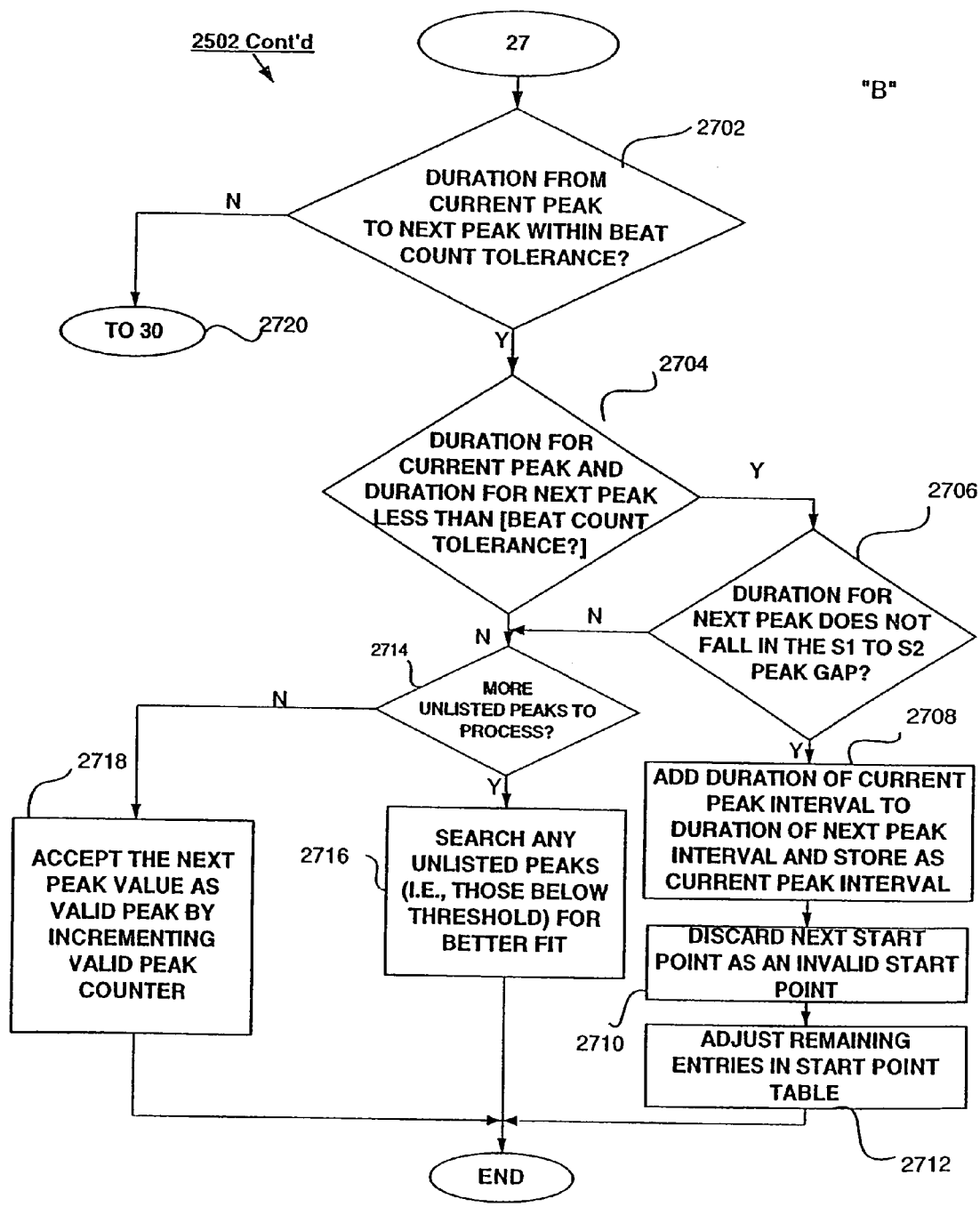
FIG. 27 continues the flow chart of FIG. 26.

Referring back to step 2604 shown in FIG. 26, if the duration from the current peak to the next peak is not less than the minimum beat duration, control passes at a step 2622 to FIG. 27. In a step 2702 in the flowchart of FIG. 27, a determination is made of whether the duration from the current peak to the next peak is within the beat count tolerance. If so, a test is then made at a step 2704 of whether the duration corresponding to the current peak combined with the duration for the next peak is less than the beat count tolerance. If so, and the duration for the next peak, as tested in a step 2706, does not fall into the S1 to S2 peak gap, then the duration corresponding to the current peak is added to the duration corresponding to the next peak, and the total is stored as the current peak interval in a step 2708. Then, in a step 2710, the next point is discarded as an invalid start point and the remaining entries in the start point table are adjusted in a step 2712. In an embodiment of the invention, this adjustment consists of moving the remaining entries in the start points table down by one entry, and adjusting all appropriate pointers and counters (including incrementing a deleted peaks counter).

If the heart beat cycle duration corresponding to the current peak, when added to the duration corresponding to the next peak, is not less than the beat count tolerance (as tested in step 2704), or if the duration corresponding to the next peak does fall into the S1 to S2 peak gap (as tested in step 2706), control passes to a step 2714. In step 2714, a determination is made of whether there are unlisted peaks to process. If so, any unlisted peaks that were not entered into the start points table because they were below the threshold are tested in a step 2716. This test will determine whether any of those unlisted peaks actually provide a better fit when compared against the beat duration estimate. If no more peaks are left to process, as tested in step 2714, the next peak value is accepted as a valid peak by incrementing the valid peak counter. Referring back to step 2702, if the duration from the current peak to the next peak is not within the beat count tolerance, control passes at a step 2120 to FIG. 30.

Figure 28:
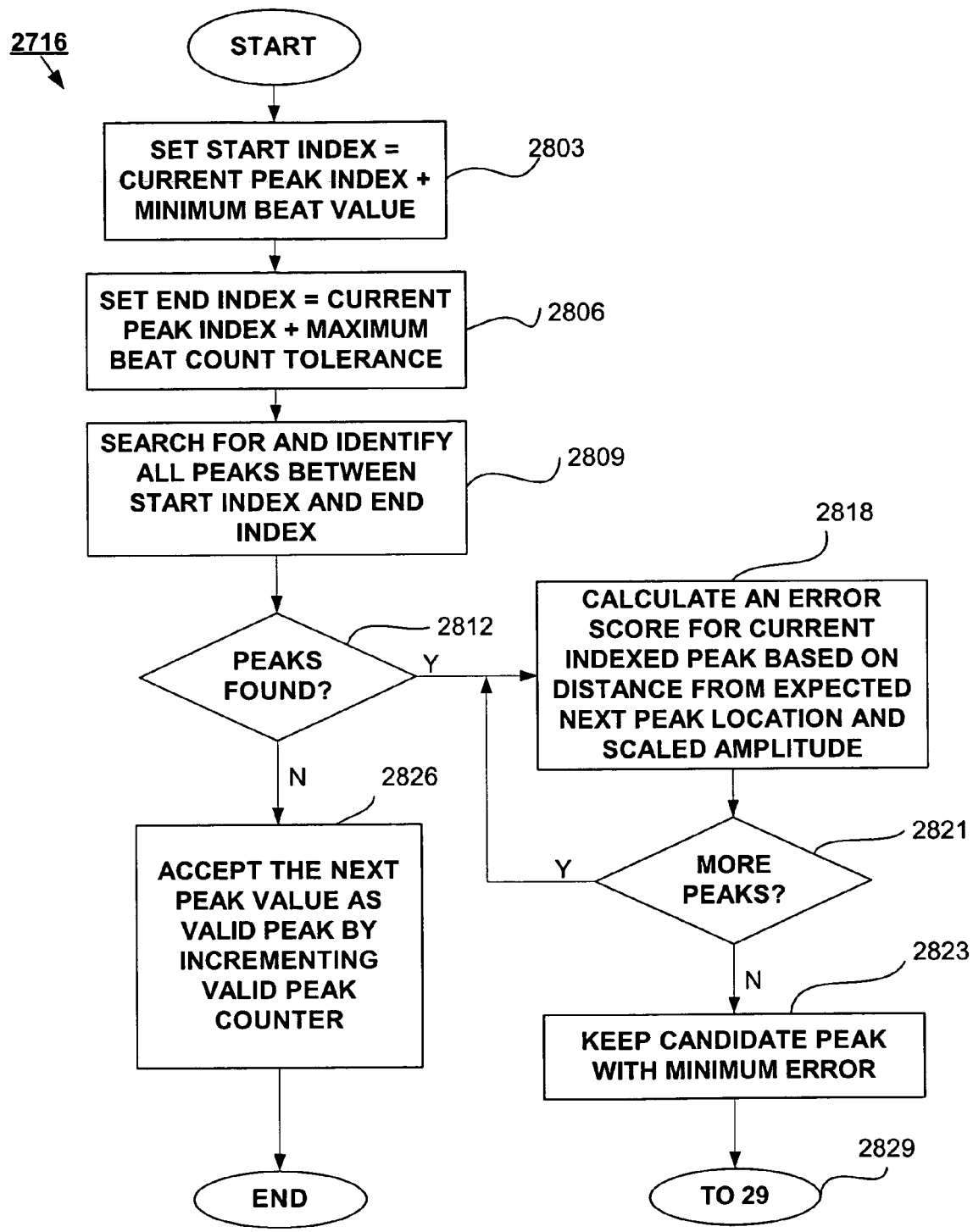
FIG. 28 is a flow chart depicting a search process for better fitting peaks.

FIG. 28 provides additional detail of the search process for unlisted peaks shown in step 2716 in FIG. 27. In particular, at a step 2803, a start index is set to a value equal to the index for the current peak plus the minimum beat value. At a step 2806, an end index is set to a value equal to index for the current peak plus the maximum beat count tolerance. In a step 2809, a search is then performed that identifies all peaks between the start index and the end index. If no peaks were found, as tested in a step 2812, the next peak value is accepted as a valid peak value in a step 2826 by incrementing the valid peak counter. If, however, peaks were found in step 2809, as tested in step 2812, an error score for the current indexed peak is calculated in a step 2818. This error score is based on the distance from the expected next peak location and the scaled amplitude. The error score will be used to determine which candidate peak to keep. In a step 2821, a determination is made of whether any more peaks exist between the start index and end index that need to have an error score calculated for them. If so, control passes to step 2818 and the next peak is processed. If no more peaks exist that need to have an error score calculated for them, the candidate unlisted peak with the smallest error value is retained in a step 2823. Control then passes at a step 2829 to FIG. 29.

Figure 29:
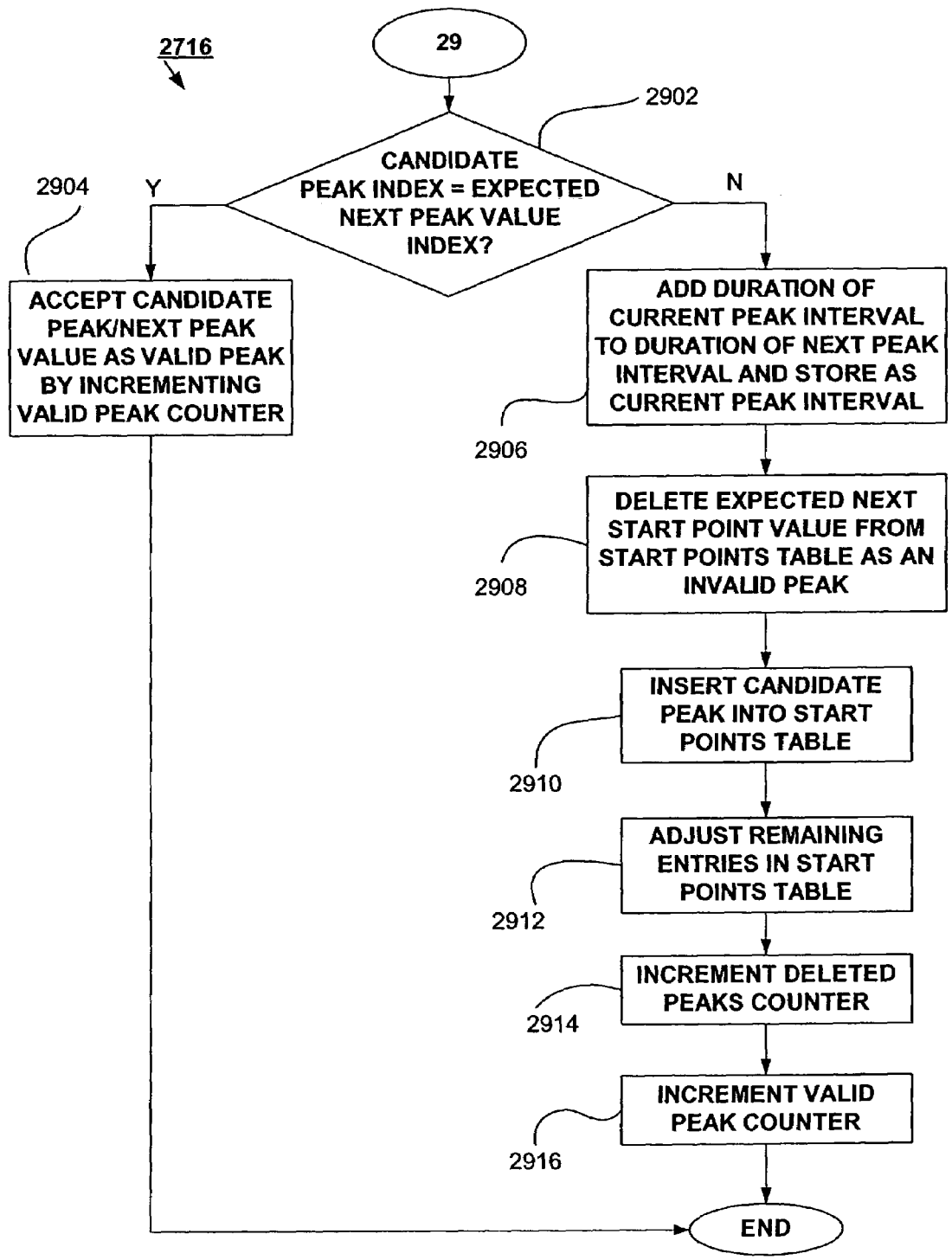
FIG. 29 continues the flow chart of FIG. 28.

FIG. 29 continues detailing the process of searching for unlisted peaks, according to one embodiment of the invention. In FIG. 29, the candidate peak with the smallest error that was determined in step 2823 is further tested. In a step 2902, a determination is made of whether the candidate peak index is equal to the index value of the expected next peak. If so, the candidate peak is accepted in a step 2904 as a valid peak by incrementing the valid peak counter. If, however, the candidate peak index is not equal to the index value of the expected next peak, further processing must be done prior to accepting the peak as a valid start point. In particular, at a step 2906, the duration corresponding to the current peak is added to the duration corresponding to the next peak. The resulting sum is stored as the interval value corresponding to the current peak. Next, in a step 2908, the peak that would be the next expected start point after the current and next peak (i.e., the current peak location plus two), is deleted from the start points table as an invalid peak. Instead, the current candidate peak is inserted into the start points table in a step 2910. In a step 2912, the remaining entries in the start points table are adjusted. In an embodiment of the invention, this adjustment consists of moving the remaining entries in the start points table down by one entry and adjusting all appropriate pointers and counters (such as the incrementing of the deleted peaks counter in a step 2914 and the incrementing of the valid peak counter in a step 2916).

Figure 30:
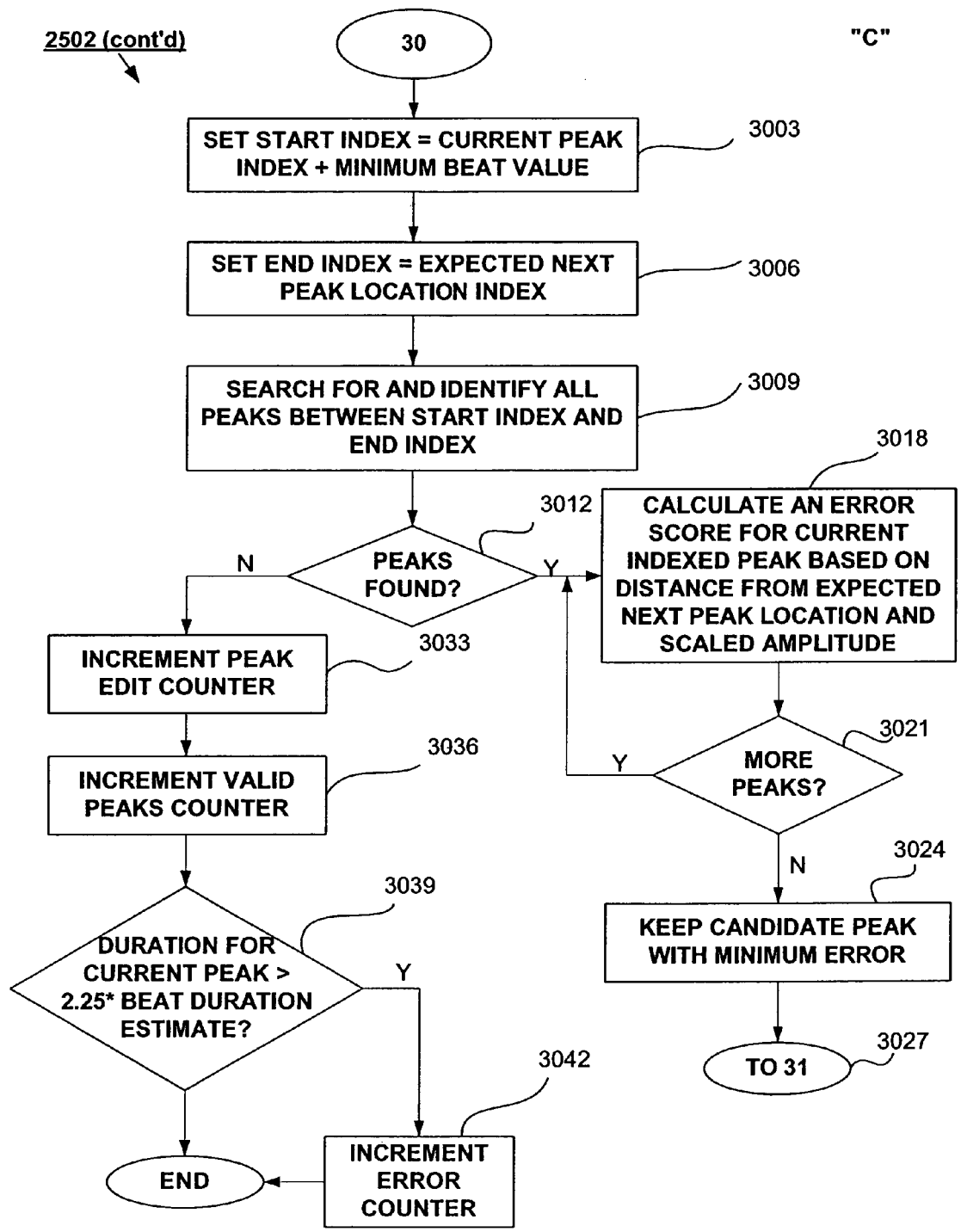
FIG. 30 continues the flow chart of FIG. 27.

Referring back to the test in step 2702 of the flow chart in FIG. 27, if the duration from the current peak to the next peak is not within the beat count tolerance (and that same duration is greater than the minimum beat duration as tested in step 2604 of FIG. 26), control is passed at step 2120 to FIG. 30, which further details the process shown in step 2502 of evaluating each peak in the start point table.

In a step 3003, a start index is set to a value equal to the index for the current peak plus the minimum beat value. At a step 3006, an end index is set to a value equal to the index for the next peak location. In a step 3009, a search is then performed that identifies all unlisted peaks between the start index and the end index. If no peaks were found, as tested in a step 3012, a peak edit counter (which keeps track of peaks which have been modified) is incremented in a step 3033 and the next peak value is accepted as a valid peak value in a step 3036 by incrementing the valid peak counter. In one embodiment, a test is then performed in a step 3039 of whether the duration corresponding to the current peak is greater than 225% of the beat duration estimate. If so, the error count is incremented in a step 3042.

If, however, unlisted peaks were found in step 3009, as tested in step 3012, an error score for the current indexed peak is calculated in a step 3018. This error score is based on the distance from the expected next peak location and the scaled amplitude. The error score will be used to determine which candidate peak to keep. In a step 3021, a determination is made of whether any more peaks exist between the start index and end index that need to have an error score calculated for them. If so, control passes to step 3018 and the next peak is processed. If no more peaks exist that need to have an error score calculated for them, the candidate peak with the smallest error value is retained in a step 3024. Control then passes at a step 3027 to FIG. 31, which further details the process shown in step 2502 of evaluating each peak in the start point table.

Figure 31:
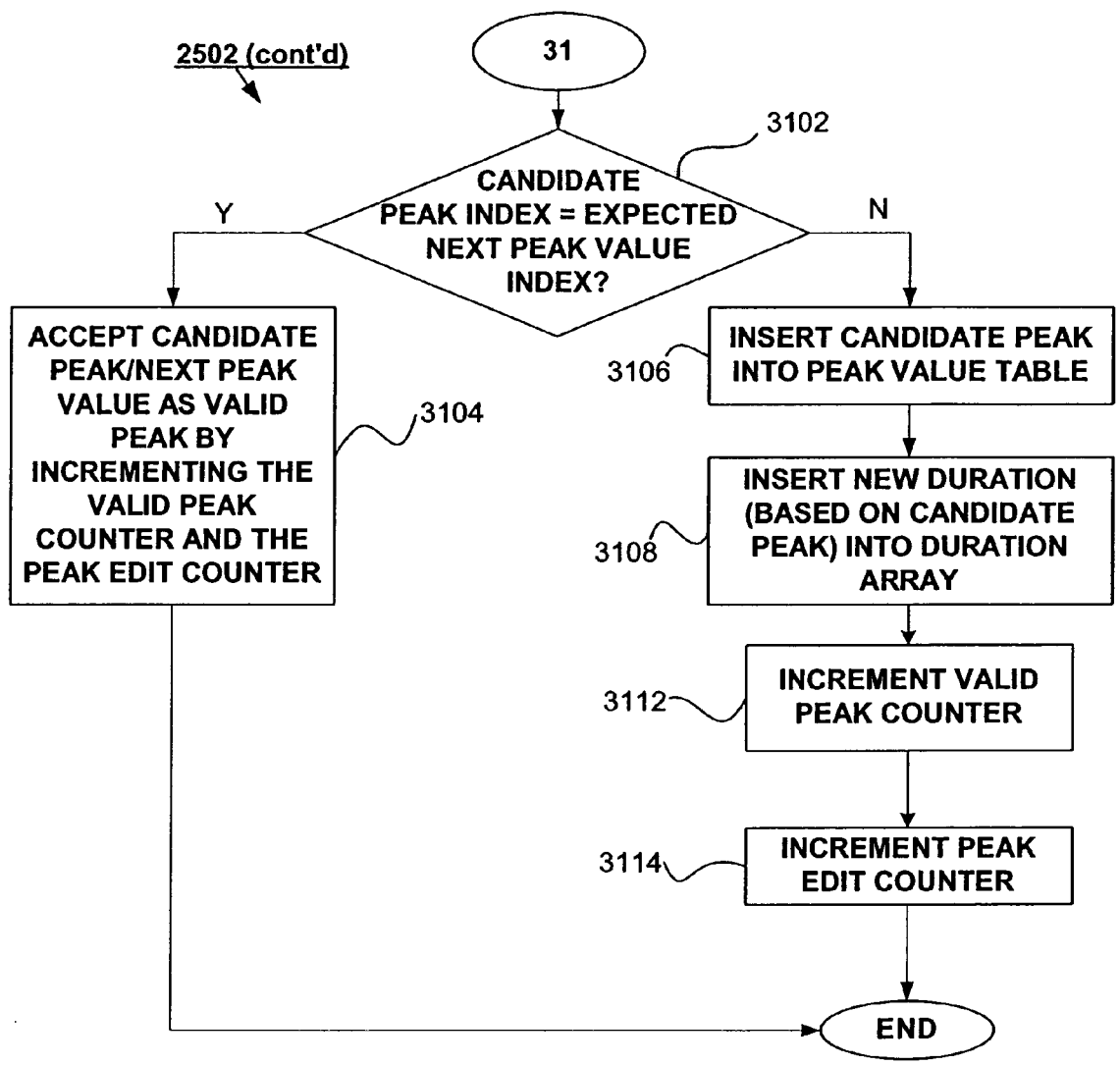
FIG. 31 continues the flow chart of FIG. 30.

FIG. 31 continues detailing the process shown in step 2502 of evaluating each peak in the start point table, according to one embodiment of the invention. In FIG. 31, the candidate peak with the smallest error that was determined in step 3027 is further tested. In a step 3102, a determination is made of whether the candidate peak index is equal to the index value of the expected next peak. If so, the candidate peak is accepted in a step 3104 as a valid peak by incrementing the valid peak counter and incrementing the peak edit counter. If, however, the candidate peak index is not equal to the index value of the expected next peak, further processing must be done prior to accepting the peak as a valid start point. In particular, at a step 3106, the candidate peak is inserted into the peak value table, and at a step 3108 the new duration, which is based on the current candidate peak, is inserted into the duration array. Then, in a step 3112 the valid peak counter is incremented and in a step 3114, the peak edit counter is incremented.

Referring again to FIG. 25, after the peaks in the start point table have been evaluated, a test is then made at a step 2504 of whether the last peak in the cardiovascular sound signals is too close to the end of the file of cardiovascular sound signals. If the last peak is too close, the last entry from the start point table and its corresponding duration is removed in a step 2506 and the peak value counter is decremented in a step 2508. In a step 2510 a parsing score is computed by subtracting 0.1 for peak error and 0.01 for peak edits from a perfect score of one.

The preceding discussion of FIG. 23 through FIG. 31 described the process shown in step 2235 of FIG. 7, which are the steps, according to one embodiment of the invention, for parsing the cardiovascular sound signals and extracting the start point of each heart cycle signal based on the current convolution of the smoothed cardiovascular sound signals with either the bootstrap filter (if the first time through the loop shown in FIG. 7) or the currently indexed beat (if not the first time through the loop).

A parsing score based on the parsing process is calculated in a step 2240 of FIG. 6. In one embodiment, the parsing score is calculated as:

parsing score=valid peaks/(number of peaks+error counter−1)−0.01 (peak edit counter+deleted peaks counter)     [1]

Thus, the parsing score will only be equal to one where the number of valid peaks determined by the steps above is equal to the total number of peaks chosen as candidate peaks (i.e., peaks above a predefined threshold), and also where the peak edits counter and deleted peaks counter are both zero (i.e., no edits were made to either the peaks or the durations during the previously described steps of extracting the start point of each heart cycle signal).

If, as a result of the parsing process discussed in the preceding steps, the predicted start point of each heartbeat interval aligns with all of the peaks shown in FIG. 22, a perfect parsing score of one results. The calculated parsing score is checked in a step 2245 of FIG. 7 against the current best parsing score. If the parsing score is greater than the current best parsing score, the current parsing score is made the current best parsing score at step 2250. Next, the current best parsing score is checked in step 2255 to determine if a perfect parsing score of one has been calculated.

If the current best parsing score is not equal to a perfect parsing score of one, then a check is made in step 2260 of whether there are additional smoothed cardiovascular heartbeat cycle sound signals to be processed. If there are additional smoothed cardiovascular sound signals to process, the index into the peak detect signal is updated to point to the next predicted beat. This new beat is then convolved in step 2265 with the smoothed cardiovascular sound signals in waveform 820 of FIG. 9 to produce a new set of cross-correlation peaks. The loop described above consisting of step 2230 through step 2255 is then repeated until a parsing score of one is reached or there are no more peak detect signals available.

If the current best parsing score is equal to one or if there are no further peak detect signals to process, a determination is made in step 2275 of whether an incomplete beat exists at the end of the smoothed cardiovascular sound signals. If so, the incomplete beat is discarded in step 2280. Otherwise, the process continues without discarding anything.

If the highest parsing score of one is obtained from this search, then the relative phase of S1 in the best segment is measured and compared with that of the heartbeat average that matched the original waveform estimate. This establishes the S1 start point phase of the heartbeat segment with the highest parsing score.

After all correlation searches are completed, the results from the search having the best parsing score are stored for the file under process. This table of data lists the starting indices of each heartbeat. A table of the differences of adjacent start points is calculated to provide the duration of each heartbeat interval.

An example of this table for 44 heart beats is shown in Table 3 below.

Example of the result returned from Peak Analysis
Parsing Score=0.920 Number Syncs 44
Syncs and Duration Arrays are in Narrowband Time Sample Points

TABLE 3

| Heart beat start indices | | |
|---|---|---|
| Beat | Sync | Duration |
| 1 | 216 | 297 |
| 2 | 507 | 285 |
| 3 | 795 | 301 |
| 4 | 1095 | 291 |
| 5 | 1398 | 297 |
| 6 | 1695 | 297 |
| 7 | 1987 | 287 |
| 8 | 2271 | 292 |
| 9 | 2570 | 306 |
| 10 | 2867 | 279 |
| 11 | 3145 | 233 |
| 12 | 3381 | 348 |
| 13 | 3729 | 291 |
| 14 | 4023 | 292 |
| 15 | 4313 | 277 |
| 16 | 4597 | 310 |
| 17 | 4901 | 290 |
| 18 | 5195 | 288 |
| 19 | 5482 | 274 |
| 20 | 5758 | 311 |
| 21 | 6054 | 285 |
| 22 | 6339 | 287 |
| 23 | 6633 | 287 |
| 24 | 6913 | 280 |
| 25 | 7199 | 296 |
| 26 | 7494 | 290 |
| 27 | 7786 | 276 |
| 28 | 8068 | 286 |
| 29 | 8353 | 307 |
| 30 | 8652 | 290 |
| 31 | 8946 | 276 |
| 32 | 9217 | 285 |
| 33 | 9501 | 293 |
| 34 | 9805 | 305 |
| 35 | 10104 | 273 |
| 36 | 10379 | 288 |
| 37 | 10668 | 305 |
| 38 | 10966 | 287 |

TABLE 3-continued

Heart beat start indices

| Beat | Sync | Duration |
|---|---|---|
| 39 | 11256 | 276 |
| 40 | 11535 | 281 |
| 41 | 11813 | 309 |
| 42 | 12116 | 286 |
| 43 | 12408 | 286 |
| 44 | 12688 | 273 |

Although the search results at this point are fairly accurate, in accordance with one embodiment, further processing is carried out to further improve the results. For example, a Vernier fine tuning process can be performed in a step 2285 that can improve the determined start of each heart cycle signal. The center of the convolution result can then be searched to see if even greater correlation occurs between the respective pulse waveforms, by shifting the subsequent peak detected signal by a slight shift along the time axis. If greater correlation does result, the start of the synch index for the next heart cycle signal is then shifted by the correlation offset. This process is repeated throughout the entire set of parsed heart cycle signals. Other fine tuning processes could include comparisons of the onset of S1 or the alignment of the peaks of S1.

Figure 32:
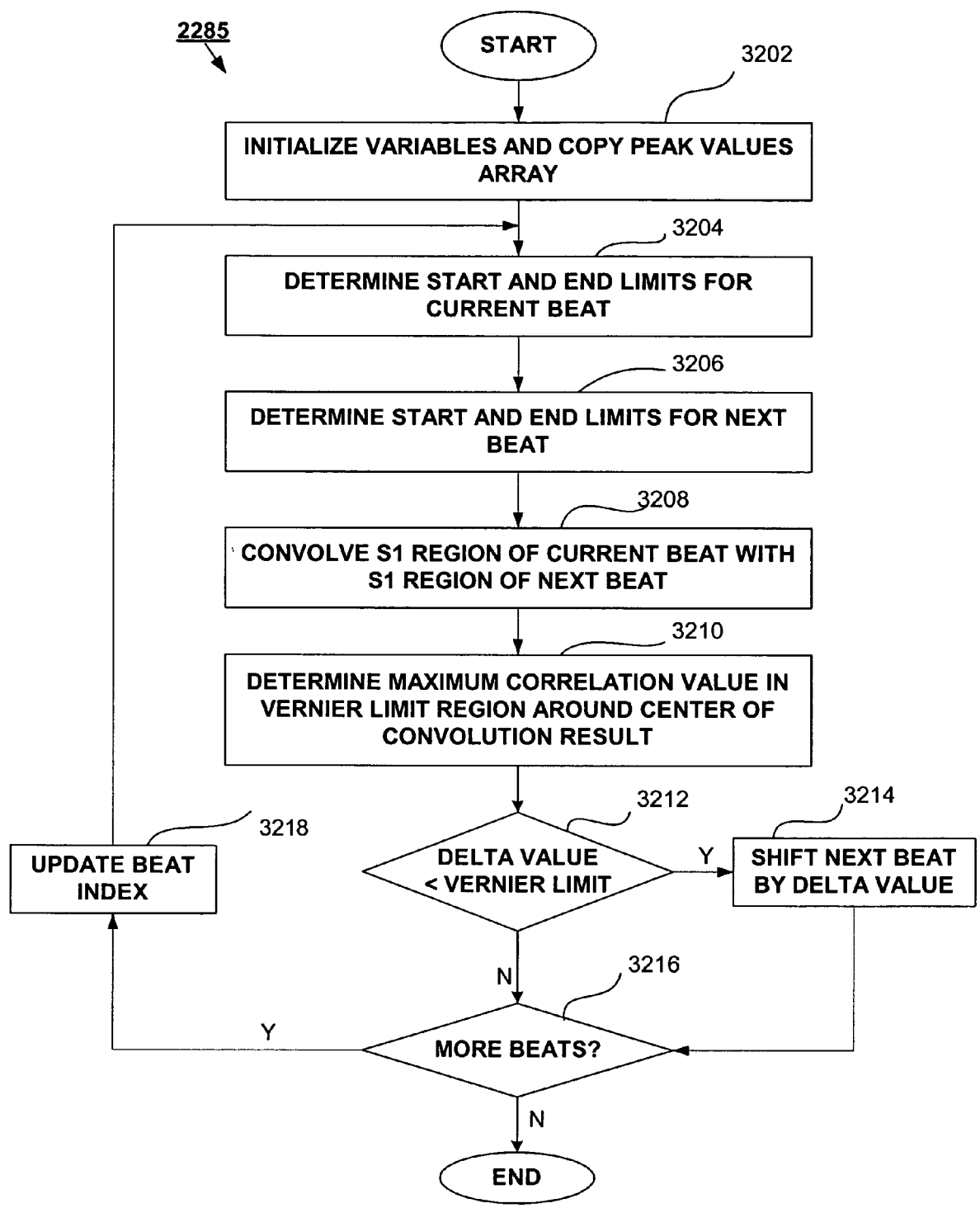
FIG. 32 is a flow chart depicting a Vernier tuning process.

As shown in the detail of FIG. 32, this Vernier fine tuning process can loop through each of the heart cycle signals convolving a section of the narrowband time waveform from the current heart cycle signal with the next heart cycle signal. In particular, at a step 3202 of FIG. 32, a set of variables are initialized and the peak values array is copied into local storage for the Vernier tuning process. In a step 3204, the start and end limits for the currently indexed heart cycle signal are determined and in a step 3206, the start and end limits for the next heart cycle signal are determined. In a step 3208, the S1 region of the currently indexed heart cycle signal is convolved with the next heart cycle signal. In a step 3210, a maximum correlation value is determined in a previously determined Vernier limit region around the center of the convolution result and a corresponding delta shift value is determined. If the delta shift value is less than a previously defined limit, as tested in a step 3212, then the next peak value is shifted by the delta shift value in a step 3214. If the delta shift value is not less than a previously defined limit, a determination is made in a step 3216 of whether there are more beats to process. If so, the beat index is updated in a step 3218 and control passed back to step 3204.

As an interim summary, the above described process of determining the start point of each heart cycle signal within the acquired cardiovascular sound signals (as depicted in FIG. 6 through FIG. 32) is summarized in the input/output detail in FIG. 33. Specifically, with an input autocorrelation of the filtered and smoothed heart audio signals shown in signal 3310 in FIG. 33, a math model filter such as the one shown in signal 3320 can result. Similarly, when the math model filter and bootstrap filters have been determined, they can be used to establish the start point locations of the heart cycle signals, as depicted in signal 3330 of FIG. 33.

Determine Start or End of Heartbeat Phases

Referring back to FIG. 5, once the start point of each heart cycle signal has been determined in step 2200, a determination is then made in a step 2400 of a start point and/or end point of one or more of the phases of each heart cycle signal, including S1 and S2, preferably including S1 through S4. In one embodiment, the parsing of the cardiovascular sound signals and the identification of the phases of each heart cycle signal occurs without a separate reference signal, such as an ECG, that indicates the start of a heart beat. As described above, four intervals, S1, S2, diastole, and systole, are associated with each heartbeat cycle, as reflected in each heart cycle signal. Average measurements of these intervals are used in subsequent processing, as described below. The measurement of these intervals is depicted in the flowchart shown in FIG. 34.

Figure 34:
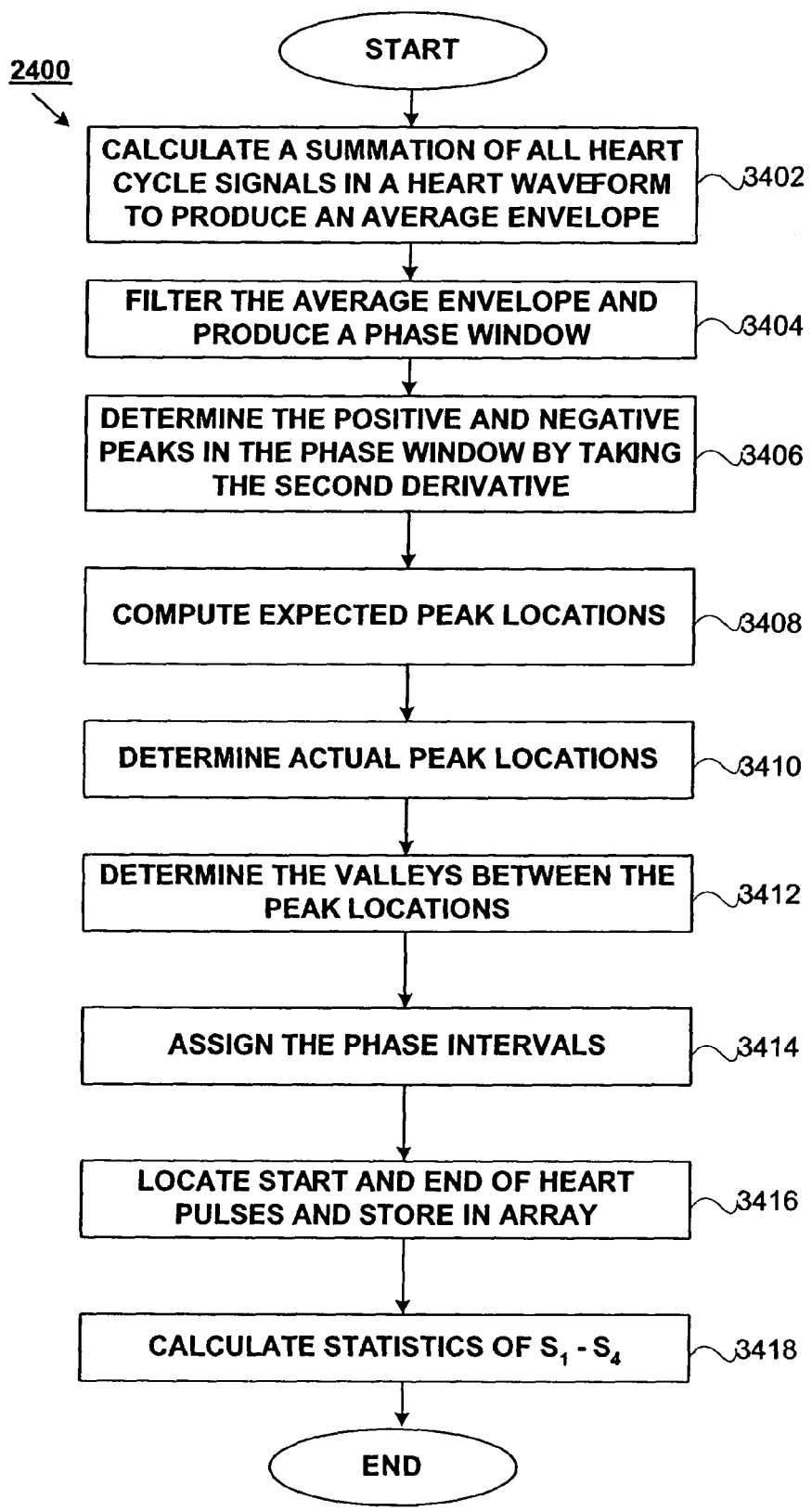
FIG. 34 is a flow chart depicting the process of determining a start point or end point of one or more phases of each heart cycle signal.
Figure 35:
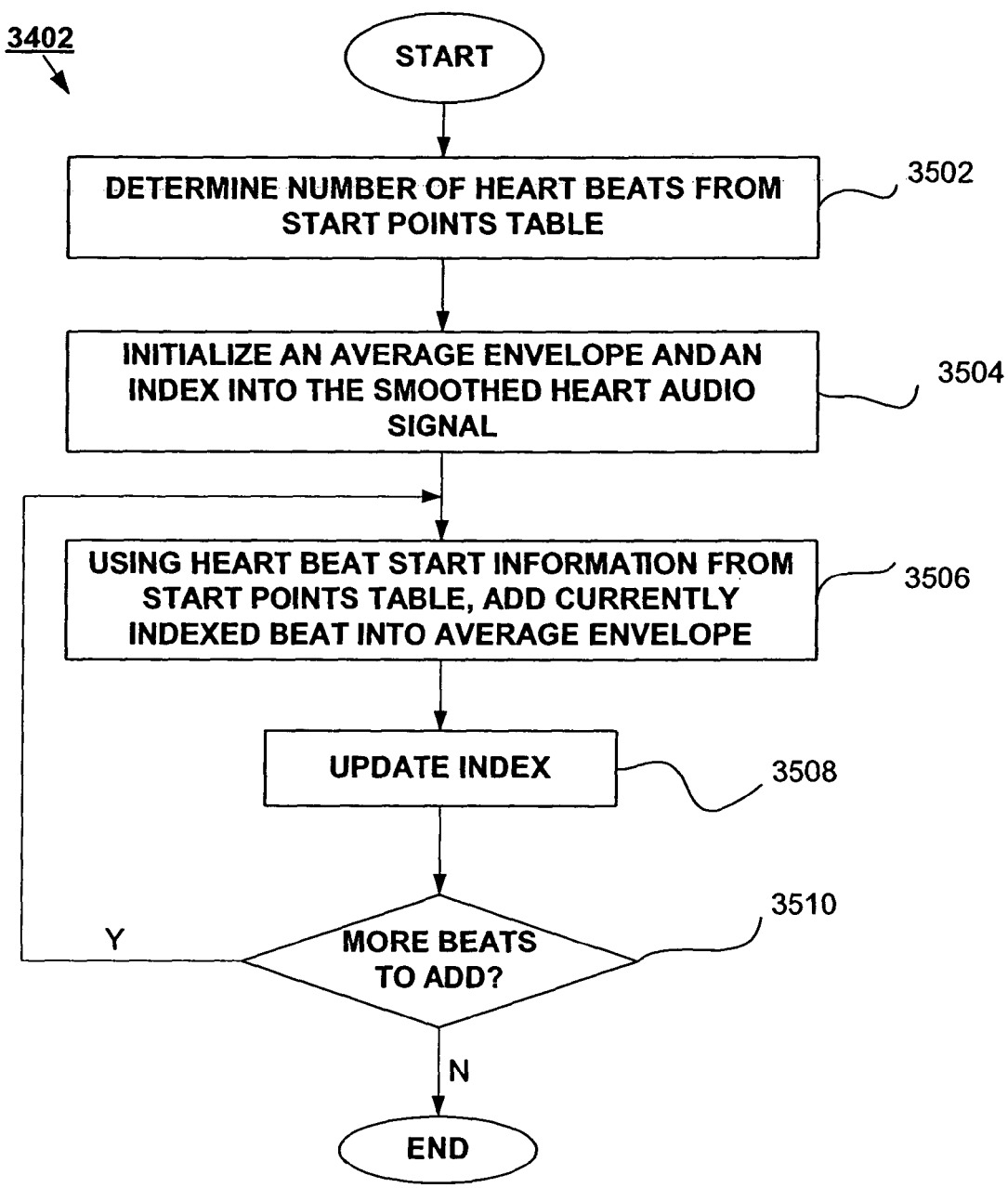
FIG. 35 is a flow chart depicting the calculation of an average envelope.

All of the heart cycle signals in the filtered cardiovascular sound signals (a portion of which is shown in FIG. 46) are summed in a step 3402 of FIG. 34 to build an average envelope that emphasizes S1 and S2. In particular, as further detailed in step 3502 of FIG. 35, the average envelope calculation begins with a determination of the number of heart cycle signals from the start points table. In a step 3504, an average envelope is initialized, in one embodiment, to all zeroes. Likewise, in that same step an index into the smoothed cardiovascular sound signals is determined. Using the start point information from the start points table, each point from the currently indexed heart cycle signal gets added into the average envelope. In a step 3508, the index into the start points table is updated and a determination is made in a step 3510 of whether any more heart cycle signals need to be added to the average envelope or if the averaging portion of the process is done.

Figure 36:
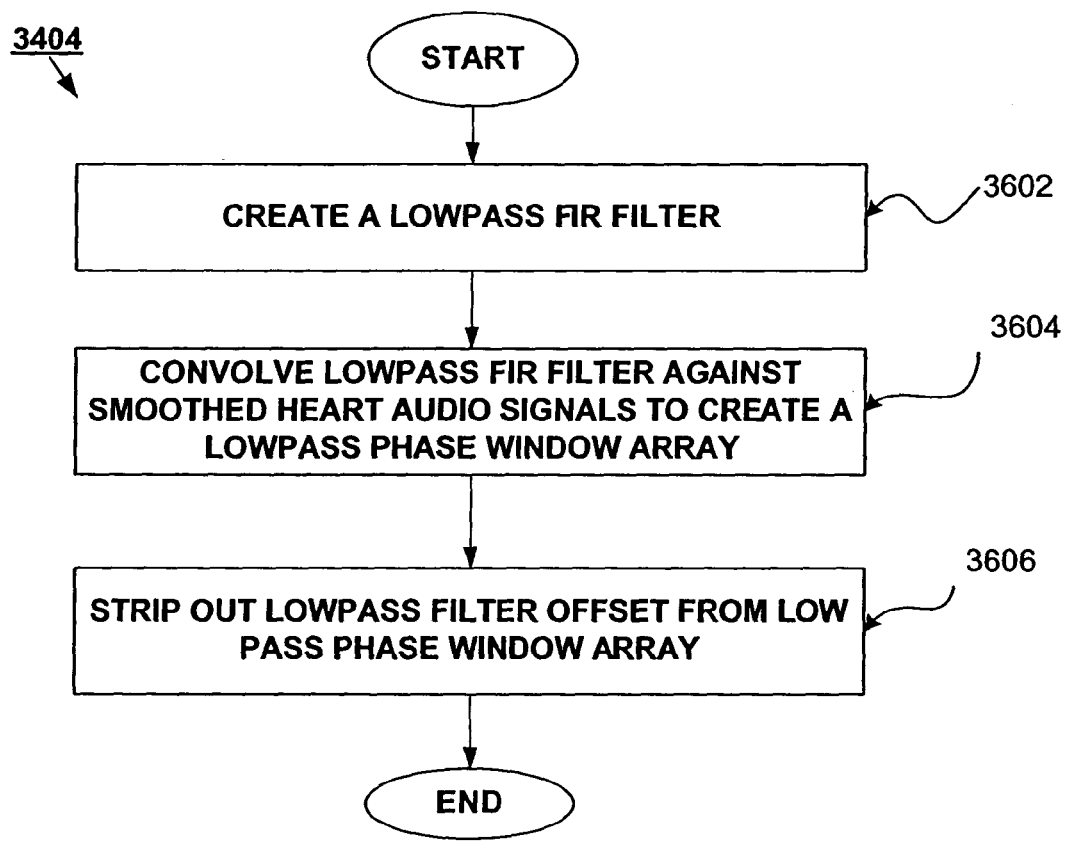
FIG. 36 is a flow chart depicting the calculation of a phase window.
Figure 48:
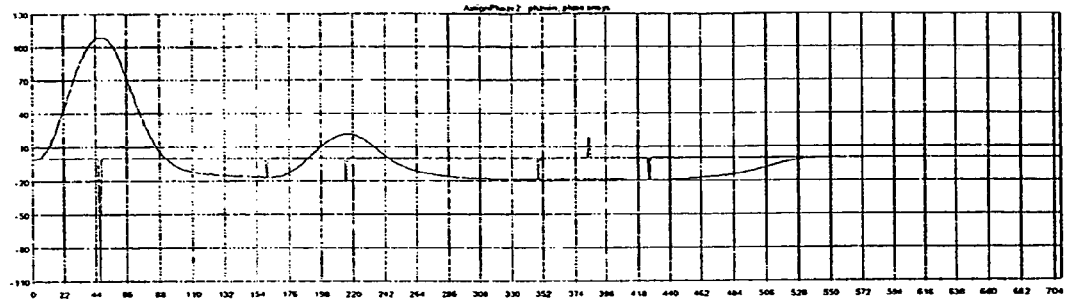
FIG. 48 shows a graphical representation of a phase window and an array of S1 through S4 indices.

In a step 3404 of FIG. 34, the average envelope is filtered to enhance the frequencies most prevalent in the S1 and S2 pulses. These frequencies typically range from 20 Hz to 60 Hz. As shown in the details of step 3404 that are shown in FIG. 36, a low pass finite impulse response (FIR) filter is created in a step 3602 and convolved against the smoothed cardiovascular sound signals in a step 3604 to create a phase window. In a step 3606, the low pass filter offset from the phase window is stripped out (i.e., the widening caused by the low pass filter process). Waveform 4810 of FIG. 48 shows the audio waveform after the low pass filtering and convolution process used to enhance S1 and S2.

Once the phase window has been calculated, a second derivative of the phase window is calculated in a step 3406 to determine whether the extrema in the phase window are positive (i.e., peaks) or negative (i.e., valleys). After the peaks and valleys are determined, the expected peak locations in all of the heart cycle signals are computed in a step 3408. The expected peak locations for S1 and S2 are calculated relative to the average beat duration and previously measured S1 to S2 spacing.

Figure 37:
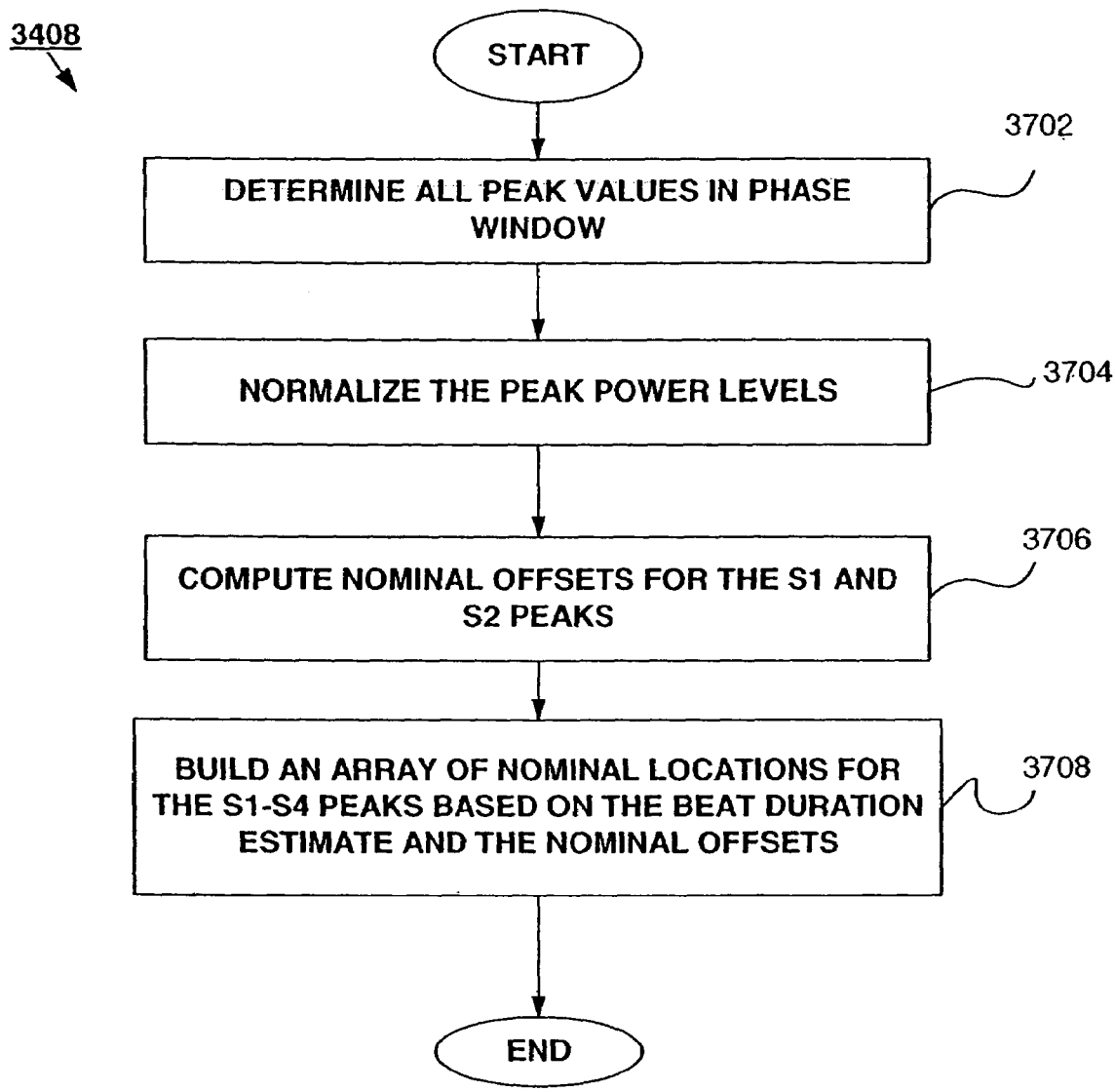
FIG. 37 is a flow chart depicting the computation of the expected peak locations.

FIG. 37 provides further detail on the peak/valley determination of step 3408. In a step 3702 of FIG. 37, all peak values in the phase window are determined and identified. In a step 3704, those peak value locations are normalized by, in one embodiment, subtracting the minimum power in the phase window. Next, in a step 3706, nominal offsets for the S1 and S2 peaks are computed. In one embodiment, the S1 offset is calculated from the index of the first occurrence of S1 in the start points table. The S2 offset is then calculated based on the S1 offset, and is limited to be within the first half of the computed beat duration estimate. Finally, in a step 3708, an array of nominal locations for the S1–S4 peaks is built, based on the nominal offsets calculated in step 3706.

Referring back to FIG. 34, a determination is made in a step 3410 comparing the actual peak locations to the predicted peak locations, and generating a score for each predicted peak location. The best scores for each S1 through S4 candidate peak are then used to assign the actual peak locations.

Figure 38:
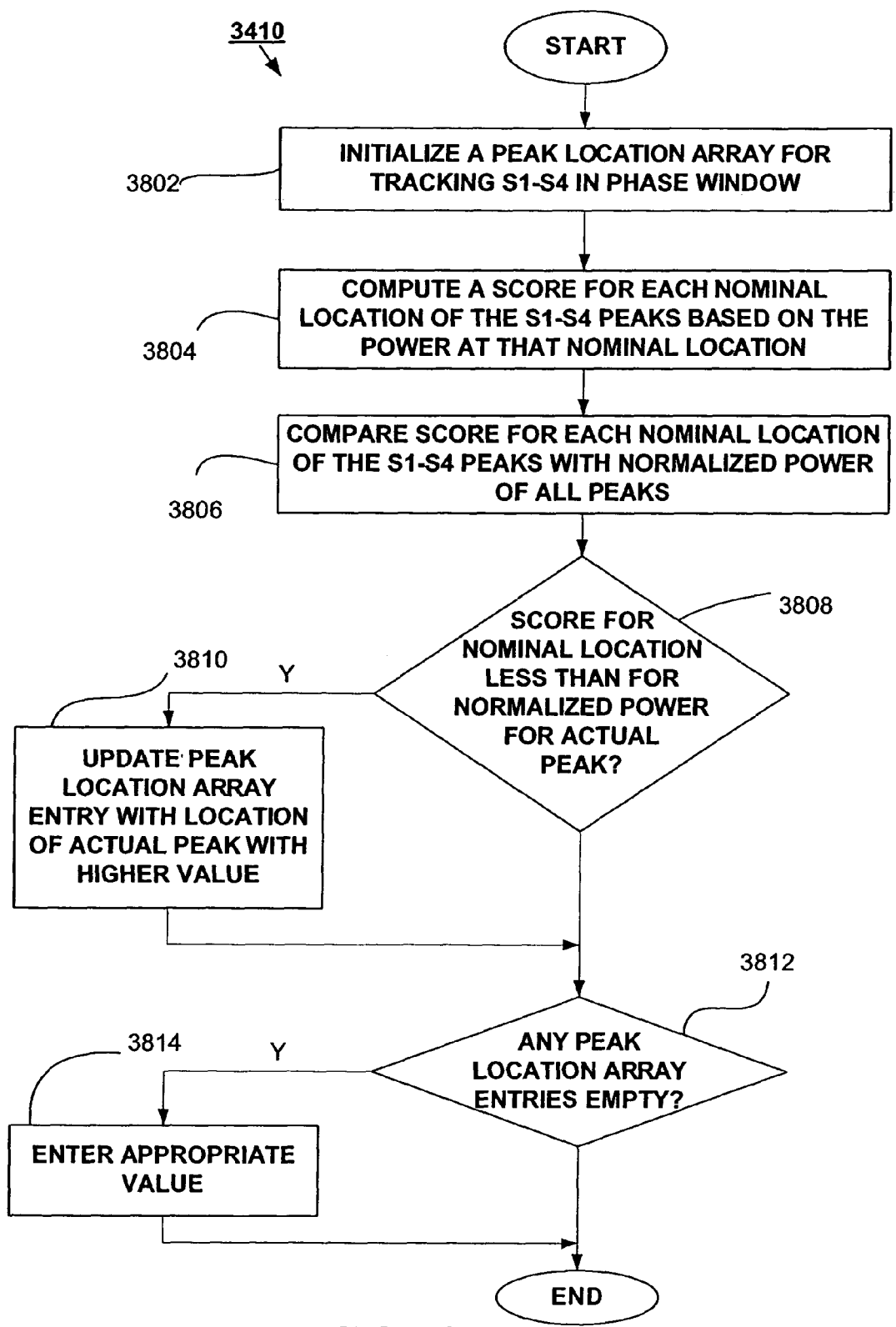
FIG. 38 is a flow chart depicting the determination of the actual peak locations.

FIG. 38 provides further detail on the peak location and scoring processes of step 3410 of FIG. 34. In a step 3802, a peak location array is initialized for tracking the S1 to S4 locations in the phase window. In a step 3804, a score for each nominal S1 to S4 peak location is computed, based on the power at that nominal location. In a step 3806, a comparison is made between the score for each nominal location and the score for the normalized power of all peaks. If the score for the nominal location is less than the normalized power for the actual peak location (as checked in a step 3808), then the S1 to S4 peak location array entries are updated with the location of the peak with the higher value.

In a step 3812, a determination is made of whether any of the S1 to S4 peak location array entries are empty. If so, those empty peak location array entries are populated. In one embodiment, they can be filled with predetermined values. In another embodiment, they can be populated with values extrapolated from other populated locations.

In a step 3412, all of the valley locations in all of the heart cycle signals are determined in a fashion similar to the determinations of the peak locations. The identification of all of the phase intervals for all of the heart cycle signals in a heart waveform (or heart cycle signal) consists of computing the approximate regions of S1 through S4 based on the peaks and valleys identified in the preceding steps. If the peaks and valleys were not able to be properly identified, an estimate of the regions is made, relative to the average beat duration for the current heart waveform.

Figure 39:
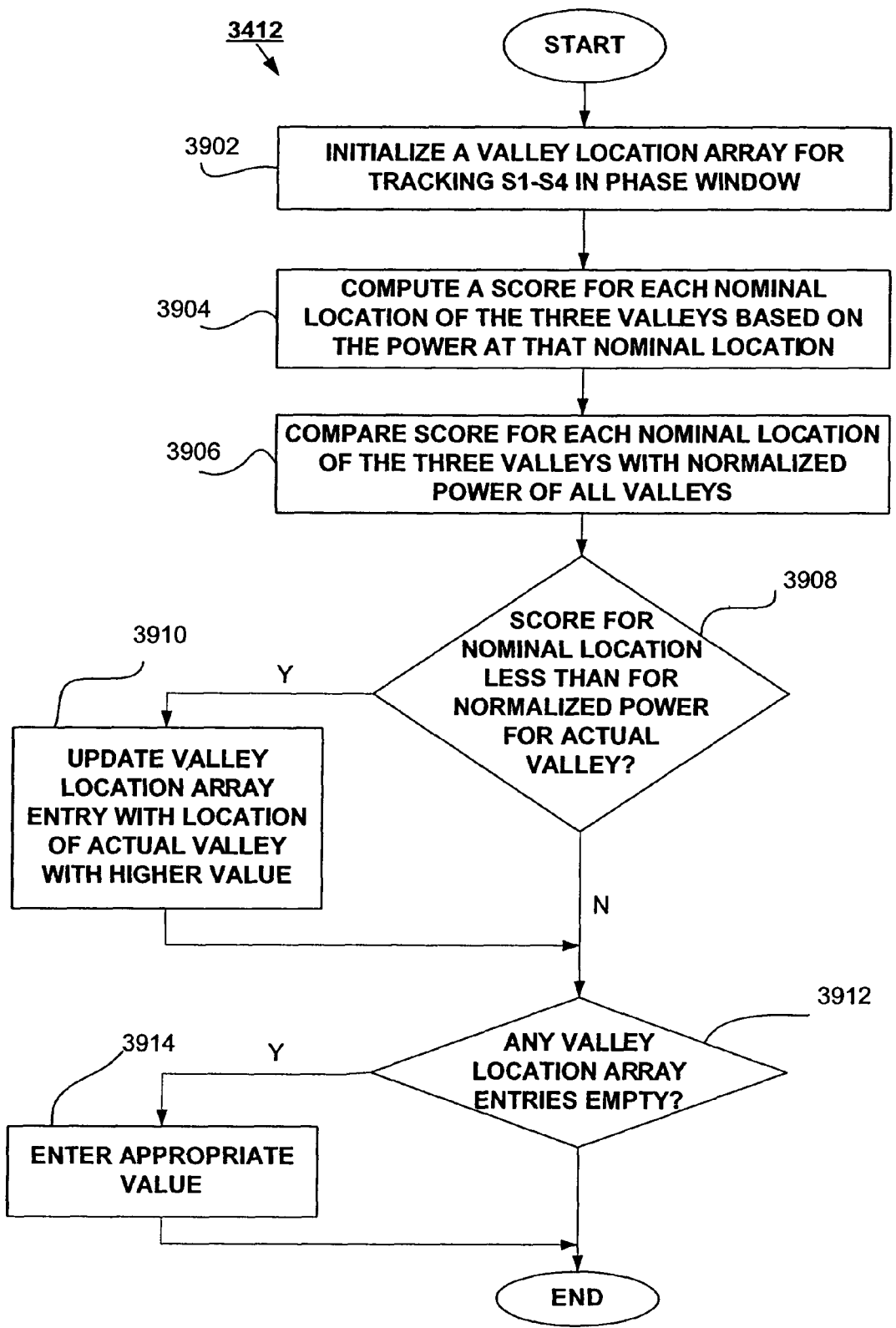
FIG. 39 is a flow chart depicting the determination of the valleys between the peak locations determined in the flow chart of FIG. 38.

FIG. 39 provides further detail on the valley location and scoring processes of step 3412 of FIG. 34. In a step 3902, a valley location array is initialized for tracking the S1 to S4 locations in the phase window. In a step 3904, a score for each nominal S1 to S4 valley location is computed, based on the power at that nominal location. In a step 3906, a comparison is made between the score for each nominal location and the score for the normalized power of all valleys. If the score for the nominal location is less than the normalized power for the actual valley location (as checked in a step 3908), then the S1 to S4 valley location array entries are updated with the location of the valley with the higher value.

Figure 40:
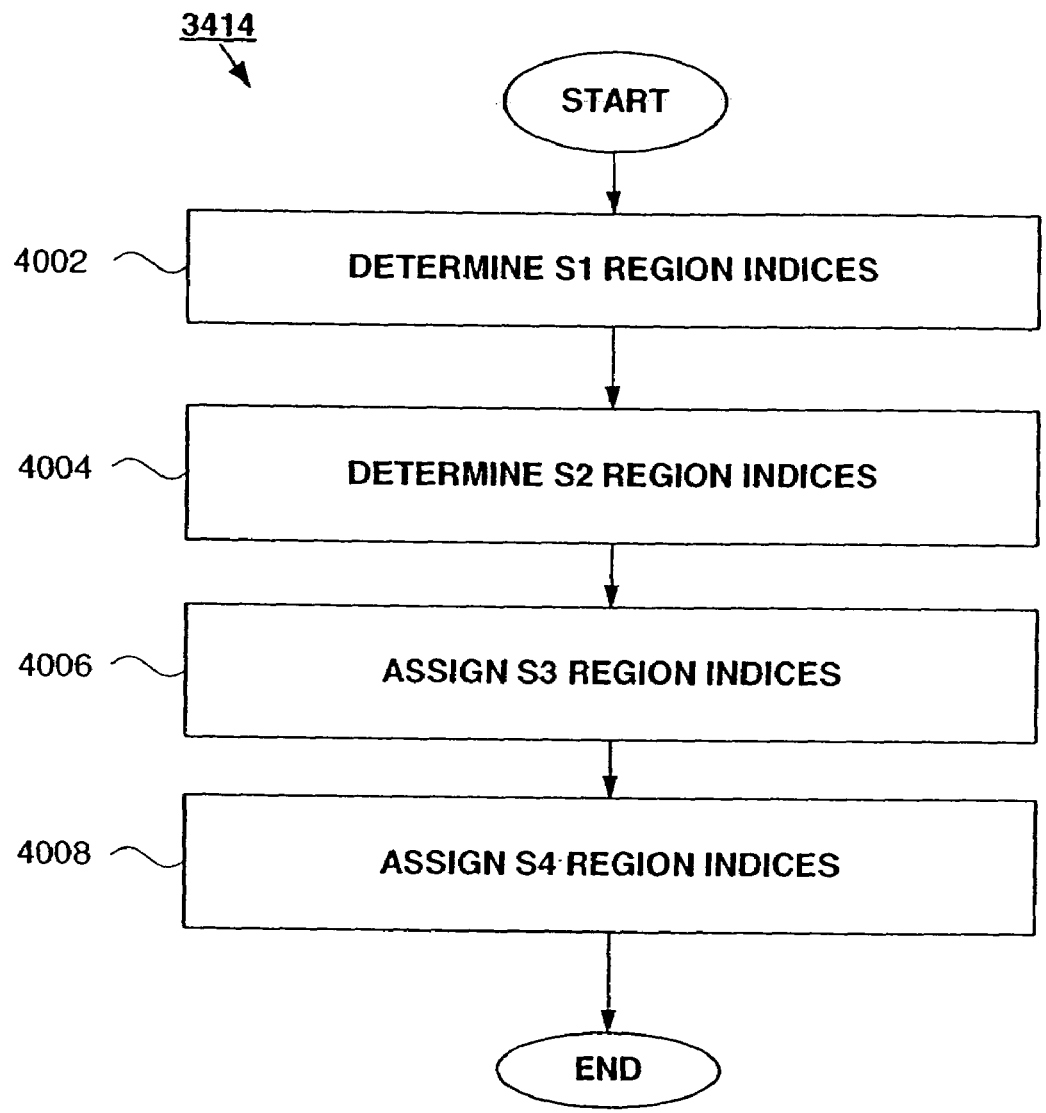
FIG. 40 is a flow chart depicting assignment of the S1 through S4 phase intervals.

FIG. 40 then provides further detail on step 3414 shown in FIG. 34, depicting the phase interval assignment for each heart cycle signal. In step 4002 through 4008, the indices for each of the S1 through S4 regions is determined for all heart cycle signals in the file containing the cardiovascular sound signals.

Figure 41:
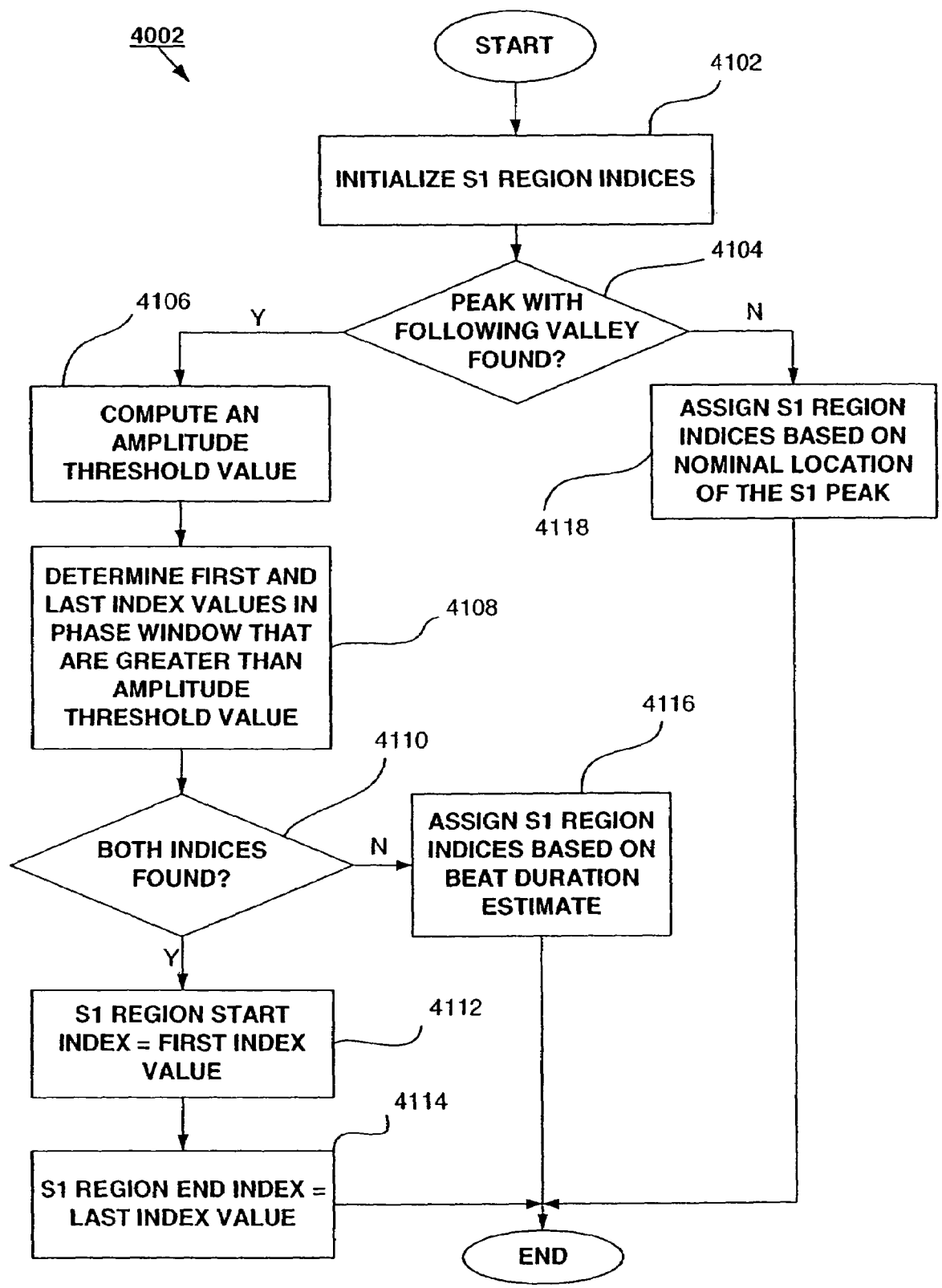
FIG. 41 is a flow chart depicting the determination of the S1 region indices.

FIG. 41 depicts the process in step 4002 of FIG. 40 by which the S1 indices are determined. In a step 4102, the S1 region indices are initialized. At step 4104, a determination is made of whether a peak with a following valley was found, based on the values in the peak and valley locations arrays. If no such peaks with following valleys are detected, the S1 region indices are assigned based on the nominal location of the S1 peak at a step 4118. If, however, peaks with following valleys were detected, an amplitude threshold value is computed in a step 4106. Then, in a step 4108, the first and last index values in the phase window that are greater than the amplitude threshold value are determined. If both such indices are found (based on a test at a step 4110), the S1 region start index is set equal to the first index value in a step 4112 and the S1 region end index is set equal to the last index value in a step 4114. If both such indices were not found in step 4110, the S1 region indices are assigned in a step 4116 based on the beat duration estimate calculated earlier, as would be apparent.

Figure 42:
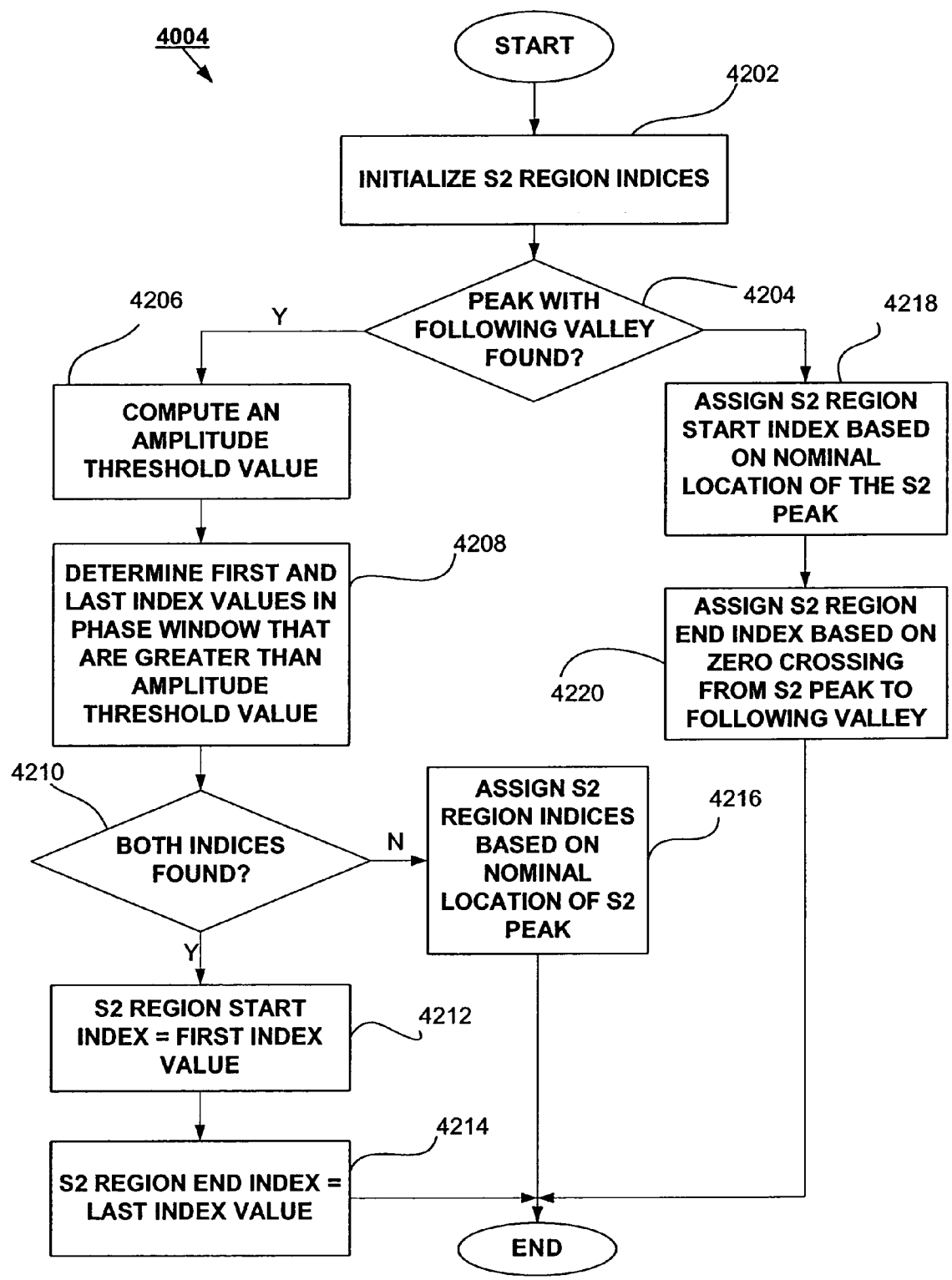
FIG. 42 is a flow chart depicting the determination of the S2 region indices.

Similar to the process in FIG. 41, FIG. 42 depicts the process in step 4004 of FIG. 40 by which the S2 indices are determined. In a step 4202, the S2 region indices are initialized. At step 4204, a determination is made of whether a peak with a following valley was found, based on the values in the peak and valley locations arrays. If no such peaks with following valleys are detected, the S2 region start index is assigned based on the nominal location of the S2 peak at a step 4218. At a step 4220, the S2 region end index is assigned based on the zero crossing from the S2 peak to the following valley, as would be apparent.

If peaks with following valleys were detected in step 4204 of FIG. 42, an amplitude threshold value is computed in a step 4206. Then, in a step 4208, the first and last index values in the phase window that are greater than the amplitude threshold value are determined. If both such indices are found in the test at a step 4210, the S2 region start index is set equal to the first index value in a step 4212 and the S2 region end index is set equal to the last index value in a step 4214. If both such indices were not found in step 4210, the S2 region indices are assigned in a step 4216 based on the nominal location of the S2 peak.

Once the S1 and S2 phase indices have been determined as detailed above, the S3 and S4 phase can also be determined. If the S3 peak is missing, the start of the S3 phase location is assigned based on the location of the valley between the S2 peak and the third peak. The mid point of the S3 phase is determined from the first point to be ¾ in value of the leading edge of the $3^{rd}$ peak. Similarly, if the s4 peak is missing, the start of the S4 phase location is assigned using the starting location of the $4^{th}$ peak.

To illustrate the above process, FIG. 47 shows the results of the parsing operation that causes the windowing of the S1 and S2 heart pulses. FIG. 47 also shows weak signals at 0.7 and 0.82 seconds, which are S3 and S4 pulses common in many patient's heartbeat.

Heart Pulse Statistics

Once the start points of the heart cycle signals are found, and the corresponding phases have been assigned, data can be accumulated on the individual pulse data found within each heartbeat. In particular, the start, duration and relative power in all individual pulses can be found. Pulses are then assigned for S1 through S4 according to the previously determined phase assignment.

Figure 43:
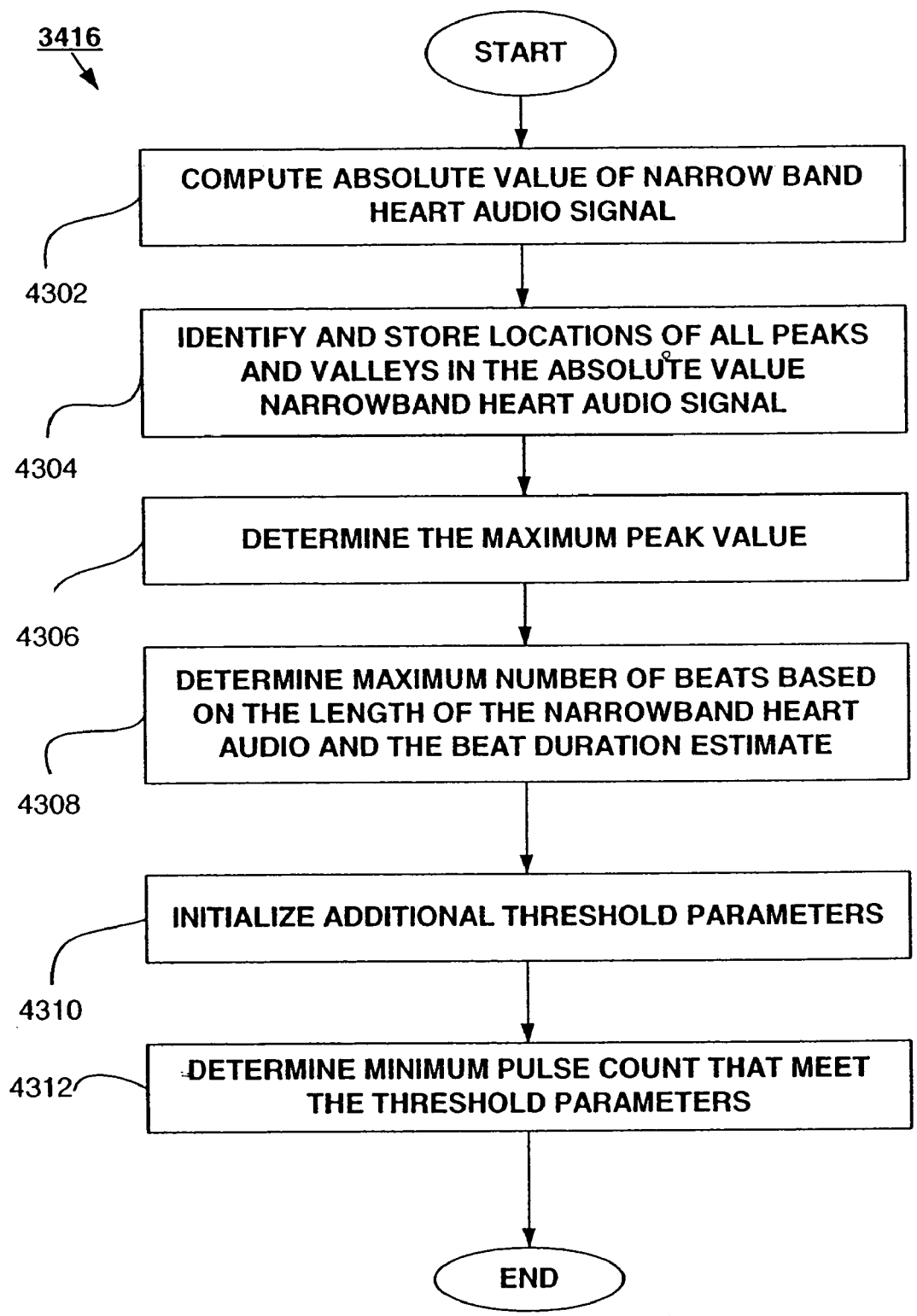
FIG. 43 is a flow chart depicting the creation of an array of locations corresponding to the start and end indices of each of the actual S1 through S4 pulses.

The actual the start and end points of all of the S1–S4 heart pulses in the heart cycle signals are next determined in step 3416 of FIG. 34. The process of finding the pulses locates those points in the waveform that are above a pre-defined threshold, as follows. The flow chart shown in FIG. 43 depicts the process of identifying the start and end points of the S1–S4 heart cycle signals. The process begins by smoothing out unwanted high frequency components of the heart audio. To do so, the narrow band waveform described earlier is band-pass filtered in step 4302 with a center pass-frequency of 40 Hz and 3 dB skirts at 20 and 60 Hz. Also in step 4302, the filtered waveform is transformed by an absolute value function. In a step 4304, the locations of all peaks and valleys in the signal computed in step 4302 are identified and stored, followed by the identification of the maximum peak value in a step 4306.

In a step 4308 a number of additional threshold parameters are determined. The threshold parameters consist of, in one embodiment, the maximum number of beats in the cardiovascular sound signals, a gap run time (which is the minimum length in seconds of the gap between the pulses), the pulse length threshold (which is the minimum acceptable length in seconds of pulses), a minimum pulse count (which is the minimum number of pulses to search to locate the S1 to S4 pulses), an amplitude threshold (which is the fraction of the maximum signal to consider), a minimum amplitude threshold, a threshold step value, and a minimum threshold step value.

In one embodiment, an initial amplitude threshold is set equal to a value that is one quarter of the maximum peak in the waveform. In defining valid pulses in one embodiment, they have a duration greater than 0.035 seconds. Additionally, individual pulses separated by less than 0.055 seconds are combined as one pulse. This forces a connection for the positive and inverted negative segments of the pulse.

Since a typical heartbeat has an S1 and S2 pulse, and may have S3 and/or S4 pulse, the search algorithm generally tests to see whether the pulse count is at least four times the number of heartbeats in the sample. If the pulse count is insufficient, then the amplitude threshold is lowered a small amount and a new set of pulses is extracted. This process will continue until an amplitude threshold limit is reached or the pulse count decreases by a predetermined amount. The limit is set to avoid extracting noise pulses.

Figure 44:
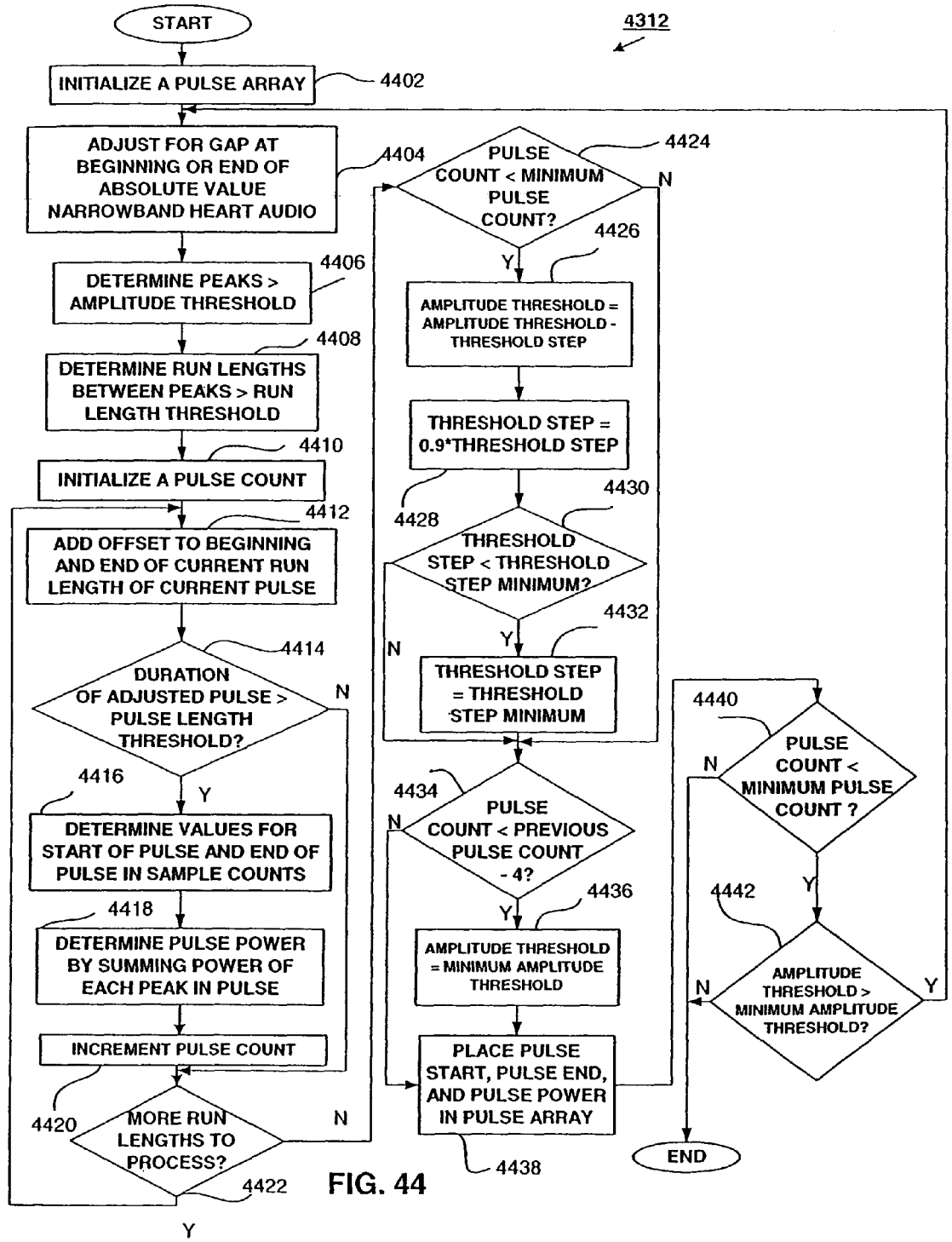
FIG. 44 is a flow chart depicting the determination of a pulse count that meets a set of threshold parameters.

In particular, as shown in FIG. 44, the S1 to S4 pulse determination process commences with a pulse array being initialized in a step 4402. This array will, upon completion of the process, contain indices for those S1 to S4 pulses that were identifiable in the heart cycle signals. In a step 4404, an adjustment is made for any gaps that might exist at the beginning or end of the absolute value narrowband cardiovascular sound signals. Next, any peaks that are greater than a peak (or clip) threshold are isolated in a step 4406. In a step 4408, a determination is made of whether the current run length is greater than a predetermined run length threshold. Specifically, a run length is defined as the amount of time during which a set of peaks that make up a pulse remain greater than the run length threshold.

Once all of the run lengths above the run length threshold have been determined, a check is made to determine whether the run lengths can be considered as actual S1 to S4 pulses. To begin, a pulse count is initialized in a step 4410. In a step 4412, an offset is added to the beginning and end of each run length. In one embodiment, this offset is set equal to one quarter (25%) of a typical or nominal 25 Hz heart cycle. The offset is added to account for the fact that a pulse actually begins approximately one quarter of a cycle before the first peak and finished approximately one quarter of a cycle after the last peak finishes.

After adding the offsets in step 4412, a test is made in a step 4414 of whether the duration of the adjusted pulse is greater than the predetermined pulse length threshold. If so, a determination is made in a step 4416 of the start and end values for the pulse (in sample counts). In a step 4418, a determination is made of the power of the pulse by summing the power of each peak that comprises the pulse. Again referring to FIG. 47, an S1 pulse of one heart cycle signal is shown framed at about 0.2 seconds and an S2 pulse of what is presumed to be the same heart cycle signal is shown framed at approximately 0.5 seconds. The pulse power determination just described would entail summing the power for each of the peaks within those framed pulses.

In a step 4420, the pulse counter is incremented and in a step 4422, a test is made of whether there are further run lengths to process. If there are further runs to process, control passes back up to step 4412 where the next run is processed. If there are no further runs to process, a test is then performed in a step 4424 of whether the current pulse count is less than the predetermined minimum pulse count.

If the current pulse count is less than the minimum pulse count at step 4424, the amplitude threshold is updated on the expectation that additional peaks will then be detected as part of one or more run lengths, thereby increasing the pulse count. To update the amplitude threshold in one embodiment, the amplitude threshold is first decremented by the threshold step in a step 4426. The threshold step is then updated by reducing it by 10% in a step 4428. A test is then made in a step 4430 to determine if the threshold step is less than the threshold step minimum. If the threshold step is less than the threshold step minimum (meaning that a suitable number of peaks has not been found even though the threshold step has been reduced to its minimum value), the threshold step is set equal to the minimum threshold step value in a step 4432.

At a step 4434, a test is made to determine whether the current pulse count is less than the previous pulse count minus four. This test is made to account for split S1 and S2 pulses which may disappear as the amplitude threshold is reduced. In particular, the gaps between the composite peaks at higher amplitude that make up an S1 or S2 signal may go away when the amplitude threshold is lowered. If the current pulse count meets the test (i.e., a previous amplitude threshold value produced as good as or better results than the current amplitude threshold value, the amplitude threshold is forced to the minimum amplitude threshold (which will cause an early exit from the processing loop at a step 4442.

Figure 45:
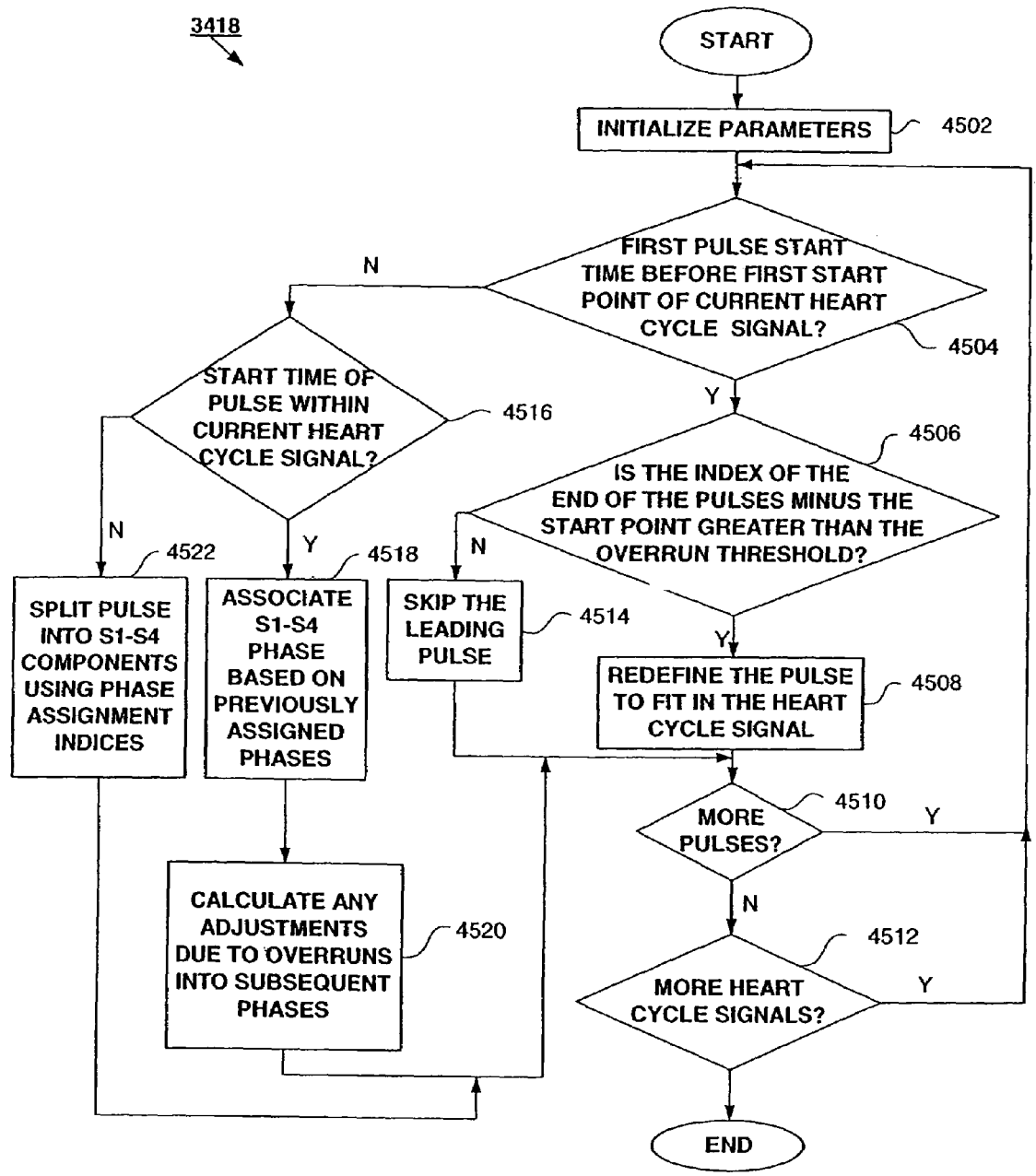
FIG. 45 is a flow chart depicting calculation of statistics of the S1 through S4 pulses.

If the current pulse count is acceptable at step 4434, control passes to a step 4438. In one embodiment, once a suitable pulse count is obtained (or the amplitude limit is reached) the pulse start, pulse end, and total pulse power are logged in the pulse table in step 4438. The relative power is calculated from the square of the sum of the sample values across the pulse. In an alternative embodiment that involves ancillary pulse data (described in FIG. 45), the pulse start, pulse duration, and pulse power are determined as shown in Table 4 below, which contains the first seven entries of an exemplary pulse table.

TABLE 4

| PULSE TABLE | | | |
| --- | --- | --- | --- |
| Pulse | Start | Duration | Power |
| 1 | 70 | 50 | 64 |
| 2 | 205 | 42 | 83 |
| 3 | 428 | 60 | 166 |
| 4 | 559 | 35 | 87 |
| 5 | 775 | 65 | 162 |
| 6 | 914 | 44 | 79 |
| 7 | 1134 | 46 | 68 |

Referring back to FIG. 44, a determination is next made at a step 4440 of whether the current pulse count is less than a predetermined minimum pulse count. If so, a test is then performed at step 4442 to determine whether the current amplitude threshold is greater than the minimum amplitude threshold. If both of these tests are true (i.e., a minimum number of pulses has not yet been determined and the amplitude threshold is not at its minimum value), control returns to step 4404 with a lowered amplitude threshold value. Otherwise, the process completes.

Given the pulse table shown in Table 4 above and the heartbeat phase information determined in step 3414 and step 3416 of FIG. 34, each pulse can be assigned a phase within the heartbeat. The assignment algorithm checks the location of the start of the pulse within a given heartbeat and determines whether the pulse overruns into the next heartbeat phase. If the overrun is excessive, then the pulse is split to report pulse energy from two or more phases according to the extent of the pulse. Often an S4 pulse will merge with the S1 pulse of the next heartbeat.

The tabulated data for nine heartbeats of the heart audio example used here are listed in table 5 below. Only two weak S4's were found and no S3's are reported. The pulse-start referenced to the start of the heartbeat and pulse-duration are reported in units of the narrow band Sample Index Heartbeat Data: Heartbeat Pulses—Times in Sample Indices If the start time of the current pulse is not within the current heart cycle signal (as checked in step 4516), the current pulse is split into appropriate S1 to S4 components using the previously determined phase assignment indices. This case covers the situation where the start time of the current pulse is in the next heartbeat.

FIG. 48 and FIG. 49 provide further information on the process described above for determining the start points and end points of one or more phases of each heart cycle signal, according to an embodiment of the invention. Chart 4810 in FIG. 48 depicts the phase window signal that is used as a more precise estimate of the location of the S1 and S2 phases across all heart cycle signals. With the filtered narrowband cardiovascular sound signals as input, in combination with

TABLE 5

| Beat | Start Index | Duration | Strt | S1 Dur | Pwr | Strt | S2 Dur | Pwr | Strt | S3 Dur | Pwr | Strt | S4 Dur | Pwr |
|---|---|---|---|---|---|---|---|---|---|---|---|---|---|---|
| 1 | 62 | 360 | 8 | 50 | 64 | 143 | 42 | 83 | 0 | 0 | 0 | 0 | 0 | 0 |
| 2 | 422 | 352 | 6 | 60 | 166 | 137 | 35 | 87 | 0 | 0 | 0 | 0 | 0 | 0 |
| 3 | 774 | 351 | 1 | 65 | 162 | 140 | 44 | 79 | 0 | 0 | 0 | 0 | 0 | 0 |
| 4 | 1125 | 359 | 9 | 46 | 68 | 145 | 33 | 84 | 0 | 0 | 0 | 0 | 0 | 0 |
| 5 | 1484 | 355 | 7 | 50 | 69 | 142 | 42 | 75 | 0 | 0 | 0 | 319 | 16 | 12 |
| 6 | 1839 | 343 | 2 | 65 | 187 | 138 | 34 | 86 | 0 | 0 | 0 | 0 | 0 | 0 |
| 7 | 2182 | 339 | 3 | 58 | 159 | 140 | 26 | 67 | 0 | 0 | 0 | 0 | 0 | 0 |
| 8 | 2521 | 344 | 6 | 53 | 130 | 145 | 35 | 65 | 0 | 0 | 0 | 0 | 0 | 0 |
| 9 | 2865 | 339 | 6 | 53 | 85 | 148 | 30 | 51 | 0 | 0 | 0 | 290 | 19 | 14 |

Statistics on the start and end points (and associated intervals) are determined in a step 3418 of FIG. 34. In an embodiment (as illustrated in the flowchart shown in FIG. 45), such statistics can include pulse duration and pulse power. At a step 4502 in FIG. 45, a set of parameters is initialized. In one embodiment, such parameters can include an overrun threshold set to 5% of the beat duration estimate, a new duration threshold, and a counter of the number of start points. At a step 4504, the start time of the first pulse of the current heart cycle signal is checked to determine if it is before the start point of that heart cycle signal. If so, a check is then performed at a step 4506 of whether the index of the end of the pulses for the current heart cycle signal minus the start point for the current heart cycle signal is greater than the overrun threshold. If so, the current pulse is redefined in a step 4508 to fit in the current heart cycle signal. Then a check is made in a step 4510 if any more pulses need to be processed and, if not, whether any more heart cycle signals need to be processed in a step 4512.

If the index of the end of the pulses for the current heart cycle signal minus the start point for the current heart cycle signal is not greater than the overrun threshold (as tested in step 4506), then the current pulse is determined to be a leading pulse not in the parsed set of heartbeats and is discarded in a step 4514. Control then passes to step 4510, where a check is made of whether any more pulses need to be processed and, if not, whether any more heart cycle signals need to be processed in a step 4512.

If the start time of the first pulse of the current heart cycle signal is not before the start point of that heart cycle signal (as checked in step 4504), a check is then made in a step 4516 of whether the start time of the current pulse is within the current heart cycle signal. If so, the S1 through S4 phase values are associated based on the previously assigned phases in a step 4518. Then, in a step 4520, appropriate adjustments are made due to any overruns into subsequent phases.

the phase window in chart 4810, array 4820 is produced, which shows the generalized S1 through S4 regions for all heart cycle signals.

FIG. 49 contains an exemplary pulse array 4910 (similar to that shown in Table 4) that includes a pulse index, pulse start value, pulse length value, and a pulse power value. FIG. 49 also contains pulse statistics array 4920 showing the ancillary pulse data information for each heartbeat (similar to the data shown in Table 5).

Identify Bruit Candidates

Referring again to FIG. 4, after the acquired cardiovascular sound signals have been parsed at step 2000, bruit candidates are identified from high frequency anomalies at a step 3000. In one embodiment, the system identifies bruit candidates that occur in the diastolic interval. In another embodiment, the below described processing is similarly used to identify bruit candidates in systole. In yet another embodiment, the process described below with respect to step 3000 can be used to identify bruit candidates in the background noise signals, which can then be used in the noise cancellation process described further below.

Generally speaking, at step 3000, in the illustrated embodiment of the system 100, the processing algorithm seeks anomalies in the acquired cardiovascular sound signals, such anomalies being defined as having peak energies in the 300 to 1800 Hz frequency bands. As will be discussed in further detail below, anomalies meeting certain predefined criteria will be identified as bruit candidates. In the case of coronary artery disease, these identified bruit candidates are believed to be indicative of blockages in coronary arteries.

Figure 50:
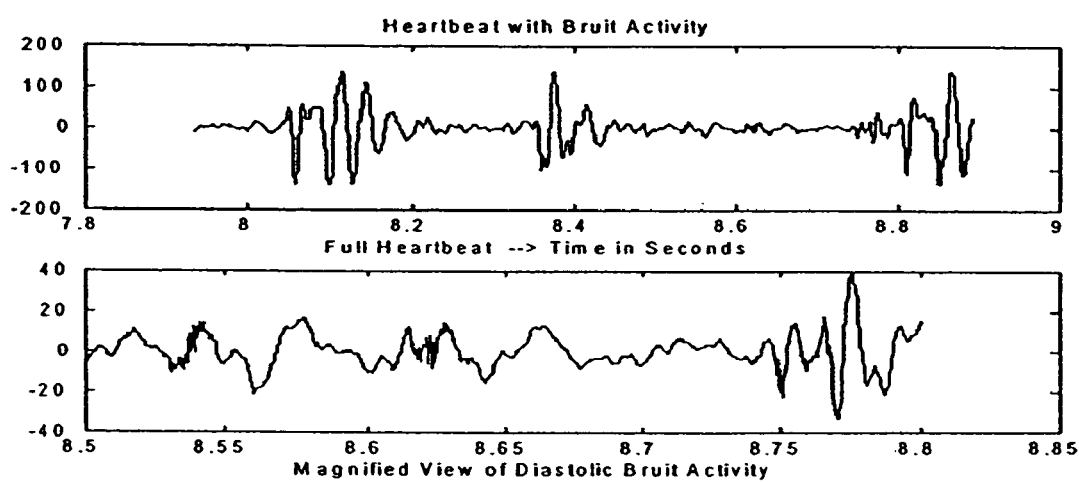
FIG. 50 contains a signal that contains bruits, along with a magnification of those bruits.

FIG. 50 shows one heartbeat with a magnified view of bruits occurring in diastole, which are indicated by three bursts of high frequency energy at approximately 8.54, 8.63, and 8.75 seconds. Signals such as these are not normally seen from patients without heart disease.

Figure 51:
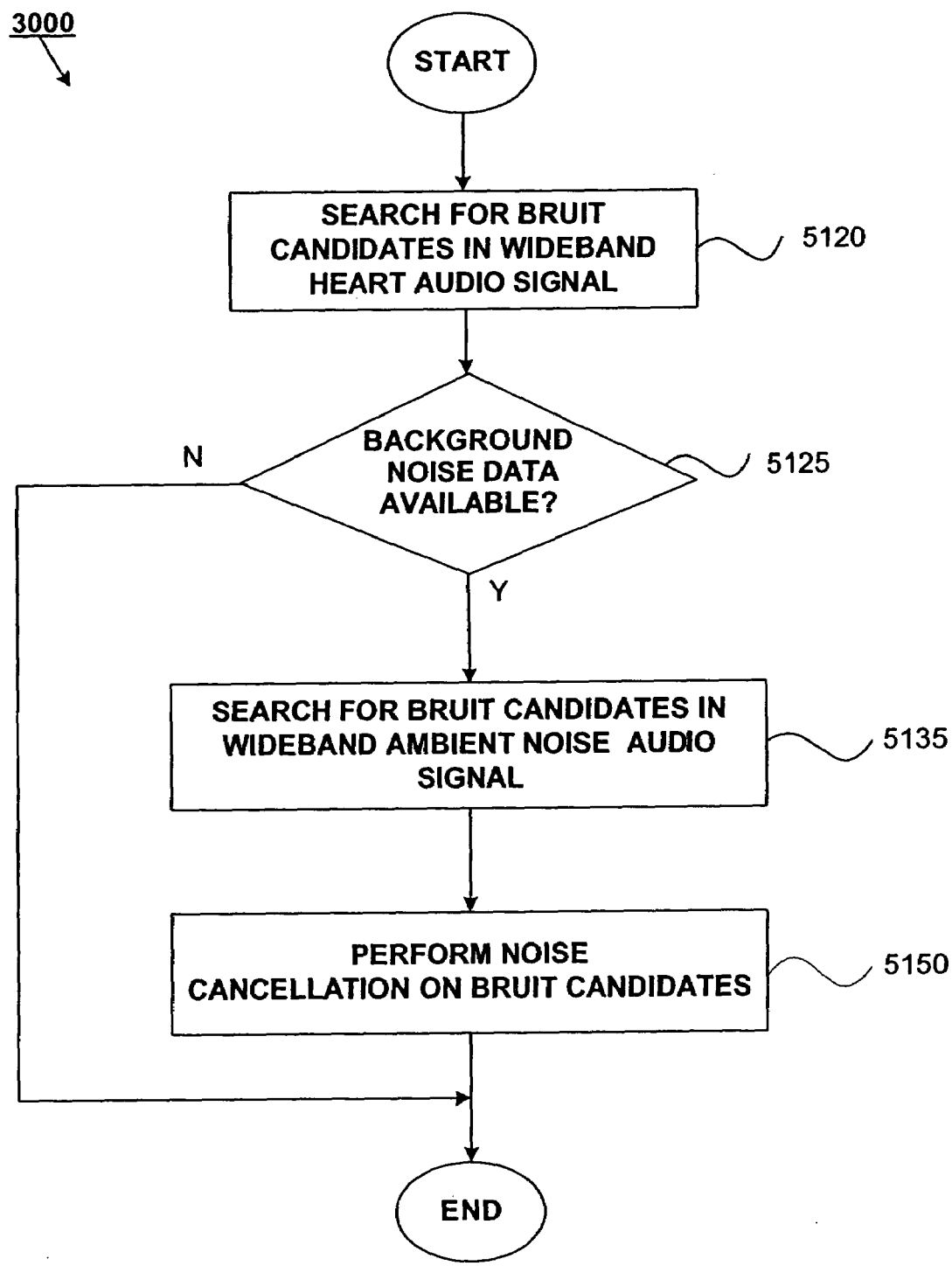
FIG. 51 is a flow chart depicting the process of identifying bruit candidates.

Flowchart 3000 in FIG. 51 illustrates the process of identifying bruit candidates in each heart cycle in one or more heart waveforms of the acquired cardiovascular sound signals. In order to identify bruit candidates, all cardiovascular sound signals with peak frequency components in the 300 to 1800 Hz band are logged and weighted to participate in a final probability of repetitive bruits. A set of bruit detection parameters has been defined and adjusted to screen out any anomalies not necessary for the process. The primary bruit detection parameters are listed below along with a brief description of their purpose. Their use will become clearer in the discussions to follow.

| Parameter | Description | Value |
| --- | --- | --- |
| NoiseAvgWindowFact | Fractional Heartbeat Period for Spectral Averaging | 1.0 |
| SkewCutoffThreshold | Anomalies with greater Skew are ignored | 0.75 |
| BruitDetectionThreshold HA | Anomalies with less spectral energy are ignored - Heart Audio | 14.0 dB |
| BruitDetectionThreshold BN | Anomalies with less spectral energy are ignored - Background Noise | 11.5 dB |
| LowFrequencyLimit | Low Frequency limit | 300 Hz |
| HighFrequencyLimit | High Frequency limit | 1800 Hz |
| FFTSize | Size of FFT in wideband sample points | 128 |
| SpectrumOffset | Spectrum overlap ratio | 0.5 |
| MeanTimePowerThreshold HA | Time data energy rejection threshold - Heart Audio | 0.96 |
| MeanTimePowerThreshold BN | Time data energy rejection threshold - Background Noise | 0.49 |
| Spectrum Notch Threshold HA | Width of spectrum rejection zone in Hertz around located bruit candidate: Heart Audio | 2205 Hz |
| Spectrum Notch Threshold BN | Width of spectrum rejection zone in Hertz around located bruit candidate: Background Noise | 400 Hz |
| FreqSepLim | Noise cancellation frequency separation limit | 1200 Hz |

FIG. 51 illustrates the processing used to detect bruit candidates in each heart cycle. The characteristics of bruits are such that they are distinguishable by measurements made in the frequency domain. The ultimate goal of deriving the probability of bruits in diastole begins with spectral measurements of the cardiovascular sound signals. In order to suppress any transient effects from segments of low frequency signal envelopes, the cardiovascular sound signals are first high pass filtered. In an embodiment, frequencies from 300 Hz and up are retained while those below 200 Hz are heavily attenuated.

Figure 64:
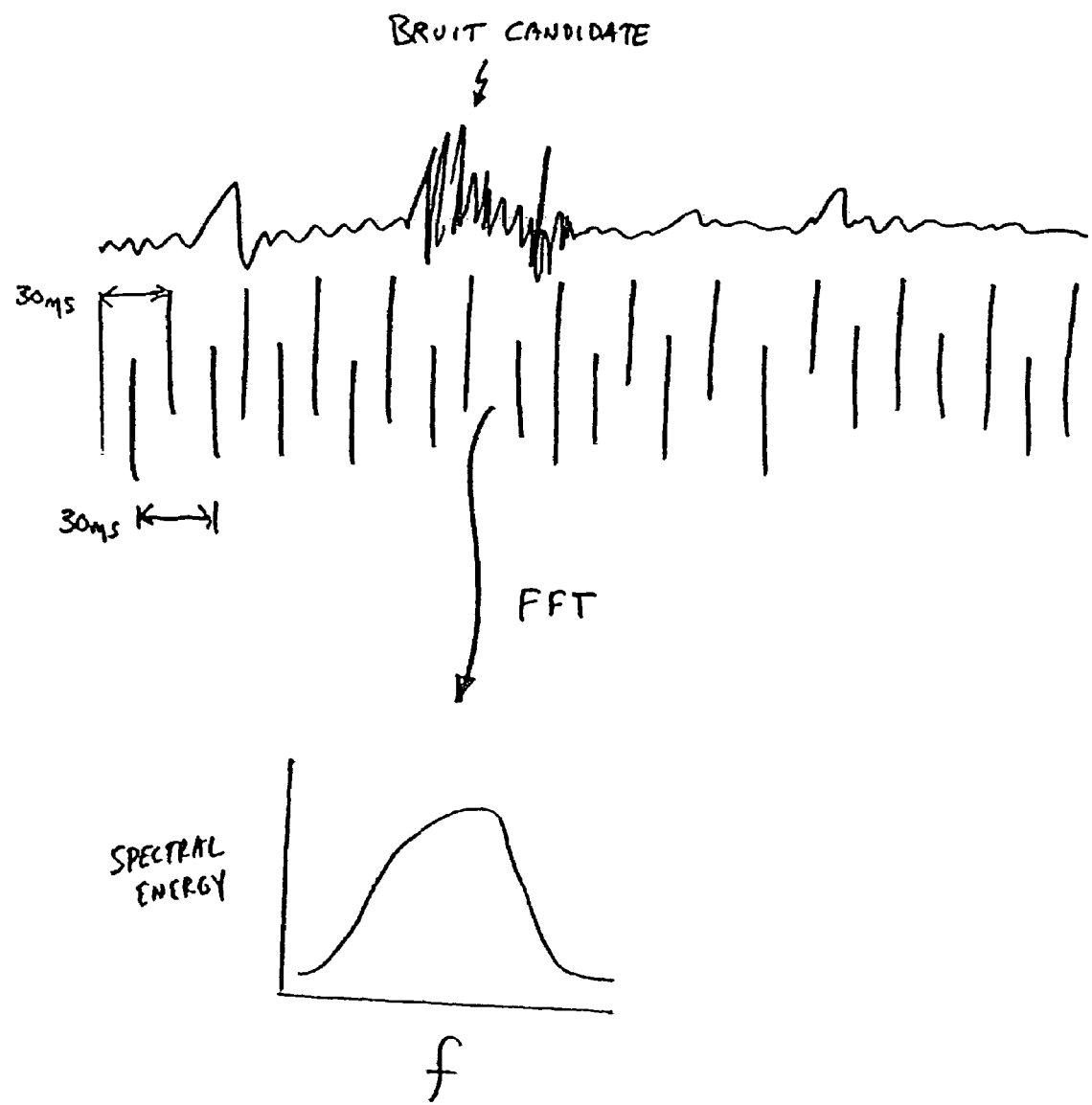
FIG. 64 shows the overlapping segments used in the spectral calculations.

Each filtered heart cycle signal is then segmented into nominal 15 millisecond intervals (also known as windows or segments) for evaluation. In one embodiment, each heart cycle signal is processed in numerous sample sets each having 128 time samples from the data sampled at 4.4 kHz. Each of the sample sets is nominally 30 milliseconds in duration. Successive spectra (frequency and magnitude) are calculated from sample sets that overlap adjacent sample sets by 64 time samples. The use of a binary number of time samples (e.g., 128) enables the use of Fast Fourier Transform or other processing to expedite calculation of the spectra. A windowing function (such as a Blackman or Kaiser Window) is applied to each sample set to suppress the contribution of time samples at the beginning and end of each sample set. The windowing suppresses sample edge transients that can corrupt the resultant spectrum. Further, the spectrum for each time window or segment, though calculated over a time window nearly 30 milliseconds wide, favors only the signals from the central 15 milliseconds. FIG. 64 graphically illustrates a representation of this segmenting across a portion of a heart cycle having a bruit candidate. The mean time data energy sum of each FFT time window is computed in the process described above for FIG. 51 through FIG. 55.

More specifically, as shown in FIG. 51, bruit candidates in the wideband heart audio signal for each heart beat cycle signal are detected in a step 5120. As discussed in further detail below with respect to FIG. 52 through FIG. 60, to detect bruit candidates, the spectrum of each 15-millisecond time window within systole or diastole, normalized by the ratio to a noise floor, is inspected to see if any spectra have cells with an energy ratio above a bruit power detection cutoff. If found, the mean time data power for the spectrum window is compared to a mean time power threshold. If it is greater than the mean time power threshold, the skew ratio is computed. If the skew ratio is less than a skew cutoff threshold, the bruit candidate's time coordinate, the frequency of the spectral peak of the bruit candidate, and the ratio of the bruit candidate spectral power to the local spectral average (SNR) are inserted into the bruit candidate table. A search for multiple bruit candidates can be made within each spectrum slice.

In one embodiment, a heart waveform includes a number of heart cycles, where the heart waveform was sensed at one location on a patient. As illustrated by step 5120 of FIG. 51 and the steps in FIG. 52, the heart audio waveform is run through steps 5202 through 5206 to identify bruit candidates in each heart cycle signal. In accordance with a preferred embodiment, this process is repeated for each heart cycle of each heart audio waveform sensed at each of the nine previously described locations. As mentioned above and described below, the information collected on each bruit candidate, is entered into a table in step 5208 of FIG. 52.

Figure 52:
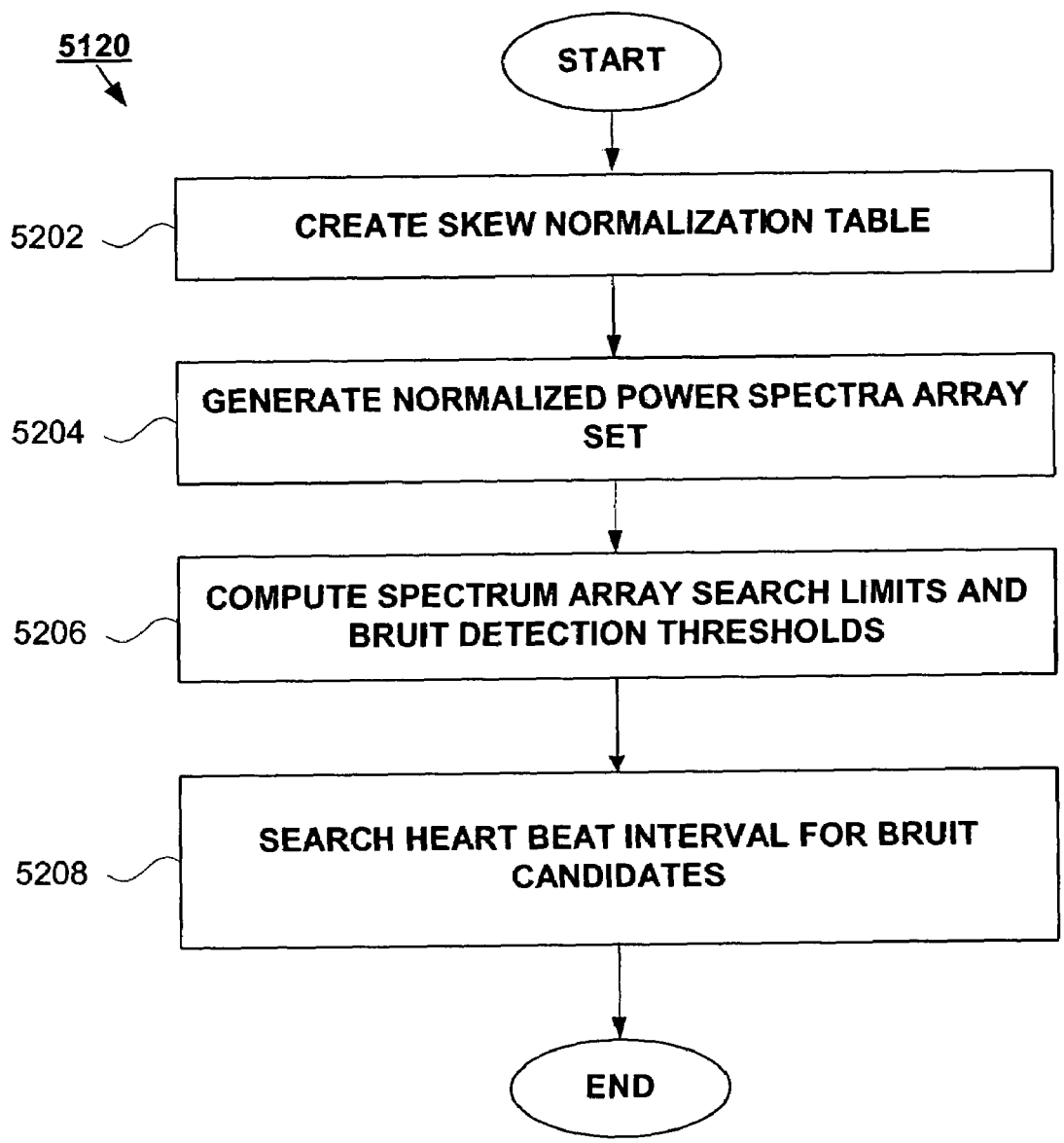
FIG. 52 is a flow chart depicting the process of detecting bruit candidates in each heart cycle signal.
Figure 53:
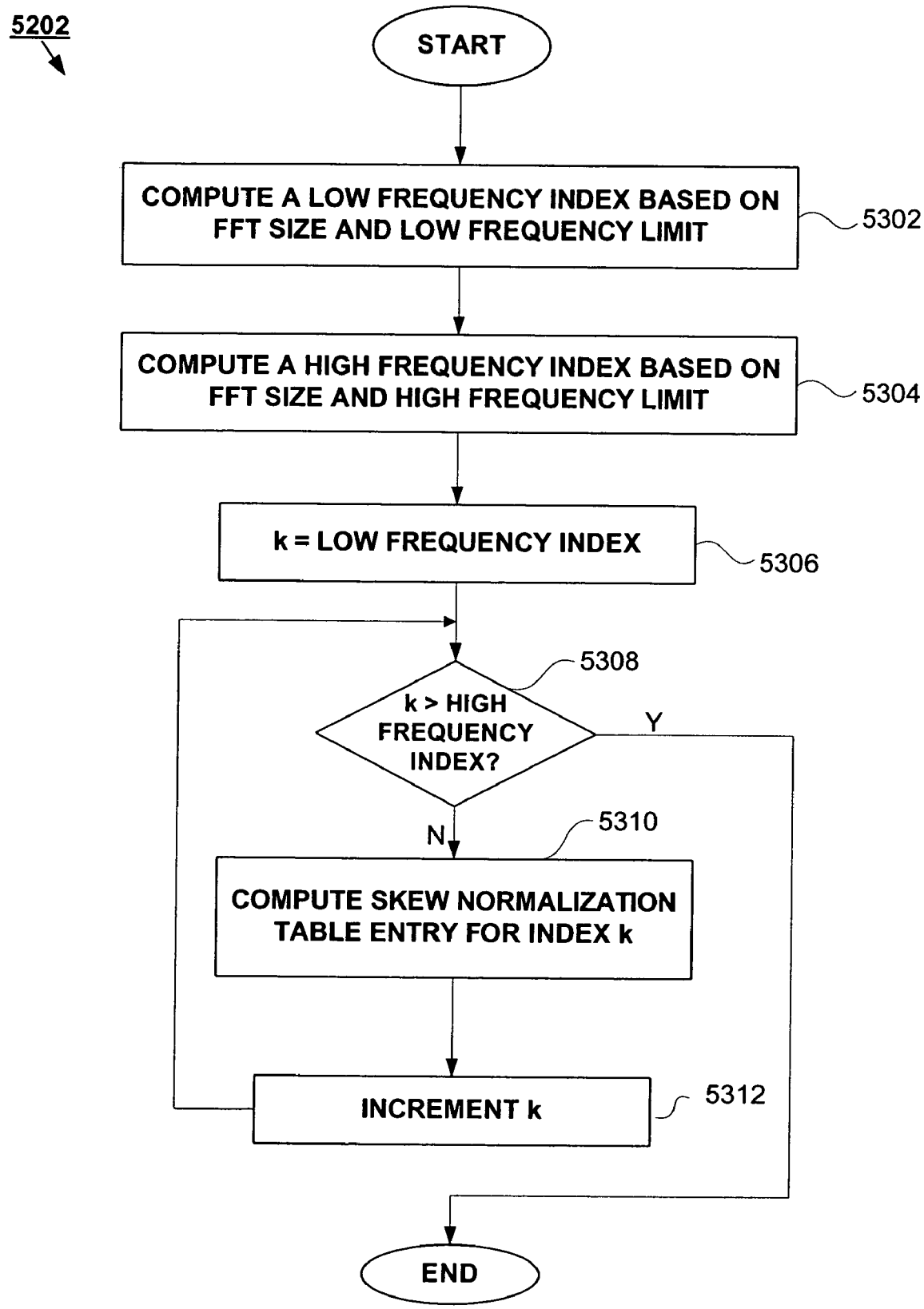
FIG. 53 is a flow chart depicting the calculation of skew normalization factors.

FIG. 52 provides further detail on the process in step 5120 of detecting bruit candidates. At a step 5202, a table of skew normalization factors is created that is a function of the frequency index of the amplitude peak of the bruit spectrum. FIG. 53 is a flowchart depicting the details of the process in step 5202 of creating a table of skew normalization factors, as part of the overall process of detecting bruit candidates. In particular, at a step 5302, a low frequency index is determined based on the size of the FFT to be used in the process and a predetermined low frequency limit. Similarly, at a step 5304, a high frequency index is determined based on the size of the FFT to be used in the process and a predetermined high frequency limit. At a step 5306, a counter is set to the value of the low frequency index. Entering a loop at a step 5308, a determination is made of whether the current counter is greater than the high frequency index. At a step 5310, the skew normalization factor is computed for the filter index in the spectral frequency range. The skew normalization computation is discussed in greater detail in the description of the skew ratio processing below. The process is repeated for all indexes in the spectrum frequency search range as shown in a step 5308 and 5312.

Figure 54:
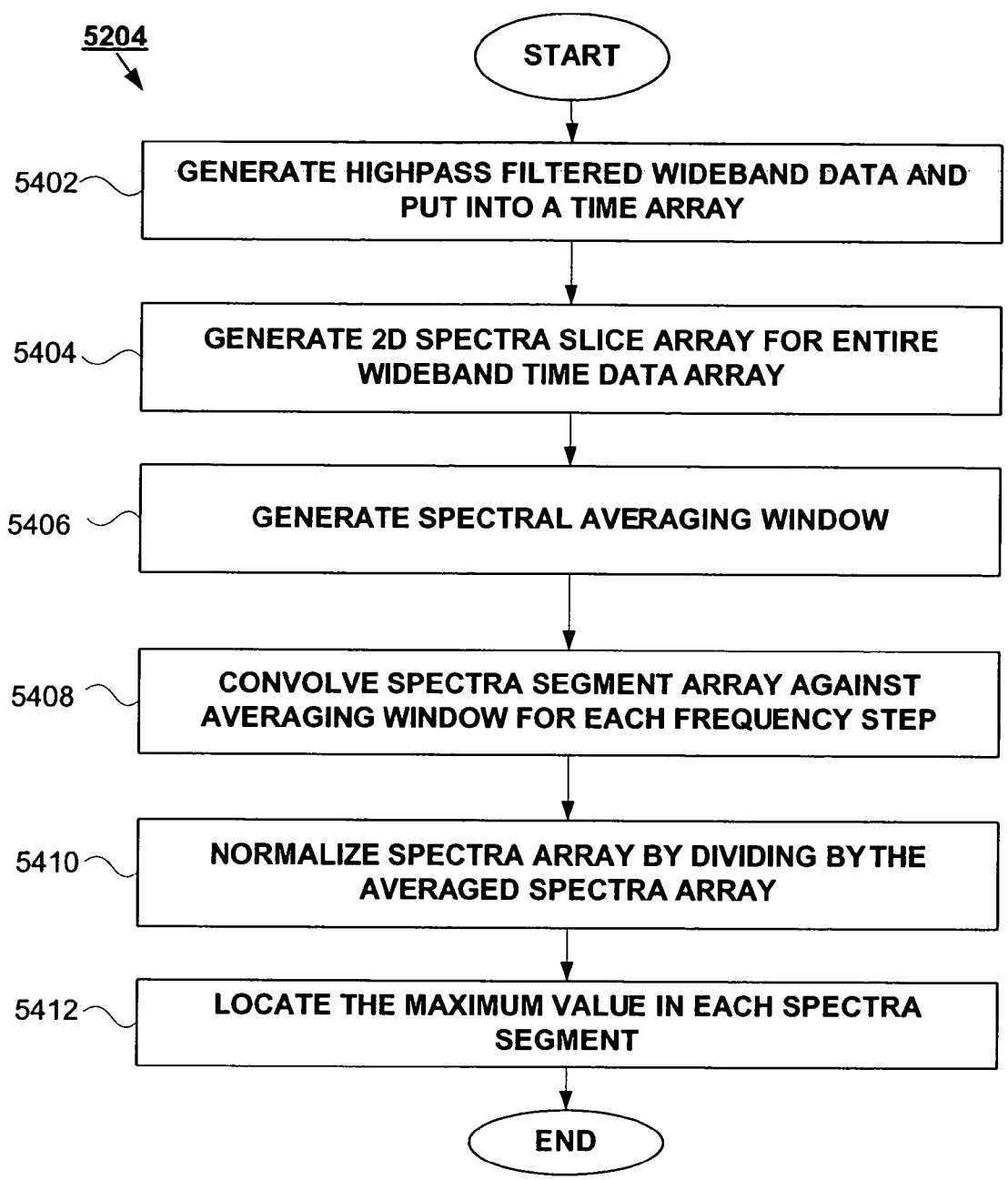
FIG. 54 is a flow chart depicting the creation of a table of spectral amplitude ratios.

At a step 5204 in FIG. 52, a normalized and averaged 2 dimensional spectrum array is generated from the high pass filtered time signal. FIG. 54 is a flowchart depicting the details of the process in step 5204 of creating a table of frequency amplitude ratios that form a normalized power spectra array set, as part of the overall process of detecting bruit candidates. In particular, at a step 5402, the wideband audio signals are band pass filtered and put into a time array. At a step 5404, a spectra slice array is generated for the entire time array. This produces a spectral value for each time segment of nominal width.

Figure 55:
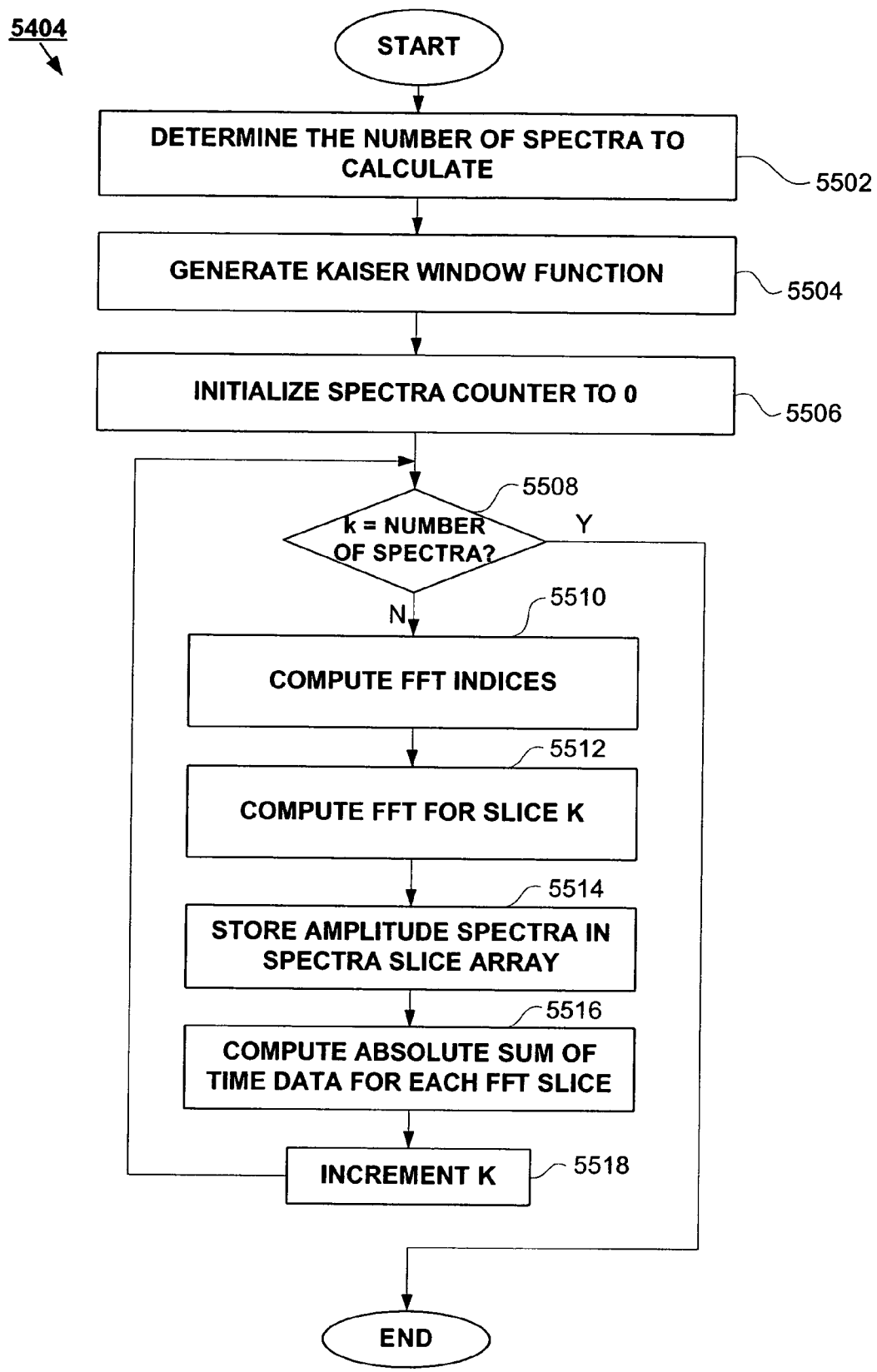
FIG. 55 is a flow chart depicting the spectral data calculation process.

FIG. 55 provides further detail on the process of generating the spectra slice array, as shown in step 5404 of FIG. 54. In a step 5502, the number of spectra to calculate is determined, based on the length of the wideband cardiovascular sound signals and the size of the FFT. In one embodiment, the number of spectra to calculate is equal to one less than two times the length of the time array data divided by the size of the FFT. At a step 5504, a Kaiser window is computed of a length equal to the size of the FFT. In a step 5506, a spectrum counter is initialized to 0. At a step 5508, a decision is made about whether the spectrum counter is equal to the number of spectra to be determined. If so, the process completes. If not, the process continues at a step 5510, wherein FFT indices are computed based on the spectrum counter, the spectrum offset, and the FFT size. In one embodiment, the FFT size is 128. Next, in a step 5512, an FFT for the current time slice is calculated. In an embodiment, the FFT is calculated on the product of the Kaiser window and the time array. After calculating the FFT, the amplitude spectrum is stored in a step 5514 and the time data sum for each spectrum slice is calculated in a step 5516. In a step 5518, the spectrum counter is incremented and control returns to step 5508.

Once the raw spectral measurements have been made as described above, additional measurements are made to isolate high frequency anomalies of interest. These anomalies are isolated by comparing normalized spectral energy measurements at each 15-millisecond interval with pre-defined frequency and energy thresholds. The amplitude comparison is invariant to the scaling of the input signal amplitude. That is, variations in the gain settings at the time of the recording do not affect the results of a bruit detection process. This is accomplished by replacing the raw spectral measurements with their ratios to the local spectral average. Since the local spectral average is typically a noise floor, these ratios, or Signal-to-Noise Ratios (SNR), are not overly sensitive to the amplitude level of the input waveform. As described in further detail below, local spectral averages are computed by averaging the signal across each spectrum filter frequency over a Kaiser-Bessel or similar window that is a fraction of the duration of the heartbeat. The central portion of the window is set to zero to suppress contribution from the actual signal. In one embodiment, the noise averaging window factor is one mean heart cycle duration. Since detection is dependent upon a pre-defined SNR, extraneous background noise in the heart audio channel is preferably kept to a minimum so as not to suppress the bruit detection sensitivity.

Figure 65:
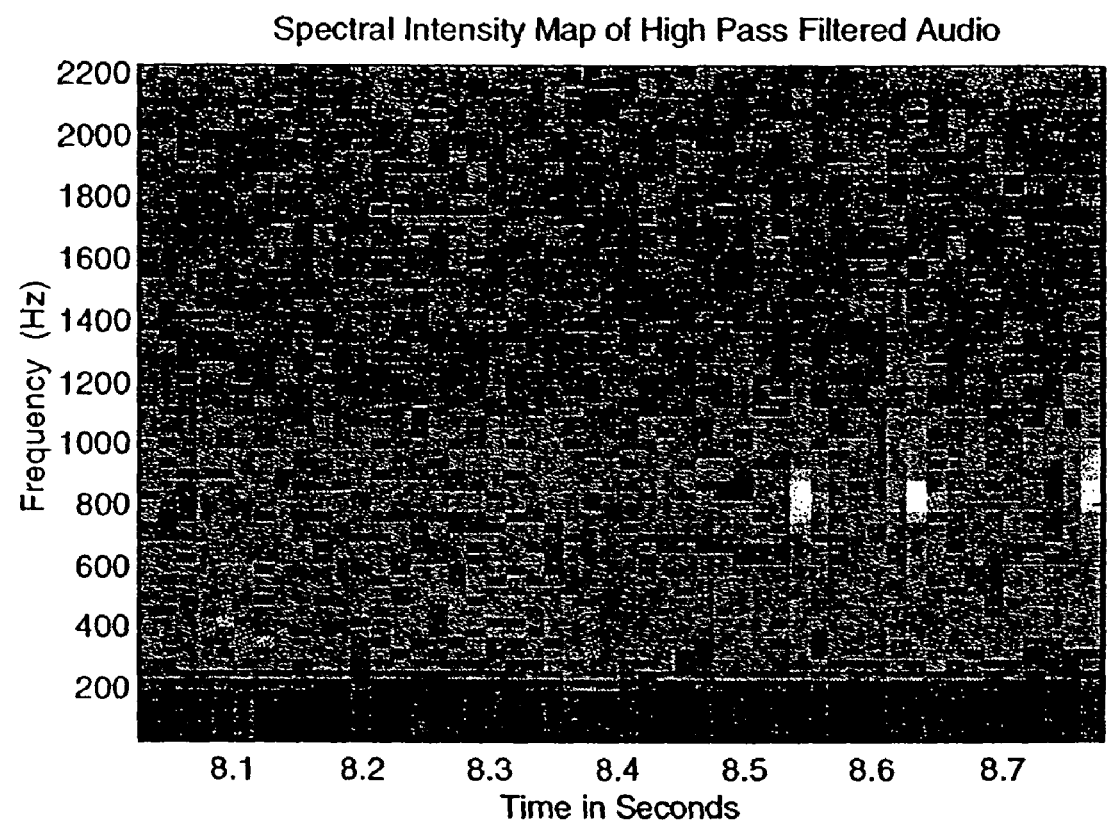
FIG. 65 shows a two-dimensional graphical representation of the likelihood of bruits.

The set of normalized spectra calculated for the heartbeat shown in FIG. 50 is exhibited in FIG. 65. Spectral amplitude is indicated in FIG. 65 by the gray scale plot in which black corresponds to negligible amplitude; while increasing amplitudes are correspond to lighter shades. Note that three bruits manifest themselves as relatively strong bursts of energy with peak frequencies just above 800 Hz and having durations on the order of 30 milliseconds. Energy on the far right of the plot is associated with high frequencies of the S1 pulse of the next heartbeat.

Figure 56:
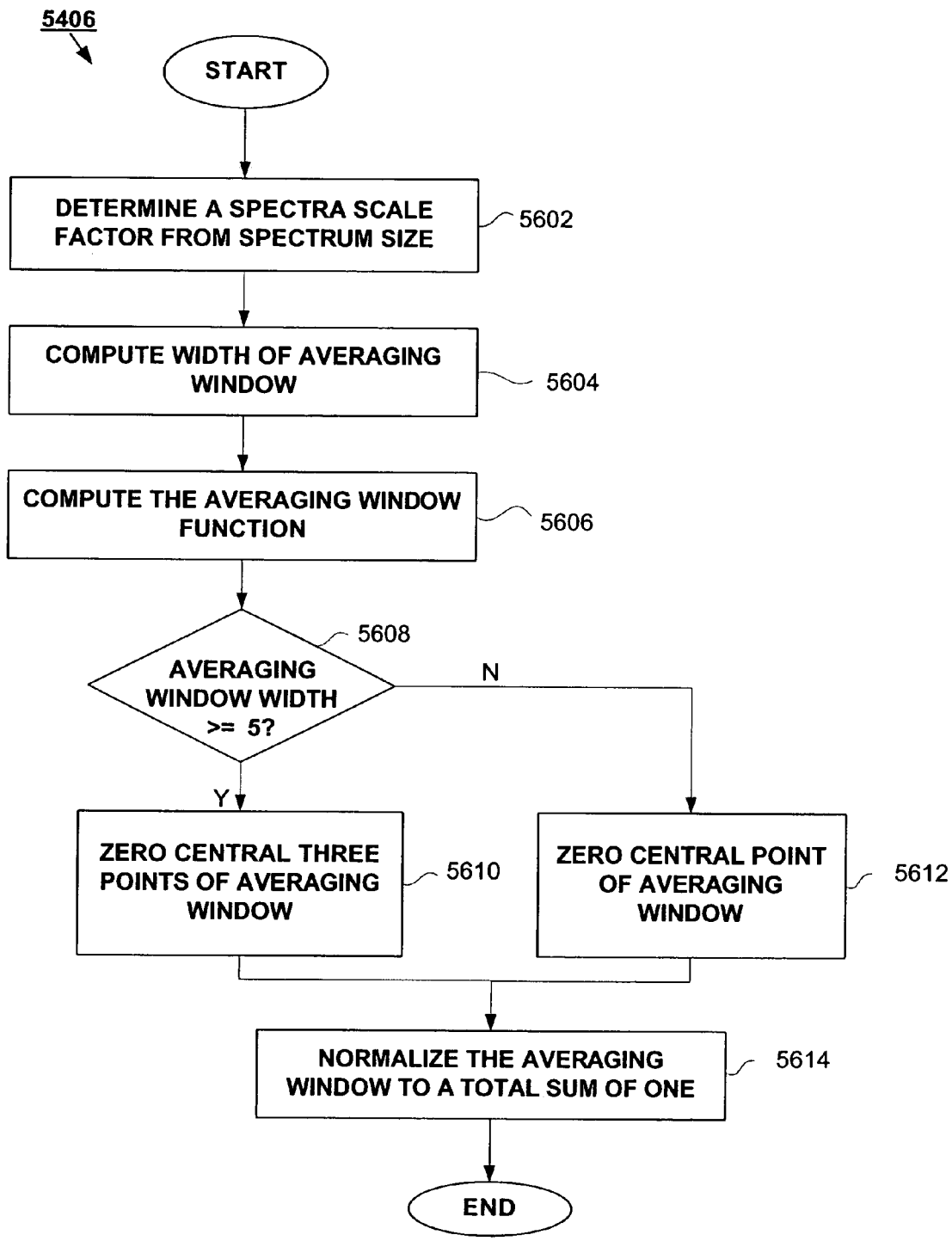
FIG. 56 is a flow chart depicting the spectral averaging process.
Figure 57:
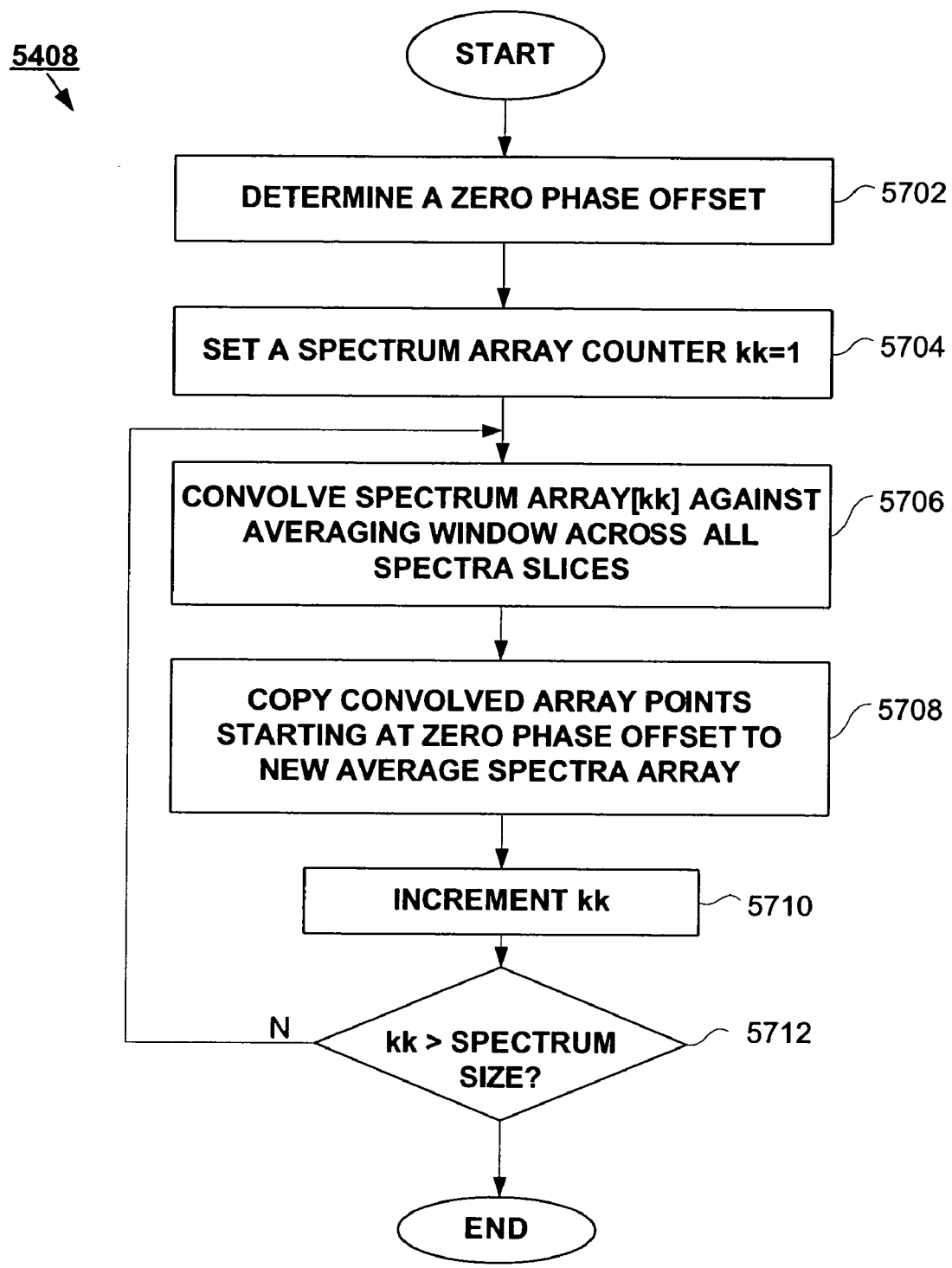
FIG. 57 is a flow chart depicting further details of the spectral averaging process.

Referring back to FIG. 54, in a step 5406, spectral averaging is performed to eliminate any constant frequency noise, thus producing an averaging window. FIG. 56 provides further detail on the process of performing spectral averaging and producing an averaging window. In a step 5602 in FIG. 56, a spectra scale factor is determined from the spectrum size. In one embodiment, the spectra scale factor is set equal to ten divided by the spectrum size. In a step 5604, the width of the averaging window is computed based on the mean heart beat duration and in a step 5606 the averaging window is computed. In one embodiment, this consists of setting up a Kaiser-Bessel window that rolls to −10 dB at the margin. In a step 5608, a determination is made of whether the averaging window has a width of five or more. If so, the central three peaks of the averaging window are set to zero in a step 5610. Otherwise, only the central peak is set to zero in a step 5612. In both cases, the setting of the central peak or peaks to zero will avoid the suppression of peaks that could occur when performing subsequent convolutions. In a step 5614, the averaging window is normalized to a value of one.

The averaging window described above is used in a step 5408 in FIG. 54. In that step, each spectral slice array is convolved against the averaging window produced in step 5406. Further detail on this process is shown in the flow chart of FIG. 57. In a step 5702 a zero phase offset is determined based on half of the width of the averaging window. In a step 5704, a spectrum array counter is initialized to a value of one, in one embodiment. In a step 5706, the spectrum array at a frequency index kk is convolved against the averaging window by stepping through the frequency cells to produce a windowed spectrum array set. In a step 5708, the local spectra average is copied to a new 2 dimensional spectrum array starting at the zero phase offset index. In a step 5710 the spectrum array counter is incremented. A test is then made at a step 5712 of whether any more convolutions are to be calculated. If so, control passes to step 5706; otherwise the process completes.

Next, in a step 5410 shown in FIG. 54, the spectra are normalized as ratios to the local noise floor. In an embodiment, the normalization involves dividing the raw spectra value by the average spectral values for the frequency of interest. After normalization, the maximum value in each spectral slice is determined in a step 5412.

Figure 58:
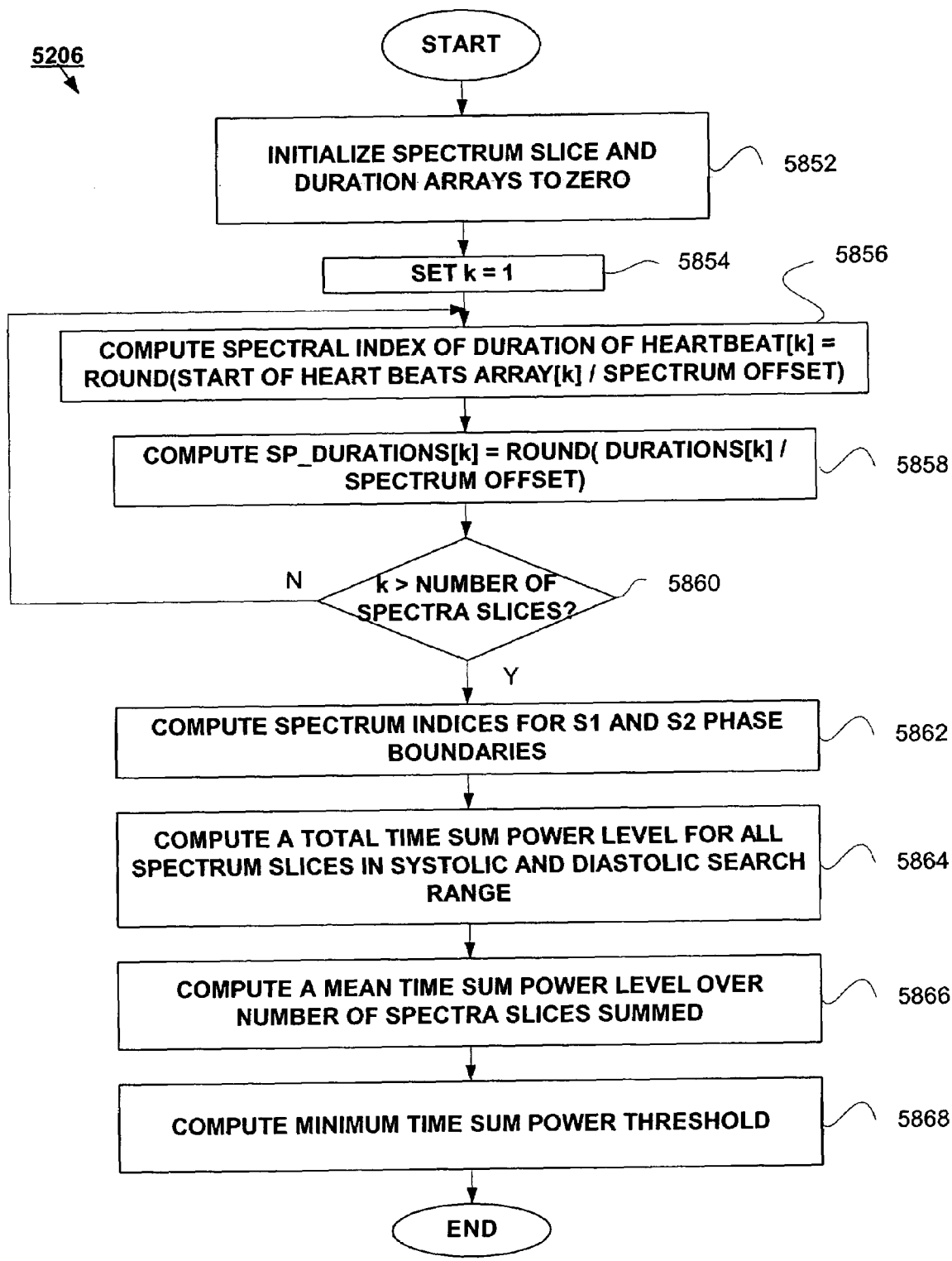
FIG. 58 is a flow chart depicting the power calculation process.

Referring back to FIG. 52, at a step 5206, the spectrum slice index search limits are computed from the frequency search limits and bruit detection power thresholds are computed from their dB thresholds. FIG. 58 provides details on the computation of these limits and thresholds. In steps 5852 to 5860, the bruit search ranges (in units of spectrum indices) are computed for the start and duration of each parsed heart beat cycle in the time data. In a step 5852, the start and duration index arrays for each beat are initialized to zero for the number of beats detected. In a step 5854, the beat index k is initialized to one. In a step 5856, the spectral index for the start of each heart beat cycle is computed from the time sample index stored in the synchs array. In a step 5858, the spectral index count for the duration of each heart beat cycle is computed from the time sample count stored in the duration array. In a step 5860, this process is repeated until indexes for all the parsed beats have been computed. In a step 5862, the spectral index offsets for the S1 and S2 phase boundaries locations are computed from the S1 and S2 phase index table. In the steps 5864 through 5868, a time power sum threshold is computed to be used in the bruit detection process to filter out false weak time signal candidates. In a step 5864, the total sum of the time power measurements made for each spectrum slice which falls in the bruit search ranges is computed. In a step 5866, the mean time power measurement is computed by dividing the total sum by the number of spectrum slices in the bruit search ranges. In a step 5868, the time power threshold is computed by multiplying the mean time power measurement by the threshold parameter.

At a step 5208 in FIG. 52, the processed spectrum array is searched for bruit candidates for each detected heart beat cycle in the signal data.

Figure 59:
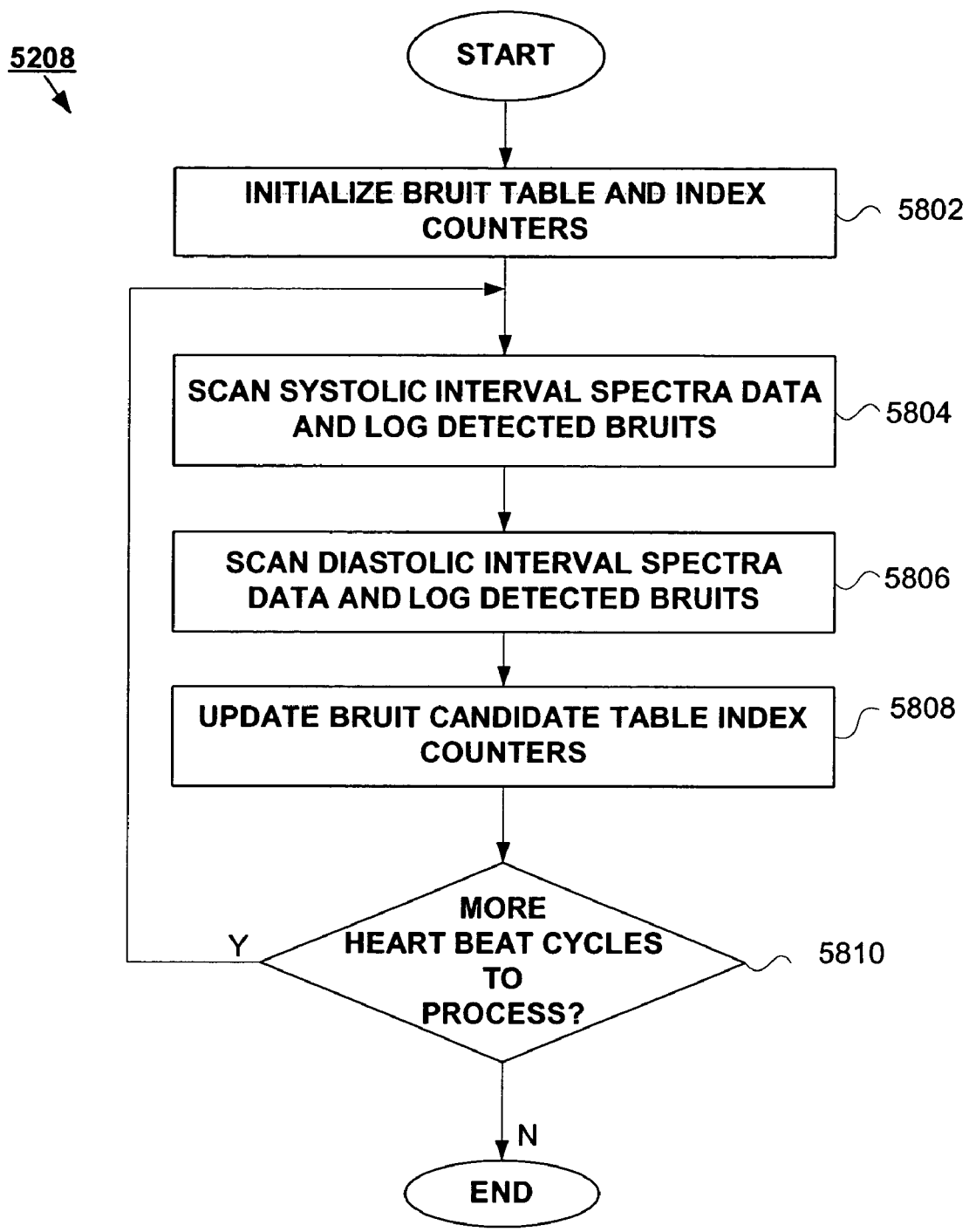
FIG. 59 is a flow chart depicting the information collection process on all bruit candidates.

As shown in FIG. 59, in a step 5802, counters and indices for the bruit candidate table creation are initialized. A loop begins at a step 5804, in which both the systolic and diastolic intervals are scanned for a single heat beat cycle signal and any detected bruit candidates are entered into the bruit candidate table. In step 5804 the systolic interval is scanned, and in step 5806 the diastolic interval is scanned.

Figure 60:
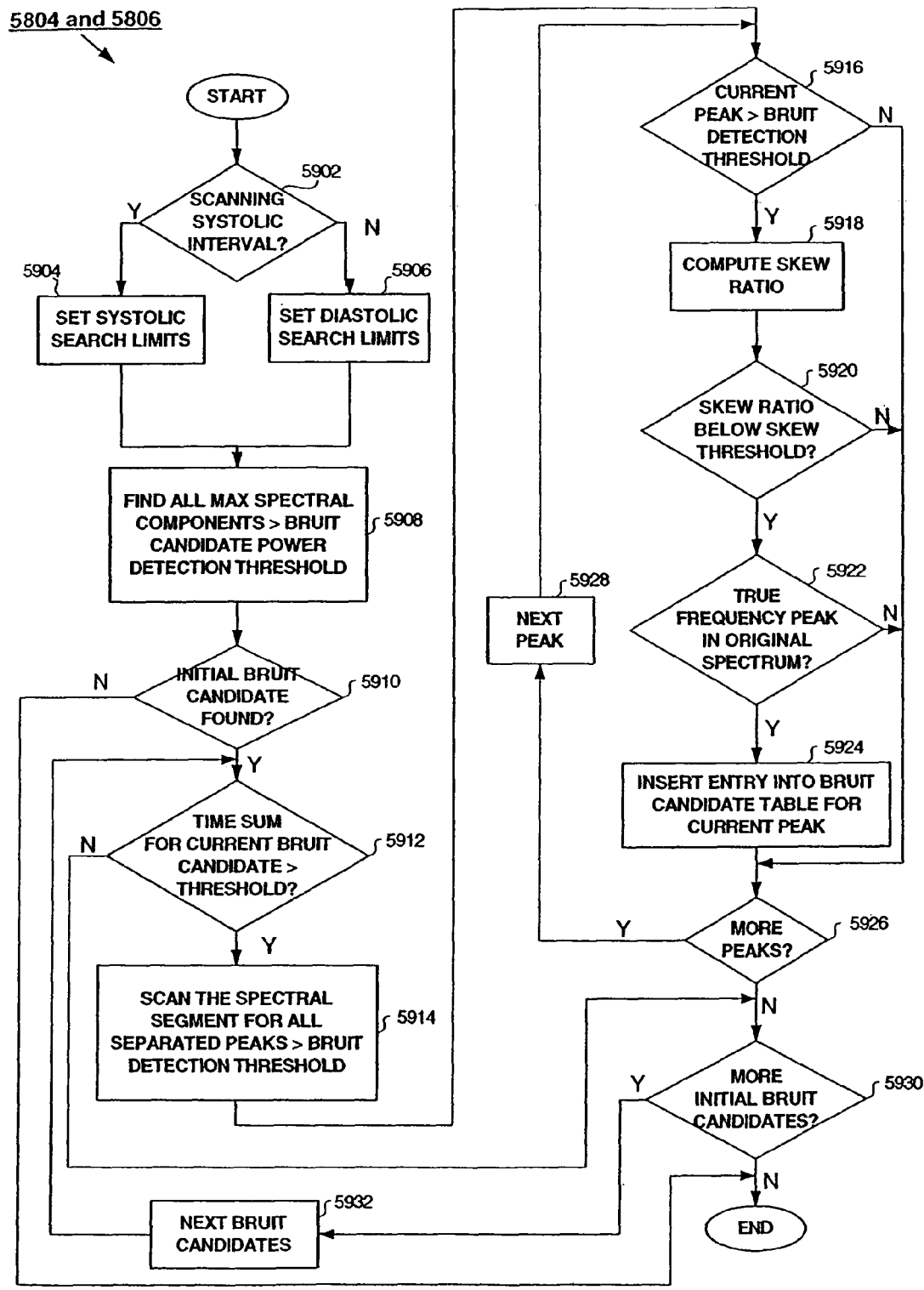
FIG. 60 is a flow chart depicting the process for scanning the systolic and diastolic intervals for bruit candidates.

FIG. 60 provides further detail on the scanning process for bruit candidates used in step 5804 and 5806 shown in FIG. 59. At a step 5902, a determination is made of which interval is to be scanned for the selected heat beat cycle. If scanning the systolic interval, the systolic search limits are set in a step 5904; if scanning the diastolic interval, the diastolic search limits are set in a step 5906. In both cases, the search limits are the set by the start and duration of the selected heat beat along with the measured S1 and S2 heart phase indices scaled to the indices of the spectral content of the wide band cardiovascular sound signals. The systolic search interval is from the end of the S1 component to the start of S2. The diastolic search interval is from the end of the S2 component to the end of the selected heart beat.

Once the search limits have been set, the peak spectral component in each spectral slice that are greater than the bruit power detection threshold are determined and stored in a initial bruit candidate array in a step 5908. Based on the results of step 5908, a test is performed in a step 5910 of whether any bruit candidates were found. If not, no information is entered into the bruit candidate table and the process exits.

If initial bruit candidates were found, a loop is entered that processes each initial bruit candidate. The first test in the loop is performed in a step 5912 of whether the time energy sum of the spectrum slice for the current candidate is above the previously computed threshold. If not, control passes to a step 5930 to see if further bruit candidates in the initial table are to be processed. If the time sum for the current bruit candidate is above a predetermined threshold, the spectral segment that contains the bruit candidate is scanned in a step 5914 for all separated peaks that are above the bruit candidate power detection threshold. The candidate peaks must be separated in frequency by a minimum spectrum notch threshold parameter which may be a different value for processing the heart audio or background noise signal.

Each candidate peak in the current spectral segment is then tested in a step 5916 for whether the peak is greater than the bruit power detection threshold. If not, control passes to step 5926 to determine whether there are more candidate peaks in the current spectral segment. If so, a skew ratio is calculated in a step 5918. Tests are then performed in steps 5920 and 5922 on the skew ratio to determine whether the peak has a skew ratio below the skew threshold and whether the peak is a true frequency peak in the original spectrum (and not a false maximum value peak at the margin on a slope at the edge of the spectrum filter search range).

A second class of high frequency anomalies, known as clicks, has been observed in younger patients who have no known heart problems. These sounds with wide band spectral energies are preferably suppressed in the identification of bruit candidates by properly setting the skew threshold. If an anomaly satisfies the frequency and energy thresholds, an additional measurement is calculated to distinguish the clicks from bruits candidates.

To distinguish clicks from bruits, a discriminant is run based upon the 'skew' of the spectral energy. Skew is the second moment associated with the spectral distribution of energy around a frequency bin with the most energy. Given the frequency bin with the highest energy, then a simplified calculation of a skew parameter for the spectrum is made as follows:

$$\text{Skew} = \text{sum}(\text{SpectRatio}(j) * ((j - \text{peakindex})^2)) / (\text{Normalization} * \text{PeakSpecRatio}) \quad [2]$$

for j=low filter index to high filter index where Normalization=sum((j−peakindex)^2)

for j=low filter index to high filter index

Note that if most of the energy of the spectrum is in the peak frequency bin, the value for skew approaches zero; if all the frequency bins have the same energy as the peak filter, the skew is a maximum of one.

The skew calculation envelope is not symmetric in that a spectral peak close to 300 Hz or close to 1800 Hz will have most of its neighbors above or below the peak. Under these conditions, a distant signal peak may have an undesirably strong effect on the skew measurement as defined by the trial discriminant. For this reason ramp weighting decreases the emphasis of the distant frequency peaks. The modified calculation of spectral skew is as follows:

$$\text{SpecSkew} = \text{sqrt}(\text{sum}(\text{xprod}(j))/\text{xden}) \quad [3]$$

where:

$$\text{xprod}(j) = (1 - \text{abs}((j - \text{PeakIndex}))/(\text{HiFilterindex} - \text{LowFilterindex})) * \text{SpecRatio}(j) * ((j - \text{PeakIndex})^2)$$
(for j=low filter index to high filter index)

and:

$$\text{xden} = (\text{Normalization} * \text{PeakSpectralRatio}) \quad [4]$$

where:

$$\text{Normalization} = \text{sum}((1 - \text{abs}(((j - \text{PeakIndex}))/(\text{HiFilterIndex} - \text{LowFilterindex})) * (j - \text{PeakIndex})^2)$$

Testing of heart cycle signals containing clicks and bruits has revealed that most bruits have a lower skew ratio while clicks usually have a higher skew ratio. In one embodiment, a skew ratio rejection threshold is utilized to distinguish clicks from bruits.

If both conditions are met in steps 5920 and 5922 (i.e., the current peak has a skew below the skew threshold just discussed and the current peak is a true frequency peak in the original spectrum), the current bruit candidate under scrutiny is entered into the bruit candidate table in a step 5924. In one embodiment, the heart beat count index, the spectral peak power, the skew ratio, and the time at the start of the spectrum slice are entered into the bruit candidate table. After the bruit candidate is entered into the bruit candidate table (or if either of the immediately preceding conditions is not met), a test is done at a step 5926 of whether there are more candidates to process for the current spectrum slice. If so, the bruit candidate peak indices are updated in a step 5928 and control passes to step 5916.

If there are no more spectral peaks to process for the current spectrum, a determination is then made at step 5930 of whether there are more initial bruit candidates to process for the systolic or diastolic interval. If so, the bruit candidate indices are updated in a step 5932 and control passes to step 5912. In one embodiment, if there are no more bruit candidates to process, the bruit candidate detection process shown in FIG. 60 is complete. as shown in FIG. 59 to process the next heart beat cycle until all parsed heart beat cycles have been processed.

Referring again to FIG. 59, after both the systolic and diastolic intervals have been processed in steps 5804 and 5806, the processing returns to a step 5808, where all counters and indices are updated. At step 5810, a test is made of whether further heart beat cycle signals need to be processed. If so, the loop continues at step 5806, otherwise the process completes.

A sample of the bruit candidate table for one heart waveform of a patient file is shown in FIG. 66. Note that a column for the value of a bruit probability indicator ("mbProb") has been initialized to all zeroes. This will be used in subsequent steps to store the values calculated for the bruit candidate probability indicators.

Once the bruit candidate table in FIG. 66 has been assembled and there are no more heart cycle signals to process (as tested for in step 5810 of FIG. 59), noise cancellation is performed. As discussed earlier, a second channel can be used to provide a background noise signal. This background noise signal can be used to detect false bruit candidates that may actually have been caused by events external to the patient, such as fan hum, talking, etc. Referring back to FIG. 51, if background noise signal data is available (as tested in a step 5125), a separate bruit candidate table is generated in a step 5135 from the background noise signal to be used in the noise cancellation process. The background noise bruit detection uses the same process, but a different spectrum power and time data energy power threshold, as compared to the bruit detection used with the heart audio signals in the process described above.

Figure 61:
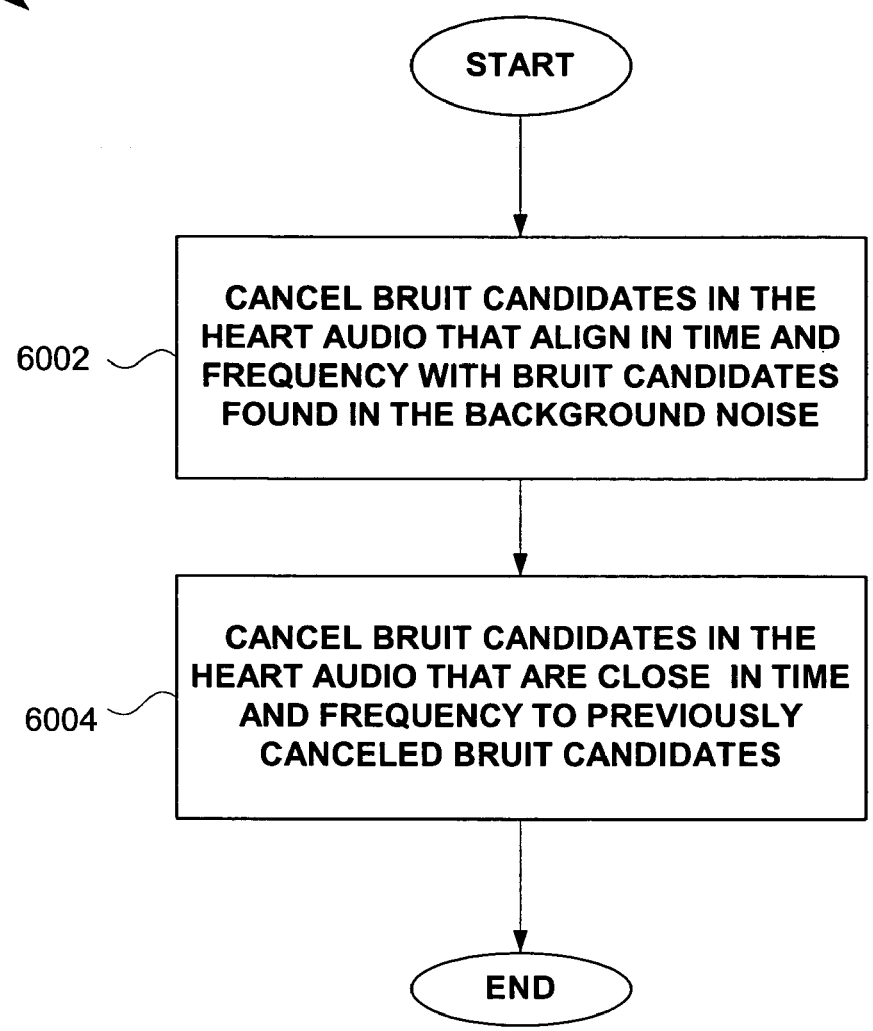
FIG. 61 is a flow chart depicting the noise cancellation process.

In one embodiment, noise cancellation is performed on the bruit candidates as shown in step 5150 of FIG. 51 and described in further detail with respect to FIG. 61. The noise cancellation process uses a two-pass approach. As shown in a step 6002 of FIG. 60, the first noise cancellation pass compares the heart audio bruit candidate table to the background noise bruit candidate table. Each entry in the heart audio bruit candidate table is scanned in sequence with a subsequent scan of the background noise bruit candidate table. If a background noise bruit candidate is detected that is close in peak frequency and in time to the heart audio bruit candidate, the heart audio bruit candidate is cancelled by replacing the skew ratio value with a high value near one.

Figure 62:
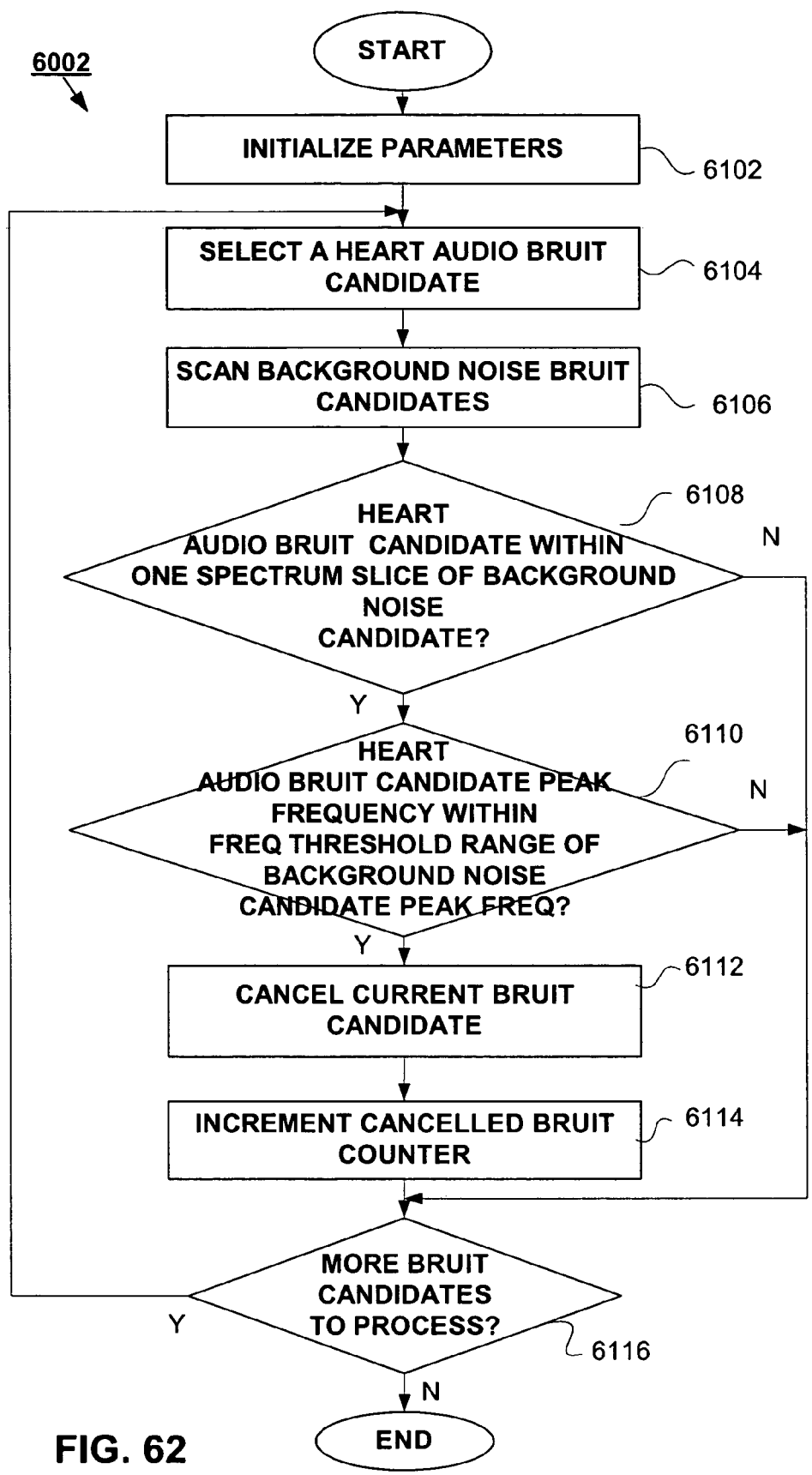
FIG. 62 is a flow chart depicting further details of the noise cancellation process.

FIG. 62 provides further detail on the first noise cancellation pass. In a step 6102, noise cancellation parameters (derived from observations of noise induced bruits) are initialized. A loop is entered at a step 6104, wherein a heart audio bruit candidate is selected. In a step 6106, the background noise bruit candidates are scanned and a determination is made in a step 6108 of whether the bruit candidate from the heart sound signal was within one spectrum segment in time (that is, within 15 milliseconds) of the background noise bruit candidate. This is the maximum time difference expected for events appearing in both channels. If so, then in a step 6110, the peak frequency of the heart audio bruit candidate is compared to the peak frequency of the background noise bruit candidate. If the peak frequency separation is less than the noise cancel frequency separation threshold of 1200 Hz times the heart audio bruit candidate skew ratio, the current heart audio bruit candidate is canceled in the bruit candidate table in a step 6112 by, for example, replacing the measured skew ratio with a high value near one. The high skew ratio value in an embodiment (i.e., close to the value one) will have the effect of removing the bruit candidate from contributing to the computation of the probability discussed below. If the bruit candidate was cancelled, a cancelled bruit counter is incremented in a step 6114. At a step 6116, a determination is made of whether there are any more bruit candidates to process. If so, control passes back up to step 6104. Otherwise, the first noise cancellation pass ends.

The second noise cancellation pass, illustrated in step 6004 of FIG. 60, examines the heart audio bruit candidate table only. Each entry is examined for cancelled skew ratios. In an embodiment, if the skew ratio values indicate a cancelled bruit candidate, the adjacent entries in the table are examined to see if either one should be cancelled as well. If an uncancelled bruit candidate is from a spectrum segment next to one that was previously canceled and has a peak frequency within the peak frequency separation threshold, it is cancelled. This could, for example, be within a range of 400 Hz times 0.65, which represents a nominal skew ratio.

Figure 63:
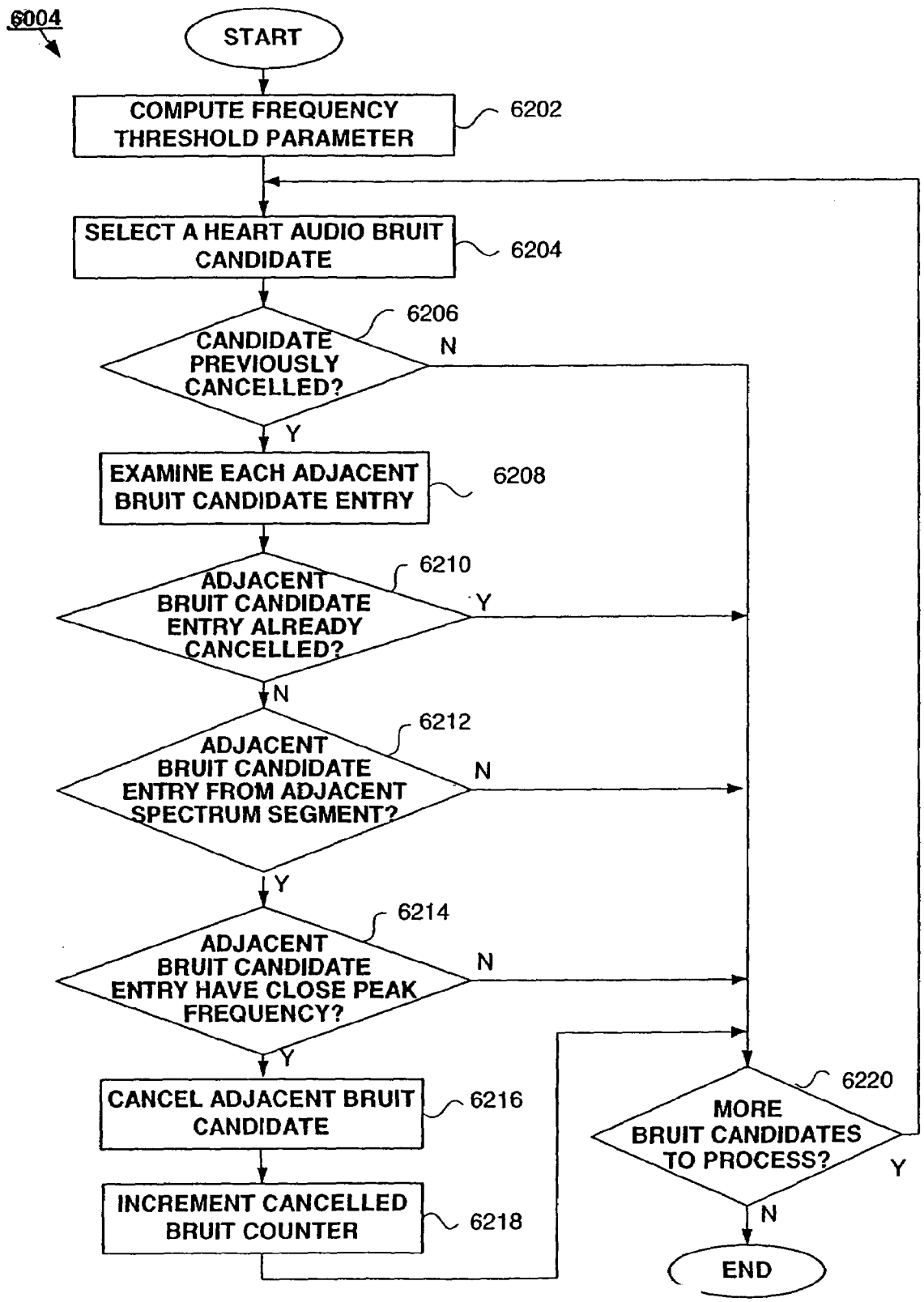
FIG. 63 is a flow chart depicting further details of the noise cancellation process.

FIG. 63 provides further detail on the second noise cancellation pass. In a step 6202, appropriate noise cancellation parameters are initialized. A loop is entered at a step 6204, wherein a bruit candidate is selected. In a step 6206, a determination is made of whether the selected bruit candidate was cancelled in the first noise cancellation pass. If so, in a step 6208, each bruit candidate entry adjacent to the canceled entry in the table is examined for three conditions. In a step 6210, the adjacent candidate entry is examined to see if it has already been canceled. If yes, control passes to a step 6220. If not, then in a step 6212, the candidate entry is examined to determine if the candidate is from a spectrum segment next to the cancelled bruit candidate. If not, control passes to a step 6220. If the entry is from an adjacent spectrum segment, then a test is performed in a step 6214 whether the peak frequency of the adjacent candidate entry is close to the current cancelled bruit candidate in frequency and time. If so, the adjacent candidate entry is then cancelled a step 6216 by, for example, replacing the measured skew ratio with a value close to one and a cancelled bruit counter is incremented in a step 6218. A determination is then made in a step 6220 of whether there are any more bruit candidates to process. If so, control passes back up to step 6204. Otherwise, the second noise cancellation pass ends.

Processing Bruit Candidates

Referring back to FIG. 4, following the generation of the bruit candidate table as part of step 3000 described above, the bruit candidates are then processed at a step 4000 to determine the degree to which a patient has repetitive bruits. The method of assigning a probability of repetitive bruits causes each bruit candidate to contribute in a cumulative process to the overall Flow Murmur Score. This contribution occurs since each bruit candidate will have a probability associated with it that the bruit candidate is an actual bruit and, therefore, that the patient has CHD.

The important parameters associated with the development of a probability indicator of coronary heart disease (Flow Murmur Score) are listed below. A brief description of their purpose is included. The use of the parameters is explained further in subsequent text.

| Parameter | Description | Nominal Value |
|---|---|---|
| Bruit/ClickThreshold | The Skew Level for Bruit/Click for 50 percent probability | 0.56 |
| Click90PercentProbability | The Skew Level for 90 percent Click Confidence | 0.38 |

-continued

| Parameter | Description | Nominal Value |
|---|---|---|
| BruitSpectralRatioThreshold | The SNR defining 50 percent Bruit Confidence | 18.5 dB |
| Bruit90PercntProbability | The SNR defining 90 percent Bruit Confidence | 24.0 dB |
| BruitCutoffProbability | SNR below this level is ignored | 14.00 dB |
| BruitsPerRespirationCycle | Expected number of Bruits per Respiration Cycle | 2.0 |
| VarianceFrequency | Uncertainty in the Bruit Frequency Measurement | 75 Hz |
| VarianceTime | Uncertainty in the Bruit Time Measurement | 20 ms |
| ProbabilityCutoffThreshold | Probability cutoff threshold | 0.09 |

The values of the skew and peak power (PkPwr) for each bruit candidate shown in the bruit candidate table in FIG. 66 comprise single values. Single values representative of energy distribution usually indicate the centroid of that energy distribution, which represents the whole amount of the energy and the center point of that energy. For example, a Fourier Transform analysis of a time waveform only analyzes frequencies that are related to the sampling rate and the number of frequencies analyzed ($F_i = i*F_{samp}/N$) as individual filters. If the time waveform contains a signal that is exactly at one of these frequencies, then the energy will be just in the one filter, but if it is slightly higher in frequency, then the energy will be distributed over the two filters, and so the centroid measurement helps refine the actual frequency measurement further.

Figure 67:
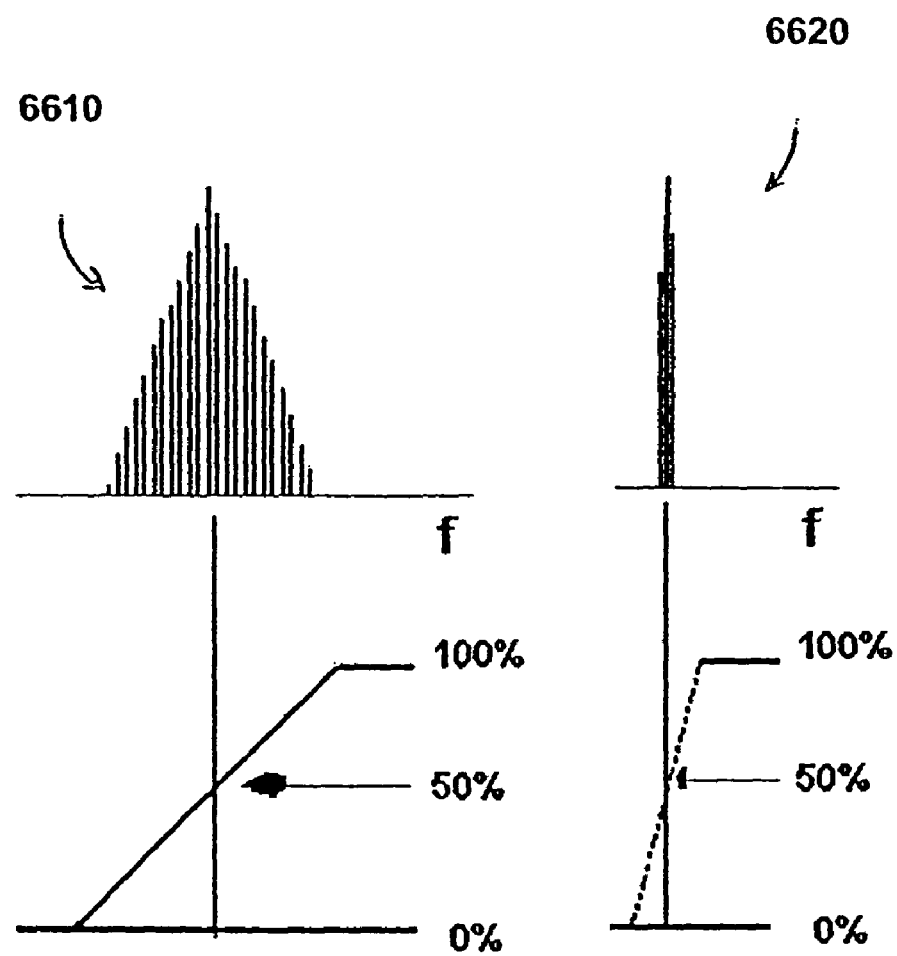
FIG. 67 shows the energy content of two different signals.

When the frequency of a waveform changes slightly during the collection interval, the energy will also be distributed over several filters. In this case it is better to consider the distribution of the energy rather than just the centroid of the energy. One could look at the total energy in the signal, and then plot the cumulative distribution contributed by all the filters, as seen in the two plots shown in FIG. 67. Wider spreading response 6610 in FIG. 67 has a longer slope than thinner spreading response 6620, so the slope could be used as an indication of the degree of spread (i.e., if s denotes the slope, a calculation of {s=100%/spectrum size} could be used to determine the slope and, consequently, an approximation of the degree of spread).

In order to calculate a probability from the spectral measurements, a probability function was designed in one embodiment that could be fit to the measured parameters. The model selected for the probability function, (P), was the Fermi factor that was initially derived for the energy distribution of charges in a conductor. The form of the function is as follows:

$$P(y) = \exp(y)/(1+\exp(y)) \quad [5]$$

which has the values shown in Table 6:

TABLE 6

Fermi function values

| y | Value | P |
|---|---|---|
| $-\infty$ | 0/(1 + 0) | 0.0 |
| 0 | 1/(1 + 1) | 0.5 |
| $\infty$ | $\infty/(1 + \infty)$ | 1.0 |

Table 6 above shows that the peak value of the signal occurs at the 50% point on the accumulative energy curve, assuming that the spreading is balanced. This means that a signal can be represented by its amplitude, frequency, and spreading factor, whereas a centroid could only give the amplitude and frequency. This same method can be used to typify a set of values that spreads over a given range. As shown, the function has a value of 0.5 for y equal to zero and rolls to either zero or one for increasing or decreasing values of y. For purposes here, the probability that an anomaly is likely to be a bruit will be a function of the SNR.

A second independent probability will be a function of the skew parameter. Considering SNR or Skew to be a value x, then y above will be defined as:

$$y = k*(x - x50) \quad [6]$$

where x50=the value of x where the probability is 0.5 and k=a constant which defines the slope of the probability function This function rolls from zero through 0.5 at x50, to one, (or vice-versa depending on the sign of k), with a slope determined by the constant, k. The value of k controls the slope of the probability function. A sharp discriminant will switch from 0 to 1 with a small change in x. When the numerator of the equation above ($P(y)=\exp(y)/(1+\exp(y))$) is 9, the function has a value of nine tenths corresponding to a 0.9 probability. Initial settings for k can be established by making a judgment as to when a bruit could be asserted with 90 percent confidence. When the value of x is assigned as having a 0.9 probability (x90), then k can be evaluated yielding:

$$k = \log(9)/(x90 - x50) \quad [7]$$

where x90 and x50 can be estimated as discussed below.

Figure 70:
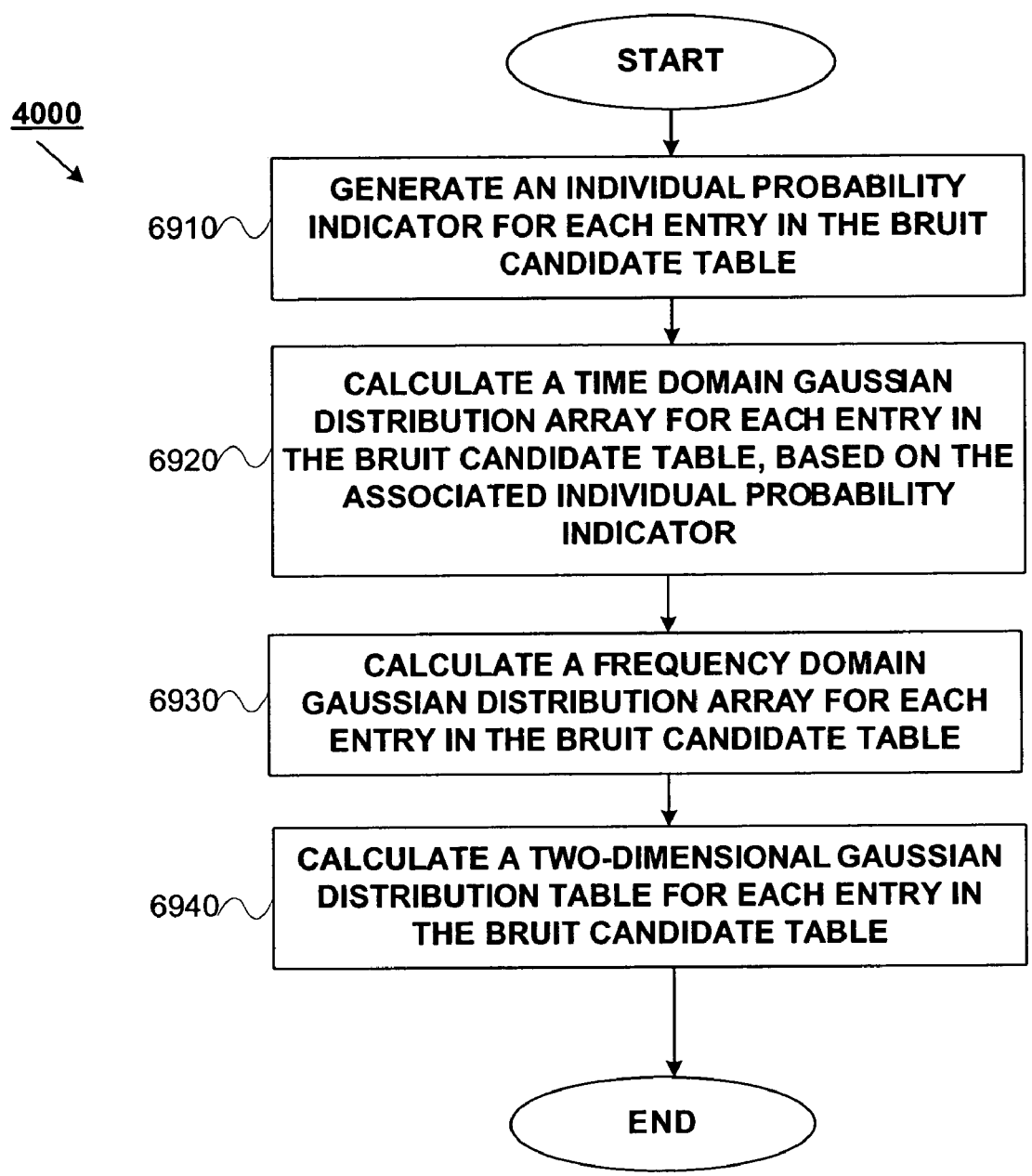
FIG. 70 is a flow chart depicting the processing of the identified bruit candidates.

FIG. 70 provides further detail on step 4000 in FIG. 4 of processing the identified bruit candidates. In FIG. 70, an individual probability indicator is generated in step 6910 for each entry in the bruit candidate table. As described above, the individual probability indicator referenced in step 6910 utilizes two independent probability functions to develop the probability that a spectral anomaly is a bruit candidate. As each anomaly has a time position in diastole and a peak frequency, a 2-dimensional probability function is built for each of the bruit candidates and thereafter assessed. As each heartbeat is processed, each bruit candidate listed in the bruit candidate table will build up the 2-dimensional probability indicator according to the SNR, diastolic time, frequency, and the skew characteristics of the bruit candidate. In an embodiment, the skew threshold, where an anomaly was equally likely to be a bruit or a Click was found to be very close to 0.56. Thus a skew of 0.56 corresponded to x50 for the Click-bruit discriminant. An inspection of many detected anomalies revealed that Clicks and bruits can be effectively discriminated if the skew ratio was lower than the threshold value by 0.18. Hence x90 is set to approximately 0.38, the value establishing the anomaly as a bruit with 90 percent confidence. These parameters can be given slight adjustments to improve the probability results as patients with known heart conditions are processed.

From the values adopted above and using the Fermi equation discussed earlier, the probability that an anomaly is a bruit (not a click) is given by:

$$P(\text{Bruit}/\text{Click}) = \text{aterm}/(1+\text{aterm}) \quad [8]$$

Where aterm=exp(A*(skew−0.56))
And A=log(9)/(0.38−0.56)

A second probability function can be defined to take into account the SNR at the spectral peak. Although a detection threshold close to 7.5 dB has been used in listing anomalies, testing has shown that a power ratio close to 18.5 dB corresponds to a 50 percent probability of being a bruit. Further, it was estimated from experimental observations that at a SNR close to 24 dB, the anomaly was a bruit with 90 percent certainty. These values are used to evaluate a probability of an anomaly being a bruit based upon the SNR.

$$P(\text{Bruit})=\text{bterm}/(1+\text{bterm}) \quad [9]$$

Where bterm=exp(B*(SNR−18.5))
And B=log(9)/(24−18.5)

Figure 68:
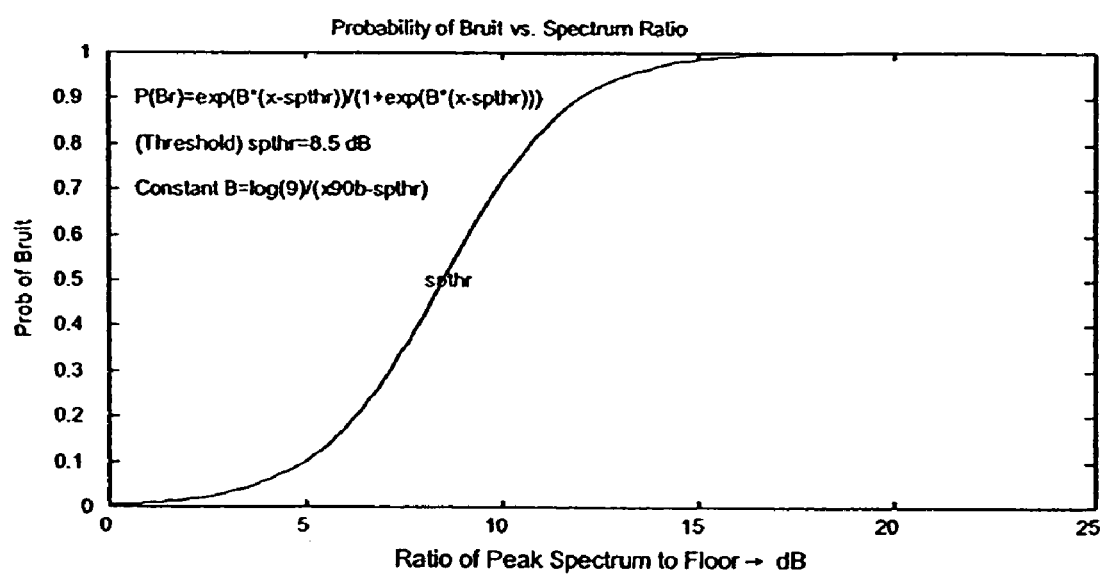
FIG. 68 shows a graph of the probability of a bruit as a function of the spectral signal-to-noise ratio.

In an embodiment, the signs of the terms A and B are opposite producing a bruit probability function which decreases for increasing Skew, but increases with increasing SNR. FIG. 68 shows the values of an example probability function over the operable SNR range with a threshold at 8.5 dB and a 90 percent confidence level 4 dB above the threshold.

Since probability of a bruit and the probability of a click are independent functions, then the probability that an anomaly is a bruit is simply the complement of the product of the two probabilities that the anomaly is not a bruit. The use of the product of probabilities of 'No Bruit' has been used to consolidate the probability measurements.

As described above, the anomalies that are listed in the bruit candidate table carry a peak frequency and a time stamp. The data from the heartbeat-parsing algorithm then makes it possible to specify when the anomaly occurs relative to S1 or S2 heartbeat pulses as desired. Plotting the values of the individual probability indicators for each entry in the bruit candidate table would produce a figure such as that shown in FIG. 69.

Since attention here is focused on diastole, a time relative to S2 is most meaningful. Significant bruits are those which repeat themselves at nearly the same audio frequency and the same time within the diastolic period. To allow such repetitive bruits to build a strong probability, the probability indicator for each bruit can be expanded into a 2-dimensional probability function with a time and a frequency axis.

In order to accurately plot the 2-dimensional probability plot for a single anomaly, it is helpful to specify the character of the function for a single bruit candidate. If there were no uncertainty in the time or the frequency measurement, a single resolution point could be assigned the probability calculated above. In reality, however, it is not realistic to think that a 'similar' bruit will repeat its time and frequency parameters exactly. Hence, it is helpful to specify an uncertainty in each dimension and extend the envelope of the probability measurement as a 2-dimensional envelope, such as a Gaussian envelope, decreasing in value as the distance from the measured position increases in time and frequency.

Figure 71:
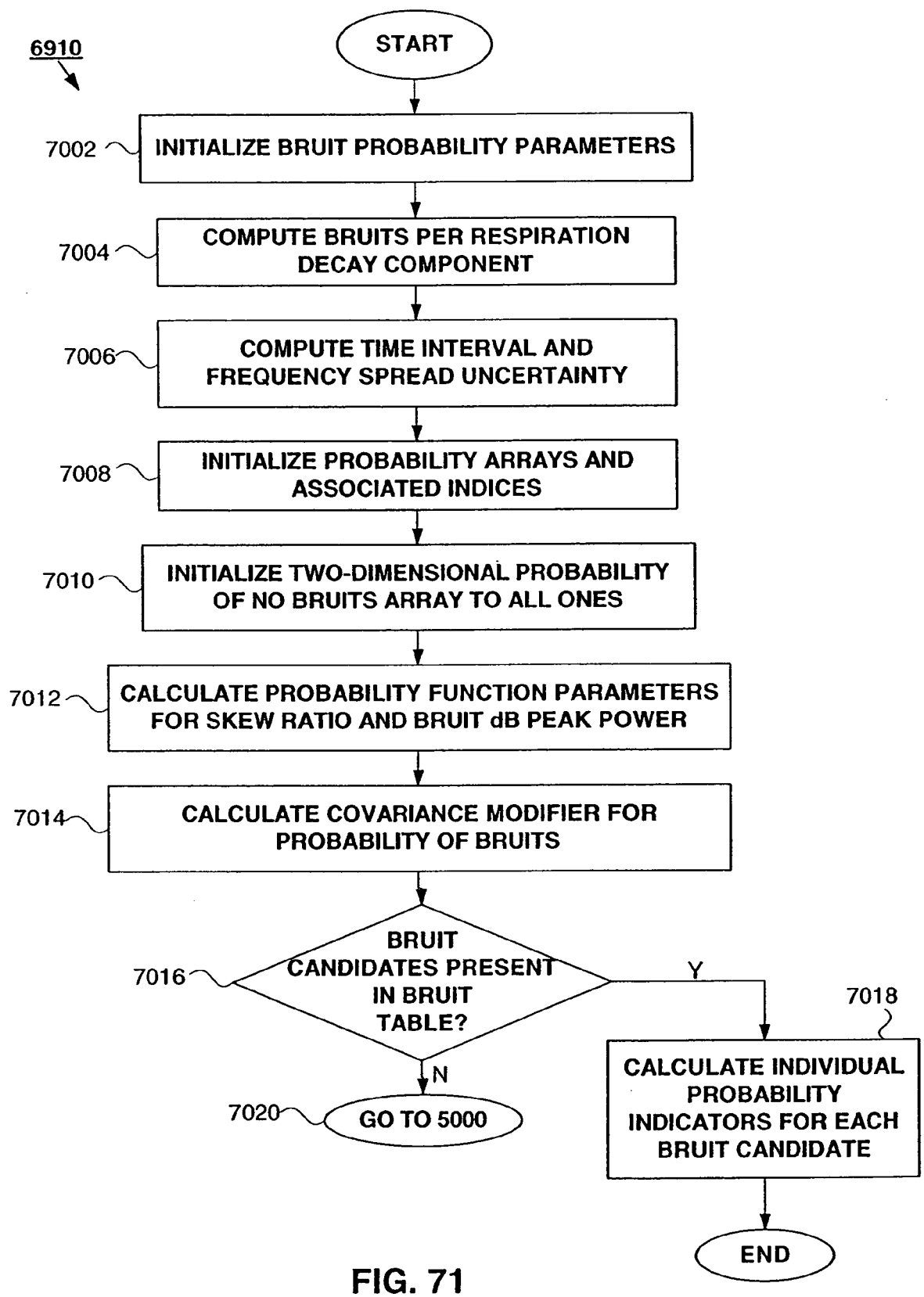
FIG. 71 is a flow chart depicting the generation of an individual probability indicator for each bruit candidate.

In an embodiment, the time and frequency projections of the probability envelopes for a measurement can take the form:

$$\text{GaussEnvelope}=\exp(-(((x-xo)/\text{widthx50})^2)) \quad [10]$$

Where x=time or frequency
x0=the coordinate position of the anomaly
and widthx50=the displacement from x0 at which the function is at half its peak FIG. 71 provides further detail on step 6910 in FIG. 70 of generating an individual probability indicator for each bruit candidate. In steps 7002 through 7014 of FIG. 71 a number of parameters are computed and initialized, all of which will be used in the bruit probability computation. In a step 7002, parameters for calculating the bruit probability are initialized. In a step 7004, a bruits per respiration decay component is computed for use later in the calculation of a covariance modifier. In a step 7006, values for time interval and frequency spread uncertainty are computed as expressed in equation [8] and equation [9]. In steps 7008 and 7010, the one-dimensional and two-dimensional arrays for calculating the probability indicators are initialized. In a step 7012, the probability function parameters for the skew ratio and bruit candidate peak power are calculated. In a step 7014, the covariance modifier for the probability of bruits is calculated. In a step 7016 of FIG. 70, a test is performed to determine if any bruit candidates exist in the bruit candidate table. If so, an individual probability indicator for each bruit candidate is calculated in a step 7018. If no bruit candidates exist, control passes to step 5000, whereby a single probability indicator of 0 will be generated.

Figure 72:
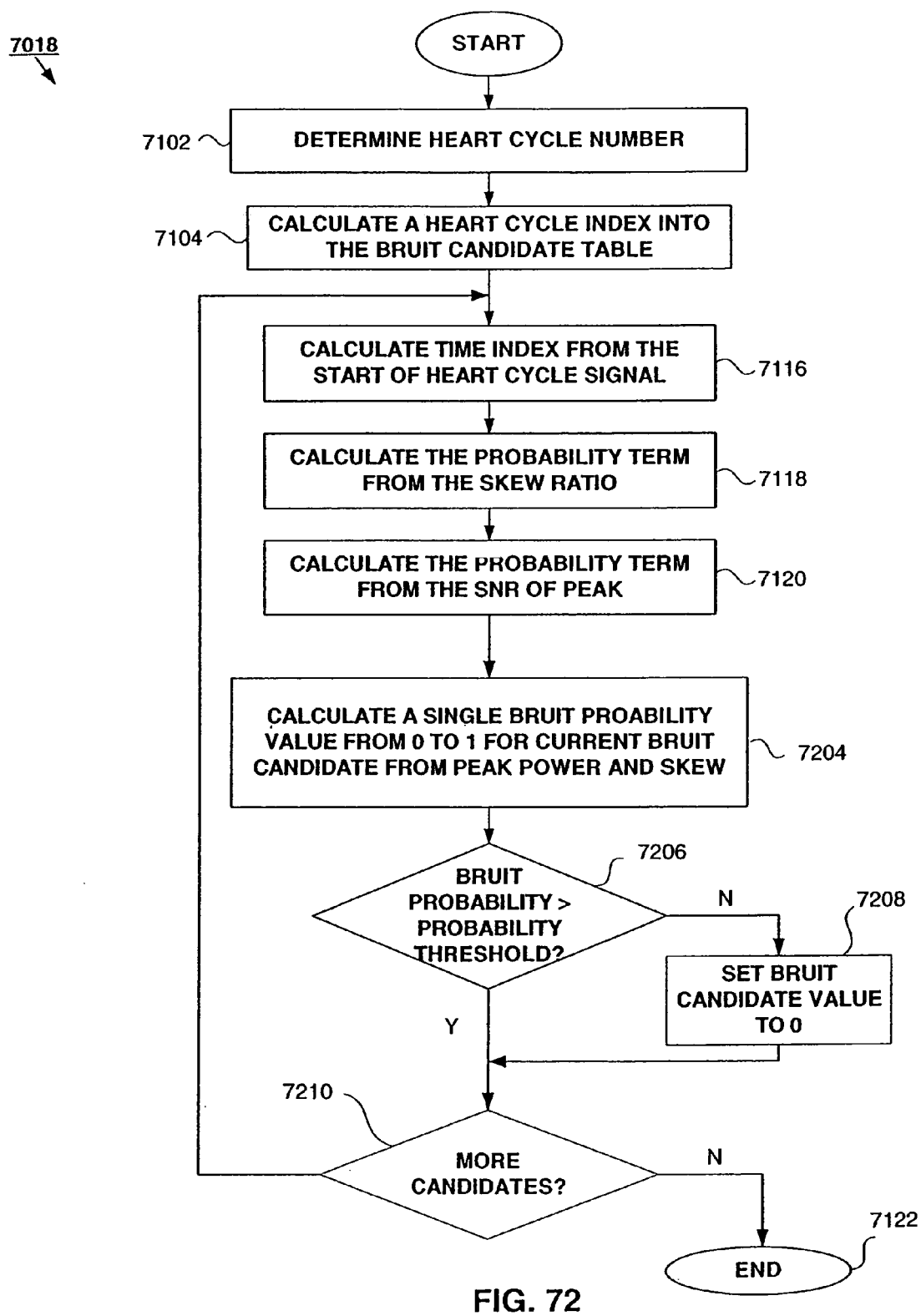
FIG. 72 is a flow chart depicting further detail on the actual calculation of an individual probability value for each bruit candidate.

FIG. 72 provides further detail on the actual calculation process of an individual probability indicator for each bruit as shown in step 7018 of FIG. 70. At a step 7102, the number of the current heart cycle signal is determined, from which a heart cycle index into the bruit candidate table is calculated in a step 7104. In a step 7116, a time index is calculated from the start of the heart cycle index. As stated earlier, each bruit candidate in the bruit candidate table comprises two values from which an individual probability can be calculated—the skew ratio and the peak power. In a step 7118, a probability term is calculated from the skew ratio. In a step 7120 a probability term is calculated from the signal-to-noise ratio of the peak. In a step 7204, the two probability terms calculated from the skew ratio and the peak power are combined to form a single bruit probability value. In an embodiment, this value is between zero and one.

Once the single bruit probability value has been determined and stored in step 7204, a test is then performed in a step 7206 of whether that single bruit probability value is greater than a previously selected probability threshold. At a step 7206, a check is made of whether the bruit probability just calculated is greater than the predefined minimum probability threshold. If so, the process of calculating the bruit probability value for the current bruit candidate completes. If it is not greater than the threshold, the single bruit probability value is set to a value of zero in a step 7208. A test is then performed at a step 7210 of whether further bruit candidates remain to be processed. If so, control passes back to a step 7116, otherwise the process completes.

Referring back to FIG. 70, in a step 6920, a calculation is made of the Gaussian probability envelope in the time domain for bruit candidates that meet the bruit probability threshold. This calculation will produce an array of values, with the number of values in the array being determined by the average heartbeat period of the patient divided by the sample rate of the data being used (in this case the narrow band sample rate). In an embodiment, the probability values determined at this step correspond to the probability that the bruit candidate is not indicative of cardiovascular disease (i.e., a value of zero indicates cardiovascular disease, a value of one indicates no cardiovascular disease). Thus, the array produced in step 6920 is referred to as an inverse time domain array. An example of such an array is shown in FIG. 75.

Figure 76:
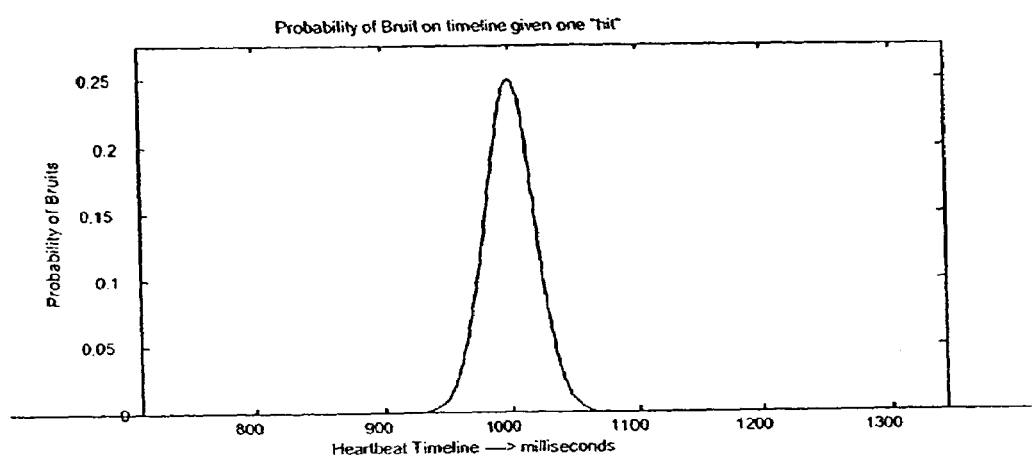
FIG. 76 is a graph showing the probability of one bruit in the time domain.

In order to plot the data points of the Gaussian function shown in FIG. 75, the values in the array are first subtracted from one, producing probability values that correspond to the probability that the bruit candidate is indicative of cardiovascular disease (i.e., a value of zero indicates no cardiovascular disease, a value of one indicates cardiovascular disease). Plotting the resulting values produces a waveform with a smooth-topped mountain with a unit height at the anomaly location. The two-dimensional projection of the Gaussian function in the time domain is illustrated in FIG. 76.

Similarly, as shown in step 6930 of FIG. 70, calculation of the Gaussian probability envelope in the frequency domain will produce an array of values, with the number of values in the array in one embodiment equal to 64. In an embodiment, the probability values determined at this step correspond to the probability that the bruit candidate is not indicative of cardiovascular disease (i.e., a value of zero indicates cardiovascular disease, a value of one indicates no cardiovascular disease). Thus, the array produced in step 6930 is referred to as an inverse frequency domain array. An example of such an array is shown in FIG. 77.

Figure 78:
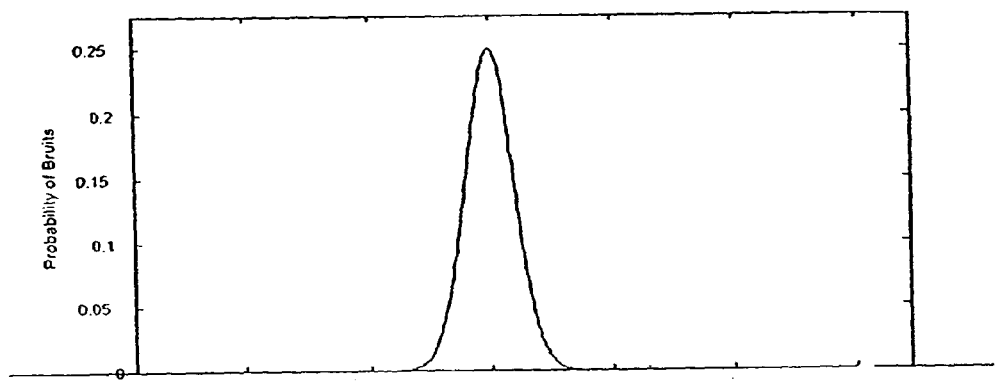
FIG. 78 is a graph showing the probability of one bruit in the frequency domain.

In order to plot the data points of the Gaussian function shown in FIG. 77, the values in the array are first subtracted from one, producing probability values that correspond to the probability that the bruit candidate is indicative of cardiovascular disease (i.e., a value of zero indicates no cardiovascular disease, a value of one indicates cardiovascular disease). Plotting the resulting values produces a waveform with a smooth-topped mountain with a unit height at the anomaly location. The two-dimensional projection of the Gaussian function in the frequency domain is illustrated in FIG. 78.

Figure 79:
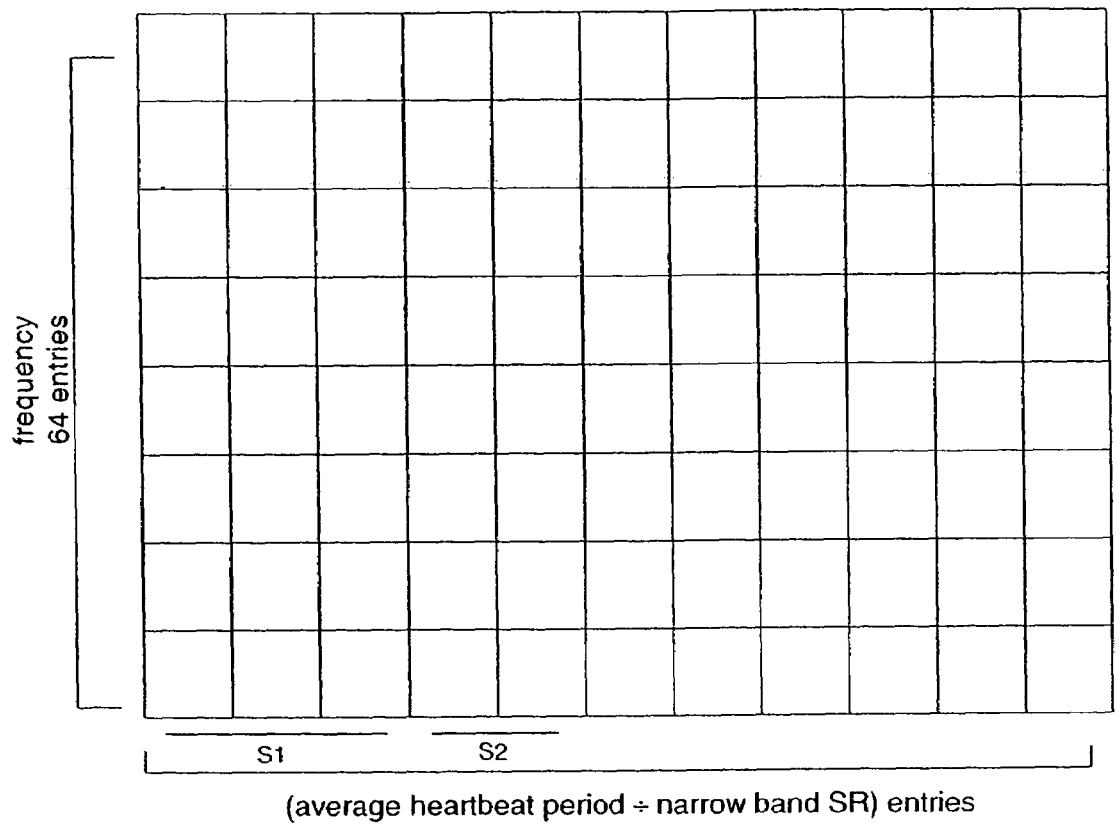
FIG. 79 is a blank two-dimensional Gaussian distribution table.
Figure 80:
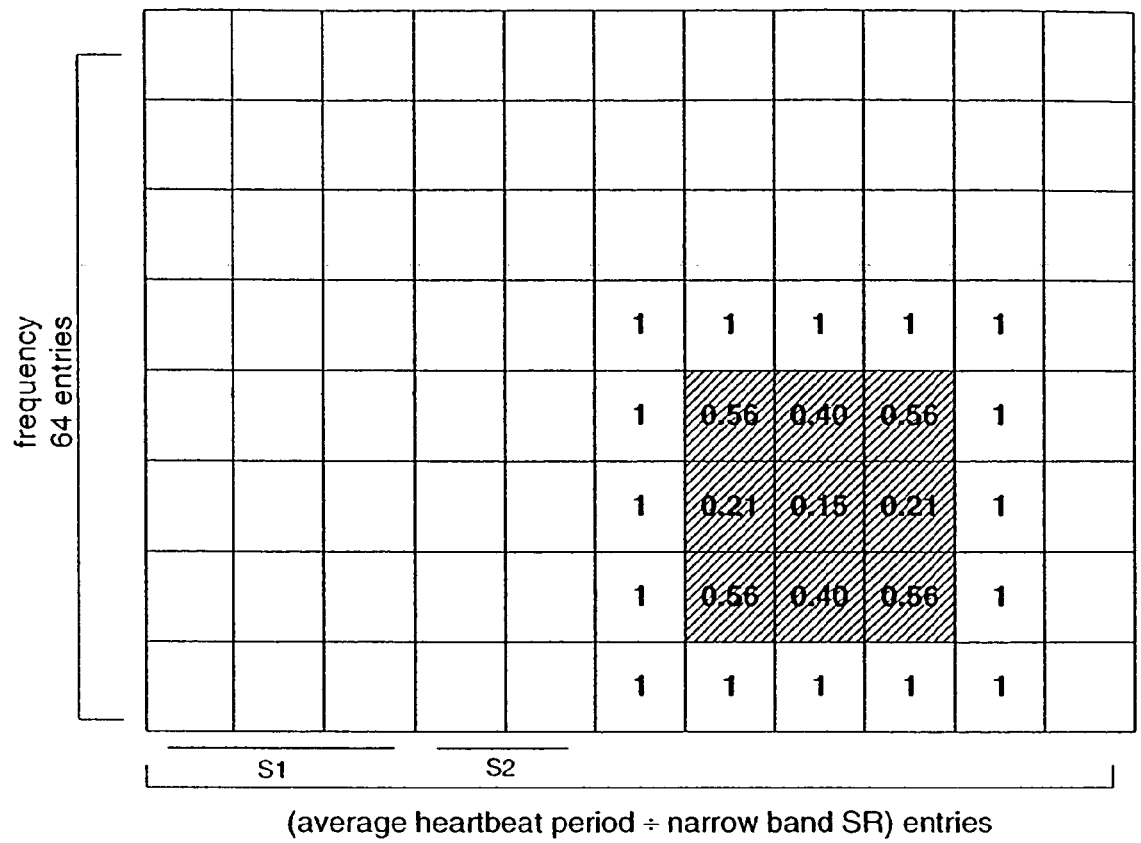
FIG. 80 is a two-dimensional Gaussian distribution table populated with sample values.
Figure 81:
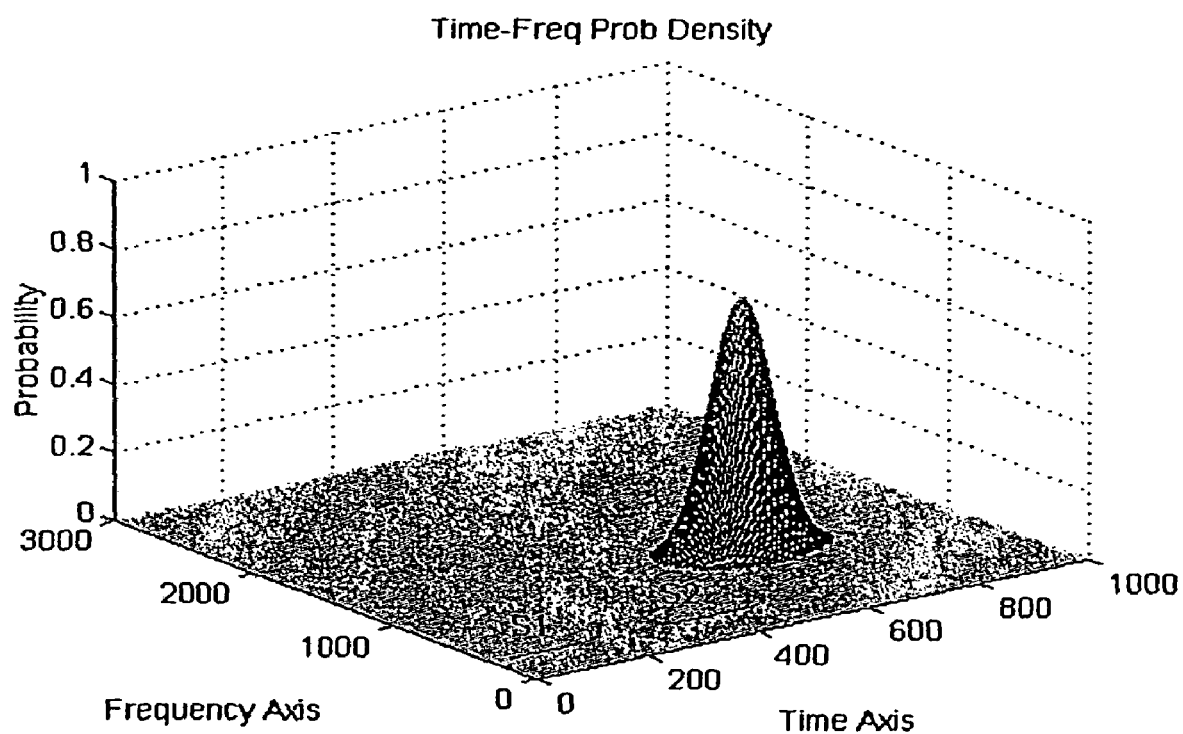
FIG. 81 is a three-dimensional representation of a probability indicator for a single bruit candidate.

As specified in step 6940 of FIG. 70, the expansion into the 2-dimensional probability of a single bruit is calculated as the vector product of the Gaussian envelopes in frequency and time all scaled by the probability that the anomaly is a bruit as calculated from SNR and skew as described above. The vector product of a one-dimensional projection of a Gaussian function in the time domain (such as in FIG. 76) and a one-dimensional projection of a Gaussian function in the frequency domain (such as in FIG. 78) results in a two-dimensional matrix, an empty example of which is shown in FIG. 79. As just one example, a bruit candidate based on the values shown in FIG. 75 and in FIG. 77 that only has a peak and one value at each location away from the peak might take on values that only populate the entries that have been shaded in FIG. 80. The center shaded entry could represent the peak and each of the perimeter entries could represent the result of the Gaussian distribution. A three dimensional plot of the matrix in FIG. 80, with an indication on the time axis of S1 and S2, is shown in FIG. 81 (not drawn to scale).

Figure 69:
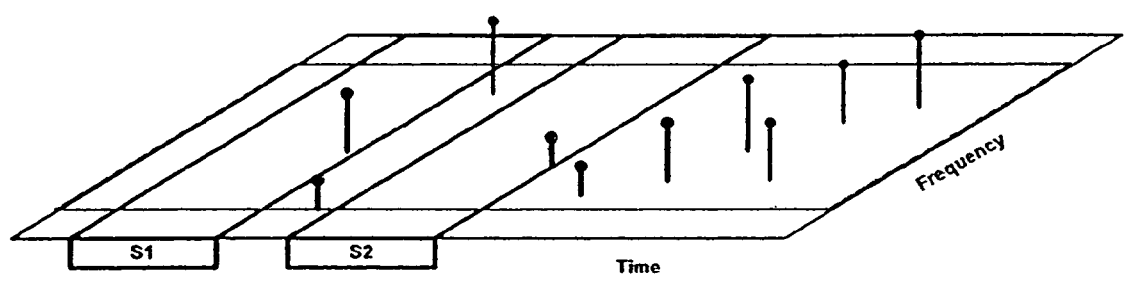
FIG. 69 shows a plot of the values of the individual probability indicators for several entries in the bruit candidate table.
Figure 73:
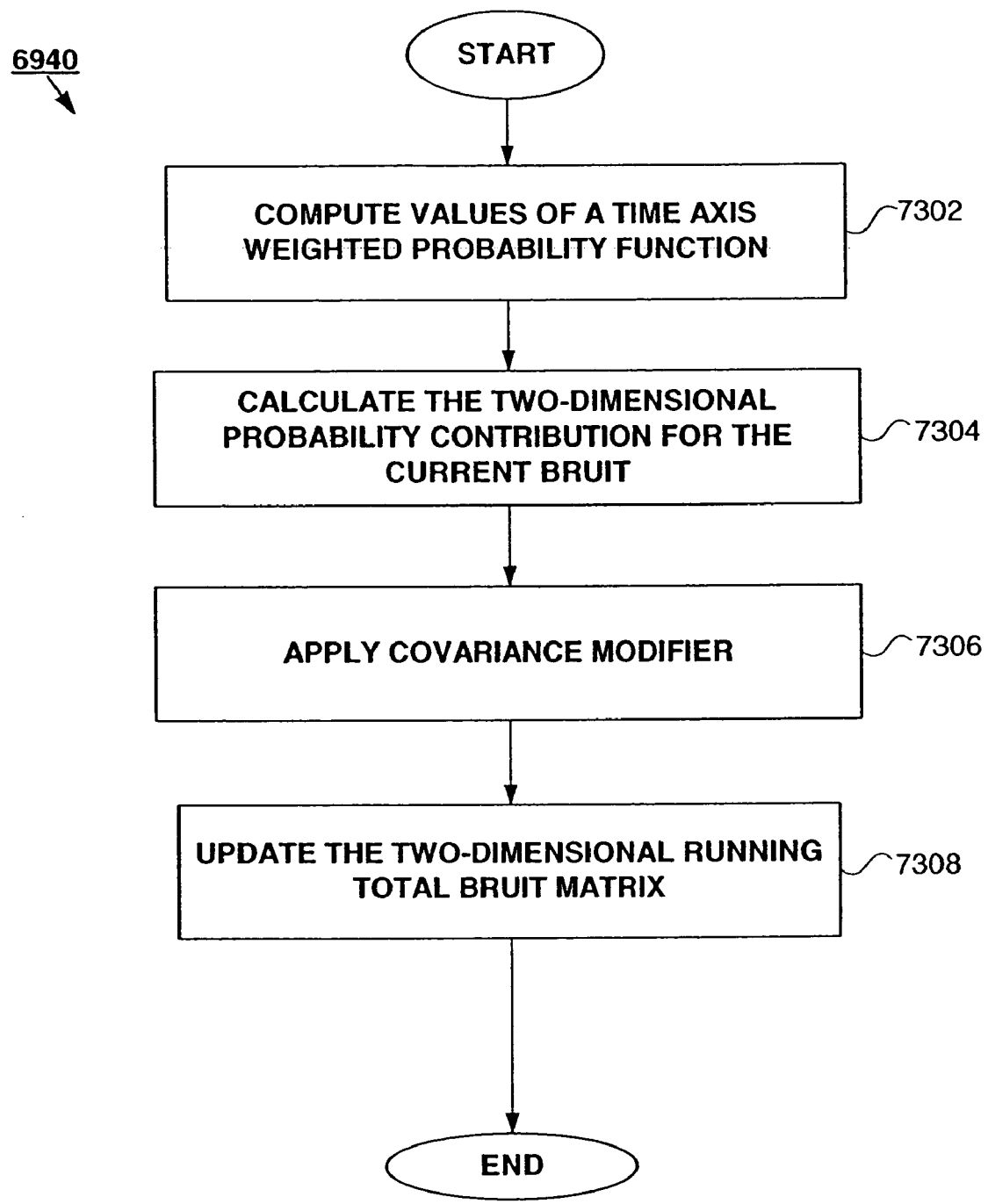
FIG. 73 is a flow chart depicting the expansion of a single bruit probability indicator into a 2-dimensional probability indicator in frequency and time.

The flow chart in FIG. 73 provides further detail of the process shown in step 6940 of FIG. 69, in which the two-dimensional Gaussian distribution for each entry in the bruit candidate table is calculated. At a step 7302, the values of a weighted probability function along the time axis are computed. In step 7304, the two-dimensional probability contribution for the current bruit is calculated by calculating an outer product of the frequency domain Gaussian distribution array and the time axis weighted probability function. In step 7306, the covariance modifier is applied to the individual two-dimensional probability contribution to account for the effects of respiration. In a step 7308 of FIG. 73, the two-dimensional running total bruit matrix is updated.

As each individual two-dimensional bruit Gaussian distribution matrix is calculated, its effects on the overall probability indicator (i.e., Flow Murmur Score) are accumulated by performing a dot product of the inverse of the Gaussian distribution envelope with a two-dimensional running total bruit matrix, which represents the current running total of the accumulated bruit probabilities for each time and frequency component of the heart cycle signals in a given heart waveform. Hence, if the first bruit candidate in the bruit candidate table corresponds to the matrix of FIG. 80, then the two-dimensional running total bruit matrix will be identical to the matrix of FIG. 80 until the second bruit candidate in the bruit candidate table is processed. For a given waveform, the two-dimensional running total bruit matrix is initially initialized to all ones (this essentially represents the probability of no bruits for a given bruit candidate) so that the initial matrix multiplications do not propagate zeroes.

Figure 82:
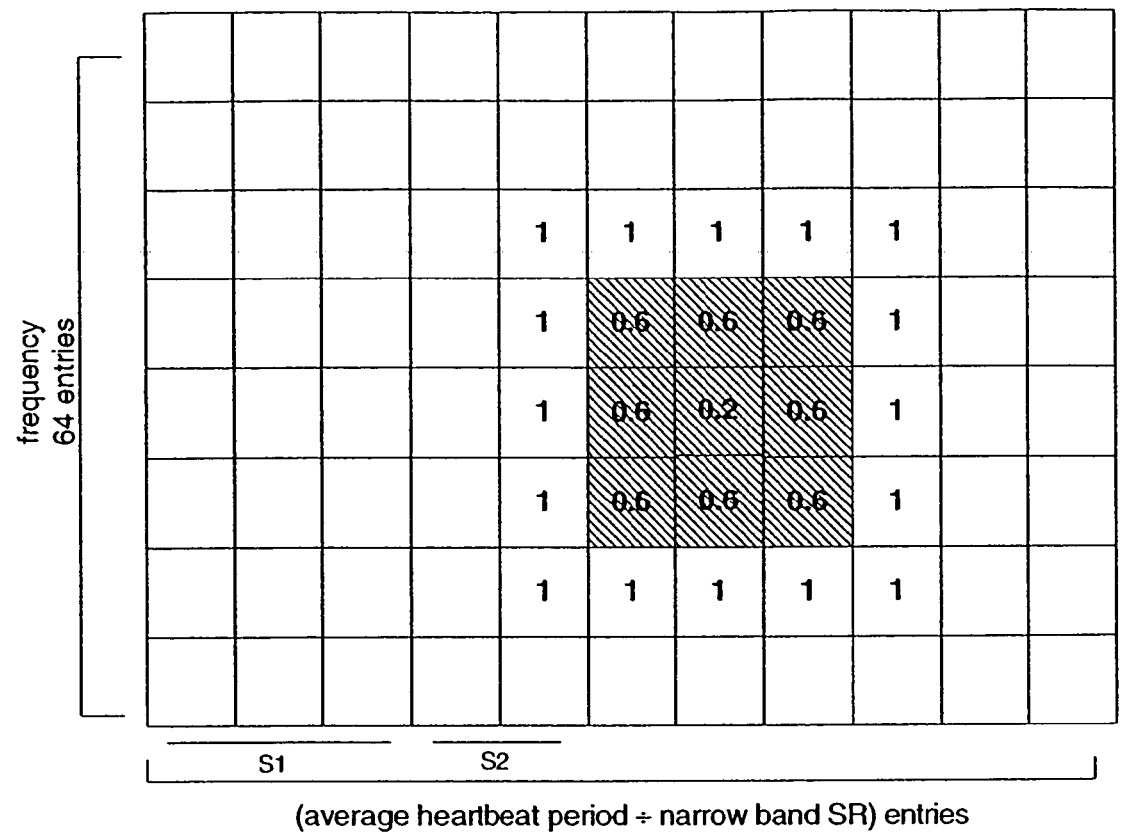
FIG. 82 is a two-dimensional Gaussian distribution table populated with sample values for a second bruit candidate.
Figure 83:
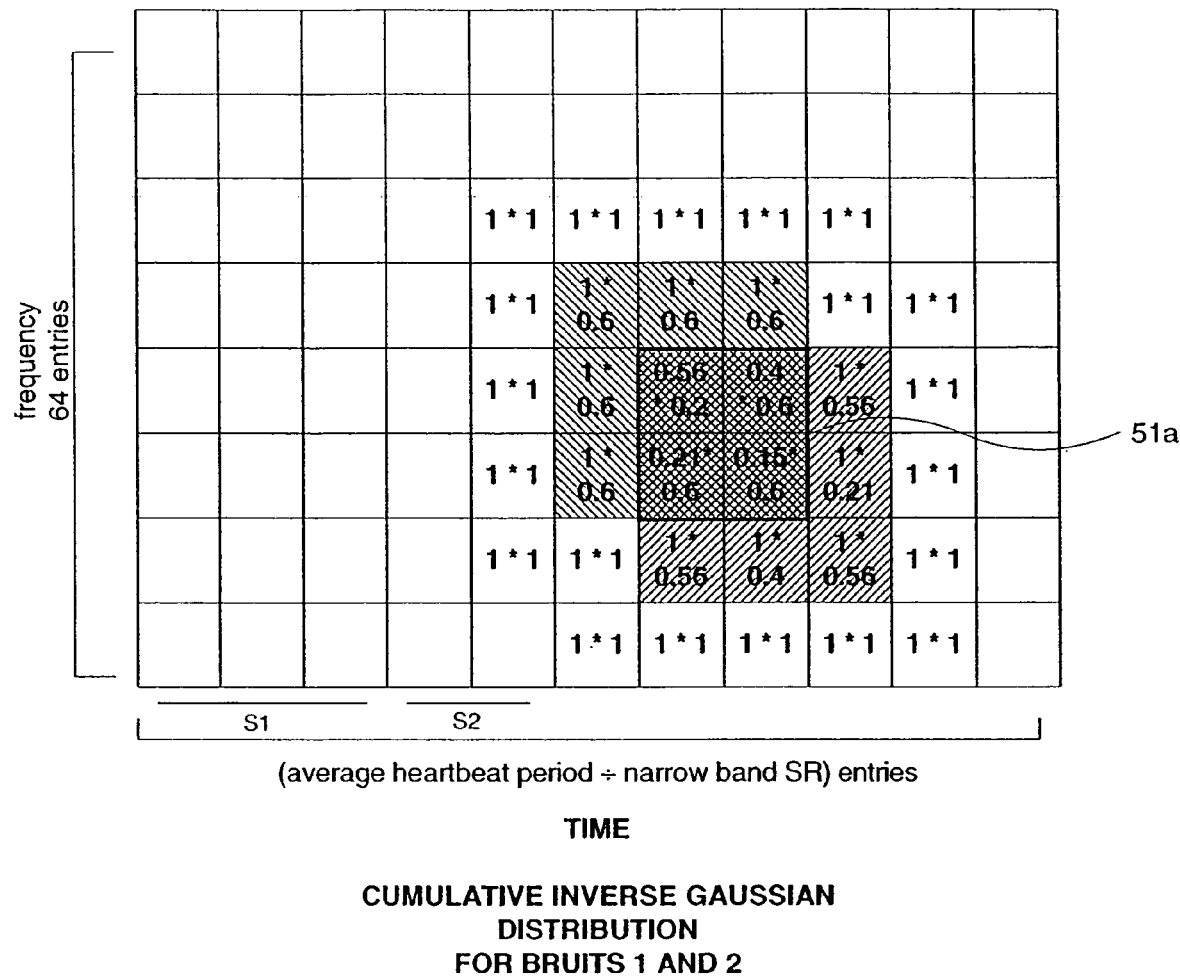
FIG. 83 is a two-dimensional running total Gaussian distribution table populated with sample values.
Figure 84:
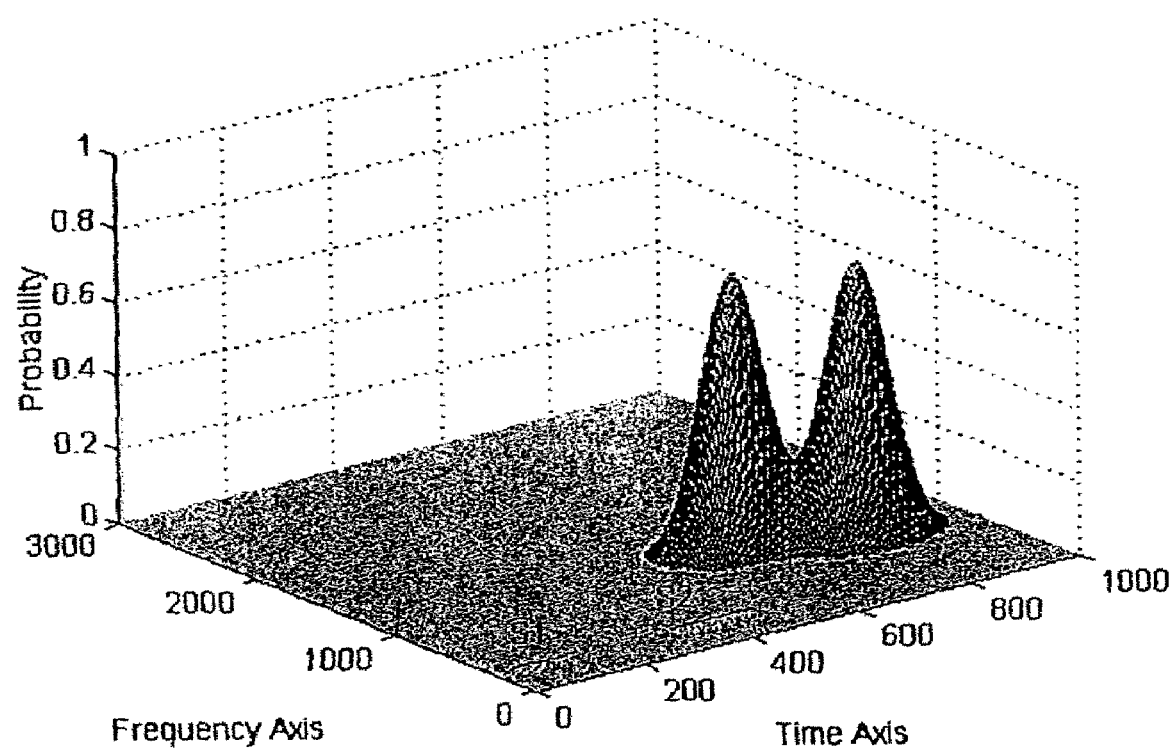
FIG. 84 is a three-dimensional representation of a probability indicator for multiple bruit candidates.

Plotting the results of one exemplary bruit Gaussian distribution for a second bruit candidate will take the form of the two-dimensional bruit Gaussian distribution matrix shown in FIG. 82. After the first bruit candidate is processed as just described, the two-dimensional bruit Gaussian distribution matrix of the second bruit candidate is inverted and then multiplied by the two-dimensional running total bruit matrix to obtain an updated two-dimensional running total bruit matrix as shown in FIG. 83. The cross-hatch section labeled 51a illustrates the time and frequency overlap of the Gaussian bruit distributions of the two bruit candidates. In three dimensions, the overlapping phenomenon between adjacent bruits could produce the figure shown in FIG. 84.

The above process of calculating two-dimensional bruit Gaussian distribution matrices is repeated for each bruit candidate within a given heart cycle and then for each bruit candidate in subsequent heart cycles until the entire heart waveform signal has been processed to produce a completed two-dimensional running total bruit probability matrix for a given heart waveform. The process is then completed for each of the heart waveform signals to produce nine separate completed two-dimensional running total bruit probability matrices for each of the respective nine heart waveform signals in the illustrated embodiment. As will be appreciated, the overlapping of the bruit candidates in time and frequency is emphasized by the multiplication of the matrices, which in turn contributes to the calculation of the likelihood of the patient having coronary heart disease. That is, when bruit candidates fall within the same time and frequency windows within one heart cycle or within different heart cycles, this is viewed as increasing the likelihood that the patient has coronary heart disease and the embodiments of the invention emphasize this in the above-described manner, which is ultimately reflected in the later generated probability indicator of coronary heart disease for each individual heart waveform and in the overall probability indicator of coronary heart disease for all the waveforms.

Figure 85:
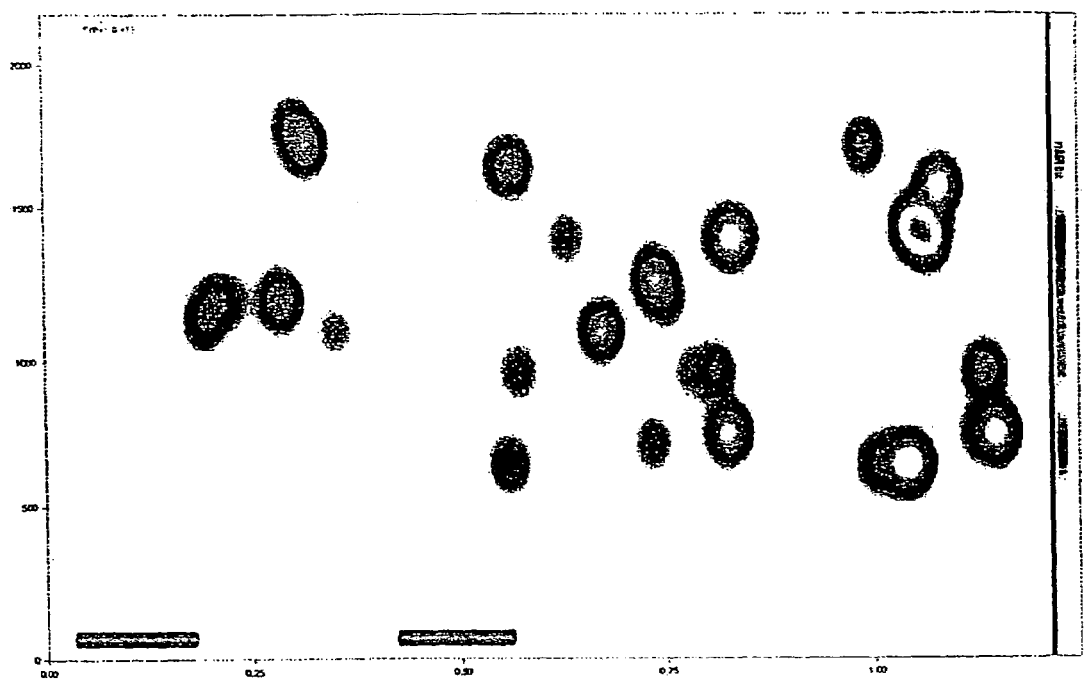
FIG. 85 is a graphical representation of all bruit candidates for one file of cardiovascular sound signals.

In summary, initial probability data on each bruit candidate is mapped in the two-dimensional bruit candidate matrix. The relative time of the anomaly in the bruit candidate in each bruit candidate heartbeat is on one axis of the matrix while the frequency of the signal maximum is on the other axis of the matrix. Each bruit candidate is spread over a narrow time and frequency region using a two-dimensional Gaussian wave function, which may be plotted in three dimensions, with peak probability equal to the calculated probability indicator of the bruit candidate. The dimensions of the Gaussian wave in time and frequency represent regions of uncertainty associated with the respective measurements. This function is then inverted and vector multiplied by the running total bruit matrix for all bruit candidates in a given heart waveform. The matrix data of the two-dimensional bruit Gaussian distribution array and the two-dimensional running total bruit matrix are maintained as probability of bruit so that the completed two-dimensional running total bruit matrix may be collapsed to a single number, as described below, which represents the probability of no bruit for a given waveform and thus the probability of no coronary heart disease for the given waveform. By subtracting the final complementation from one (1−P[NB]), the probability is returned to that of repetitive bruits. FIG. 85 illustrates a grayscale map representation of the two-dimensional probability of repetitive bruits for the heart-audio file example carried throughout this algorithm description.

As discussed above, each anomaly logged as a bruit candidate is evaluated in a statistical manner and combined in a summary probability calculation. Since the operative search here is for repetitive bruits, the process considers the peak audio frequency of the bruit as well as the relative time of occurrence of the bruit in the diastolic interval. The algorithm described above includes the accumulation of all bruit candidates in a time-frequency probability function. Independent bruit candidate events are then consolidated into a repetitive bruit probability as a function of frequency that is then further consolidated into a single repetitive bruit probability value for a single patient file.

Further, and as also described above, two additional processing steps produce a probability of repetitive bruits that applies to one heart waveform of a patient file. The first step is a consolidation via multiplication of each of the probability indicators of the completed two dimensional running total matrix along the time domain axis for each frequency index. The one-dimensional grayscale plot labeled 8820 on the right hand side of FIG. 86 shows the results of this first consolidation.

Figure 74:
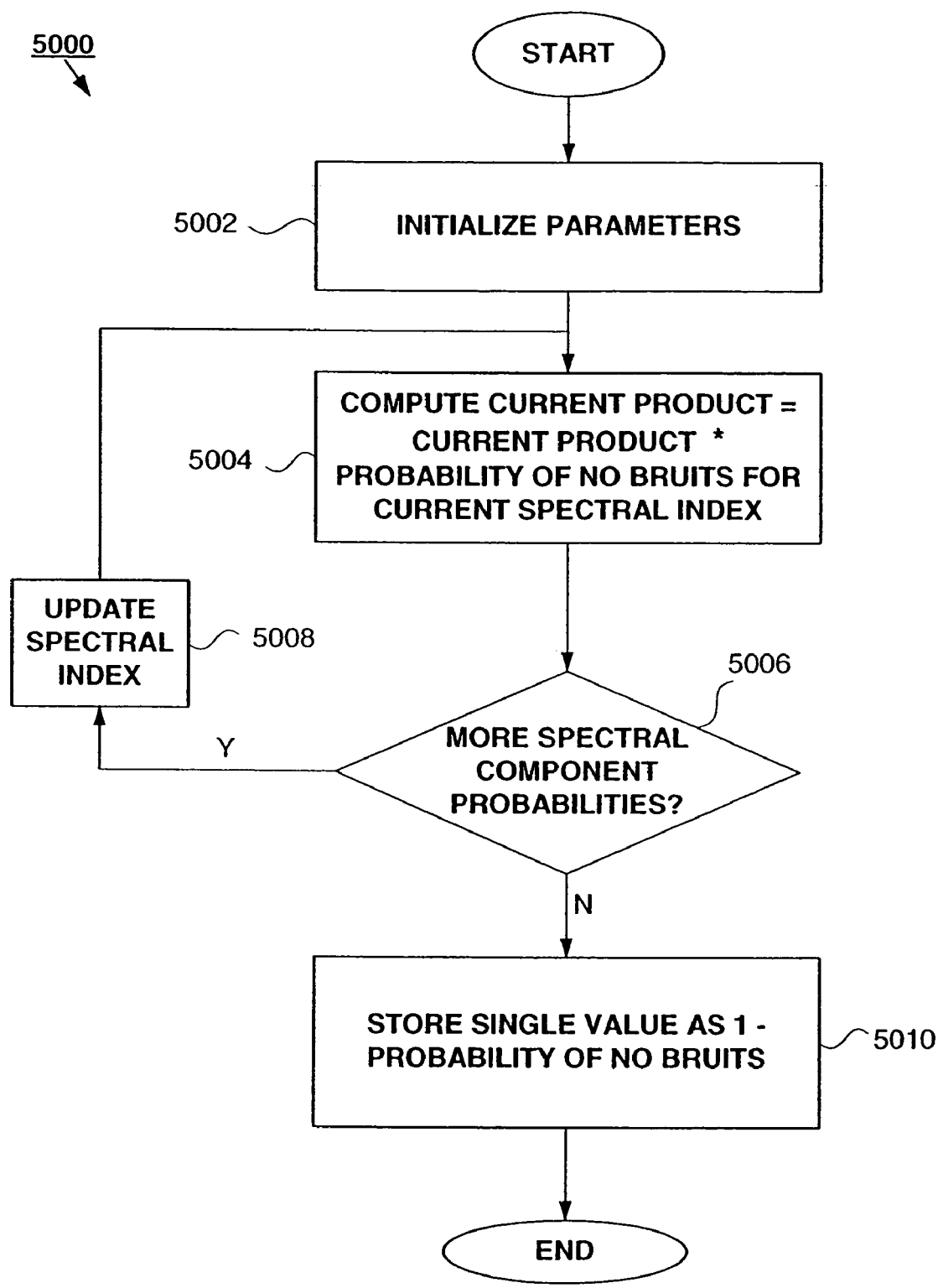
FIG. 74 is a flow chart depicting the consolidation of all probability indicators into a single overall probability indicator.

The consolidation across the time domain axis is followed by a consolidation via multiplication of each of the probability indicators across the frequency domain axis into a probability indicator of coronary heart disease for the given heart sound signal, as shown in step 5000 of FIG. 2. The flow chart in FIG. 74, along with the discussion below, provides further details on this consolidation process. At a step 5002, parameters associated with the consolidation process that will generate a single value probability indicator are initialized. At a step 5004, a new current product is calculated by multiplying the old current product value by the probability of no bruits for the current spectral index. At a step 5006 a check is performed of whether there are further spectral component probabilities to process. If so, the spectral index is updated in a step 5008 and control then passes to step 5004. If there are no further spectral component probabilities to process, a probability of bruits is calculated in a step 5010 by subtracting the single resulting value (corresponding to the probability of no bruits) from one.

Figure 86:
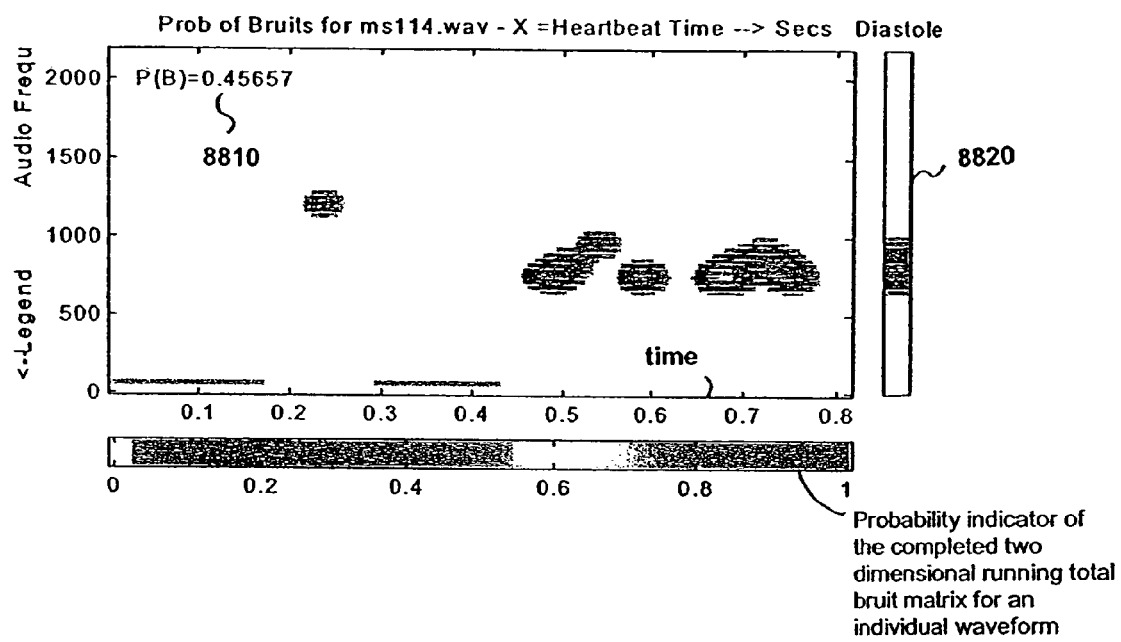
FIG. 86 is a two-dimensional probability graph of the probability of repetitive bruits, with a single probability of bruits value also displayed.

The single probability indicator of bruits (corresponding to the probability of coronary heart disease) for the given waveform of the final file consolidation is reported by the number designated as 8810 in the upper left hand corner of the main plot in FIG. 86. This probability indicator of coronary heart disease is repeated for each given heart waveform.

The intent of the first consolidation described above is to combine time data across diastole at each frequency in a manner such that a high level of confidence could be placed on a final probability at each audio frequency. This has required that the initial probability of a bruit measurement for each time cell had to be reduced in scale by some factor. The factor for achieving this confidence was based upon the expected repetitive nature of serious bruits. A criterion was established so that bruits must be recurring through the audio recording at some predefined rate. It must be noted that the choice of parameters has been guided by the angiography data from a known patient set. An arbitrary, but logical, choice was to expect the bruits to recur in pairs at a nominal respiration rate, that is, every five seconds. In order to derive a scale factor for the first consolidation, it was assumed that a sequence of anomalies at one frequency, each with 50 percent probability of being a bruit and occurring twice every five seconds, should consolidate into a single probability also equal to 0.5. The basic consolidation of the probability data is a calculation by products of the probability of No bruit, given the events that have been detected. This is the product of the No bruit probabilities for each frequency across the time line. The time line is windowed to encompass approximately 600 milliseconds after the onset of S2. Hence the consolidation of our adjusted hypothetical bruits occurring with 50 percent probability is given by the expression:

$$P'(NB) = (1 - \text{alpha} * 0.5)^{B\text{perR}} = 0.5 \text{ [Adjusted Probability]} \quad [11]$$

where $$B\text{perR} = 2 * \text{RecordingTime}/5; \text{ [Bruits per Recording]}$$

Solving for Alpha, we have:

$$\text{Alpha} = (1 - 10^{\wedge}(\log 10(0.5)/B\text{perR}))/0.5 \text{ [Modifier for Prob(Bruit)]} \quad [12]$$

The following equation, (C4), has been used to calculate a probability of repetitive bruits as a function of frequency.

$$P'(NB) = \text{PRODUCTS of } (1 - \text{alpha} * P(ti)) \text{ for independent } ti \quad [13]$$

The time indices (ti), of the product terms are just far enough apart to be independent. Recalling that a Gaussian envelope represented the probability function for each anomaly, the separation for independence is a function of the slope of the Gaussian envelope set by its half-width. Recall that this calculation is the probability of No bruits. Given:

$$\text{GaussEnvelope} = \exp(-(((x-xo)/\text{width}x50)^{\wedge}2)) \quad [14]$$

then $$\text{delta\_}t = 1.69 * \text{width}x50 \text{ [the separation for independence]} \quad [15]$$

Although any one set of points on the probability distribution separated by delta_t can be multiplied together to produce a consolidated probability, the resultant value will fluctuate according to the particular set selected. A better result is obtained by using the average of all the discrete sets that have delta_t separation. Once the averages have been calculated for all discrete filter frequencies, the time variable has been eliminated and a consolidated probability of repetitive bruits as a function of frequency has been realized.

Since appropriately separated frequency probabilities can be considered independent measurements, they can be consolidated in a second consolidation using equation (C4) with an Alpha substituted by Beta as set forth below. However, repetitive bruits at 300 Hz do not carry the same level of significance as those of higher frequency. This is because more constricted flow will produce stronger turbulence and associated higher frequencies. For this reason, a weighting factor has been arbitrarily assigned that lowers the associated bruit probability for the lower frequency. This weighting function is given by the expression:

$$\text{Beta}(\text{Frequency}) = \min \{1, \text{sqrt}(\text{Frequency}/1000)\} \quad [16]$$

The square root function causes the weight to increase rapidly from 0.5 at 300 Hz to 0.84 at 700 Hz. The value is limited to one for frequencies above 1000 Hz. Alpha in equation (C4) is replaced with Beta to consolidate the frequency data into a single probability of repetitive bruits for the file. The terms are weighted by increasing frequency to accentuate the contributions of the higher frequencies. As in the consolidation across the time axis, all available sets of measurements with independent separations of 1.69 times the half-frequency width of the Gaussian envelope are averaged. The result is a single probability of repetitive bruits for one file. The results of this probability calculation are displayed in the upper left hand corner of each 2-dimensional probability plot.

Finally, a third consolidation process combines the multiple file summaries into one patient summary for a file set, usually nine audio recordings from sites positioned in a 3×3 array on the chest over the heart. The probability of repetitive bruits measure for each of the nine recording sites must be consolidated into a single Flow Murmur Score for the patient. Based on current evidence, there is no clear basis for assuming that the data in the audio from neighboring chest locations is independent. There is evidence in the summary patient plots that sounds from a common source appear in audio recordings taken from adjacent positions. The individual file probabilities are presumed covariant and have been consolidated using a method similar to equation (C4) with an Alpha of 0.5.

Given a bruit Source that can be equally heard from two sites, then the constraint of the calculation is that the cumulative probability from the two recording sites match either one individually. This implies that some scale factor, a, can be applied to yield the desired result.

$$(1-a*P1(NB))*(1-a*P2(NB))=1-P(NB), \text{ with}$$
$$P=P1=P2, (NB)\text{-->No bruit} \qquad [17]$$

Then solving for a*P(NB):

$$a*P(NB)=\text{sqrt}(P(NB)) \qquad [18]$$

The desired result merely requires taking the square root of the probabilities of no bruit, which results in an even simpler calculation that produced results very similar to previously used methods. However, the new approach provided more separation in results between normal and diseased patients. A slightly different but useful calculation of a composite probability can be obtained from the product of the square of the individual probabilities of bruits.

Using the methodology described above, a differential analysis was undertaken to determine whether the methodology could discriminate between various degrees of coronary artery lesions. For twenty-two patients undergoing a percutaneous coronary intervention, FMS scores (i.e., overall probability indicators) were computed both before and after the intervention. A statistically significant decrease in FMS occurred after intervention (p=0.02), indicating that the methodology indeed found fewer bruits after the coronary artery lesion was reduced.

Set forth in detail above are aspects of at least one embodiment of the invention. Each of the features set forth above may be implemented in one system, method, and/or computer executable code in accordance with an embodiment of the invention. Alternatively, each of the features set forth above may be separately implemented in different systems, methods, and/or computer executable codes in accordance with embodiments of the invention.

Furthermore, the principles, preferred embodiments, and modes of operation of the invention have been described in the foregoing description. However, the invention that is intended to be protected is not to be construed as limited to the particular embodiments disclosed. Further, the embodiments described herein are to be regarded as illustrative rather than restrictive. Others may make variations and changes, and equivalents employed, without departing from the spirit of the invention. Accordingly, it is expressly intended that all such variations, changes and equivalents which fall within the spirit and scope of the invention as defined in the foregoing claims be embraced thereby.

What is claimed is:

1. A method comprising:
   determining a first time window within which a first bruit candidate is located;
   determining a second time window within which a second bruit candidate is located; and
   if the first time window and the second time window overlap in time with respect to a common reference, then emphasizing the overlap of the first time window and the second time window in a generation of a likelihood of cardiovascular disease.

2. The method of claim 1, the first and second time windows each having an accuracy greater than at least half of a duration of either diastole or systole.

3. The method of claim 1, the first bruit candidate and the second bruit candidate each being within one heart cycle.

4. The method of claim 1, the first bruit candidate being within a first heart cycle and the second bruit candidate being within a second heart cycle.

5. The method of claim 4, the first heart cycle being part of a first heart waveform signal corresponding to a first location of a patient where cardiovascular sound signals were acquired, the second heart cycle being part of a second heart waveform signal corresponding to a second location of the patient where cardiovascular sound signals were acquired.

6. The method of claim 4, the first heart cycle and the second heart cycle being part of a single heart waveform signal corresponding to one location of a patient where cardiovascular sound signals were acquired.

7. A method comprising:
   determining, to an accuracy greater than at least half of a duration of either diastole or systole, a first time window within which a first bruit candidate is located;
   determining, to an accuracy greater than at least half of a duration of either diastole or systole, a second time window within which a second bruit candidate is located; and
   generating a likelihood of cardiovascular disease, an overlapping in time of the first time window and the second time window contributing to the generated likelihood.

8. A method for processing acquired cardiovascular sound signals of a patient, the cardiovascular sound signals corresponding to at least a first heart cycle and a second heart cycle of the patient, the method comprising:
   defining a plurality of time windows of the acquired cardiovascular sound signals, each of the time windows being a portion of a whole of diastole or systole of the first and second heart cycles of the patient;
   determining a location of a first bruit candidate in the first heart cycle based on information collected from the time windows;
   determining a location of a second bruit candidate in the second heart cycle based on information collected from the time windows; and
   generating a likelihood that the patient has cardiovascular disease, the determined location of the first bruit candidate and the determined location of the second bruit candidate contributing to the generated likelihood.

9. The method of claim 8, the generated likelihood including a numerical indicator.

10. The method of claim 9, the numerical indicator being between 0 and 1 or between 0 and 100%.

11. The method of claim 8, the acquired cardiovascular sound signals including one heart waveform signal corresponding to a location of the patient where the cardiovascular sound signals were acquired, the heart waveform signal including the first and second heart cycles of the patient.

12. The method of claim 8, the acquired cardiovascular sound signals including one heart waveform signal corresponding to a location of the patient where the cardiovascular sound signals were acquired, the heart waveform signal including the first heart cycle of the patient.

13. The method of claim 12, the one heart waveform signal being a first heart waveform signal, the cardiovascular sound signals further including a second heart waveform signal corresponding to second location of the patient where the cardiovascular sound signals were acquired, the second heart waveform signal including the second heart cycle of the patient.

14. The method of claim 8, the determined location of the first bruit candidate and the determined location of the second bruit candidate each being measured relative to a common reference of the first and the second heart cycles.

15. The method of claim 14, the common reference being a common time location in the first and second heart cycles.

16. The method of claim 15, the common time location being the start or end of S1.

17. The method of claim 15, the common time location being the start or end of S2.

18. The method of claim 14, further comprising:
determining the common reference using a signal derived from electrical potential heart signals.

19. The method of claim 14, further comprising:
determining the common reference without the assistance of a signal derived from electrical potential heart signals.

20. The method of claim 8, the generated likelihood being based on a power of the first bruit candidate and a power of the second bruit candidate.

21. The method of claim 8, the generated likelihood being based on a frequency of the first bruit candidate and a frequency of the second bruit candidate.

22. The method of claim 8, the generated likelihood being based on a duration of the first bruit candidate and a duration of the second bruit candidate.

23. The method of claim 8, the cardiovascular sound signals corresponding to a third heart cycle of the patient, the method further comprising:
determining a location of a third bruit candidate in the third heart cycle based on information collected from the time windows, the determined location of the third bruit candidate contributing to the generated probability indicator.

24. A method comprising:
generating from acquired cardiovascular sound signals a likelihood that a patient has cardiovascular disease based on whether signals indicative of bruit occur within a same time window of at least two different heart cycles of the patient, the same time window being measured relative to a common reference in the two different heart cycles and being a portion of a whole of diastole or systole of each of the at least two different heart cycles.

25. A method for processing cardiovascular sound signals of a patient, the cardiovascular sound signals corresponding to at least two different heart cycles of the patient, each of the different heart cycles having one of a systole or a diastole divided into a plurality of time windows, each of the different heart cycles having a common reference, the method comprising:
generating a likelihood that the patient has cardiovascular disease based on whether bruit candidates occur within at least one same time window of the plurality of time windows of the two different heart cycles of the patient, the same time window being measured relative to the common reference.

26. A method comprising:
identifying a first bruit candidate in a first heart cycle of a patient based on acquired cardiovascular signals of the patient;
identifying a second bruit candidate in a second heart cycle of the patient based on the acquired cardiovascular signals of the patient; and
determining a time location of the identified first bruit candidate and a time location of the second bruit candidate, both relative to a common reference in each of the first and second heart cycles of the patient.

27. A method comprising:
generating a two dimensional distribution matrix of probability indicators for at least two bruit candidates in one heart cycle or in different heart cycles.

28. A method comprising:
generating a two dimensional distribution matrix of probability indicators for each of a plurality of heart waveform signals, each of the heart waveform signals corresponding to a different location where cardiovascular sound signals were acquired.

29. A method comprising:
generating a two dimensional running total bruit matrix for a first heart waveform; and
generating a two dimensional running total bruit matrix for a second heart waveform.

30. The method of claim 29, further comprising:
generating a likelihood of cardiovascular disease from the two dimensional running total bruit matrix for the first heart waveform and the two dimensional running total bruit matrix for the second heart waveform.

31. A system comprising:
means for determining, to an accuracy greater than at least half of a duration of either diastole or systole, a first time window within which a first bruit candidate is located;
means for determining, to an accuracy greater than at least half of a duration of either diastole or systole, a second time window within which a second bruit candidate is located; and
means for generating a likelihood of cardiovascular disease, an overlapping in time of the first time window and the second time window contributing to the generated likelihood.

32. A computer readable medium containing computer program instructions for:
determining, to an accuracy greater than at least half of a duration of either diastole or systole, a first time window within which a first bruit candidate is located;
determining, to an accuracy greater than at least half of a duration of either diastole or systole, a second time window within which a second bruit candidate is located; and
generating a likelihood of cardiovascular disease, an overlapping in time of the first time window and the second time window contributing to the generated likelihood.

33. A computer readable medium containing computer program instructions for:
- identifying a first bruit candidate in a first heart cycle of a patient based on acquired cardiovascular sound signals of the patient;
- identifying a second bruit candidate in a second heart cycle of the patient based on the acquired cardiovascular sound signals of the patient; and
- determining a time location of the first bruit candidate and a time location of the second bruit candidate, both relative to a common reference in each of the first and second heart cycles of the patient.

34. A method comprising:
- determining a start point or an end point of at least one of S1, S2, S3, and S4 within each of a plurality of heart cycle signals independently of a signal derived from electrical potential or optical heart signals, each of the plurality of heart cycle signals corresponding to a different heart cycle.

35. The method of claim 34, further comprising:
- identifying any possible bruit signals in each heart cycle within a time window located relative to the determined start point or determined end point.

36. The method of claim 35, further comprising:
- generating a probability indicator indicative of the likelihood that the patient has cardiovascular disease based on at least some of identified possible bruit signals.

37. The method of claim 34, said determining including determining the end point of S2.

38. The method of claim 37, further comprising:
- identifying in each heart cycle within a time window located relative to the end point of S2 any possible bruit signals.

39. The method of claim 34, said determining including determining the end point of S1.

40. The method of claim 39, further comprising:
- identifying in each heart cycle within a time window located relative to the end point of S1 any possible bruit signals.

41. The method of claim 34, said determining the start point of at least one of S1, S2, S3, and S4 within each of the plurality of heart cycle signals comprising:
- applying at least one low pass filter to each of said heart cycle signals to obtain a low pass filter set for each heart cycle; and
- decimating the low pass filter set to obtain a decimated sample set for each heart cycle.

42. The method of claim 41, said determining the start point of at least one of S1, S2, S3, and S4 within each of the plurality of heart cycle signals comprising:
- convolving the decimated sample set with itself to produce an auto correlation.

43. The method of claim 42, said determining the start point of at least one of S1, S2, S3, and S4 within each of the plurality of heart cycle signals comprising:
- determining a start point of each of the heart cycle signals.

44. The method of claim 41, the low pass filter having cutoff frequency between 3000–6000 Hz.

45. The method of claim 44, the cutoff being approximately 4410 Hz.

46. The method of claim 41, the low pass filter having cutoff frequency between 300–600 Hz.

47. The method of claim 46, the cutoff being approximately 441 Hz.

48. A computer readable medium containing computer program instructions for:
- determining a start point or an end point of at least one of S1, S2, S3, and S4 within each of a plurality of heart cycle signals independently of a signal derived from electrical potential or optical heart signals, each of the plurality of heart cycle signals corresponding to a different heart cycle.

* * * * *

UNITED STATES PATENT AND TRADEMARK OFFICE
CERTIFICATE OF CORRECTION

PATENT NO.        : 7,190,994 B2                                        Page 1 of 5
APPLICATION NO.   : 10/390172
DATED             : March 13, 2007
INVENTOR(S)       : Sailor Hampton Mohler et al.

It is certified that error appears in the above-identified patent and that said Letters Patent is hereby corrected as shown below:

On the Title Page

In the Abstract, Line 3, "diesclosed" should be changed to --disclosed--.
In the Abstract, Line 5, "overlapping in time" should be changed to --overlapping-in-time--.

In the Drawings

Sheet 7, FIG. 7, the lead line at the top of the block "UPDATE INDEX INTO SMOOTHED HEART
    AUDIO", located between blocks labeled 2260 and 2265, should be changed so as to
    associate with previously-unassociated reference character "2270" located to the right of the
    block.
Sheet 11, FIG. 13:
    a "Y" label should added in association with the arrow between decision blocks 1302 and
        1306, and in association with the arrow between decision block 1308 and the block
        labeled "IGNORE ANY 3$^{RD}$ PEAKS";
    a "N" label should be added in association with the arrow between decision blocks 1306 and
        1308, and in association with the arrow between decision blocks 1308 and 1310; and
    the arrow from the "Y" branch of decision block 1308 should be extended and shifted so as to
        connect to the connector leading to the block labeled "IGNORE ANY 3$^{RD}$ PEAKS".
Sheet 13, FIG. 15:
    multi-line reference sign "1508" should be changed to --1508--; and
    reference sign --2215-- should be added together with a lead line directed at the entire flow
        chart.
Sheet 14, FIG. 16, reference sign "1104" should be changed to --2215--.
Sheet 15, FIG. 17, reference sign "1104" should be changed to --2215--.
Sheet 56, FIG. 61, reference sign "5130" should be changed to --5150--.

Signed and Sealed this
Twenty-ninth Day of September, 2015

Michelle K. Lee
*Director of the United States Patent and Trademark Office*

CERTIFICATE OF CORRECTION (continued)
U.S. Pat. No. 7,190,994 B2

In the Specification and Claims

Column 1, Lines 58 and 65, "where" should be changed to --wherein-- (two occurrences).
Column 2, Line 50, "signals" should be changed to --signal--.
Column 3:
    Line 33, "Vernier" should be changed to --vernier--; and
    Line 35, a (--.--) should be inserted after "signals".
Column 4, Lines 51-52, "single bruit probability indicator" should be changed to
    --pair of bruit probability indicators--.
Column 5:
    Line 25, --estimate-- should be inserted after "likelihood"; and
    Line 27, --anomolies-- should be changed to "anomalies".
Column 6, Line 45, "an" should be changed to --and--.
Column 7, Line 18, "percordium" should be changed to --precordium--.
Column 7, Lines 50 and 66; and Column 14, Line 2,
    "dc" should be changed to --DC-- (3 occurrences).
Column 8:
    Lines 14-15, "or within proximity to" should be changed to --, or within proximity to,--;
    Line 29, a (--,--) should be inserted after "110"; and
    Line 31, a (--,--) should be inserted after "120".
Column 10, Line 45, "include" should be changed to --includes--.
Column 11:
    Line 24, "HeartBeat" should be changed to --Heartbeat--; and
    Line 30, "Heart Beat" should be changed to --Heartbeat--.
Column 14, Lines 7-8, --signal-- should be inserted after "wide band".
Column 14, Lines 28, 30, 33-34 and 47-48 (4 occurrences); Column 15, line 55;
    Column 28, Lines 33, 36, 38 and 39 (4 occurrences); and
    Column 56, Lines 4, 5 and 6 (Claim 41, 3 occurrences); Line 20 (Claim 44); and
    Line 25 (Claim 46), "low pass" should be changed to --low-pass-- (14 occurrences in total).
Column 15:
    Line 48, "band pass" should be changed to --band-pass--;
    Line 57, "one" should be deleted before "each"; and
    Line 57, "band passed" should be changed to --band-passed--.
Column 16, Line 31, --1040-- should be inserted after "sub-peaks".
Column 17, Lines 29-30, "sound signals" should be changed to --data set--.
Column 18:
    Line 25, "sub peaks" should be changed to --sub-peaks--;
    Lines 27, 28 (two occurrences), 38 and 44,
        "sub peak" should be changed to --sub-peak-- (five occurrences in total);
    Line 36, "subpeak" should be changed to --sub-peak--;
    Line 41, "later-occurring" should be changed to --latter-occurring--;
    Line 62, "means" should be changed to --mean--; and
    Line 67, "(2)" should be changed to --(b)--.

Column 20:
    Line 14, "low-pass filtered version of the" should be deleted; and
    Lines 38-39, a (--,--) should be inserted after "envelope".

Column 21:
    Line 5, "at a step 1914" should be changed to --, at a step 1914,--;
    Lines 29-30, --smoothed-- should be inserted before "cardiovascular";
    Line 59, "+1s" should be changed to --+1's--; and
    Line 60, "narrowband" should be deleted before "cardiovascular".

Column 22, Line 2, a (--,--) should be inserted after "2402".

Column 23, Line 40, --then, in step 2718,-- should be inserted after "step 2714,".

Column 23, Line 44, and Column 24, Line 33, "2120" should be changed to --2720--
    (two occurrences).

Column 25:
    Lines 24-25, "subtracting 0.1 for peak error and 0.01 for peak edits from a perfect score of
        one" should be changed to
        --calculating the ratio of the valid peak counter over the sum of number of peaks plus
        the error count minus one and then subtracting 0.01 times the sum of the peak edit
        counter plus the deleted peak counter. The maximum parsing score is a value of 1.--;
    Line 26, "FIG. 23 through FIG. 31" should be changed to --FIGS. 23 and 24--;
    Line 36, "FIG. 6" should be changed to --FIG. 7--;
    Lines 38-40, Equation [1] should be replaced with:
        --parsing score = ( valid peaks / (number of peaks + error counter - 1)) -
            (0.01 * (peak edit counter + deleted peaks counter)).--; and
    Line 65, --in step 2270-- should be inserted after "updated".

Column 26, Line 6, a (--,--) should be inserted after "one".

Column 27:
    Lines 16, 28, 34 and 41, "Vernier" should be changed to --vernier-- (four occurrences); and
    Line 54, "FIG. 6" should be changed to --FIGS. 7--.

Column 28:
    Line 22, "Using" should be changed to --In step 3506, using--; and
    Line 55, "value locations" should be changed to --values--.

Column 29:
    Line 14, --, in step 3810,-- should be inserted after "then";
    Line 18, --in step 3814,-- should be inserted before "those";
    Line 42, --, in step 3910,-- should be inserted after "then";
    Line 44, --In step 3912, a determination is made of whether any of the S1 to S4 valley
        location array entries are empty. If so, in step 3914, those empty valley location array
            entries are populated.-- should be inserted after "value.";
    Line 47, "step" should be changed to --steps--;
    Line 48, "is determined" should be changed to --are respectively determined or assigned--;
        and
    Line 55, "locations" should be changed to --location--.

Column 30:
    Line 11, "At" should be changed to --Then, at--;
    Line 31, "s4" should be changed to --S4--; and

CERTIFICATE OF CORRECTION (continued)
U.S. Pat. No. 7,190,994 B2

Line 38, "heartbeat." should be changed to --heartbeats.--.

Column 31:
- Line 9, --in step 4310,-- should be inserted after "embodiment,";
- Line 17, --in step 4312,-- should be inserted after "pulse,"; and
- Line 26, --of step 4312-- should be inserted after "process".

Column 32:
- Line 27, "value," should be changed to --value),--; and
- Line 28, "threshold (which" should be changed to --threshold, which--.

Column 33:
- Line 8, "table 5" should be changed to --Table 5--; and
- Lines 11-12, "narrow band
    Sample Index" should be changed to --narrow band Sample Index.--.

Column 35:
- Line 16, "SkewCutoftThreshold" should be changed to -- SkewCutoffThreshold--; and
- Line 24, "LowFreguencyLimit" should be changed to --LowFrequencyLimit--.

Column 35, Line 51; and Column 36, Line 64,
    "high pass" should be changed to --high-pass-- (2 occurrences).

Column 36:
- Line 33, "5206" should be changed to --5208--; and
- Lines 61, "a step" should be changed to --steps--.

Column 37, Line 3, "band pass" should be changed to --band-pass--.

Column 38, Line 10, "margin" should be changed to --margins--.

Column 39:
- Lines 11, 18, and 22, "heat" should be changed to --heart-- (three occurrences);
- Line 16, "step" should be changed to --steps--; and
- Line 30, "component" should be changed to --component(s)--.

Column 40:
- Line 2, "bruits" should be changed to --bruit--;
- Line 12, a (--,--) should be inserted after "high filter index";
- Line 13, a (--,--) should be inserted after "2)";
- Line 14, a (--,--) should be inserted after "high filter index";
- Line 31, a blank line should be inserted before the fifth line of Equation [3],
    i.e. before "(for j=low filter index to high filter index)"; and
- Lines 35-36, the third and fourth lines of Equation [4] should be replaced with:
    --Normalization = sum((1 - (abs (j - PeakIndex) /
    (HiFilterIndex-LowFilterindex))) * (j-PeakIndex)^2).--.

Column 41:
- Lines 1-3, "as shown in FIG. 59 to process the next heart beat cycle until all parsed heart beat cycles have been processed." should be deleted; and
- Line 9, "5806" should be changed to --5804 to process the next heart beat cycle until all parsed heart beat cycles have been processed--.

Column 41, Line 37, and Column 42, Line 8, "FIG. 60" should be changed to --FIG. 61-- (two occurrences).

Column 44:
    Line 15, a (--,--) should be inserted after "0.5";
    Line 17, a (--.--) should be inserted after "function";
    Line 62, "Where" should be changed to --where--, and
        a (--,--) should be inserted after "))"; and
    Line 63, "And" should be changed to --and--, and
        a (--.--) should be inserted after "0.56)".

Column 45:
    Line 8, "Where" should be changed to --where--, and
        a (--,--) should be inserted after "))";
    Line 9, "And" should be changed to --and--, and
        a (--.--) should be inserted after "18.5)";
    Line 11, a (--,--) should be inserted after "opposite";
    Line 12, "Skew" should be changed to --skew--;
    Line 53, Equation [10], "xo" should be changed to --x0--;
    Line 54, "Where" should be changed to --where--, and
        a (--,--) should be inserted after "frequency";
    Line 55, a (--,--) should be inserted after "anomaly"; and
    Line 57, a (--.--) should be inserted after "peak".

Column 46:
    Line 10, "FIG. 70" should be changed to --FIG. 71--;
    Line 25, --SNR of the-- should be inserted before "peak power"; and
    Lines 35-36, "At a" should be changed to --At--.

Column 47, Line 47, "FIG. 69" should be changed to --FIG. 70--.

Column 49, Line 33, "FIG. 2" should be changed to --FIG. 4--.

Column 50:
    Line 18, "5; [" should be changed to --5. [--;
    Line 20, Equation [12]:
        "log 10" should be changed to --log10--; and
        "0.5 [" should be changed to --0.5. [--;
    Line 22, ", (C4)," should be deleted;
    Line 26, the (--,--) after "indices (ti)" should be deleted;
    Line 32, Equation [14], "xo" should be changed to --x0--; and
    Line 34, Equation [15], "50 [" should be changed to --50. [--.

Column 50, Lines 47 and 60, and Column 51, Line 22, "(C4)," should be changed to --[13]--.

Column 51:
    Line 24, "Source" should be changed to --source--;
    Line 30, Equation [17], a (--.--) should be inserted after "(NB)-->No bruit"; and
    Line 32, Equation [18], a (--.--) should be inserted after "sqrt(P(NB))".